(12) United States Patent
Nakamura et al.

(10) Patent No.: US 10,202,461 B2
(45) Date of Patent: Feb. 12, 2019

(54) ANTI-HUMAN TROP-2 ANTIBODY HAVING AN ANTITUMOR ACTIVITY IN VIVO

(71) Applicant: CHIOME BIOSCIENCE INC., Tokyo (JP)

(72) Inventors: Koji Nakamura, Tokyo (JP); Kentaro Okamura, Kanagawa (JP); Maki Tamura, Kanagawa (JP); Hiroyuki Yanai, Kanagawa (JP); Toru Kanke, Kanagawa (JP); Naoya Tsurushita, Palo Alto, CA (US); Shankar Kumar, Pleasanton, CA (US)

(73) Assignee: Chiome Bioscience Inc., Tokyo (JP)

( * ) Notice: Subject to any disclaimer, the term of this patent is extended or adjusted under 35 U.S.C. 154(b) by 6 days.

(21) Appl. No.: 15/169,109

(22) Filed: May 31, 2016

(65) Prior Publication Data

US 2016/0333110 A1 Nov. 17, 2016

Related U.S. Application Data

(62) Division of application No. 13/682,319, filed on Nov. 20, 2012, now Pat. No. 9,427,464.

(60) Provisional application No. 61/562,672, filed on Nov. 22, 2011.

(51) Int. Cl.
| | |
|---|---|
| *G01N 33/574* | (2006.01) |
| *C07K 16/30* | (2006.01) |
| *C07K 16/28* | (2006.01) |
| *A61K 39/395* | (2006.01) |
| *A61K 47/68* | (2017.01) |
| *A61K 39/00* | (2006.01) |

(52) U.S. Cl.
CPC .... *C07K 16/3053* (2013.01); *A61K 39/39558* (2013.01); *A61K 47/6851* (2017.08); *C07K 16/30* (2013.01); *C07K 16/303* (2013.01); *C07K 16/3023* (2013.01); *C07K 16/3038* (2013.01); *C07K 16/3046* (2013.01); *C07K 16/3069* (2013.01); *C07K 16/3076* (2013.01); *G01N 33/57438* (2013.01); *G01N 33/57488* (2013.01); *G01N 33/57492* (2013.01); *A61K 2039/505* (2013.01); *A61K 2039/545* (2013.01); *C07K 2317/24* (2013.01); *C07K 2317/33* (2013.01); *C07K 2317/34* (2013.01); *C07K 2317/56* (2013.01); *C07K 2317/73* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,840,854 | A | 11/1998 | Hellstrom et al. |
| 6,653,104 | B2 | 11/2003 | Goldenberg |
| 7,420,040 | B2 | 9/2008 | Young et al. |
| 7,420,041 | B2 | 9/2008 | Young et al. |
| 2004/0001825 | A1 | 1/2004 | Govindan et al. |
| 2007/0202043 | A1 | 8/2007 | Young et al. |
| 2007/0202113 | A1 | 8/2007 | Young et al. |
| 2008/0131428 | A1 | 6/2008 | Young et al. |
| 2013/0089872 | A1 | 4/2013 | Nakamura et al. |

FOREIGN PATENT DOCUMENTS

| | | |
|---|---|---|
| EP | 2573120 A1 | 3/2013 |
| JP | 2001-501801 A | 2/2001 |
| JP | 2006-502698 A | 1/2006 |
| JP | 2009-527230 A | 7/2009 |
| JP | 2009-528995 A | 8/2009 |
| JP | 2010-528056 A | 8/2010 |
| WO | 97/14796 A1 | 4/1997 |
| WO | 03074566 A2 | 9/2003 |
| WO | 2007095748 A1 | 8/2007 |
| WO | 2007095749 A1 | 8/2007 |
| WO | 2008144891 A1 | 12/2008 |
| WO | 2010089782 A1 | 8/2010 |
| WO | 2011145744 A1 | 11/2011 |

OTHER PUBLICATIONS

Maynard, J. et al., "Antibody Engineering", Annual Review of Biomedical Engineering, vol. 2, Jan. 1, 2000, pp. 339-376, XP009039750.
Panka, D.J. et al., "Variable region framework differences result in decreased or increased affinity of variant anti-digoxin antibodies", Proceedings of the National Academy of Sciences, vol. 85, No. 9, May 1, 1988, pp. 3080-3084, XP000611718.
Summons to attend oral proceedings pursuant to Rule 115(1) EPC issued in European Application No. 11783675.9, dated Nov. 4, 2016.
Paul, W.E. "Fundamental Immunology", 3rd Edition, 1993, pp. 292-295.
Rudikoff, S. et al. "Single amino acid substitution altering antigen-binding specificity", Proc. Natl. Acad. Sci. USA, 1982, vol. 79, pp. 1979-1983.
De Pascalis, R. et al. "Grafting of 'Abbreviated'Complementarity-Determining Regions Containing Specificity-Determining Residues Essential for Ligand Contact to Engineer a Less Immunogenic Humanized Monoclonal Antibody", The Journal of Immunology, 2002, vol. 169, pp. 3076-3084.
Casset, F. et al. "A peptide mimetic of an anti-CD4 monoclonal antibody by rational design", Biochemical and Biophysical Research Communications, 2003, 307, pp. 198-205.

(Continued)

Primary Examiner — Michael Allen
(74) Attorney, Agent, or Firm — McDermott Will & Emery LLP

(57) ABSTRACT

The present invention provides: an antibody which specifically reacts with hTROP-2 and has anti-tumor activity in vivo (particularly, a humanized antibody); a hybridoma which produces the aforementioned antibody; a conjugate of the aforementioned antibody and a drug; a pharmaceutical composition for diagnosing or treating a tumor; a method for detecting a tumor; and a kit for detecting or diagnosing a tumor.

14 Claims, 74 Drawing Sheets

Specification includes a Sequence Listing.

(56) References Cited

OTHER PUBLICATIONS

U.S. Office Action issued in U.S. Appl. No. 14/729,953 dated Sep. 13, 2016.
W. P. Faulk, et al., Antigens of human trophoblasts: A working hypothesis for their role in normal and abnormal pregnancies, Proc. Natl. Acad. Sci. USA, vol. 75, No. 4, pp. 1947-1951, Apr. 1978.
M. Lipinski, et al., Human trophoblast cell-surface antigens defined by monolonal antibodies, Proc. Natl. Acad. Sci. USA, vol. 78, No. 8, pp. 5147-5150, Aug. 1981.
A. J. Linnenbach, et al., Sequence investigation of the major gastrointestinal tumor-associated antigen gene family, GA733, Proc. Natl. Acad. Sci. USA, vol. 86, pp. 27-31, Jan. 1989.
A. Basu, et al., The epithelial/carcinoma antigen EGP-1, recognized by monoclonal antibody RS7-3G11, is phosphorylated on Serine 303, Int. J. Cancer: 62, pp. 472-479, 1995.
M. Fornaro, et al., Cloning of the gene encoding TROP-2, a cell-surface glycoprotein expressed by human carcinomas, Intl. J. Cancer: 62, pp. 610-618, 1995.
E. Ripani, et al., Human TROP-2 is a tumor-associated calcium signal transducer, Intl. J. Cancer: 76, pp. 671-676, 1998.
G. Calabrese, et al., Assignment of TACSTD1 (alias TROP1, M4S1) to human chromosome 2p21 and refinement of mapping of TACSTD2 (alias TROP2, M1S1) to human chromosome 1p32 by in situ hybridization, Cytogenet Cell Genet 92: pp. 164-165, 2001.
T. E. Sewedy, et al., Cloning of the murine TROP2 gene: conservation of a PIP2- binding sequence in the cytoplasmic domain of TROP-2, Intl. J. Cancer: 75, pp. 324-330, 1998.
R. Cubas, et al., Trop2: A possible therapeutic target for late stage epithelial carcinomas, Biochimica et Biophysica Acta, 1796, pp. 309-314, 2009.
T. Ohmachi, et al., Clinical Significance of TROP2 Expression in Colorectal Cancer, Clin. Cancer Res., 12, pp. 3057-3063, 2006.
Y. J. Fang, et al., Elevated expressions of MMP7, TROP2, and survivin are associated with survival, disease recurrence, and liver metastasis of colon cancer, Int. J. Colorectal Dis., 24, pp. 875-884, 2009.
D. Fong., et al., High expression of TROP2 correlates with poor prognosis in pancreatic cancer, British Journal of Cancer, 99, pp. 1290-1295, 2008.
D. Fong, et al., TROP2: a novel prognostic marker in squamous cell carcinoma of the oral cavity, Modem Pathology, 21, pp. 186-191, 2008.
A. D. Santin, et al., Gene expression profiles in primary ovarian serous papillary tumors and normal ovarian epithelium: identification of candidate molecular markers for ovarian cancer diagnosis and therapy, Intl. J. Cancer: 112, pp. 14-25, 2004.
J. Wang, et al., Identification of TROP-2 as an oncogene and an attractive therapeutic target in colon cancers, Mol. Cancer Ther., 7(2), pp. 280-285, Feb. 2008.
An International Search Report, dated Mar. 12, 2013, which issued during the prosecution of International Application No. PCT/JP2012/080800, which corresponds to the present application.
A Supplementary European Search Report, dated Sep. 12, 2013, which issued during the prosecution of European Application No. 11 78 3675.9, which is related to the present application.
Truong et al., "520 Poster, A monoclonal antibody targeting Trop-2 exhibits anti-tumor efficacy in human cancer models as a monotherapy and demonstrates efficacy in combination therapy", European Journal of Cancer, Supplement, Pergamon, Oxford, GB, vol. 6, No. 12, Oct. 1, 2008, pp. 165, XP025534584.
Truong et al., "AR47A6.4.2, a naked monoclonal antibody targeting Trop-2, exhibits anti-tumor efficacy in multiple human cancer models as a monotherapeutic agent and demonstrates efficacy in combination therapy", American Association for Cancer Research, Proceedings of the Annual Meeting, vol. 49, Apr. 1, 2008, pp. 948, XP001539271.
Truong et al., "Functional antibodies targeting Trop-2 demonstrate in vivo efficacy in human pancreatic and other solid tumor xenograft models", Americal Association for Cancer Research, Proceedings of the Annual Meeting, vol. 48, Apr. 1, 2007, pp. 217, XP001539272.
Hahn et al., "Antibodies targeting the tumor-associated antigen TROP-2 demonstrate anti-tumor effects in human pancreatic cancer models", Proceedings of the American Association for Cancer Research Annual Meeting & 97th Annual Meeting of the American-Association-for-Cancer-Research (AACR), vol. 47, Apr. 1, 2006, pp. 877, XP001525503.
S. V. Govindan et al., Poster Presentations—Monoclonal Antibodies 1, Abstract 2438: Efficacious therapies of two human pancreatic cancer xenografts and an aggressive human lymphoma xenograft with redesigned antibody-SN-38 conjugates, Cancer Research, Apr. 2010, vol. 70, Issue 8, Supplement 1, Abstract 2438.
Office Action, dated Feb. 5, 2014, which issued during the prosecution of U.S. Appl. No. 13/698,201, which is related to the present application.
Communication pursuant to Article 94(3) EPC, dated Jun. 25, 2014, which issued during the prosecution of European Patent Application No. 11 783 675.9, which is related to the present application.
Holt et al., "Domain antibodies: proteins for therapy," Trends in Biotechnology vol. 21, No. 11, Nov. 2003, pp. 484-490.
Notice of Allowance, dated Feb. 12, 2015, which issued during the prosecution of U.S. Appl. No. 13/698,201, which is related to the present application.
European Search Report dated Jun. 15, 2015 issued in corresponding EP Application No. 12852269.5.
J. Varughese et al., Gynecologic Oncology, Academic Press, London, GB, vol. 122, No. 1, Mar. 3, 2011, pp. 171-177.
J. Varughese et al., Cancer, vol. 117, No. 14, Jul. 15, 2011, pp. 3163-3172.
Rhoda Raji et al., Journal of Experimental & Clinical Cancer Research, vol. 30, No. 1, Jan. 1, 2011, p. 106.
J. Varughese et al., American Journal of Obstetrics & Gynecology, Mosby, St. Louis, MO, US, vol. 205, No. 6, Jun. 29, 2011, pp. 567.e1567.e7.
T.M. Cardillo et al., Clinical Cancer Research, vol. 17, No. 10, Mar. 3, 2011, pp. 3157-3169.
Alberti, S., et al. "Biochemical Characterization of Trop-2, a Cell Surface Molecule Expressed by Human Carcinomas: Formal Proof that the Monoclonal Antibodies T16 and MOv-16 Recognize Trop-2", HYBRIDOMA, vol. 11, No. 5, 1992, pp. 539-545.
Eurasian Search Report issued in Eurasian Application No. 201500219, dated Oct. 30, 2015.
Paul, Fundamental Immunology, 3rd Edition, 1993, pp. 292-295.
Bendig M. M. (Methods: A Companion to Methods in Enzymology, 1995, 8:83-93.
U.S. Office Action issued in U.S. Appl. No. 13/682,319 dated May 12, 2014.
U.S. Office Action issued in U.S. Appl. No. 13/682,319 dated Feb. 12, 2015.
U.S. Office Action issued in U.S. Appl. No. 13/682,319 dated Oct. 22, 2015.
U.S. Notice of Allowance issued in U.S. Appl. No. 13/682,319 dated Mar. 4, 2016.

Fig. 1 Affinity

BxPC-3

Other cancer cell lines

Other cancer cell lines

Reactivity with EpCAM/hTROP-1

K5-70 / Treatment

K5-70 /BxPC-3

K5-70/dose-dependent prevention

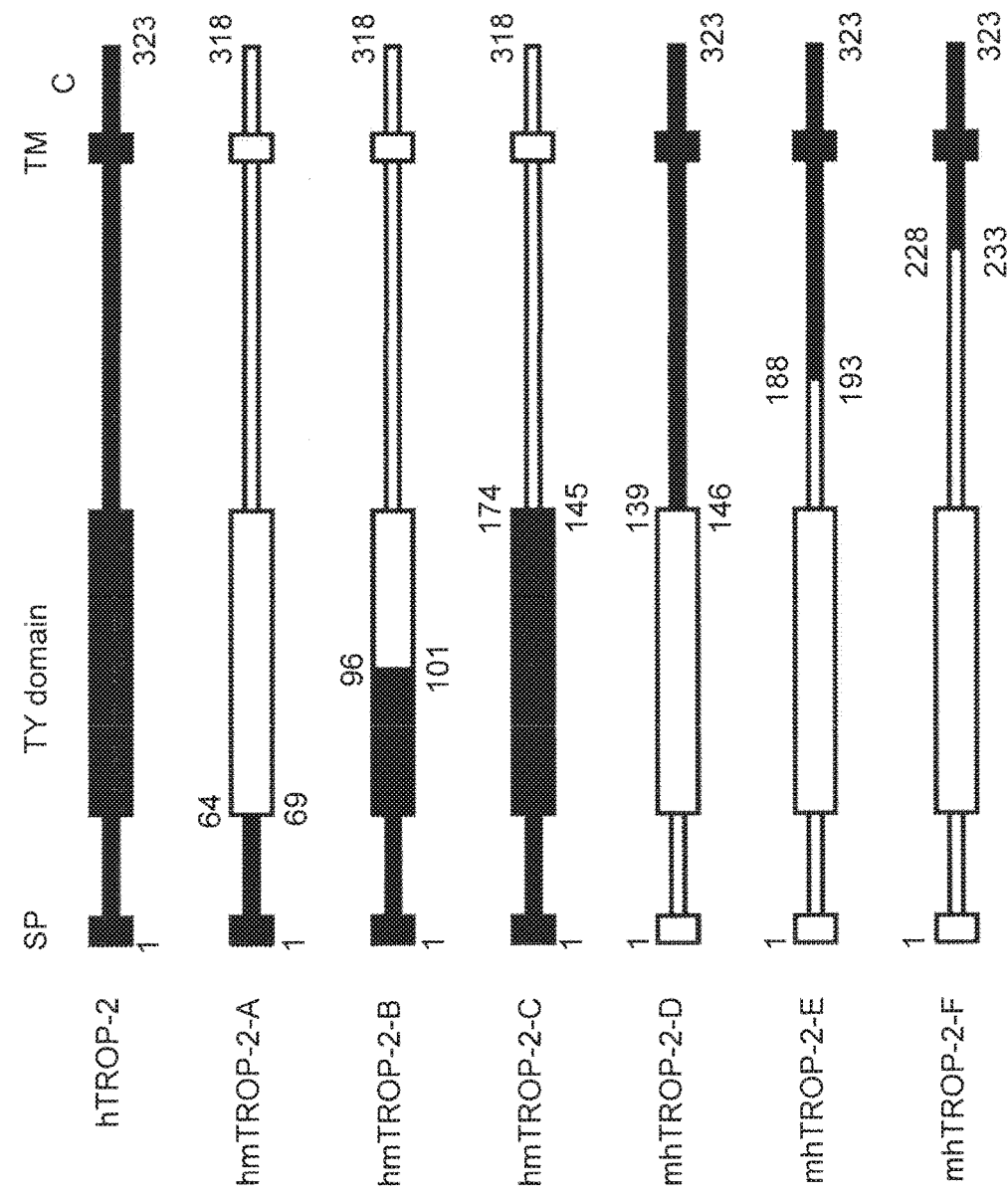

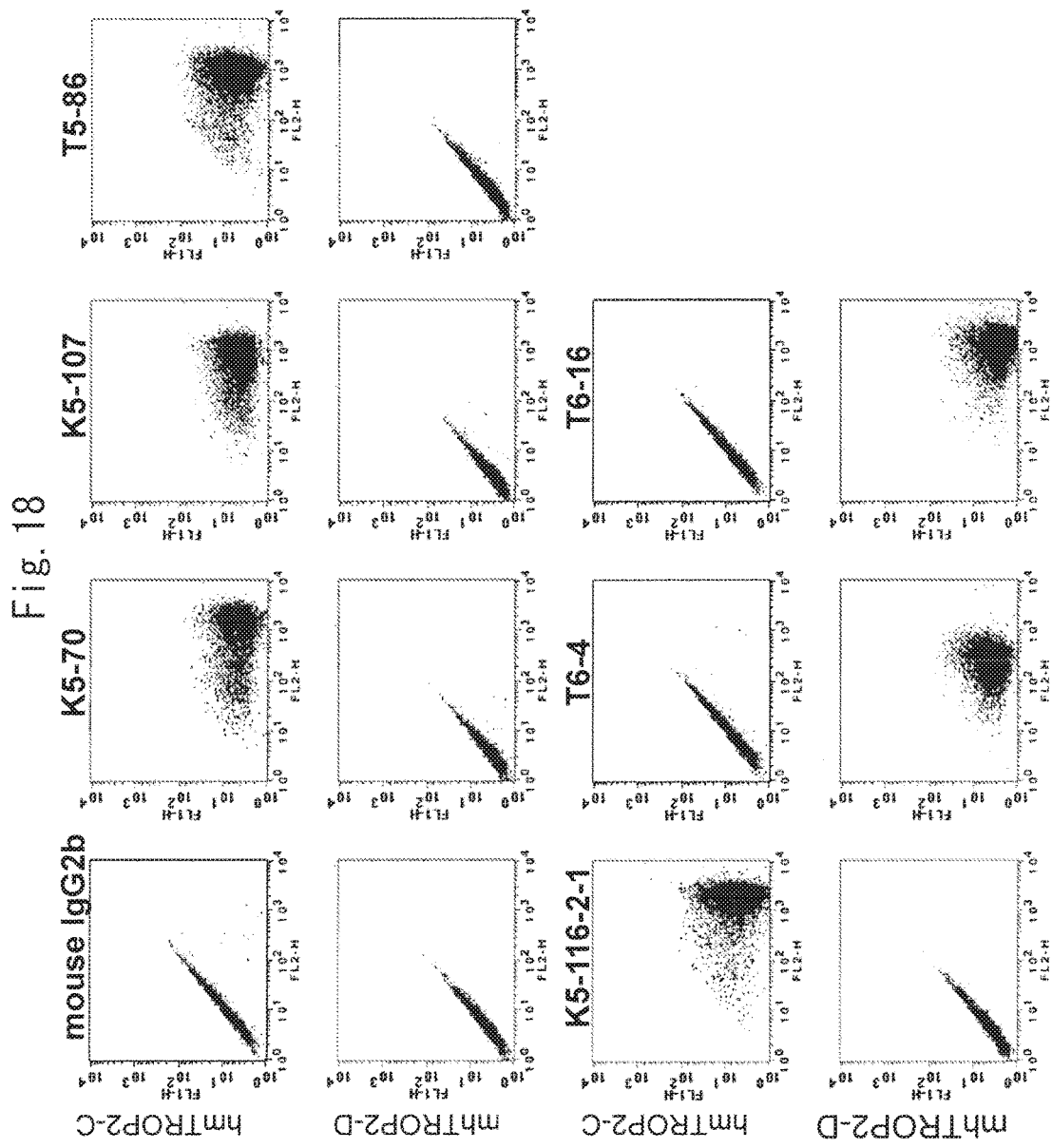

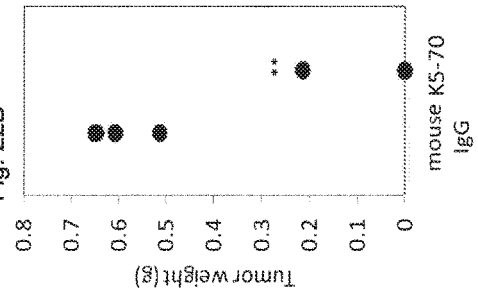
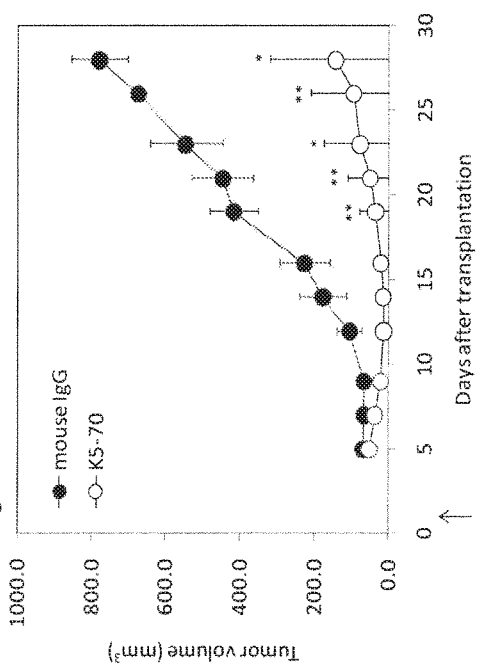
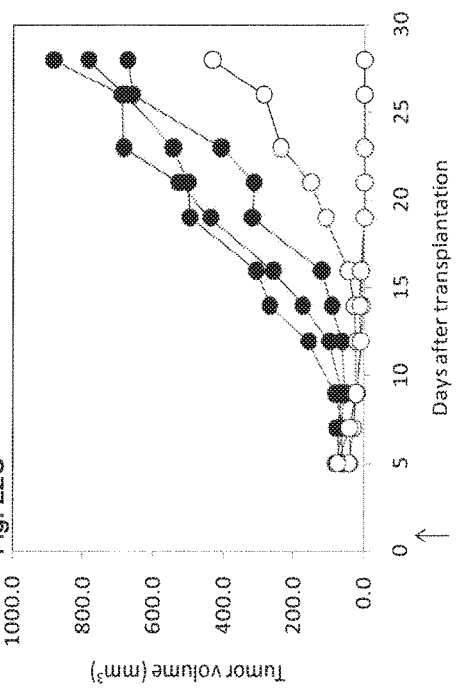

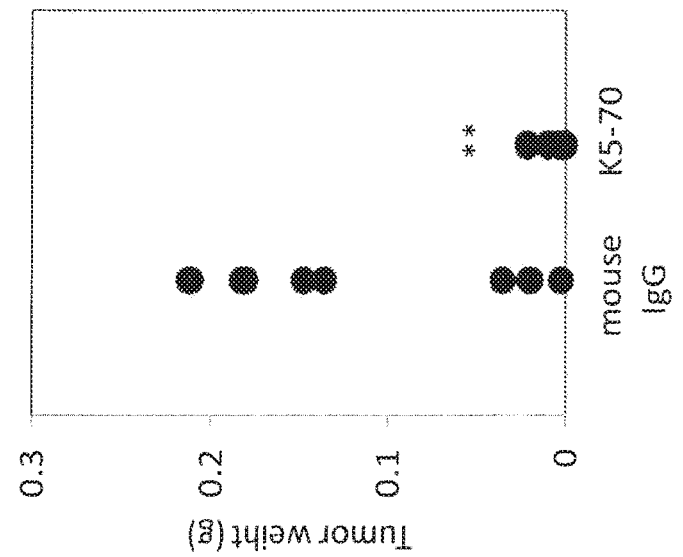
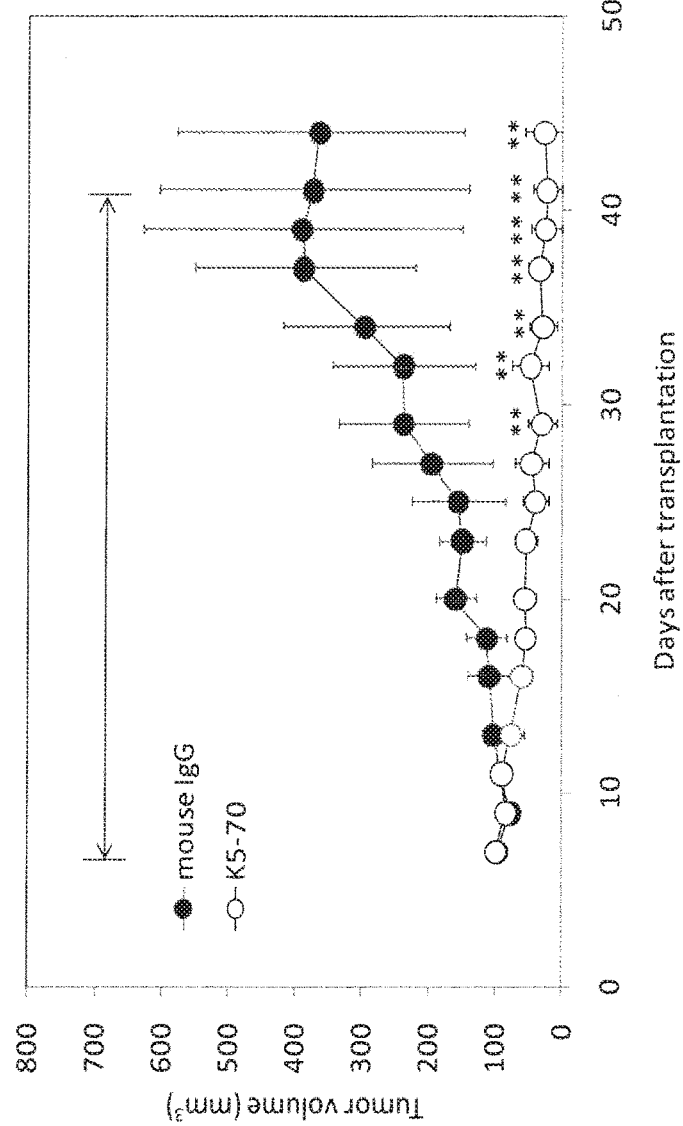
Fig. 23A
Fig. 23B

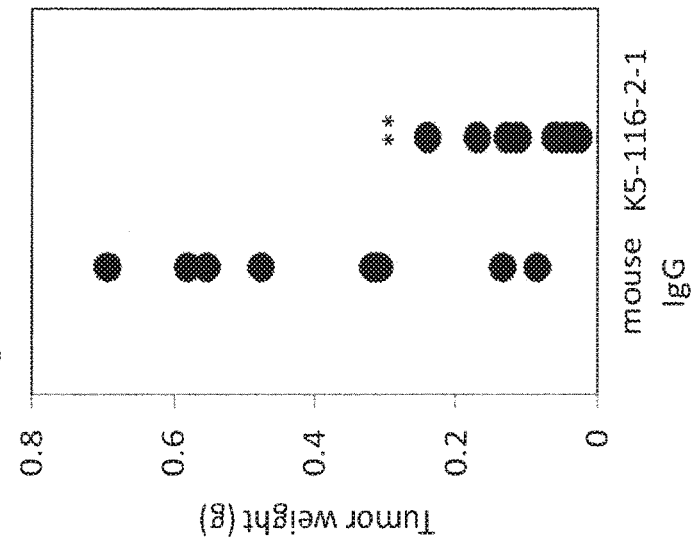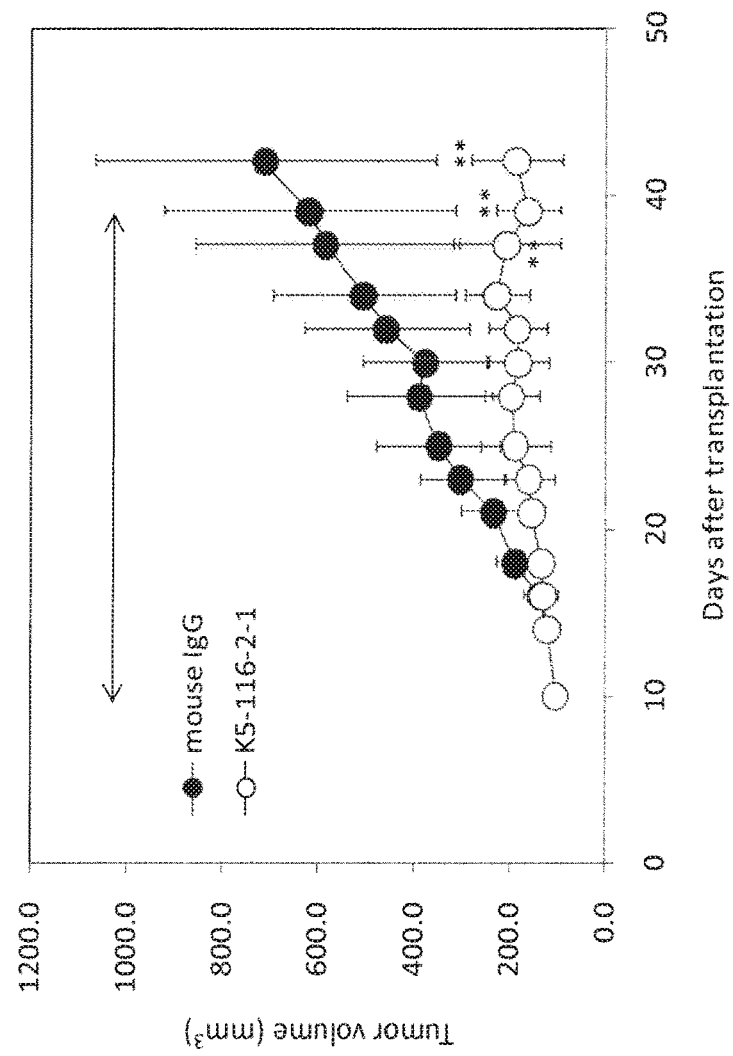
Fig. 24A
Fig. 24B

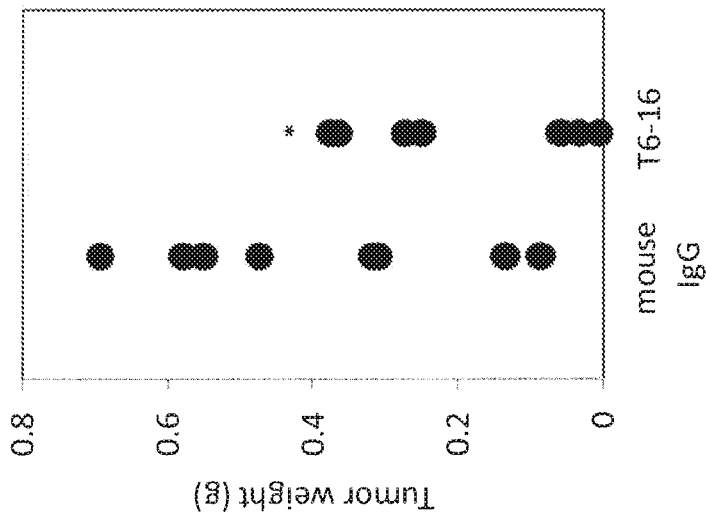
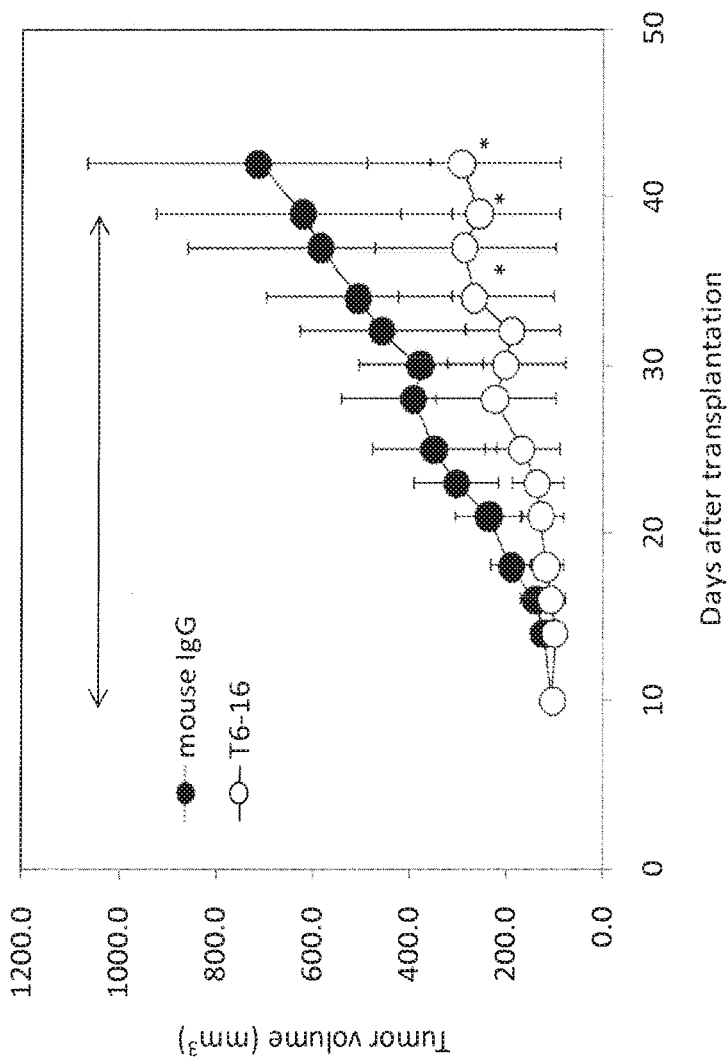
Fig. 25A
Fig. 25B

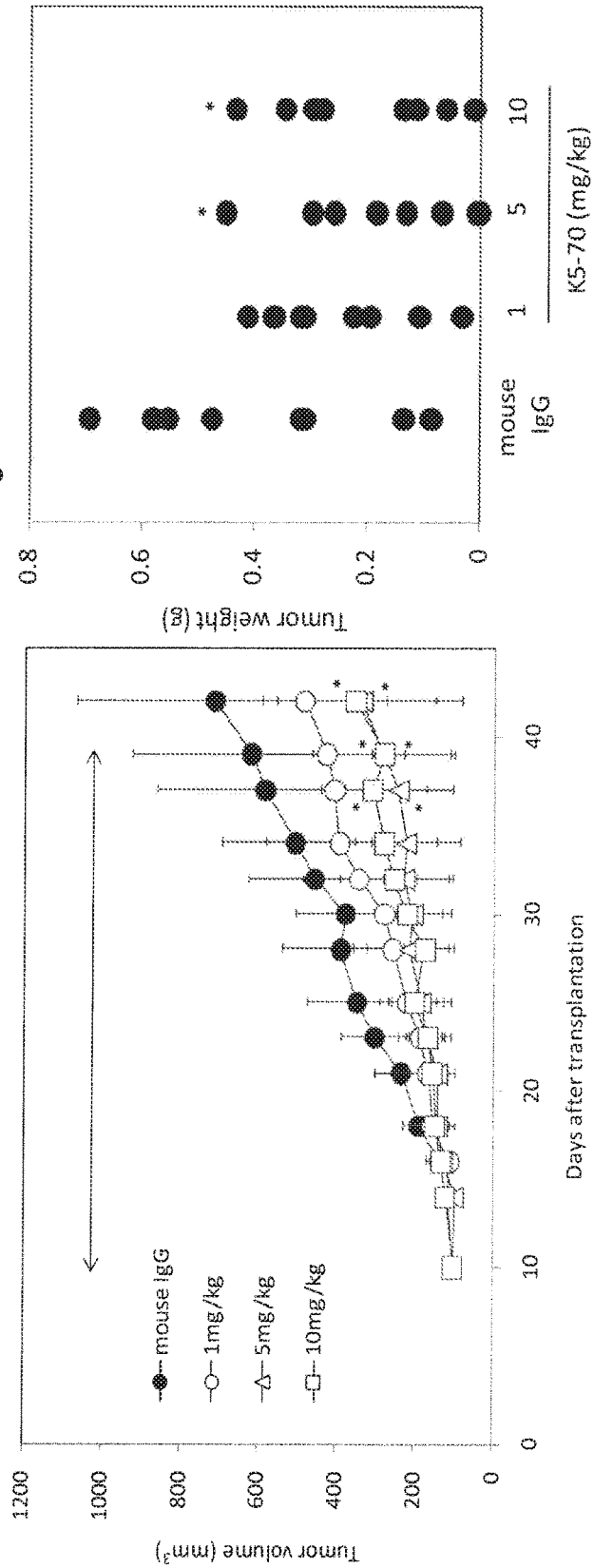

SEQ ID NO: 34  ATGGGATGGAGCTGTATCATCCTCTTCTTGGTAGCAACAGGTACAGGTGTCCACTCCCAG
SEQ ID NO: 35   M  G  W  S  C  I  I  L  F  L  V  A  T  A  T  G  V  H  S  Q

GTCCAACTGCAGCAGCCTGGGGCTGAGCTGGTGAGGCCTGGGGCTTCAGTGAAGCTGTCC
 V  Q  L  Q  Q  P  G  A  E  L  V  R  P  G  A  S  V  K  L  S

TGCAAGGCTTCTGGCTACACCTTCACCATCTACTGGATAAACTGGGTGAAACAGAGGCCT
 C  K  A  S  G  Y  T  F  T  I  Y  W  I  N  W  V  K  Q  R  P      SEQ ID NO: 36

GGACAAGGCCTTGAGTGGATGGAATGGATTGGAAATATTTATCCTTCTGATAGTTATACTAACTACAAT
 G  Q  G  L  E  W  I  G  N  I  Y  P  S  D  S  Y  T  N  Y  N

CAAAAGTTCAAGGACAAGGCCACATTGACTGTAGACAAATCCTCCAGCACACAGCCTACATG
 Q  K  F  K  D  K  A  T  L  T  V  D  K  S  S  S  T  A  Y  M      SEQ ID NO: 37

CAGCTCAGCAGCCCGACATCTGAGGACTCTGCGGTCTATTACTGTACAAGAACGTCTATG
 Q  L  S  S  P  T  S  E  D  S  A  V  Y  Y  C  T  R  T  S  M

GCGGACTACTGGGGCCAAGGCACCACTCTCACAGTCTCCTCA
 A  D  Y  W  G  Q  G  T  T  L  T  V  S  S                         SEQ ID NO: 38

SEQ ID NO:39 ATGGTATCCACACCTCAGTTCCTTGTATTTTTGCTTTTCTGGATTCCAGCCTCCAGAGGT
SEQ ID NO:40 M V S T P Q F L V F L L F W I P A S R G

GACATCTTGCTGACTCAGTCTCCAGCCATCCTGTCTGAGTCCAGGAGAAAGAGTCAGT      SEQ ID NO: 41
D I L L T Q S P A I L S V S P G E R V S

TTCTCCTGCAGGGCCAGTCAGAGCATTGGCACAGAGCATACACTGGTATCAGCAAGAACA
F S C R A S Q S I G T S I H W Y Q Q R T

AATGGTTCTCCAAGGCTTCTCATAAAGTATGCTTCTGAGTCTATCTCTGGGATCCCTTCC   SEQ ID NO:42
N G S P R L L I K Y A S E S I S G I P S

AGGTTTAGTGGCAGTGGATCAGGGACAGATTTTACTCTTAGCATCAACAGTGTGGAGTCT
R F S G S G S G T D F T L S I N S V E S

GAAGATATTGCAGATTATTACTGTCAACAAAGTAATAGCTGGCCATTCACGTTCGGCTCG   SEQ ID NO: 43
E D I A D Y Y C Q Q S N S W P F T F G S

GGGACAAAGTTGGAAATAAAA
G T K L E I K

SEQ ID NO: 44  ATGGGATGGAGCTGTATCATCCTCTTCTTGGTAGCAACAGCTACAGGTGTCCACTCCCAG
SEQ ID NO: 45   M  G  W  S  C  I  I  F  L  V  A  T  A  T  G  V  H  S  Q

GTCCAACTGCAGCAACTGGGTCTGAGCTGGTGAGACCTGGAGCTTCAGTGAAGCTGTCC
 V  Q  L  Q  Q  P  G  S  E  L  V  R  P  G  A  S  V  K  L  S

TGCAAGGCTTCTGGCTACACATTCACCAGCTACTGGATGCACTGGGTGAAGCAGAGGCAT
 C  K  A  S  G  Y  T  F  T  S  Y  W  M  H  W  V  K  Q  R  H       SEQ ID NO: 46

GGACAAGGCCTTGAGTGGATTGGAAATATTTATCCTGGTGGTGGTTATACTAACTACGAT
 G  Q  G  L  E  W  I  G  N  I  Y  P  G  G  G  Y  T  N  Y  D

GAGAAGTTCAAGAGCAAGGCAACTGACTGTAGACATCCTCCAGCACCAGCCTACATG
 E  K  F  K  S  K  G  T  L  T  V  D  T  S  S  S  T  A  Y  M       SEQ ID NO: 47

CACCTCAGCAGCCTGACATCTGAGGACTCTGCGGTCTATTACTGTACAAGATCATCCGTT
 H  L  S  S  L  T  S  E  D  S  A  V  Y  Y  C  T  R  S  S  V

TTTGACTACTGGGGCCAAGGCACCACTCTCACAGTCCTCA
 F  D  Y  W  G  Q  G  T  T  L  T  V  S  S                          SEQ ID NO: 48

SEQ ID NO: 49  ATGGTATCCACACCTCAGTTCCTTGTATTTTTGCTTTTCTGGATTCCAGCCTCCAGAGGT
SEQ ID NO: 50   M  V  S  T  P  Q  F  L  V  F  L  L  F  W  I  P  A  S  R  G

GACATCTTGCTGACTCAGTCTCCAGCCATCCTGTCTGTGAGTCCAGGAGAAAGAGTCAGT
 D  I  L  L  T  Q  S  P  A  I  L  S  V  S  P  G  E  R  V  S

TTCTCCTGCAGGGCCAGTCAGAACATTGGCACAAGCATACACTGGTTTCAGCAAAGAACA         SEQ ID NO: 51
 F  S  C  R  A  S  Q  N  I  G  T  S  I  H  W  F  Q  Q  R  T

AATGGTTCTCCAAGGCTTCTCATAAAGTATGCTTCTGAGTCTATCTCTGGGATCCCTTCC         SEQ ID NO: 52
 N  G  S  P  R  L  L  I  K  Y  A  S  E  S  I  S  G  I  P  S

AGGTTTAGTGGCAGTGGATCAGGGACAGATTTTACTCTTAGCATCAACAGTGTGGAGTCT
 R  F  S  G  S  G  S  G  T  D  F  T  L  S  I  N  S  V  E  S

GAAGATATTGCAGATTATTACTGTCAACAAAGTAATAGCTGGCCATTCACGTTCGGCTCG         SEQ ID NO: 53
 E  D  I  A  D  Y  Y  C  Q  Q  S  N  S  W  P  F  T  F  G  S

GGGACAAAGTTGGAAATAAAA
 G  T  K  L  E  I  K

SEQ ID NO: 54  ATGGGATGGAGCTGTATCATCCTCTTCTTGGTAGCAACAGCTACAGGTGTCCACTCCCAG
SEQ ID NO: 55  M  G  W  S  C  I  I  L  F  L  V  A  T  A  T  G  V  H  S  Q

GTCCAACTGCAGCAGCCTGGGGCTGAGCTGGTGAGGCCTGGGGCTTCAGTGAAGCTGTCC
 V  Q  L  Q  Q  P  G  A  E  L  V  R  P  G  A  S  V  K  L  S

TGCAAGGCTTCTGGCTACACCTTCACCAGCTACTGGATAACCTGGGTGAAGCAGAGGCCT      SEQ ID NO: 56
 C  K  A  S  G  Y  T  F  T  S  Y  W  I  T  W  V  K  Q  R  P

GGACAAGGCCTTGAGTGGATGGAAATATTTATCCTTCTGATAGTTATACTAACTACAAT
 G  Q  G  L  E  W  I  G  N  I  Y  P  S  D  S  Y  T  N  Y  N

CAAAAGTTCAGGGACAAGGCCACATTGACTGTAGACAAATCCTCCAGTACAGCCTACATG      SEQ ID NO: 57
 Q  K  F  R  D  K  A  T  L  T  V  D  K  S  S  S  T  A  Y  M

CAGCTCAGCAGCCCGACATCTGAGGACTCTGCGGTCTATTACTGTTCAGCCCTCTTTGAC
 Q  L  S  S  P  T  S  E  D  S  A  V  Y  Y  C  S  A  L  F  D

TACTGGGGCCAAGGCACCACTCTCACAGTCTCCTCA                              SEQ ID NO: 58
 Y  W  G  Q  G  T  T  L  T  V  S  S

SEQ ID NO: 59  ATGGTATCCACACCTCAGTTCCTTGTATTTTTGCTTTTTCTGGATTCCAGCCTCCAGAGT
SEQ ID NO: 60   M  V  S  T  P  Q  F  L  V  F  L  L  F  W  I  P  A  S  R  G

GACATCTTGCTGACTCAGTCTCCAGCCATCCTGTCTGTGAGTCCAGGAGAAAGAGTCAGT
 D  I  L  L  T  Q  S  P  A  I  L  S  V  S  P  G  E  R  V  S

TTCTCCTGCAGGGCCAGTCAGAGCATTGGCACAAGCATATACACTGGTATCAGCAAAGAACA         SEQ ID NO: 61
 F  S  C  R  A  S  Q  S  I  G  T  S  I  H  W  Y  Q  Q  R  T

AATGGGTTCTCCAAGGCTTCTCATAAAGTATGCTTTCTGAGTCTATCTCTGGGATCCCTTCC         SEQ ID NO: 62
 N  G  S  P  R  L  L  I  K  Y  A  S  E  S  I  S  G  I  P  S

AGGTTTAGTGGCAGTGGATCAGGGACAGATTTTATTCTTAGCATCAACAGTGTGGAGTCT
 R  F  S  G  S  G  S  G  T  D  F  I  L  S  I  N  S  V  E  S

GAAGATATTGCAGATTATTACTGTCAACAAAGTAATAGCTGGCCATTCACGTTCGGCTCG         SEQ ID NO: 63
 E  D  I  A  D  Y  Y  C  Q  Q  S  N  S  W  P  F  T  F  G  S

GGGACAAAGTTGGAAATAAAA
 G  T  K  L  E  I  K

SEQ ID NO: 64 ATGGGATGGAGCTGGATCTTTCTCTTCCTCCTGTCAGGAACTGCAGGCGTCCACTCTGAG
SEQ ID NO: 65  M  G  W  S  W  I  F  L  F  L  L  S  G  T  A  G  V  H  S  E

GTCCAGCTTCAGCAGTCAGGACCTGAGCTGGTGAAACCTGGGGCCTCAGTGAAGATTTCC
 V  Q  L  Q  Q  S  G  P  E  L  V  K  P  G  A  S  V  K  I  S

TGCAAGGCTTCTGGATACACATTCACTGACTACAATATGCACTGGGTGAAGCAGAGCCAT          SEQ ID NO: 66
 C  K  A  S  G  Y  T  F  T  D  Y  N  M  H  W  V  K  Q  S  H

GGAAAGAACCTTGAATGGATTGGATATATTTATCCTTACAATGGTGGTACTGGCTACAAC
 G  K  N  L  E  W  I  G  Y  I  Y  P  Y  N  G  G  T  G  Y  N

CAGAGGTTCAAGAGCAGGGCCACAATGACTGTAGACAAATCCTCCAGCACCAGCCTACATG          SEQ ID NO: 67
 Q  R  F  K  S  R  A  T  M  T  V  D  K  S  S  S  T  A  Y  M

GAGCTCCGCAGCCTGACATCTGATGACTCTGCAGTCTATTACTGTGCAAGAGAAGACTAC
 E  L  R  S  L  T  S  D  D  S  A  V  Y  Y  C  A  R  E  D  Y

GGTAGTAGCCCCTCTTATGCTATGGACTATTGGGGTCAAGGAACCTCAGTCATCGTCTCC          SEQ ID NO: 68
 G  S  S  P  S  Y  A  M  D  Y  W  G  Q  G  T  S  V  I  V  S

TCA
 S

SEQ ID NO: 69 ATGAAGTTGCCTGTTAGGCTGTTGGTGCTGTTGATGTTCTGGATTCCTGCTTCCAGCAGTGAT
SEQ ID NO: 70  M  K  L  P  V  R  L  L  V  L  M  F  W  I  P  A  S  S  S  D
GTTGTGATGACCCAAACTCCACTCTCCCTGCCTGTCAGTCTTGGAGATCAGGCCTCCATC
 V  V  M  T  Q  T  P  L  S  L  P  V  S  L  G  D  Q  A  S  I
TCTTGCAGATCTAGTCAGAGCCTTGTACACGGTAATGGAAACACCTATTTACATTGGTAC     SEQ ID NO: 71
 S  C  R  S  S  Q  S  L  V  H  G  N  G  N  T  Y  L  H  W  Y
CTGCAGAAGCCAGGCCAGTCTCCAAAGCTCCTGATCTACAAAGTTTCCAACCGATTTTCT
 L  Q  K  P  G  Q  S  P  K  L  L  I  Y  K  V  S  N  R  F  S     SEQ ID NO: 72
GGGGTCCCAGACAGGTTCAGTGGCAGTGGATCAGGGACGGATTTCACACTCAAGATCAGC
 G  V  P  D  R  F  S  G  S  G  S  G  T  D  F  T  L  K  I  S
AGAGTGGAGGCTGAGGATCTGGGAGTTTATTTCTGCTCTCAAACTACACATGTTCCCACG
 R  V  E  A  E  D  L  G  V  Y  F  C  S  Q  T  T  H  V  P  T     SEQ ID NO: 73
TTCGGCTCGGGGACAAAGTTGGAAATAAAA
 F  G  S  G  T  K  L  E  I  K

Fig. 41

```
                              1                   2                   3                   4
                      123456789 0123456789 0123456789 0123456789 0123456789
SEQ ID NO: 35  K5-70     VH   QVQLQQPGA ELVRPGASVK LSCKASGYTF TIYWINWVKQ RPGQGLEWIG
SEQ ID NO: 75  HuK5-70   VH   QVQLVQSGA EVKKPGASVK VSCKASGYTF TIYWINWVRQ APGQRLEWIG
SEQ ID NO: 85  DA980102  VH   QVQLVQSGA EVKKPGASVK VSCKASGYTF T----WVRQ APGQRLEWMG
                                  5                   6                   7                   8
                              0122234 56789 0123456789 0123456789 0122223456789
                                   a                                              abc
               K5-70     VH   NIYPSDSYTNY NQKFKDKATL TVDKSSSTAY MQLSSPTSEDSAV
               HuK5-70   VH   NIYPSDSYTNY NQKFKDKATL TVDTSASTAY MELSSLRSEDTAV
               DA980102  VH   ---------- ---RVTL TSDTSASTAY MEMSSLRSEDTAV
                                        1              1
                                        0              1
                              0123456789 0123456789 0123
               K5-70     VH   YYCTRTSMA- -DYWGQGTTL TVSS
               HuK5-70   VH   YYCTRTSMA- -DYWGQGTLV TVSS
               DA980102  VH   VHYYCAR--- -WGQGTLV TVSS
```

Fig. 42

```
                              1               2              3
                     123456789 0123456789 0123456789 0123456789
SEQ ID NO: 40 K5-70    VL      DILLTQSPA  ILSVSPGERV SFSCRASQSI GTSIHWYQQR
SEQ ID NO: 77 HuK5-70  VL      EIVLTQSPA  TLSLSPGERA TLSCRASQSI GTSIHWYQQK
SEQ ID NO: 87 L41174   VL      EIVLTQSPA  TLSLSPGERA TLSC------ -----WYQQK 4          5          6          7
                     0123456789 0123456789 0123456789 0123456789
K5-70     VL         TNGSPRLLIK YASESISGIP SRFSGSGSGT DFTLSINSVE
HuK5-70   VL         PGQAPRLLIK YASESISGIP ARFSGSGSGT DFTLTISSLE
L41174    VL         PGQAPRLLIY -------GIP ARFSGSGSGT DFTLTISSLE 1
                         8          9                  0
                     0123456789 0123456789         01234567
K5-70     VL         SEDIADYYCQ QSNSWPFTFG         SGTKLEIK
HuK5-70   VL         PEDFAVYYCQ QSNSWPFTFG         QGTKVEIK
L41174    VL         PEDFAVYYC- --------FG         QGTKVEIK
```

Fig. 43

```
                              1          2          3          4
                      123456789 0123456789 0123456789 0123456789 0123456789
SEQ ID NO: 65 T6-16    VH    EVQLQQSGP ELVKPGASVK ISCKASGYTF TDYNMHWVKQ SHGKNLEWIG
SEQ ID NO: 79 HuT6-16  VH1   QVQLVQSGA EVKKPGASVK VSCKASGYTF TDYNMHWVRQ APGQGLEWIG
SEQ ID NO: 81 HuT6-16  VH2   QVQLVQSGA EVKKPGASVK VSCKASGYTF TDYNMHWVRQ APGQGLEWIG
SEQ ID NO: 88 DA935238 VH    QVQLVQSGA EVKKPGASVK VSCKASGYTF T-----WVRQ APGQGLEWMG 5          6          7         8
                      0122345678 9 0123456789 0123456789 012222234 56789
                               a                          abc
T6-16    VH          YIYPYNGGTGY NQRFKSRATM TVDKSSSTAY MELRSLTSDDSAV
HuT6-16  VH1         YIYPYNGGTGY NQRFKSRATM TVDKSTSTAY MELRSLRSDDTAV
HuT6-16  VH2         YIYPYNGGTGY NQRFKSRATM TVDTSTSTAY MELRSLRSDDTAV
DA935238 VH          ---------- -----RVTM TVDTSTSTAY MELRSLRSDDTAV 9          10         1
                      0123456789 0000000123 456789 0123
                               abcde
T6-16    VH          YYCAREDYGS SPSYAMDYWGQGTSV IVSS
HuT6-16  VH1         YYCAREDYGS SPSYAMDYWGQGTMV TVSS
HuT6-16  VH2         YYCAREDYGS SPSYAMDYWGQGTMV TVSS
DA935238 VH          YYCAR----- ---------WGQGTMV TVSS
```

Fig. 44

```
                    1          2                    3
           123456789 0123456789 0123456677777789 0123456789
                                      abcde
SEQ ID NO: 70  T6-16 VL    DVVMTQTPL SLPVSLGDQA SISCRSSQSLVHGNG NTYLHWYLQK
SEQ ID NO: 83  HuT6-16 VL  DIVMTQSPL SLPVTPGEPA SISCRSSQSLVHGNG NTYLHWYLQK
SEQ ID NO: 90  M99608 VL   DIVMTQSPL SLPVTPGEPA SISC---------- ----WYLQK 4              5          6              7
              0123456789 0123456789 0123456789 0123456789
T6-16 VL      PGQSPKLLIY KVSNRFSGVP DRFSGSGSGT DFTLKISRVE
HuT6-16 VL    PGQSPQLLIY KVSNRFSGVP DRFSGSGSGT DFTLKISRVE
M99608 VL     PGQSPQLLIY ------GVP DRFSGSGSGT DFTLKISRVE 8          9          1
              0123456789 0123456789 01234567
T6-16 VL      AEDLGVYFCS QTTHVP-TFG SGTKLEIK
HuT6-16 VL    AEDVGVYYCS QTTHVP-TFG GGTKVEIK
M99608 VL     AEDVGVYYC- ------FG GGTKVEIK
```

Fig. 45
HuK5-70
VH

SEQ ID NO: 74
SEQ ID NO: 75

GAA TTC ACC ATG GGG TGG AGC TGT ATC ATC CTC TTC TTG GTA GCA ACA GCT GGC
            M   G   W   S   C   I   I   L   F   L   V   A   T   A   G

GTT CAC TCA CAG GTT CAG CTA GTG CAG TCT GGA GCT GAG GTG AAG AAA CCA GGG GCA TCT
 V   H   S   Q   V   Q   L   V   Q   S   G   A   E   V   K   K   P   G   A   S

GTC AAA GTG AGC TGT AAG GCC TCT GGC TAT ACC TTC ACC ATA TAC TGG ATC AAT TGG GTG
 V   K   V   S   C   K   A   S   G   Y   T   F   T   I   Y   W   I   N   W   V

AGG CAA GCT CCT GGA CAA CGG TTG GAA TGG ATT GGC AAC ATC TAT CCC TCA GAC AGC TAC
 R   Q   A   P   G   Q   R   L   E   W   I   G   N   I   Y   P   S   D   S   Y

ACC AAC TAC AAT CAG AAG TTC AAG GAC AGA GCC ACT CTC ACC GTA GAT ACC TCT TCC ACC
 T   N   Y   N   Q   K   F   K   D   R   A   T   L   T   V   D   T   S   S   T

ACA GCC TAT ATG GAG CTG AGC AGC CTG AGA TCT GAG GAT ACA GCC GTG TAC TAC TGC ACC
 T   A   Y   M   E   L   S   S   L   R   S   E   D   T   A   V   Y   Y   C   T

AGA ACC TCC ATG GCT GAC TAT TGG GGT CAG GGA ACT CTG GTC ACT GTC AGC TCC GCT AGC
 R   T   S   M   A   D   Y   W   G   Q   G   T   L   V   T   V   S   S   A   S

Fig. 46

HuK5-70
VL

SEQ ID NO: 76
SEQ ID NO: 77

```
ACC GGT ACC ACC ATG GTA AGC ACA CCC CAG TTC GTC GGT TTC CTG CTG TTT CTG ATT CCC
                 M   V   S   T   P   Q   F   V   G   F   L   L   F   L   I   P

GCA AGT AGA GGG GAG ATC GTC ATG ACA CAG AGT CCT GCC ACA CTG TCT CTT TCA CCA GGA
 A   S   R   G   E   I   V   M   T   Q   S   P   A   T   L   S   L   S   P   G

GAA AGG GCA ACA CTT AGC TGT TGG GGA GCT TCT CAG AGT ATT GGC ACC TCC ATA CAC TGG TAT
 E   R   A   T   L   S   C   W   G   A   S   Q   S   I   G   T   S   I   H   W  Y

CAG CAG AAA CCG GGA CAA GCT CCA CGG TTA CTG ATC AAG TAT GCC TCC GAA AGC ATC TCT
 Q   Q   K   P   G   Q   A   P   R   L   L   I   K   Y   A   S   E   S   I   S

GGG ATT CCT GCA CGC TTT AGC GGA AGT GGT AGT GGT ACC GAC TTC ACT CTG ACC ATA TCC
 G   I   P   A   R   F   S   G   S   G   S   G   T   D   F   T   L   T   I   S

TCA CTA GAA CCC GAG GAT TTT GCC GTC TAC TAC TGC CAG CAG TCC AAC TCA TGG CCT TTC
 S   L   E   P   E   D   F   A   V   Y   Y   C   Q   Q   S   N   S   W   P   F

ACC TTT GGC CAA GGG ACC AAA GTG GAG ATC AAG CGT ACC
 T   F   G   Q   G   T   K   V   E   I   K
```

Fig. 47

HuT6-16
VH1

```
GAA TTC ACC ACC ATG GGA TGG TCT TGT ATC TTT CTC TTG CTG TCT GGA ACA GCT GGA
            M   G   W   S   C   I   F   L   L   L   S   G   T   A   G
---------------------------------------------------------------------------
GTG CAT TCC CAA GTT CAG CTG GTC CAG TCC GGA GCT GAA GTT AAA AAG CCC GGG GCC AGC
 V   H   S   Q   V   Q   L   V   Q   S   G   A   E   V   K   K   P   G   A   S
---------------------------------------------------------------------------
GTC AAA GTG TCC TGC AAG GCA TCC GGG TAT ACT TTT ACC GAT TAT AAC ATG CAC TGG GTG
 V   K   V   S   C   K   A   S   G   Y   T   F   T   D   Y   N   M   H   W   V
---------------------------------------------------------------------------
CGC CAA GCA CCC GGC CAG GGC CTG GAG TGG ATT GGC TAT ATC TAT CCT TAT AAT GGA GGG
 R   Q   A   P   G   Q   G   L   E   W   I   G   Y   I   Y   P   Y   N   G   G
---------------------------------------------------------------------------
ACC GGC TAC AAC CAG AAG TTC AAG AGC AGA GCC ACC ATG ACA GTG GAT ACA TCT ACC AGC
 T   G   Y   N   Q   K   F   K   S   R   A   T   M   T   V   D   T   S   T   S
---------------------------------------------------------------------------
ACT GCC TAT ATG GAG CTG CGG AGC CTG AGA TCC GAC GAC ACA GCC GTG TAC TAC TGT GCC
 T   A   Y   M   E   L   R   S   L   R   S   D   D   T   A   V   Y   Y   C   A
---------------------------------------------------------------------------
CGC GAG GAT TAC AGC AGC CCA TAC GCC ATG GAT TAC TGG GGC CAA GGC ACT ATG
 R   E   D   Y   S   S   P   Y   A   M   D   Y   W   G   Q   G   T   M
---------------------------------------------------------------------------
GTC ACC GTG AGC AGC GCT AGC
 V   T   V   S   S   A   S
```

SEQ ID NO: 78
SEQ ID NO: 79

Fig. 48
HuT6-16
VH2

SEQ ID NO: 80
SEQ ID NO: 81

Fig. 49

HuT6-16
VL

SEQ ID NO: 82
SEQ ID NO: 83

```
ACC GGT ACC ACC ATG AAG CTC CCA GTG CTG CTC CTG GTC CTG CTG ATG TTC TGG ATT CCC GCT
                M   K   L   P   V   L   L   L   V   L   L   M   F   W   I   P   A

TCC TCT AGT GAT ATT GTC ATG ACC CAA TCC CAA CTG TCT CCA TCT GTG ACA CCA GGC GAA
 S   S   S   D   I   V   M   T   Q   S   Q   L   S   P   S   V   T   P   G   E
                                         ------------------------------

CCT GCA TCT ATT AGC TGT AGA AGC AGC CAG AGC CTG GGA CAG AGC TTT AGC GGC ACA GCC TAT
 P   A   S   I   S   C   R   S   S   Q   S   L   G   Q   S   F   S   G   T   A   Y
            ------------------------------------------------------------

CTG CAC TGG TAC CTG CAG AAA CCT GGA CAG AGC CCC CAG CTG CTG ATC TAC AAA GTC AGC
 L   H   W   Y   L   Q   K   P   G   Q   S   P   Q   L   L   I   Y   K   V   S
 -----------------------                                  ---------------

AAT AGA TTT AGC GGG GTG CCC GAC AGG TTT AGC GGC AGC GGC AGC GGC ACA GAT TTC ACC
 N   R   F   S   G   V   P   D   R   F   S   G   S   G   S   G   T   D   F   T
 ------

CTG AAA ATC TCC CGG GTC GAG GCC GAC GAT GTT GGG GTT TAT TAC TGC AGC CAG ACA ACC
 L   K   I   S   R   V   E   A   D   D   V   G   V   Y   Y   C   S   Q   T   T
                                                            --------------

CAT GTG CCC ACT TTC GGG GGC ACT AAG GTG GAG ATC AAG ACG
 H   V   P   T   F   G   G   T   K   V   E   I   K
 ----------
```

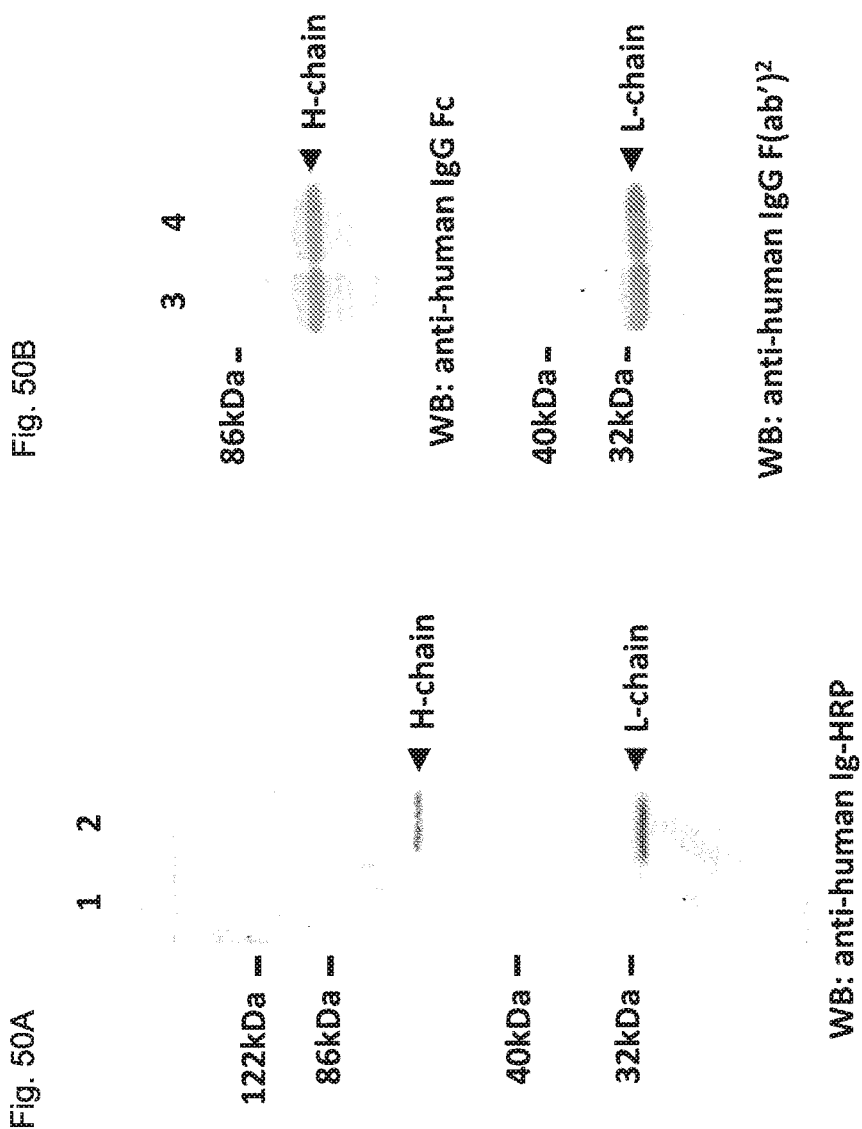

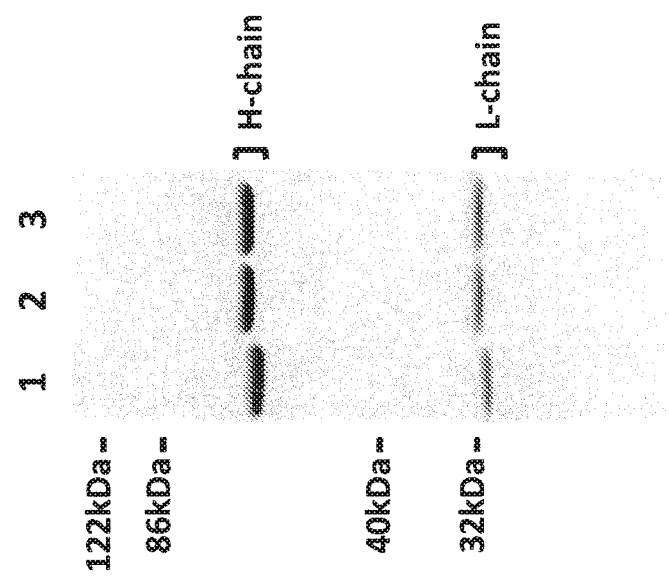

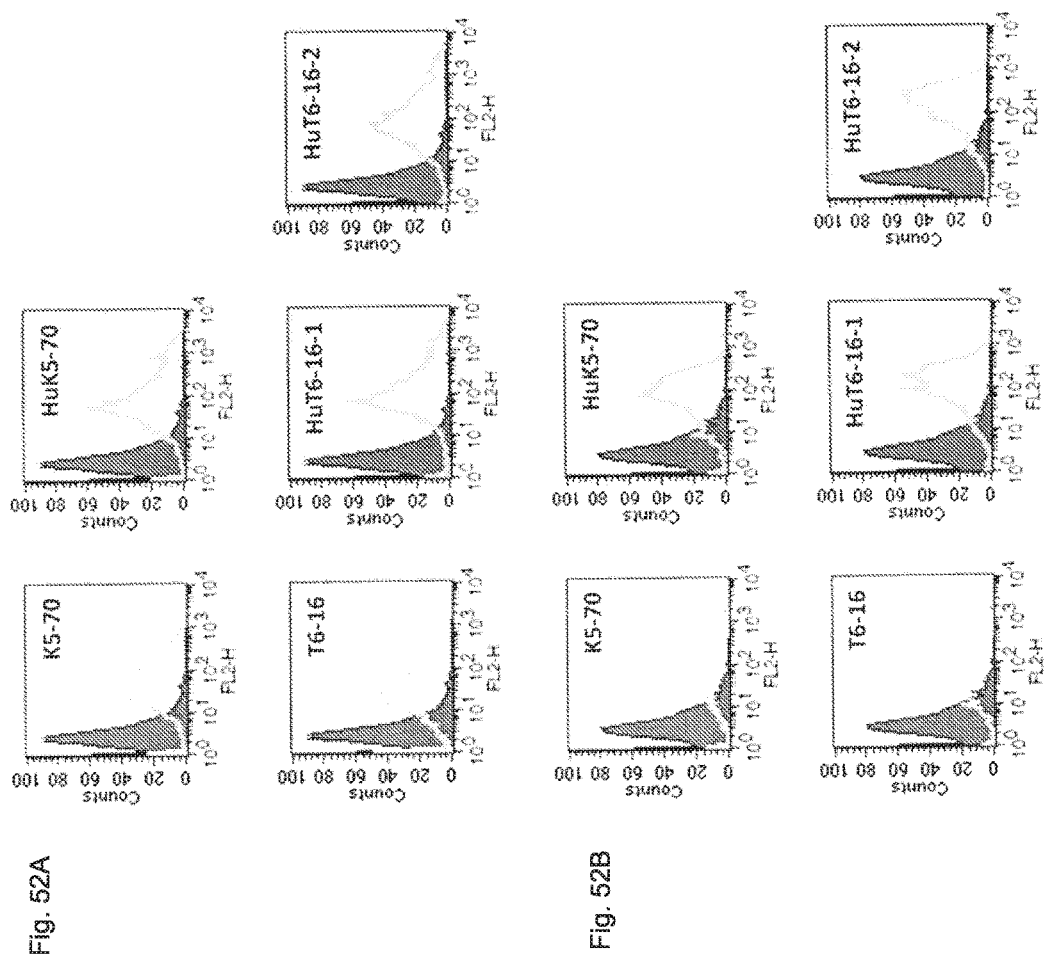

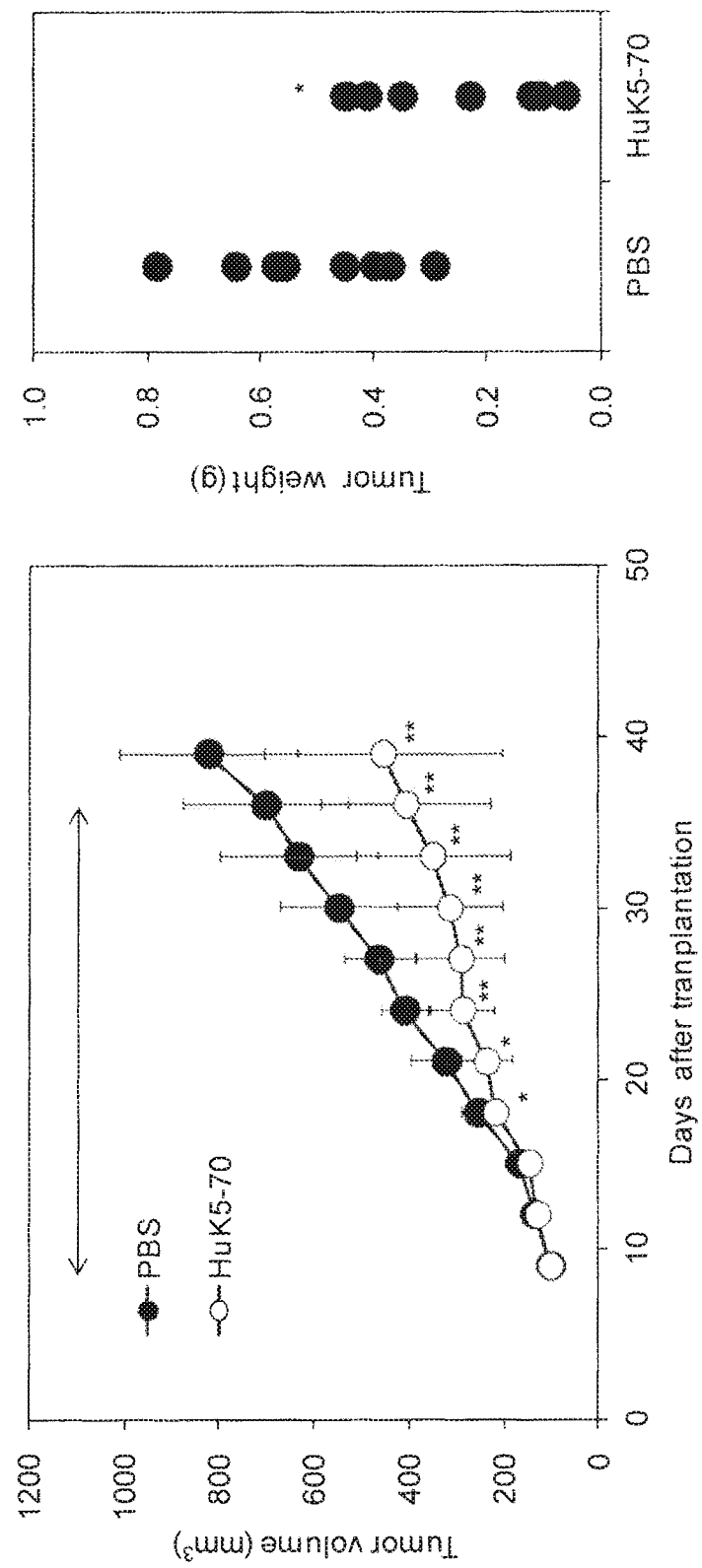

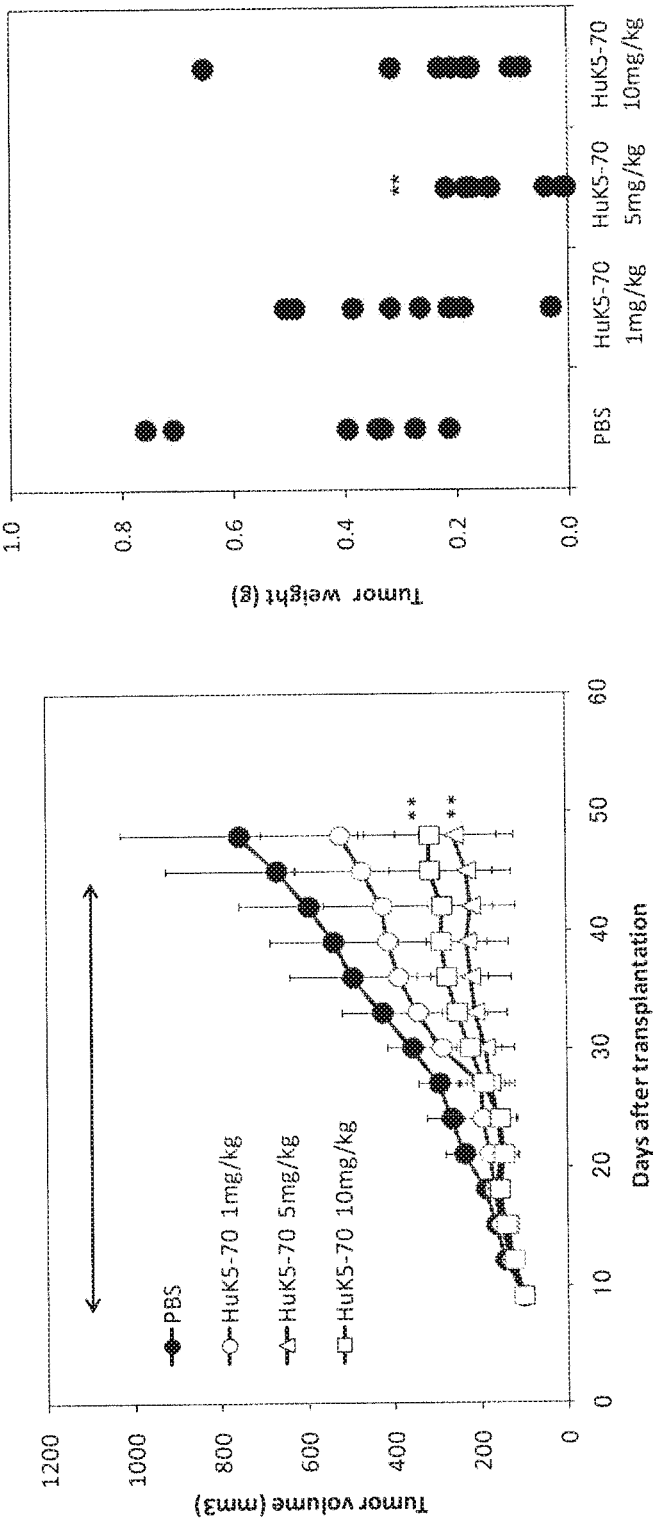

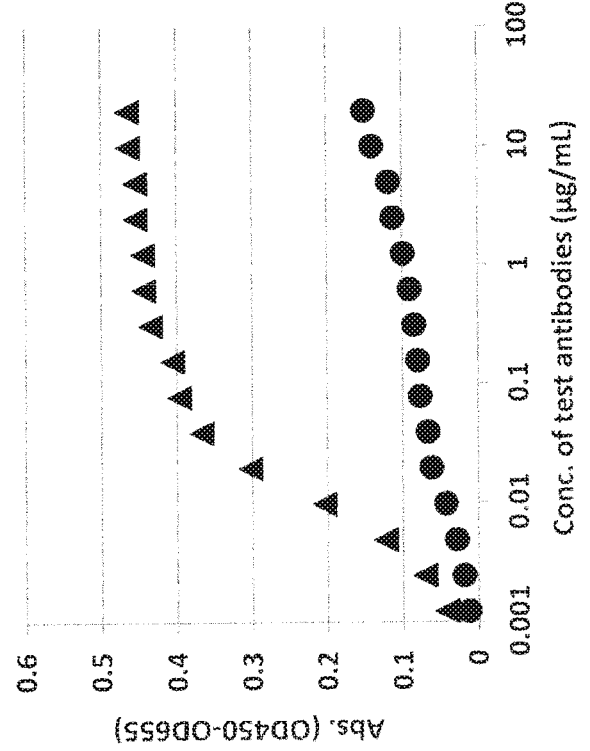

Fig. 64

```
         EcoRI  Kozak
SEQ ID NO:99 GAA TTC ACC ACC ATG GGA TGG TCC TGC ATT ATT CTC TTT CTC GTC GCC ACC GCC ACA GGC
SEQ ID NO: 35                M   G   W   S   C   I   I   L   F   L   V   A   T   A   T   G GTG CAC AGC CAG GTT CAA CTG CAG CAA CCT GGG GCA GAG CTG GTT CGG CCA GGG GCC TCC
          V   H   S   Q   V   Q   L   Q   Q   P   G   A   E   L   V   R   P   G   A   S GTC AAA CTG TCC TGC AAA GCT TCT GGC TAC ACT TTC ACC ATC TAC TGG ATC AAC TGG GTG
          V   K   L   S   C   K   A   S   G   Y   T   F   T   I   Y   W   I   N   W   V                SEQ ID NO: 36

AAG CAG AGG CCC GGC CAG GGC CTG GAA TGG ATC GGA AAT ATC TAT CCT AGC GAT TCT TAC
          K   Q   R   P   G   Q   G   L   E   W   I   G   N   I   Y   P   S   D   S   Y

ACA AAT TAC AAC CAG AAG TTC AAG GAC AAG GCT ACC CTG ACC GTG GAC AAA TCT AGC TCC
          T   N   Y   N   Q   K   F   K   D   K   A   T   L   T   V   D   K   S   S   S                SEQ ID NO:37

ACA GCC TAC ATG CAG CTG AGC AGC CCC ACT AGT GAG GAT AGC GCA GTG TAT TAT TGT ACC
          T   A   Y   M   Q   L   S   S   P   T   S   E   D   S   A   V   Y   Y   C   T

NheI
         AGA ACC AGC ATG GCC GAC TAT TGG GGA CAG GGC ACA ACT CTG ACC GTG AGC AGC GCT AGC
          R   T   S   M   A   D   Y   W   G   Q   G   T   T   L   T   V   S   S                        SEQ ID NO:38
```

Fig. 65

SEQ ID NO: 100

```
     AgeI    Kozak
     ACC GGT ACC ACC ATG GTT AGC ACA CCT CAA TTT CTG GTC TTC CTC TTC TGG ATT CCT
                      M   V   S   T   P   Q   F   L   V   F   L   F   W   I   P
```
SEQ ID NO: 40

```
GCC AGC AGA GGA GAT ATC CTC CTG ACA CAA AGC CCC GCA ATC CTG AGC GTG TCC CCC GGA
 A   S   R   G   D   I   L   L   T   Q   S   P   A   I   L   S   V   S   P   G

GAG CGC GTG AGC TTT AGC TGC CGG GCC AGC CAG AGC ATT GGA ACC AGC ATC CAC TGG TAT    SEQ ID NO: 41
 E   R   V   S   F   S   C   R   A   S   Q   S   I   G   T   S   I   H   W   Y

CAG CAG AGA ACC AAC GGG TCT CCC AGG CTG CTG ATT AAA TAC GCT TCT GAG TCT ATT TCC    SEQ ID NO: 42
 Q   Q   R   T   N   G   S   P   R   L   L   I   K   Y   A   S   E   S   I   S

GGG ATC CCA AGC AGA TTC TCC GGC AGC GGC ACT GAT TTT ACT CTG TCT ATC AAC
 G   I   P   S   R   F   S   G   S   G   T   D   F   T   L   S   I   N

AGC GTG GAG TCC GAG GAC ATC GCC GAC TAC TAT TGT CAG CAG AGC AAT TCC TGG CCA TTC
 S   V   E   S   E   D   I   A   D   Y   Y   C   Q   Q   S   N   S   W   P   F
                                                          BsiWI
ACC TTT GGC AGC GGC ACC AAG CTG GAA ATC AAG CGT ACG                                 SEQ ID NO: 43
 T   F   G   S   G   T   K   L   E   I   K
```

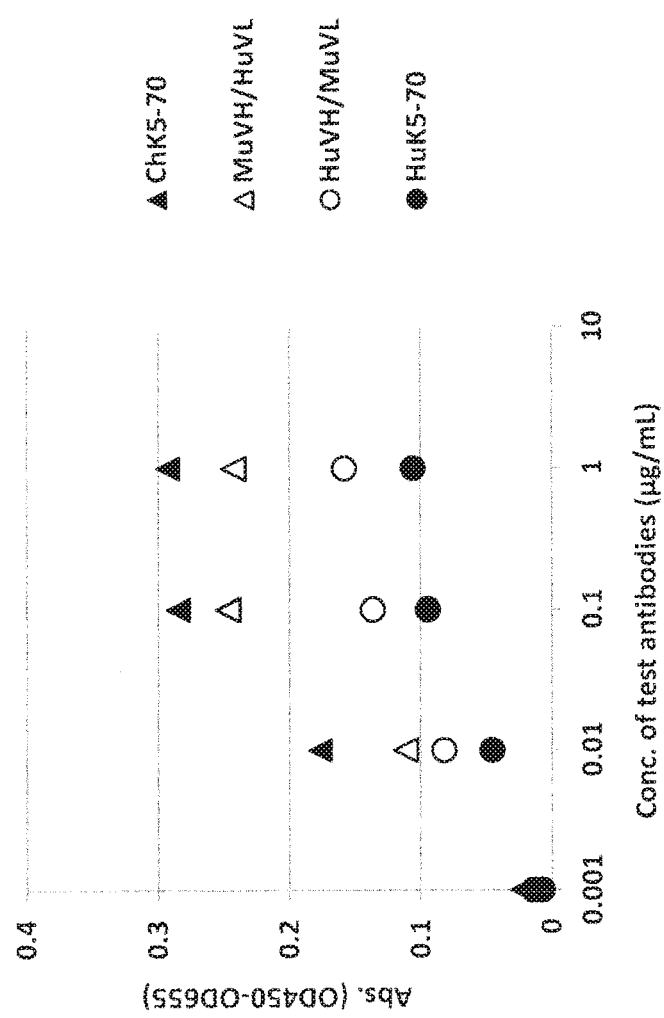

Fig. 67

```
                                        1          2          3          4          5
                              123456789 0123456789 0123456789 0123456789 0123456789
                                                                                   a
SEQ ID NO: 75   HuK5-70 VH    QVQLVQSGA EVKKPGASVK VSCKASGYTF TIYWINWVRQ APGQRLEWIG NIYPSDSYTNY
SEQ ID NO. 235  V5Q           ----Q---- ---------- ---------- ---------- ---------- -----------
SEQ ID NO. 236  S7P           ------P-- ---------- ---------- ---------- ---------- -----------
SEQ ID NO. 237  V11L          --------- -L-------- ---------- ---------- ---------- -----------
SEQ ID NO. 238  K12V          --------- --V------- ---------- ---------- ---------- -----------
SEQ ID NO. 239  K13R          --------- ---R------ ---------- ---------- ---------- -----------
SEQ ID NO. 240  V20L          --------- ---------- L--------- ---------- ---------- -----------
SEQ ID NO. 241  R38K          --------- ---------- ---------- --------K- ---------- -----------
SEQ ID NO. 242  A40R          --------- ---------- ---------- ---------- R--------- -----------
SEQ ID NO. 243  R44G          --------- ---------- ---------- ---------- ----G----- -----------
SEQ ID NO. 245  T73K          --------- ---------- ---------- ---------- ---------- -----------
SEQ ID NO. 246  A75S          --------- ---------- ---------- ---------- ---------- -----------
SEQ ID NO. 247  E81Q          --------- ---------- ---------- ---------- ---------- -----------
SEQ ID NO. 248  L82cP         --------- ---------- ---------- ---------- ---------- -----------
SEQ ID NO. 249  R83T          --------- ---------- ---------- ---------- ---------- -----------
SEQ ID NO. 250  T87S          --------- ---------- ---------- ---------- ---------- -----------
SEQ ID NO. 251  L108T         --------- ---------- ---------- ---------- ---------- -----------
SEQ ID NO. 252  V109L         --------- ---------- ---------- ---------- ---------- -----------
SEQ ID NO. 244  V11L/R38K     --------- -L-------- ---------- --------K- ---------- -----------

1          1
                                                                       0          1
                            6          7          8          9         0          0
                            0123456789 0123456789 0122223456789 0123456789 0123456789
                                                   abc
                HuK5-70 VH  NQKFKDKATL TVDTSASTAY MELSSLRSEDTAV YYCTRTSMA- -DYWGQGTLV TVSS
                V5Q         ---------- ---------- ------------- ---------- ---------- ----
                S7P         ---------- ---------- ------------- ---------- ---------- ----
                V11L        ---------- ---------- ------------- ---------- ---------- ----
                K12V        ---------- ---------- ------------- ---------- ---------- ----
                K13R        ---------- ---------- ------------- ---------- ---------- ----
                V20L        ---------- ---------- ------------- ---------- ---------- ----
                R38K        ---------- ---------- ------------- ---------- ---------- ----
                A40R        ---------- ---------- ------------- ---------- ---------- ----
                R44G        ---------- ---------- ------------- ---------- ---------- ----
                T73K        ---------- ---K------ ------------- ---------- ---------- ----
                A75S        ---------- -----S---- ------------- ---------- ---------- ----
                E81Q        ---------- ---------- -Q----------- ---------- ---------- ----
                L82cP       ---------- ---------- -----P------- ---------- ---------- ----
                R83T        ---------- ---------- ------T------ ---------- ---------- ----
                T87S        ---------- ---------- ----------S-- ---------- ---------- ----
                L108T       ---------- ---------- ------------- ---------- --------T- ----
                V109L       ---------- ---------- ------------- ---------- ---------L ----
                V11L/R38K   ---------- ---------- ------------- ---------- ---------- ----
```

Fig. 69

```
EcoRI    Kozak
GAA TTC  ACC ACC ATG GGC TGG AGC TGT ATT ATT CTC TTC CTC GTC GCC ACT GCA ACC GGG
                  M   G   W   S   C   I   I   L   F   L   V   A   T   A   T   G GTC CAC TCC CAG GTC CAG CTG GTG CAG AGC GGA GCT GAG GTG AAG AAG CCC GGC GCC AGC
 V   H   S   Q   V   Q   L   V   Q   S   G   A   E   V   K   K   P   G   A   S
         =

GTT AAG GTT TCT TGC AAA GCC TCT GGC TAT ACA TTC ACA ATC TAT TGG ATC AAT TGG GTG
 V   K   V   S   C   K   A   S   G   Y   T   F   T   I   Y   W   I   N   W   V

CGG CAG GCT CCA GGA CAA GGC CTG GAA TGG ATG GGC AAT ATC TAT CCT TCC GAC TCC TAC
 R   Q   A   P   G   Q   G   L   E   W   M   G   N   I   Y   P   S   D   S   Y

ACC AAC TAT AAC CAG AAA TTT AAG GAC AGA GCA ACA CTG ACC GTG GAC ACC TCT GCC AGC
 T   N   Y   N   Q   K   F   K   D   R   A   T   L   T   V   D   T   S   A   S

ACT GCT TAC ATG GAG CTG AGC AGC CTG AGA AGC GAA GAT ACT GCC GTG TAC TAC TGC ACC
 T   A   Y   M   E   L   S   S   L   R   S   E   D   T   A   V   Y   Y   C   T

NheI
AGG ACA AGC ATG GCC GAT TAC TGG GGA CAA GGG ACC CTG GTG ACC GTG AGC AGC GCT AGC
 R   T   S   M   A   D   Y   W   G   Q   G   T   L   V   T   V   S   S
```

(SEQ ID NO. 74)
(SEQ ID NO. 253)

SW480
*P< 0.05, **P < 0.01

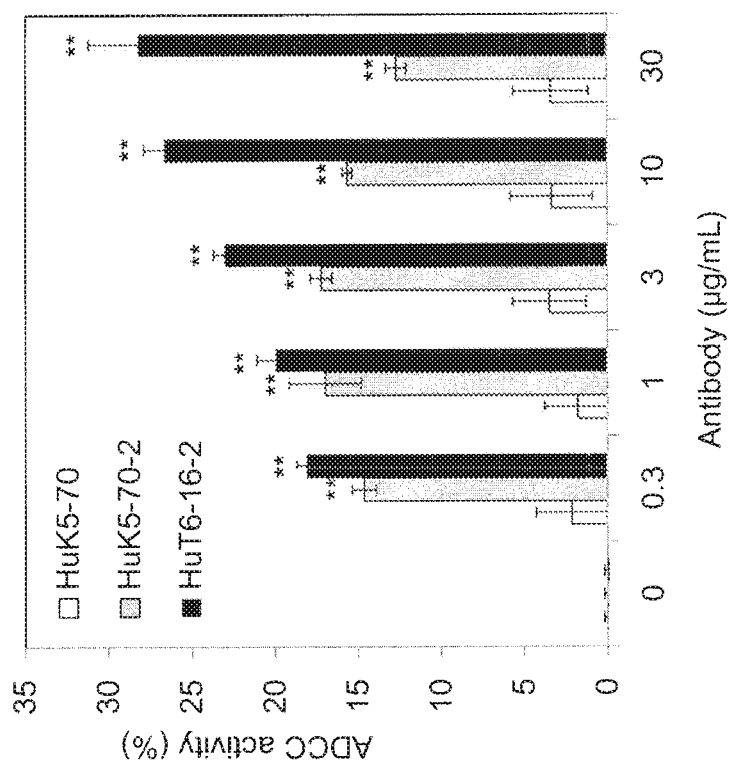

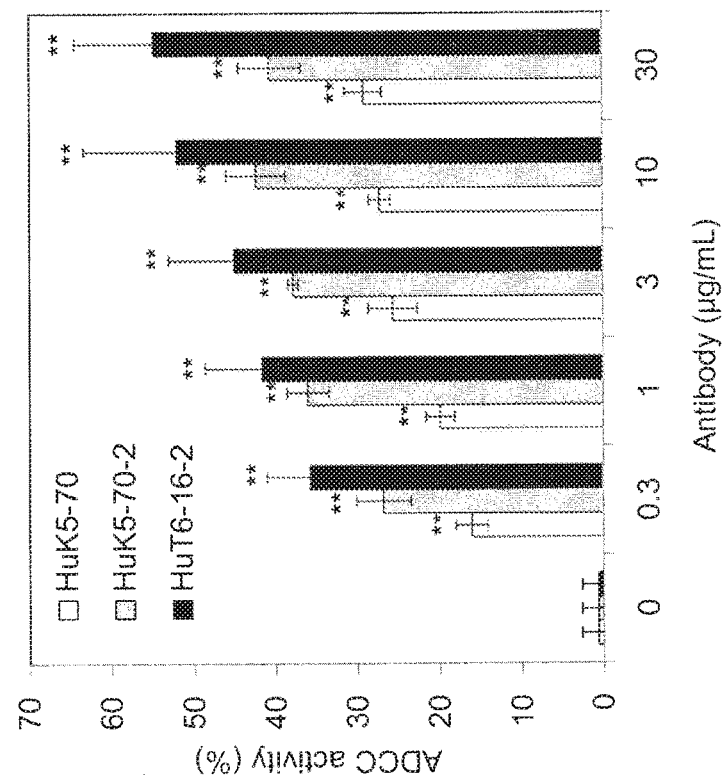

SEQUENCE LISTING

<160> NUMBER OF SEQ ID NOS: 234

<210> SEQ ID NO 1
<211> LENGTH: 2080
<212> TYPE: DNA
<213> ORGANISM: homo sapiens
<220> FEATURE:
<221> NAME/KEY: CDS
<222> LOCATION: (339)..(1310)

<400> SEQUENCE: 1

```
gcgggtcccc agaagcctac aggtgagtat cggttctccc cttcccggct ttcggtccgg      60
aggaggcggg agcagcttcc ctgttctgat cctatcgcgg cggcgcagg gccggcttgg      120 ccttccgtgg gacggggagg ggggcgggat gtgtcaccca ataccagtg gggacggtcg      180 gtggtggaac cagccgggca ggtcgggtag agtataagag ccggagggag cggccgggcg      240
gcagacgcct gcagaccatc ccagacgccg gagcccgagc cccgacgagt ccccgcgcct      300
catccgcccg cgtccggtcc gcgttcctcc gccccacc atg gct cgg ggc ccc ggc      356
                                           Met Ala Arg Gly Pro Gly
                                           1               5 ctc gcg ccg cca ccg ctg cgg ctg ccg ctg ctg ctg gtg ctg gcg              404
Leu Ala Pro Pro Pro Leu Arg Leu Pro Leu Leu Leu Val Leu Ala
            10                  15                  20 gcg gtg acc ggc cac acg gcc gcg cag gac aac tgc acg tgt ccc acc          452
Ala Val Thr Gly His Thr Ala Ala Gln Asp Asn Cys Thr Cys Pro Thr
        25                  30                  35 aac aag atg acc gtg tgc agc ccc gac ggc ccc ggc ggc cgc tgc cag          500
Asn Lys Met Thr Val Cys Ser Pro Asp Gly Pro Gly Gly Arg Cys Gln
    40                  45                  50 tgc cgc gcg ctg ggc tcg ggc atg gcg gtc gac tgc tcc acg ctg acc          548
Cys Arg Ala Leu Gly Ser Gly Met Ala Val Asp Cys Ser Thr Leu Thr
55                  60                  65                  70 tcc aag tgt ctg ctg ctc aag gcg cgc atg agc gcc ccc aag aac gcc          596
Ser Lys Cys Leu Leu Leu Lys Ala Arg Met Ser Ala Pro Lys Asn Ala
                75                  80                  85 cgc acc ctg gtg cgg ccg agt gag cac gcg ctc gtg gac aac gat ggc          644
Arg Thr Leu Val Arg Pro Ser Glu His Ala Leu Val Asp Asn Asp Gly
            90                  95                  100 ctc tac gac ccc gac tgc gac ccc gag ggc cgc ttc aag gcg cgc cag          692
Leu Tyr Asp Pro Asp Cys Asp Pro Glu Gly Arg Phe Lys Ala Arg Gln
        105                 110                 115 tgc aac cag acg tcg gtg tgc tgg tgc gtg aac tcg gtg ggc gtg cgc          740
Cys Asn Gln Thr Ser Val Cys Trp Cys Val Asn Ser Val Gly Val Arg
    120                 125                 130 cgc acg gac aag ggc gac ctg agc cta cgc tgc gat gag ctg gtg cgc          788
Arg Thr Asp Lys Gly Asp Leu Ser Leu Arg Cys Asp Glu Leu Val Arg
135                 140                 145                 150
```

```
acc cac cac atc ctc att gac ctg cgc cac cgc ccc acc gcc ggc gcc      836
Thr His His Ile Leu Ile Asp Leu Arg His Arg Pro Thr Ala Gly Ala
                155                 160                 165 ttc aac cac tca gac ctg gac gcc gag ctg agg cgg ctc ttc cgc gag      884
Phe Asn His Ser Asp Leu Asp Ala Glu Leu Arg Arg Leu Phe Arg Glu
                170                 175                 180 cgc tat cgg ctg cac ccc aag ttc gtg gcg gcc gtg cac tac gag cag      932
Arg Tyr Arg Leu His Pro Lys Phe Val Ala Ala Val His Tyr Glu Gln
                185                 190                 195 ccc acc atc cag atc gag ctg cgg cag aac acg tct cag aag gcc gcc      980
Pro Thr Ile Gln Ile Glu Leu Arg Gln Asn Thr Ser Gln Lys Ala Ala
                200                 205                 210 ggt gac gtg gat atc ggc gat gcc gcc tac tac ttc gag agg gac atc     1028
Gly Asp Val Asp Ile Gly Asp Ala Ala Tyr Tyr Phe Glu Arg Asp Ile
215                 220                 225                 230 aag ggc gag tct cta ttc cag ggc cgc ggc ggc ctg gac ttg cgc gtg     1076
Lys Gly Glu Ser Leu Phe Gln Gly Arg Gly Gly Leu Asp Leu Arg Val
                235                 240                 245 cgc gga gaa ccc ctg cag gtg gag cgc acg ctc atc tat tac ctg gac     1124
Arg Gly Glu Pro Leu Gln Val Glu Arg Thr Leu Ile Tyr Tyr Leu Asp
                250                 255                 260 gag att ccc ccg aag ttc tcc atg aag cgc ctc acc gcc ggc ctc atc     1172
Glu Ile Pro Pro Lys Phe Ser Met Lys Arg Leu Thr Ala Gly Leu Ile
                265                 270                 275 gcc gtc atc gtg gtg gtc gtg gtg gcc ctc gtc gcc ggc atg gcc gtc     1220
Ala Val Ile Val Val Val Val Val Ala Leu Val Ala Gly Met Ala Val
                280                 285                 290 ctg gtg atc acc aac cgg aga aag tcg ggg aag tac aag aag gtg gag     1268
Leu Val Ile Thr Asn Arg Arg Lys Ser Gly Lys Tyr Lys Lys Val Glu
295                 300                 305                 310 atc aag gaa ctg ggg gag ttg aga aag gaa ccg agc ttg tag              1310
Ile Lys Glu Leu Gly Glu Leu Arg Lys Glu Pro Ser Leu
                315                 320 gtacccggcg gggcagggga tggggtgggg taccggattt cggtatcgtc ccagacccaa    1370
gtgagtcacg cttcctgatt cctcggcgca aaggagacgt ttatcctttc aaattcctgc    1430 cttcccccctc ccttttgcgc acacaccagg tttaatagat cctggcctca gggtctcctt   1490
tctttctcac ttctgtcttg aaggaagcat ttctaaaatg tatccccttt cggtccaaca    1550
acaggaaacc tgactgggc agtgaaggaa gggatggcat agcgttatgt gtaaaaaaca     1610
agtatctgta tgacaacccg ggatcgtttg caagtaactg aatccattgc gacattgtga    1670
aggcttaaat gagtttagat gggaaatagc gttgttatcg ccttgggttt aaattatttg    1730
atgagttcca cttgtatcat ggcctacccg aggagaagag gagtttgtta actgggccta    1790
tgtagtagcc tcatttacca tcgtttgtat tactgaccac atatgcttgt cactgggaaa    1850
gaagcctgtt tcagctgcct gaacgcagtt tggatgtctt tgaggacaga cattgcccgg    1910
aaactcagtc tatttattct tcagcttgcc cttactgcca ctgatattgg taatgttctt    1970
ttttgtaaaa tgtttgtaca tatgttgtct ttgataatgt tgctgtaatt ttttaaaata    2030
aaacacgaat ttaataaaat atgggaaagg cacaaaccag aaaaaaaaaa               2080

<210> SEQ ID NO 2
<211> LENGTH: 323
<212> TYPE: PRT
<213> ORGANISM: homo sapiens

<400> SEQUENCE: 2
```

Met Ala Arg Gly Pro Gly Leu Ala Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
            35                  40                  45

Pro Gly Gly Arg Cys Gln Cys Arg Ala Leu Gly Ser Gly Met Ala Val
        50                  55                  60

Asp Cys Ser Thr Leu Thr Ser Lys Cys Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
            115                 120                 125

Asn Ser Val Gly Val Arg Arg Thr Asp Lys Gly Asp Leu Ser Leu Arg
        130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
        290                 295                 300

Lys Tyr Lys Lys Val Glu Ile Lys Glu Leu Gly Glu Leu Arg Lys Glu
305                 310                 315                 320

Pro Ser Leu

<210> SEQ ID NO 3
<211> LENGTH: 20
<212> TYPE: DNA
<213> ORGANISM: Artificial
<220> FEATURE:
<223> OTHER INFORMATION: synthetic DNA

<400> SEQUENCE: 3
ttcctccgcc ccaccatggc                                              20

<210> SEQ ID NO 4
<211> LENGTH: 25
<212> TYPE: DNA
<213> ORGANISM: Artificial

```
<220> FEATURE:
<223> OTHER INFORMATION: synthetic DNA

<400> SEQUENCE: 4
ctcgagcaag ctcggttcct ttctc                                              25

<210> SEQ ID NO 5
<211> LENGTH: 29
<212> TYPE: DNA
<213> ORGANISM: Artificial
<220> FEATURE:
<223> OTHER INFORMATION: synthetic DNA

<400> SEQUENCE: 5
ctcgagctcg tccaggtaat agatgagcg                                          29

<210> SEQ ID NO 6
<211> LENGTH: 23
<212> TYPE: DNA
<213> ORGANISM: Artificial
<220> FEATURE:
<223> OTHER INFORMATION: synthetic DNA

<400> SEQUENCE: 6
gatccactag tcgcgagtgg tgg                                                23

<210> SEQ ID NO 7
<211> LENGTH: 23
<212> TYPE: DNA
<213> ORGANISM: Artificial
<220> FEATURE:
<223> OTHER INFORMATION: synthetic DNA

<400> SEQUENCE: 7
aattccacca ctcgcgacta gtg                                                23

<210> SEQ ID NO 8
<211> LENGTH: 20
<212> TYPE: DNA
<213> ORGANISM: Artificial
<220> FEATURE:
<223> OTHER INFORMATION: synthetic DNA

<400> SEQUENCE: 8
tcctcgtgtc ccactcccgg                                                    20

<210> SEQ ID NO 9
<211> LENGTH: 25
<212> TYPE: DNA
<213> ORGANISM: Artificial
<220> FEATURE:
<223> OTHER INFORMATION: synthetic DNA

<400> SEQUENCE: 9
ctcgagtgca ttgagttccc tatgc                                              25

<210> SEQ ID NO 10
<211> LENGTH: 30
<212> TYPE: DNA
<213> ORGANISM: Artificial
<220> FEATURE:
<223> OTHER INFORMATION: synthetic DNA

<400> SEQUENCE: 10
cctgagccta cgctgcgacg aagtggtgcg                                         30
```

<210> SEQ ID NO 11
<211> LENGTH: 30
<212> TYPE: DNA
<213> ORGANISM: Artificial
<220> FEATURE:
<223> OTHER INFORMATION: synthetic DNA

<400> SEQUENCE: 11
cgcaccactt cgtcgcagcg taggctcagg                              30

<210> SEQ ID NO 12
<211> LENGTH: 30
<212> TYPE: DNA
<213> ORGANISM: Artificial
<220> FEATURE:
<223> OTHER INFORMATION: synthetic DNA

<400> SEQUENCE: 12
gactgctcca cgctgacttc caagtgcctg                              30

<210> SEQ ID NO 13
<211> LENGTH: 30
<212> TYPE: DNA
<213> ORGANISM: Artificial
<220> FEATURE:
<223> OTHER INFORMATION: synthetic DNA

<400> SEQUENCE: 13
caggcacttg gaagtcagcg tggagcagtc                              30

<210> SEQ ID NO 14
<211> LENGTH: 30
<212> TYPE: DNA
<213> ORGANISM: Artificial
<220> FEATURE:
<223> OTHER INFORMATION: synthetic DNA

<400> SEQUENCE: 14
ctcgtggaca acgatggcct ctacgacccg                              30

<210> SEQ ID NO 15
<211> LENGTH: 30
<212> TYPE: DNA
<213> ORGANISM: Artificial
<220> FEATURE:
<223> OTHER INFORMATION: synthetic DNA

<400> SEQUENCE: 15
cgggtcgtag aggccatcgt tgtccacgag                              30

<210> SEQ ID NO 16
<211> LENGTH: 31
<212> TYPE: DNA
<213> ORGANISM: Artificial
<220> FEATURE:
<223> OTHER INFORMATION: synthetic DNA

<400> SEQUENCE: 16
ccaaagcctg cgctgcgatg agctggtgcg c                            31

<210> SEQ ID NO 17
<211> LENGTH: 31
<212> TYPE: DNA
<213> ORGANISM: Artificial
<220> FEATURE:
<223> OTHER INFORMATION: synthetic DNA

<400> SEQUENCE: 17
gcgcaccagc tcatcgcagc gcaggctttg g                          31

<210> SEQ ID NO 18
<211> LENGTH: 30
<212> TYPE: DNA
<213> ORGANISM: Artificial
<220> FEATURE:
<223> OTHER INFORMATION: synthetic DNA

<400> SEQUENCE: 18
agcttcctat ccgcggtgca ctacgagcag                            30

<210> SEQ ID NO 19
<211> LENGTH: 30
<212> TYPE: DNA
<213> ORGANISM: Artificial
<220> FEATURE:
<223> OTHER INFORMATION: synthetic DNA

<400> SEQUENCE: 19
ctgctcgtag tgcaccgcgg ataggaagct                            30

<210> SEQ ID NO 20
<211> LENGTH: 30
<212> TYPE: DNA
<213> ORGANISM: Artificial
<220> FEATURE:
<223> OTHER INFORMATION: synthetic DNA

<400> SEQUENCE: 20
gacattaaag gcgagtctct attccagggc                            30

<210> SEQ ID NO 21
<211> LENGTH: 30
<212> TYPE: DNA
<213> ORGANISM: Artificial
<220> FEATURE:
<223> OTHER INFORMATION: synthetic DNA

<400> SEQUENCE: 21
gccctggaat agagactcgc ctttaatgtc                            30

<210> SEQ ID NO 22
<211> LENGTH: 21
<212> TYPE: DNA
<213> ORGANISM: Artificial
<220> FEATURE:
<223> OTHER INFORMATION: synthetic DNA

<400> SEQUENCE: 22
ctactccacc ccaccctggc g                                     21

<210> SEQ ID NO 23
<211> LENGTH: 25
<212> TYPE: DNA
<213> ORGANISM: Artificial
<220> FEATURE:
<223> OTHER INFORMATION: synthetic DNA

<400> SEQUENCE: 23
ctcgagcaag ctaggttcgc ttctc                                 25

<210> SEQ ID NO 24

```
<211> LENGTH: 12
<212> TYPE: DNA
<213> ORGANISM: Artificial
<220> FEATURE:
<223> OTHER INFORMATION: synthetic DNA

<400> SEQUENCE: 24 tccakagttcca                                                            12

<210> SEQ ID NO 25
<211> LENGTH: 12
<212> TYPE: DNA
<213> ORGANISM: Artificial
<220> FEATURE:
<223> OTHER INFORMATION: synthetic DNA

<400> SEQUENCE: 25
gctgtcctga tc                                                           12

<210> SEQ ID NO 26
<211> LENGTH: 45
<212> TYPE: DNA
<213> ORGANISM: Artificial
<220> FEATURE:
<223> OTHER INFORMATION: synthetic DNA

<400> SEQUENCE: 26
ctaatacgac tcactatagg gcaagcagtg gtatcaacgc agagt               45

<210> SEQ ID NO 27
<211> LENGTH: 22
<212> TYPE: DNA
<213> ORGANISM: Artificial
<220> FEATURE:
<223> OTHER INFORMATION: synthetic DNA

<400> SEQUENCE: 27
ctaatacgac tcactatagg gc                                                22

<210> SEQ ID NO 28
<211> LENGTH: 23
<212> TYPE: DNA
<213> ORGANISM: Artificial
<220> FEATURE:
<223> OTHER INFORMATION: synthetic DNA

<400> SEQUENCE: 28
gggaartarc ccttgaccag gca                                               23

<210> SEQ ID NO 29
<211> LENGTH: 23
<212> TYPE: DNA
<213> ORGANISM: Artificial
<220> FEATURE:
<223> OTHER INFORMATION: synthetic DNA

<400> SEQUENCE: 29
gggaartagc ctttgacaag gca                                               23

<210> SEQ ID NO 30
<211> LENGTH: 26
<212> TYPE: DNA
<213> ORGANISM: Artificial
<220> FEATURE:
<223> OTHER INFORMATION: synthetic DNA

<400> SEQUENCE: 30
```

```
cactgccatc aatvctccac ttgaca                                          26
```

<210> SEQ ID NO 31
<211> LENGTH: 23
<212> TYPE: DNA
<213> ORGANISM: Artificial
<220> FEATURE:
<223> OTHER INFORMATION: synthetic DNA

<400> SEQUENCE: 31

```
cgactggagc acgaggacac tga                                             23
```

<210> SEQ ID NO 32
<211> LENGTH: 20
<212> TYPE: DNA
<213> ORGANISM: Artificial
<220> FEATURE:
<223> OTHER INFORMATION: synthetic DNA

<400> SEQUENCE: 32

```
gccagtggat agacagatgg                                                 20
```

<210> SEQ ID NO 33
<211> LENGTH: 21
<212> TYPE: DNA
<213> ORGANISM: Artificial
<220> FEATURE:
<223> OTHER INFORMATION: synthetic DNA

<400> SEQUENCE: 33

```
gatggataca gttggtgcag c                                               21
```

<210> SEQ ID NO 34
<211> LENGTH: 402
<212> TYPE: DNA
<213> ORGANISM: homo sapiens
<220> FEATURE:
<221> NAME/KEY: CDS
<222> LOCATION: (1)..(402)

<400> SEQUENCE: 34

```
atg gga tgg agc tgt atc atc ctc ttc ttg gta gca aca gct aca ggt        48
Met Gly Trp Ser Cys Ile Ile Leu Phe Leu Val Ala Thr Ala Thr Gly
1               5                   10                  15 gtc cac tcc cag gtc caa ctg cag cag cct ggg gct gag ctg gtg agg        96
Val His Ser Gln Val Gln Leu Gln Gln Pro Gly Ala Glu Leu Val Arg
                20                  25                  30 cct ggg gct tca gtg aag ctg tcc tgc aag gct tct ggc tac acc ttc       144
Pro Gly Ala Ser Val Lys Leu Ser Cys Lys Ala Ser Gly Tyr Thr Phe
            35                  40                  45 acc atc tac tgg ata aac tgg gtg aaa cag agg cct gga caa ggc ctt       192
Thr Ile Tyr Trp Ile Asn Trp Val Lys Gln Arg Pro Gly Gln Gly Leu
        50                  55                  60 gag tgg atc gga aat att tat cct tct gat agt tat act aac tac aat       240
Glu Trp Ile Gly Asn Ile Tyr Pro Ser Asp Ser Tyr Thr Asn Tyr Asn
65                  70                  75                  80 caa aag ttc aag gac aag gcc aca ttg act gta gac aaa tcc tcc agc       288
Gln Lys Phe Lys Asp Lys Ala Thr Leu Thr Val Asp Lys Ser Ser Ser
                85                  90                  95 aca gcc tac atg cag ctc agc agc ccg aca tct gag gac tct gcg gtc       336
Thr Ala Tyr Met Gln Leu Ser Ser Pro Thr Ser Glu Asp Ser Ala Val
            100                 105                 110 tat tac tgt aca aga acg tct atg gcg gac tac tgg ggc caa ggc acc       384
Tyr Tyr Cys Thr Arg Thr Ser Met Ala Asp Tyr Trp Gly Gln Gly Thr
```

Tyr Tyr Cys Thr Arg Thr Ser Met Ala Asp Tyr Trp Gly Gln Gly Thr
            115                 120                 125 act ctc aca gtc tcc tca                                                  402
Thr Leu Thr Val Ser Ser
    130

<210> SEQ ID NO 35
<211> LENGTH: 134
<212> TYPE: PRT
<213> ORGANISM: homo sapiens

<400> SEQUENCE: 35

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ile Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Thr Ser Met Ala Asp Tyr Trp Gly Gln Gly Thr
        115                 120                 125

Thr Leu Thr Val Ser Ser
    130

<210> SEQ ID NO 36
<211> LENGTH: 5
<212> TYPE: PRT
<213> ORGANISM: homo sapiens

<400> SEQUENCE: 36

Ile Tyr Trp Ile Asn
1               5

<210> SEQ ID NO 37
<211> LENGTH: 17
<212> TYPE: PRT
<213> ORGANISM: homo sapiens

<400> SEQUENCE: 37

Asn Ile Tyr Pro Ser Asp Ser Tyr Thr Asn Tyr Asn Gln Lys Phe Lys
1               5                   10                  15

Asp

<210> SEQ ID NO 38
<211> LENGTH: 6
<212> TYPE: PRT
<213> ORGANISM: homo sapiens

<400> SEQUENCE: 38

Thr Ser Met Ala Asp Tyr
1               5

<210> SEQ ID NO 39

<211> LENGTH: 381
<212> TYPE: DNA
<213> ORGANISM: homo sapiens
<220> FEATURE:
<221> NAME/KEY: CDS
<222> LOCATION: (1)..(381)

<400> SEQUENCE: 39

| atg | gta | tcc | aca | cct | cag | ttc | ctt | gta | ttt | ttg | ctt | ttc | tgg | att | cca | 48 |
| Met | Val | Ser | Thr | Pro | Gln | Phe | Leu | Val | Phe | Leu | Leu | Phe | Trp | Ile | Pro | |
| 1   |     |     |     | 5   |     |     |     |     | 10  |     |     |     |     | 15  |     | |

| gcc | tcc | aga | ggt | gac | atc | ttg | ctg | act | cag | tct | cca | gcc | atc | ctg | tct | 96 |
| Ala | Ser | Arg | Gly | Asp | Ile | Leu | Leu | Thr | Gln | Ser | Pro | Ala | Ile | Leu | Ser | |
|     |     |     | 20  |     |     |     |     | 25  |     |     |     |     | 30  |     |     | |

| gtg | agt | cca | gga | gaa | aga | gtc | agt | ttc | tcc | tgc | agg | gcc | agt | cag | agc | 144 |
| Val | Ser | Pro | Gly | Glu | Arg | Val | Ser | Phe | Ser | Cys | Arg | Ala | Ser | Gln | Ser | |
|     |     | 35  |     |     |     |     | 40  |     |     |     |     | 45  |     |     |     | |

| att | ggc | aca | agc | ata | cac | tgg | tat | cag | caa | aga | aca | aat | ggt | tct | cca | 192 |
| Ile | Gly | Thr | Ser | Ile | His | Trp | Tyr | Gln | Gln | Arg | Thr | Asn | Gly | Ser | Pro | |
|     | 50  |     |     |     |     | 55  |     |     |     |     | 60  |     |     |     |     | |

| agg | ctt | ctc | ata | aag | tat | gct | tct | gag | tct | atc | tct | ggg | atc | cct | tcc | 240 |
| Arg | Leu | Leu | Ile | Lys | Tyr | Ala | Ser | Glu | Ser | Ile | Ser | Gly | Ile | Pro | Ser | |
| 65  |     |     |     |     | 70  |     |     |     |     | 75  |     |     |     |     | 80  | |

| agg | ttt | agt | ggc | agt | gga | tca | ggg | aca | gat | ttt | act | ctt | agc | atc | aac | 288 |
| Arg | Phe | Ser | Gly | Ser | Gly | Ser | Gly | Thr | Asp | Phe | Thr | Leu | Ser | Ile | Asn | |
|     |     |     |     | 85  |     |     |     |     | 90  |     |     |     |     | 95  |     | |

| agt | gtg | gag | tct | gaa | gat | att | gca | gat | tat | tac | tgt | caa | caa | agt | aat | 336 |
| Ser | Val | Glu | Ser | Glu | Asp | Ile | Ala | Asp | Tyr | Tyr | Cys | Gln | Gln | Ser | Asn | |
|     |     |     | 100 |     |     |     |     | 105 |     |     |     |     | 110 |     |     | |

| agc | tgg | cca | ttc | acg | ttc | ggc | tcg | ggg | aca | aag | ttg | gaa | ata | aaa | | 381 |
| Ser | Trp | Pro | Phe | Thr | Phe | Gly | Ser | Gly | Thr | Lys | Leu | Glu | Ile | Lys | | |
|     | 115 |     |     |     |     | 120 |     |     |     |     | 125 |     |     |     | | |

<210> SEQ ID NO 40
<211> LENGTH: 127
<212> TYPE: PRT
<213> ORGANISM: homo sapiens

<400> SEQUENCE: 40

Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Ser
        35                  40                  45

Ile Gly Thr Ser Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Ser Asn
            100                 105                 110

Ser Trp Pro Phe Thr Phe Gly Ser Gly Thr Lys Leu Glu Ile Lys
        115                 120                 125

<210> SEQ ID NO 41
<211> LENGTH: 11
<212> TYPE: PRT
<213> ORGANISM: homo sapiens

<400> SEQUENCE: 41

Arg Ala Ser Gln Ser Ile Gly Thr Ser Ile His
1               5                   10

<210> SEQ ID NO 42
<211> LENGTH: 7
<212> TYPE: PRT
<213> ORGANISM: homo sapiens

<400> SEQUENCE: 42

Tyr Ala Ser Glu Ser Ile Ser
1               5

<210> SEQ ID NO 43
<211> LENGTH: 9
<212> TYPE: PRT
<213> ORGANISM: homo sapiens

<400> SEQUENCE: 43

Gln Gln Ser Asn Ser Trp Pro Phe Thr
1               5

<210> SEQ ID NO 44
<211> LENGTH: 402
<212> TYPE: DNA
<213> ORGANISM: homo sapiens
<220> FEATURE:
<221> NAME/KEY: CDS
<222> LOCATION: (1)..(402)

<400> SEQUENCE: 44

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc cac tcc cag gtc caa ctg cag caa cct ggg tct gag ctg gtg agg      96
Val His Ser Gln Val Gln Leu Gln Gln Pro Gly Ser Glu Leu Val Arg
                20                  25                  30 cct gga gct tca gtg aag ctg tcc tgc aag gct tct ggc tac aca ttc     144
Pro Gly Ala Ser Val Lys Leu Ser Cys Lys Ala Ser Gly Tyr Thr Phe
            35                  40                  45 acc agc tac tgg atg cac tgg gtg aag cag agg cat gga caa ggc ctt     192
Thr Ser Tyr Trp Met His Trp Val Lys Gln Arg His Gly Gln Gly Leu
        50                  55                  60 gag tgg att gga aat att tat cct ggt ggt ggt tat act aac tac gat     240
Glu Trp Ile Gly Asn Ile Tyr Pro Gly Gly Gly Tyr Thr Asn Tyr Asp
65                  70                  75                  80 gag aag ttc aag agc aag ggc aca ctg act gta gac aca tcc tcc agc     288
Glu Lys Phe Lys Ser Lys Gly Thr Leu Thr Val Asp Thr Ser Ser Ser
                85                  90                  95 aca gcc tac atg cac ctc agc agc ctg aca tct gag gac tct gcg gtc     336
Thr Ala Tyr Met His Leu Ser Ser Leu Thr Ser Glu Asp Ser Ala Val
            100                 105                 110 tat tac tgt aca aga tca tcc gtt ttt gac tac tgg ggc caa ggc acc     384
Tyr Tyr Cys Thr Arg Ser Ser Val Phe Asp Tyr Trp Gly Gln Gly Thr
        115                 120                 125 act ctc aca gtc tcc tca                                             402
Thr Leu Thr Val Ser Ser
        130
```

<210> SEQ ID NO 45
<211> LENGTH: 134
<212> TYPE: PRT
<213> ORGANISM: homo sapiens

<400> SEQUENCE: 45

Met Gly Trp Ser Cys Ile Ile Leu Phe Leu Val Ala Thr Ala Thr Gly
1               5                   10                  15

Val His Ser Gln Val Gln Leu Gln Gln Pro Gly Ser Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg His Gly Gln Gly Leu
    50                  55                  60

Glu Trp Ile Gly Asn Ile Tyr Pro Gly Gly Gly Tyr Thr Asn Tyr Asp
65                  70                  75                  80

Glu Lys Phe Lys Ser Lys Gly Thr Leu Thr Val Asp Thr Ser Ser Ser
                85                  90                  95

Thr Ala Tyr Met His Leu Ser Ser Leu Thr Ser Glu Asp Ser Ala Val
            100                 105                 110

Tyr Tyr Cys Thr Arg Ser Ser Val Phe Asp Tyr Trp Gly Gln Gly Thr
        115                 120                 125

Thr Leu Thr Val Ser Ser
    130

<210> SEQ ID NO 46
<211> LENGTH: 5
<212> TYPE: PRT
<213> ORGANISM: homo sapiens

<400> SEQUENCE: 46

Ser Tyr Trp Met His
1               5

<210> SEQ ID NO 47
<211> LENGTH: 17
<212> TYPE: PRT
<213> ORGANISM: homo sapiens

<400> SEQUENCE: 47

Asn Ile Tyr Pro Gly Gly Gly Tyr Thr Asn Tyr Asp Glu Lys Phe Lys
1               5                   10                  15

Ser

<210> SEQ ID NO 48
<211> LENGTH: 6
<212> TYPE: PRT
<213> ORGANISM: homo sapiens

<400> SEQUENCE: 48

Ser Ser Val Phe Asp Tyr
1               5

<210> SEQ ID NO 49
<211> LENGTH: 381
<212> TYPE: DNA
<213> ORGANISM: homo sapiens
<220> FEATURE:
<221> NAME/KEY: CDS
<222> LOCATION: (1)..(381)

<400> SEQUENCE: 49 atg gta tcc aca cct cag ttc ctt gta ttt ttg ctt ttc tgg att cca    48
Met Val Ser Thr Pro Gln Phe Leu Val Phe Leu Leu Phe Trp Ile Pro
1               5                   10                  15

```
gcc tcc aga ggt gac atc ttg ctg act cag tct cca gcc atc ctg tct    96
Ala Ser Arg Gly Asp Ile Leu Leu Thr Gln Ser Pro Ala Ile Leu Ser
         20                  25                  30 gtg agt cca gga gaa aga gtc agt ttc tcc tgc agg gcc agt cag aac   144
Val Ser Pro Gly Glu Arg Val Ser Phe Ser Cys Arg Ala Ser Gln Asn
     35                  40                  45 att ggc aca agc ata cac tgg ttt cag caa aga aca aat ggt tct cca   192
Ile Gly Thr Ser Ile His Trp Phe Gln Gln Arg Thr Asn Gly Ser Pro
 50                  55                  60 agg ctt ctc ata aag tat gct tct gag tct atc tct ggg atc cct tcc   240
Arg Leu Leu Ile Lys Tyr Ala Ser Glu Ser Ile Ser Gly Ile Pro Ser
 65                  70                  75                  80 agg ttt agt ggc agt gga tca ggg aca gat ttt act ctt agc atc aac   288
Arg Phe Ser Gly Ser Gly Ser Gly Thr Asp Phe Thr Leu Ser Ile Asn
                 85                  90                  95 agt gtg gag tct gaa gat att gca gat tat tac tgt caa caa agt aat   336
Ser Val Glu Ser Glu Asp Ile Ala Asp Tyr Tyr Cys Gln Gln Ser Asn
             100                 105                 110 agc tgg cca ttc acg ttc ggc tcg ggg aca aag ttg gaa ata aaa       381
Ser Trp Pro Phe Thr Phe Gly Ser Gly Thr Lys Leu Glu Ile Lys
         115                 120                 125

<210> SEQ ID NO 50
<211> LENGTH: 127
<212> TYPE: PRT
<213> ORGANISM: homo sapiens

<400> SEQUENCE: 50

Met Val Ser Thr Pro Gln Phe Leu Val Phe Leu Leu Phe Trp Ile Pro
 1               5                  10                  15

Ala Ser Arg Gly Asp Ile Leu Leu Thr Gln Ser Pro Ala Ile Leu Ser
             20                  25                  30

Val Ser Pro Gly Glu Arg Val Ser Phe Ser Cys Arg Ala Ser Gln Asn
         35                  40                  45

Ile Gly Thr Ser Ile His Trp Phe Gln Gln Arg Thr Asn Gly Ser Pro
     50                  55                  60

Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Ser Asn
             100                 105                 110

Ser Trp Pro Phe Thr Phe Gly Ser Gly Thr Lys Leu Glu Ile Lys
         115                 120                 125

<210> SEQ ID NO 51
<211> LENGTH: 11
<212> TYPE: PRT
<213> ORGANISM: homo sapiens

<400> SEQUENCE: 51

Arg Ala Ser Gln Asn Ile Gly Thr Ser Ile His
 1               5                  10

<210> SEQ ID NO 52
<211> LENGTH: 7
<212> TYPE: PRT
<213> ORGANISM: homo sapiens

<400> SEQUENCE: 52
```

Tyr Ala Ser Glu Ser Ile Ser
1               5

<210> SEQ ID NO 53
<211> LENGTH: 9
<212> TYPE: PRT
<213> ORGANISM: homo sapiens

<400> SEQUENCE: 53

Gln Gln Ser Asn Ser Trp Pro Phe Thr
1               5

<210> SEQ ID NO 54
<211> LENGTH: 396
<212> TYPE: DNA
<213> ORGANISM: homo sapiens
<220> FEATURE:
<221> NAME/KEY: CDS
<222> LOCATION: (1)..(396)

<400> SEQUENCE: 54

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc cac tcc cag gtc caa ctg cag cag cct ggg gct gag ctg gtg agg      96
Val His Ser Gln Val Gln Leu Gln Gln Pro Gly Ala Glu Leu Val Arg
                20                  25                  30 cct ggg gct tca gtg aag ctg tcc tgc aag gct tct ggc tac acc ttc     144
Pro Gly Ala Ser Val Lys Leu Ser Cys Lys Ala Ser Gly Tyr Thr Phe
            35                  40                  45 acc agc tac tgg ata acc tgg gtg aag cag agg cct gga caa ggc ctt     192
Thr Ser Tyr Trp Ile Thr Trp Val Lys Gln Arg Pro Gly Gln Gly Leu
        50                  55                  60 gag tgg atc gga aat att tat cct tct gat agt tat act aac tac aat     240
Glu Trp Ile Gly Asn Ile Tyr Pro Ser Asp Ser Tyr Thr Asn Tyr Asn
65                  70                  75                  80 caa aag ttc agg gac aag gcc aca ttg act gta gac aaa tcc tcc agt     288
Gln Lys Phe Arg Asp Lys Ala Thr Leu Thr Val Asp Lys Ser Ser Ser
                85                  90                  95 aca gcc tac atg cag ctc agc agc ccg aca tct gag gac tct gcg gtc     336
Thr Ala Tyr Met Gln Leu Ser Ser Pro Thr Ser Glu Asp Ser Ala Val
            100                 105                 110 tat tac tgt tca gcc ctc ttt gac tac tgg ggc caa ggc acc act ctc     384
Tyr Tyr Cys Ser Ala Leu Phe Asp Tyr Trp Gly Gln Gly Thr Thr Leu
        115                 120                 125 aca gtc tcc tca                                                     396
Thr Val Ser Ser
    130
```

<210> SEQ ID NO 55
<211> LENGTH: 132
<212> TYPE: PRT
<213> ORGANISM: homo sapiens

<400> SEQUENCE: 55

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
            35                  40                  45

-continued

```
Thr Ser Tyr Trp Ile Thr Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Arg Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Ser Ala Leu Phe Asp Tyr Trp Gly Gln Gly Thr Thr Leu
            115                 120                 125

Thr Val Ser Ser
    130
```

<210> SEQ ID NO 56
<211> LENGTH: 5
<212> TYPE: PRT
<213> ORGANISM: homo sapiens

<400> SEQUENCE: 56

```
Ser Tyr Trp Ile Thr
1               5
```

<210> SEQ ID NO 57
<211> LENGTH: 17
<212> TYPE: PRT
<213> ORGANISM: homo sapiens

<400> SEQUENCE: 57

```
Asn Ile Tyr Pro Ser Asp Ser Tyr Thr Asn Tyr Asn Gln Lys Phe Arg
1               5                   10                  15

Asp
```

<210> SEQ ID NO 58
<211> LENGTH: 4
<212> TYPE: PRT
<213> ORGANISM: homo sapiens

<400> SEQUENCE: 58

```
Leu Phe Asp Tyr
1
```

<210> SEQ ID NO 59
<211> LENGTH: 381
<212> TYPE: DNA
<213> ORGANISM: homo sapiens
<220> FEATURE:
<221> NAME/KEY: CDS
<222> LOCATION: (1)..(381)

<400> SEQUENCE: 59

```
atg gta tcc aca cct cag ttc ctt gta ttt ttg ctt ttc tgg att cca      48
Met Val Ser Thr Pro Gln Phe Leu Val Phe Leu Leu Phe Trp Ile Pro
1               5                   10                  15 gcc tcc aga ggt gac atc ttg ctg act cag tct cca gcc atc ctg tct      96
Ala Ser Arg Gly Asp Ile Leu Leu Thr Gln Ser Pro Ala Ile Leu Ser
                20                  25                  30 gtg agt cca gga gaa aga gtc agt ttc tcc tgc agg gcc agt cag agc     144
Val Ser Pro Gly Glu Arg Val Ser Phe Ser Cys Arg Ala Ser Gln Ser
            35                  40                  45 att ggc aca agc ata cac tgg tat cag caa aga aca aat ggt tct cca     192
Ile Gly Thr Ser Ile His Trp Tyr Gln Gln Arg Thr Asn Gly Ser Pro
        50                  55                  60
```

```
agg ctt ctc ata aag tat gct tct gag tct atc tct ggg atc cct tcc    240
Arg Leu Leu Ile Lys Tyr Ala Ser Glu Ser Ile Ser Gly Ile Pro Ser
 65                  70                  75                  80 agg ttt agt ggc agt gga tca ggg aca gat ttt att ctt agc atc aac    288
Arg Phe Ser Gly Ser Gly Ser Gly Thr Asp Phe Ile Leu Ser Ile Asn
                 85                  90                  95 agt gtg gag tct gaa gat att gca gat tat tac tgt caa caa agt aat    336
Ser Val Glu Ser Glu Asp Ile Ala Asp Tyr Tyr Cys Gln Gln Ser Asn
            100                 105                 110 agc tgg cca ttc acg ttc ggc tcg ggg aca aag ttg gaa ata aaa        381
Ser Trp Pro Phe Thr Phe Gly Ser Gly Thr Lys Leu Glu Ile Lys
        115                 120                 125
```

<210> SEQ ID NO 60
<211> LENGTH: 127
<212> TYPE: PRT
<213> ORGANISM: homo sapiens

<400> SEQUENCE: 60

```
Met Val Ser Thr Pro Gln Phe Leu Val Phe Leu Leu Phe Trp Ile Pro
  1               5                  10                  15

Ala Ser Arg Gly Asp Ile Leu Thr Gln Ser Pro Ala Ile Leu Ser
                 20                  25                  30

Val Ser Pro Gly Glu Arg Val Ser Phe Ser Cys Arg Ala Ser Gln Ser
             35                  40                  45

Ile Gly Thr Ser Ile His Trp Tyr Gln Gln Arg Thr Asn Gly Ser Pro
         50                  55                  60

Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Ile Leu Ser Ile Asn
                 85                  90                  95

Ser Val Glu Ser Glu Asp Ile Ala Asp Tyr Tyr Cys Gln Gln Ser Asn
            100                 105                 110

Ser Trp Pro Phe Thr Phe Gly Ser Gly Thr Lys Leu Glu Ile Lys
        115                 120                 125
```

<210> SEQ ID NO 61
<211> LENGTH: 11
<212> TYPE: PRT
<213> ORGANISM: homo sapiens

<400> SEQUENCE: 61

```
Arg Ala Ser Gln Ser Ile Gly Thr Ser Ile His
  1               5                  10
```

<210> SEQ ID NO 62
<211> LENGTH: 7
<212> TYPE: PRT
<213> ORGANISM: homo sapiens

<400> SEQUENCE: 62

```
Tyr Ala Ser Glu Ser Ile Ser
  1               5
```

<210> SEQ ID NO 63
<211> LENGTH: 9
<212> TYPE: PRT
<213> ORGANISM: homo sapiens

<400> SEQUENCE: 63

Gln Gln Ser Asn Ser Trp Pro Phe Thr
1               5

<210> SEQ ID NO 64
<211> LENGTH: 423
<212> TYPE: DNA
<213> ORGANISM: homo sapiens
<220> FEATURE:
<221> NAME/KEY: CDS
<222> LOCATION: (1)..(423)

<400> SEQUENCE: 64

| atg gga tgg agc tgg atc ttt ctc ttc ctc ctg tca gga act gca ggc | 48 |
|---|---|
| Met Gly Trp Ser Trp Ile Phe Leu Phe Leu Leu Ser Gly Thr Ala Gly | |
| 1               5                   10                  15 | |

| gtc cac tct gag gtc cag ctt cag cag tca gga cct gag ctg gtg aaa | 96 |
|---|---|
| Val His Ser Glu Val Gln Leu Gln Gln Ser Gly Pro Glu Leu Val Lys | |
|             20                  25                  30 | |

| cct ggg gcc tca gtg aag att tcc tgc aag gct tct gga tac aca ttc | 144 |
|---|---|
| Pro Gly Ala Ser Val Lys Ile Ser Cys Lys Ala Ser Gly Tyr Thr Phe | |
|         35                  40                  45 | |

| act gac tac aat atg cac tgg gtg aag cag agc cat gga aag aac ctt | 192 |
|---|---|
| Thr Asp Tyr Asn Met His Trp Val Lys Gln Ser His Gly Lys Asn Leu | |
|     50                  55                  60 | |

| gaa tgg att gga tat att tat cct tac aat ggt ggt act ggc tac aac | 240 |
|---|---|
| Glu Trp Ile Gly Tyr Ile Tyr Pro Tyr Asn Gly Gly Thr Gly Tyr Asn | |
| 65                  70                  75                  80 | |

| cag agg ttc aag agc agg gcc aca atg act gta gac aaa tcc tcc agc | 288 |
|---|---|
| Gln Arg Phe Lys Ser Arg Ala Thr Met Thr Val Asp Lys Ser Ser Ser | |
|                 85                  90                  95 | |

| aca gcc tac atg gag ctc cgc agc ctg aca tct gat gac tct gca gtc | 336 |
|---|---|
| Thr Ala Tyr Met Glu Leu Arg Ser Leu Thr Ser Asp Asp Ser Ala Val | |
|             100                 105                 110 | |

| tat tac tgt gca aga gaa gac tac ggt agt agc ccc tct tat gct atg | 384 |
|---|---|
| Tyr Tyr Cys Ala Arg Glu Asp Tyr Gly Ser Ser Pro Ser Tyr Ala Met | |
|         115                 120                 125 | |

| gac tat tgg ggt caa gga acc tca gtc atc gtc tcc tca | 423 |
|---|---|
| Asp Tyr Trp Gly Gln Gly Thr Ser Val Ile Val Ser Ser | |
|     130                 135                 140 | |

<210> SEQ ID NO 65
<211> LENGTH: 141
<212> TYPE: PRT
<213> ORGANISM: homo sapiens

<400> SEQUENCE: 65

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met His Trp Val Lys Gln Ser His Gly Lys Asn Leu
    50                  55                  60

Glu Trp Ile Gly Tyr Ile Tyr Pro Tyr Asn Gly Gly Thr Gly Tyr Asn
65                  70                  75                  80

Gln Arg Phe Lys Ser Arg Ala Thr Met Thr Val Asp Lys Ser Ser Ser
                85                  90                  95

Thr Ala Tyr Met Glu Leu Arg Ser Leu Thr Ser Asp Asp Ser Ala Val
            100                 105                 110

```
            Tyr Tyr Cys Ala Arg Glu Asp Tyr Gly Ser Ser Pro Ser Tyr Ala Met
                    115                 120                 125

Asp Tyr Trp Gly Gln Gly Thr Ser Val Ile Val Ser Ser
                130                 135                 140

<210> SEQ ID NO 66
<211> LENGTH: 5
<212> TYPE: PRT
<213> ORGANISM: homo sapiens

<400> SEQUENCE: 66

Asp Tyr Asn Met His
1               5

<210> SEQ ID NO 67
<211> LENGTH: 17
<212> TYPE: PRT
<213> ORGANISM: homo sapiens

<400> SEQUENCE: 67

Tyr Ile Tyr Pro Tyr Asn Gly Gly Thr Gly Tyr Asn Gln Arg Phe Lys
1               5                   10                  15

Ser

<210> SEQ ID NO 68
<211> LENGTH: 13
<212> TYPE: PRT
<213> ORGANISM: homo sapiens

<400> SEQUENCE: 68

Glu Asp Tyr Gly Ser Ser Pro Ser Tyr Ala Met Asp Tyr
1               5                   10

<210> SEQ ID NO 69
<211> LENGTH: 390
<212> TYPE: DNA
<213> ORGANISM: homo sapiens
<220> FEATURE:
<221> NAME/KEY: CDS
<222> LOCATION: (1)..(390)

<400> SEQUENCE: 69 atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agc agt gat gtt gtg atg acc caa act cca ctc tcc ctg cct gtc     96
Ser Ser Ser Asp Val Val Met Thr Gln Thr Pro Leu Ser Leu Pro Val
                20                  25                  30 agt ctt gga gat cag gcc tcc atc tct tgc aga tct agt cag agc ctt    144
Ser Leu Gly Asp Gln Ala Ser Ile Ser Cys Arg Ser Ser Gln Ser Leu
            35                  40                  45 gta cac ggt aat gga aac acc tat tta cat tgg tac ctg cag aag cca    192
Val His Gly Asn Gly Asn Thr Tyr Leu His Trp Tyr Leu Gln Lys Pro
        50                  55                  60 ggc cag tct cca aag ctc ctg atc tac aaa gtt tcc aac cga ttt tct    240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg acg gat ttc aca    288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat ttc tgc    336
Leu Lys Ile Ser Arg Val Glu Ala Glu Asp Leu Gly Val Tyr Phe Cys
            100                 105                 110
```

```
tct caa act aca cat gtt ccc acg ttc ggc tcg ggg aca aag ttg gaa    384
Ser Gln Thr Thr His Val Pro Thr Phe Gly Ser Gly Thr Lys Leu Glu
        115                 120                 125 ata aaa                                                             390
Ile Lys
    130
```

<210> SEQ ID NO 70
<211> LENGTH: 130
<212> TYPE: PRT
<213> ORGANISM: homo sapiens

<400> SEQUENCE: 70

```
Met Lys Leu Pro Val Arg Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Gly Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Thr Thr His Val Pro Thr Phe Gly Ser Gly Thr Lys Leu Glu
        115                 120                 125

Ile Lys
    130
```

<210> SEQ ID NO 71
<211> LENGTH: 16
<212> TYPE: PRT
<213> ORGANISM: homo sapiens

<400> SEQUENCE: 71

```
Arg Ser Ser Gln Ser Leu Val His Gly Asn Gly Asn Thr Tyr Leu His
1               5                   10                  15
```

<210> SEQ ID NO 72
<211> LENGTH: 7
<212> TYPE: PRT
<213> ORGANISM: homo sapiens

<400> SEQUENCE: 72

```
Lys Val Ser Asn Arg Phe Ser
1               5
```

<210> SEQ ID NO 73
<211> LENGTH: 8
<212> TYPE: PRT
<213> ORGANISM: homo sapiens

<400> SEQUENCE: 73

```
Ser Gln Thr Thr His Val Pro Thr
1               5
```

<210> SEQ ID NO 74

```
<211> LENGTH: 402
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(402)

<400> SEQUENCE: 74 atg ggg tgg agc tgc att atc ctg ttt ctt gtc gca act gca aca ggc    48
Met Gly Trp Ser Cys Ile Ile Leu Phe Leu Val Ala Thr Ala Thr Gly
1               5                   10                  15 gtt cac tca cag gtt cag cta gtc cag tct gga gct gag gtg aag aaa    96
Val His Ser Gln Val Gln Leu Val Gln Ser Gly Ala Glu Val Lys Lys
            20                  25                  30 cca ggg gca tct gtc aaa gtg agc tgt aag gcc tct ggc tat acg ttc    144
Pro Gly Ala Ser Val Lys Val Ser Cys Lys Ala Ser Gly Tyr Thr Phe
        35                  40                  45 acg ata tac tgg atc aat tgg gtg agg caa gct cct gga caa cgg ttg    192
Thr Ile Tyr Trp Ile Asn Trp Val Arg Gln Ala Pro Gly Gln Arg Leu
    50                  55                  60 gaa tgg att ggc aac atc tat ccc tca gac tcc tac acc aac tac aat    240
Glu Trp Ile Gly Asn Ile Tyr Pro Ser Asp Ser Tyr Thr Asn Tyr Asn
65                  70                  75                  80 cag aag ttc aag gac aaa gcc act ctc acc gta gat acc agt gcc tcc    288
Gln Lys Phe Lys Asp Lys Ala Thr Leu Thr Val Asp Thr Ser Ala Ser
                85                  90                  95 aca gcc tat atg gag ctg agc agt tta cgc agc gaa gat aca gcg gtg    336
Thr Ala Tyr Met Glu Leu Ser Ser Leu Arg Ser Glu Asp Thr Ala Val
            100                 105                 110 tac tac tgc acc aga acc tcc atg gct gac tat tgg ggt cag ggt aca    384
Tyr Tyr Cys Thr Arg Thr Ser Met Ala Asp Tyr Trp Gly Gln Gly Thr
        115                 120                 125 ctg gtg act gtg agc tcc                                            402
Leu Val Thr Val Ser Ser
    130

<210> SEQ ID NO 75
<211> LENGTH: 134
<212> TYPE: PRT
<213> ORGANISM: Artificial
<220> FEATURE:
<223> OTHER INFORMATION: Synthetic Construct (recombinant protein)

<400> SEQUENCE: 75

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ile Tyr Trp Ile Asn Trp Val Arg Gln Ala Pro Gly Gln Arg Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Thr Ser Met Ala Asp Tyr Trp Gly Gln Gly Thr
```

Leu Val Thr Val Ser Ser
    130

<210> SEQ ID NO 76
<211> LENGTH: 381
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(381)

<400> SEQUENCE: 76

```
atg gta agc aca ccc cag ttc ctc gtt ttc ctc ctg ttt tgg att ccc    48
Met Val Ser Thr Pro Gln Phe Leu Val Phe Leu Leu Phe Trp Ile Pro
1               5                   10                  15 gca agt aga ggg gag atc gtc ttg act cag agt cct gcc aca ctg tct    96
Ala Ser Arg Gly Glu Ile Val Leu Thr Gln Ser Pro Ala Thr Leu Ser
            20                  25                  30 ctt tca cca gga gaa agg gcg aca ctt agc tgt cga gct tct cag agc   144
Leu Ser Pro Gly Glu Arg Ala Thr Leu Ser Cys Arg Ala Ser Gln Ser
        35                  40                  45 att ggc acg tcc ata cac tgg tat cag cag aaa ccg gga caa gct cca   192
Ile Gly Thr Ser Ile His Trp Tyr Gln Gln Lys Pro Gly Gln Ala Pro
    50                  55                  60 cgg tta ctg atc aag tat gcc tcc gaa agc atc tct ggg att cct gca   240
Arg Leu Leu Ile Lys Tyr Ala Ser Glu Ser Ile Ser Gly Ile Pro Ala
65                  70                  75                  80 cgc ttt agc gga agc ggt agt ggt acc gac ttc act ctg acc ata tcc   288
Arg Phe Ser Gly Ser Gly Ser Gly Thr Asp Phe Thr Leu Thr Ile Ser
                85                  90                  95 tca cta gaa ccc gag gat ttt gcc gtg tac tac tgc cag cag tcc aac   336
Ser Leu Glu Pro Glu Asp Phe Ala Val Tyr Tyr Cys Gln Gln Ser Asn
            100                 105                 110 tca tgg cct ttc acc ttt ggc caa ggc acc aaa gtg gag atc aag       381
Ser Trp Pro Phe Thr Phe Gly Gln Gly Thr Lys Val Glu Ile Lys
        115                 120                 125
```

<210> SEQ ID NO 77
<211> LENGTH: 127
<212> TYPE: PRT
<213> ORGANISM: Artificial
<220> FEATURE:
<223> OTHER INFORMATION: Synthetic Construct (recombinant protein)

<400> SEQUENCE: 77

Met Val Ser Thr Pro Gln Phe Leu Val Phe Leu Leu Phe Trp Ile Pro
1               5                   10                  15

Ala Ser Arg Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Ile Gly Thr Ser Ile His Trp Tyr Gln Gln Lys Pro Gly Gln Ala Pro
    50                  55                  60

Arg Leu Leu Ile Lys Tyr Ala Ser Glu Ser Ile Ser Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Ser Asn

```
                    100                 105                 110
Ser Trp Pro Phe Thr Phe Gly Gln Gly Thr Lys Val Glu Ile Lys
        115                 120                 125

<210> SEQ ID NO 78
<211> LENGTH: 423
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(423)

<400> SEQUENCE: 78 atg gga tgg tct tgg atc ttt ctc ttc ctg ctg tct ggc aca gct gga      48
Met Gly Trp Ser Trp Ile Phe Leu Phe Leu Leu Ser Gly Thr Ala Gly
1               5                   10                  15 gtg cat tcc caa gtt cag ctg gtc cag tcc gga gct gaa gtt aaa aag      96
Val His Ser Gln Val Gln Leu Val Gln Ser Gly Ala Glu Val Lys Lys
                20                  25                  30 ccc ggg gcc agc gtc aaa gtc tcc tgc aag gca tcc ggg tat act ttt     144
Pro Gly Ala Ser Val Lys Val Ser Cys Lys Ala Ser Gly Tyr Thr Phe
            35                  40                  45 acc gat tat aac atg cac tgg gtg cgc caa gca ccc ggc cag ggc ctg     192
Thr Asp Tyr Asn Met His Trp Val Arg Gln Ala Pro Gly Gln Gly Leu
        50                  55                  60 gag tgg att ggc tat atc tat cct tat aat gga ggg acc ggc tac aac     240
Glu Trp Ile Gly Tyr Ile Tyr Pro Tyr Asn Gly Gly Thr Gly Tyr Asn
65                  70                  75                  80 cag aga ttc aag agc aga gcc acc atg aca gtg gat aaa tct acc agc     288
Gln Arg Phe Lys Ser Arg Ala Thr Met Thr Val Asp Lys Ser Thr Ser
                85                  90                  95 act gcc tac atg gag ctg aga agc ctg cgg agc gac gac aca gcc gtg     336
Thr Ala Tyr Met Glu Leu Arg Ser Leu Arg Ser Asp Asp Thr Ala Val
            100                 105                 110 tac tac tgt gcc cgc gag gat tac gga agc agc cca agc tac gcc atg     384
Tyr Tyr Cys Ala Arg Glu Asp Tyr Gly Ser Ser Pro Ser Tyr Ala Met
        115                 120                 125 gat tac tgg ggc caa ggc act atg gtg acc gtg agc agc                 423
Asp Tyr Trp Gly Gln Gly Thr Met Val Thr Val Ser Ser
    130                 135                 140

<210> SEQ ID NO 79
<211> LENGTH: 141
<212> TYPE: PRT
<213> ORGANISM: Artificial
<220> FEATURE:
<223> OTHER INFORMATION: Synthetic Construct (recombinant protein)

<400> SEQUENCE: 79

Met Gly Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Asn Met His Trp Val Arg Gln Ala Pro Gly Gln Gly Leu
        50                  55                  60

Glu Trp Ile Gly Tyr Ile Tyr Pro Tyr Asn Gly Gly Thr Gly Tyr Asn
65                  70                  75                  80
```

```
Gln Arg Phe Lys Ser Arg Ala Thr Met Thr Val Asp Lys Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Asp Tyr Gly Ser Ser Pro Ser Tyr Ala Met
        115                 120                 125

Asp Tyr Trp Gly Gln Gly Thr Met Val Thr Val Ser Ser
    130                 135                 140

<210> SEQ ID NO 80
<211> LENGTH: 423
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(423)

<400> SEQUENCE: 80 atg ggc tgg tct tgg atc ttc ctc ttc ctg ctg agc ggg acc gct gga      48
Met Gly Trp Ser Trp Ile Phe Leu Phe Leu Leu Ser Gly Thr Ala Gly
1               5                   10                  15 gtc cat tct caa gtc caa ctg gtc cag tcc ggg gct gaa gtg aaa aaa      96
Val His Ser Gln Val Gln Leu Val Gln Ser Gly Ala Glu Val Lys Lys
                20                  25                  30 cca gga gca tcc gtt aag gtg tcc tgt aag gca agc gga tac acc ttt     144
Pro Gly Ala Ser Val Lys Val Ser Cys Lys Ala Ser Gly Tyr Thr Phe
            35                  40                  45 acc gac tat aac atg cac tgg gtg agg cag gcc ccc gga cag ggg ctg     192
Thr Asp Tyr Asn Met His Trp Val Arg Gln Ala Pro Gly Gln Gly Leu
        50                  55                  60 gag tgg atc ggc tat att tat cct tac aac ggg ggc act ggc tat aat     240
Glu Trp Ile Gly Tyr Ile Tyr Pro Tyr Asn Gly Gly Thr Gly Tyr Asn
65                  70                  75                  80 cag aga ttt aag agc cgc gct acc atg acc gtg gac acc tcc act tct     288
Gln Arg Phe Lys Ser Arg Ala Thr Met Thr Val Asp Thr Ser Thr Ser
                85                  90                  95 aca gcc tat atg gag ctg aga agc ctg cgg agc gat gat aca gcc gtg     336
Thr Ala Tyr Met Glu Leu Arg Ser Leu Arg Ser Asp Asp Thr Ala Val
            100                 105                 110 tac tac tgc gcc aga gaa gat tac ggc agc agc ccc agc tac gcc atg     384
Tyr Tyr Cys Ala Arg Glu Asp Tyr Gly Ser Ser Pro Ser Tyr Ala Met
        115                 120                 125 gac tac tgg ggc cag ggc aca atg gtt act gtg agc agc                 423
Asp Tyr Trp Gly Gln Gly Thr Met Val Thr Val Ser Ser
    130                 135                 140

<210> SEQ ID NO 81
<211> LENGTH: 141
<212> TYPE: PRT
<213> ORGANISM: Artificial
<220> FEATURE:
<223> OTHER INFORMATION: Synthetic Construct (recombinant protein)

<400> SEQUENCE: 81

Met Gly Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45
```

```
Thr Asp Tyr Asn Met His Trp Val Arg Gln Ala Pro Gly Gln Gly Leu
 50                  55                  60

Glu Trp Ile Gly Tyr Ile Tyr Pro Tyr Asn Gly Thr Gly Tyr Asn
 65                  70                  75                  80

Gln Arg Phe Lys Ser Arg Ala Thr Met Thr Val Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Glu Asp Tyr Gly Ser Ser Pro Ser Tyr Ala Met
        115                 120                 125

Asp Tyr Trp Gly Gln Gly Thr Met Val Thr Val Ser Ser
        130                 135                 140

<210> SEQ ID NO 82
<211> LENGTH: 390
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (1)..(390)

<400> SEQUENCE: 82 atg aag ctc cca gtg cgc ctc ctg gtc ctg atg ttc tgg att ccc gct      48
Met Lys Leu Pro Val Arg Leu Leu Val Leu Met Phe Trp Ile Pro Ala
 1               5                  10                  15 tcc tct agc gat atc gtc atg acc caa tcc cca ctg tct ctg cct gtg     96
Ser Ser Ser Asp Ile Val Met Thr Gln Ser Pro Leu Ser Leu Pro Val
                 20                  25                  30 aca cca ggc gaa cct gca tct att agc tgt aga agc agc cag tcc ctg    144
Thr Pro Gly Glu Pro Ala Ser Ile Ser Cys Arg Ser Ser Gln Ser Leu
         35                  40                  45 gtg cac gga aac gga aac acc tat ctg cac tgg tac ctg caa aaa cct    192
Val His Gly Asn Gly Asn Thr Tyr Leu His Trp Tyr Leu Gln Lys Pro
     50                  55                  60 gga cag agc ccc cag ctg ctg atc tac aaa gtc agc aat aga ttt agc    240
Gly Gln Ser Pro Gln Leu Leu Ile Tyr Lys Val Ser Asn Arg Phe Ser
 65                  70                  75                  80 ggg gtg ccc gac agg ttt agc ggc agc ggc agc ggc aca gat ttc acc    288
Gly Val Pro Asp Arg Phe Ser Gly Ser Gly Ser Gly Thr Asp Phe Thr
                 85                  90                  95 ctg aaa atc tcc cgg gtg gaa gcc gag gac gtt ggg gtt tac tat tgc    336
Leu Lys Ile Ser Arg Val Glu Ala Glu Asp Val Gly Val Tyr Tyr Cys
            100                 105                 110 agc cag aca acc cat gtg ccc act ttc ggg ggc ggc act aag gtg gag    384
Ser Gln Thr Thr His Val Pro Thr Phe Gly Gly Gly Thr Lys Val Glu
        115                 120                 125 atc aag                                                            390
Ile Lys
    130

<210> SEQ ID NO 83
<211> LENGTH: 130
<212> TYPE: PRT
<213> ORGANISM: Artificial
<220> FEATURE:
<223> OTHER INFORMATION: Synthetic Construct (recombinant protein)

<400> SEQUENCE: 83

Met Lys Leu Pro Val Arg Leu Leu Val Leu Met Phe Trp Ile Pro Ala
```

```
                1               5                    10                   15
              Ser Ser Ser Asp Ile Val Met Thr Gln Ser Pro Leu Ser Leu Pro Val
                            20                  25                  30

Thr Pro Gly Glu Pro Ala Ser Ile Ser Cys Arg Ser Ser Gln Ser Leu
                            35                  40                  45

Val His Gly Asn Gly Asn Thr Tyr Leu His Trp Tyr Leu Gln Lys Pro
                            50                  55                  60

Gly Gln Ser Pro Gln Leu Leu Ile Tyr Lys Val Ser Asn Arg Phe Ser
              65                  70                  75                  80

Gly Val Pro Asp Arg Phe Ser Gly Ser Gly Ser Gly Thr Asp Phe Thr
                            85                  90                  95

Leu Lys Ile Ser Arg Val Glu Ala Glu Asp Val Gly Val Tyr Tyr Cys
                            100                 105                 110

Ser Gln Thr Thr His Val Pro Thr Phe Gly Gly Gly Thr Lys Val Glu
                            115                 120                 125

Ile Lys
                 130

<210> SEQ ID NO 84
<211> LENGTH: 563
<212> TYPE: DNA
<213> ORGANISM: Homo sapiens
<220> FEATURE:
<221> NAME/KEY: CDS
<222> LOCATION: (102)..(458)

<400> SEQUENCE: 84
aaccacatcc ctcctcagaa gcccccagag cacaactcct taccatggac tggacctgga      60
ggatcctctt tttggtggca gcagccacag gtgcccactc c cag gtc cag ctt gtg     116
                                             Gln Val Gln Leu Val
                                              1               5 cag tct ggg gct gag gtg aag aag cct ggg gcc tca gtg aag gtt tcc       164
Gln Ser Gly Ala Glu Val Lys Lys Pro Gly Ala Ser Val Lys Val Ser
               10                  15                  20 tgc aag gct tct gga tac acc ttc act aac tat gct ctg cat tgg gtg       212
Cys Lys Ala Ser Gly Tyr Thr Phe Thr Asn Tyr Ala Leu His Trp Val
            25                  30                  35 cgc cag gcc ccc gga caa agg ctt gag tgg atg gga tgg atc aac act       260
Arg Gln Ala Pro Gly Gln Arg Leu Glu Trp Met Gly Trp Ile Asn Thr
        40                  45                  50 ggc aat ggt aac aca aaa tat tca cag aag ttc cag ggc aga gtc acc       308
Gly Asn Gly Asn Thr Lys Tyr Ser Gln Lys Phe Gln Gly Arg Val Thr
    55                  60                  65 ctt acc agt gac aca tcc gcg agc aca gcc tac atg gag atg agc agc       356
Leu Thr Ser Asp Thr Ser Ala Ser Thr Ala Tyr Met Glu Met Ser Ser
70                  75                  80                  85 ctg aga tct gaa gac acg gct gtg tat tac tgt gcg agg agc agt ggc       404
Leu Arg Ser Glu Asp Thr Ala Val Tyr Tyr Cys Ala Arg Ser Ser Gly
                90                  95                  100 tgg tac gtt tgg ttc gac ccc tgg ggc cag gga acc ctg gtc acc gtc       452
Trp Tyr Val Trp Phe Asp Pro Trp Gly Gln Gly Thr Leu Val Thr Val
            105                 110                 115 tcc tca gcttccacca agggcccatc ggttttcccc ctggcgccct gctccaggag        508
Ser Ser cacctctggg ggcacagcgg ccctgggctg cctggtcaag gactacttcc ccgaa          563

<210> SEQ ID NO 85
<211> LENGTH: 119
```

<212> TYPE: PRT
<213> ORGANISM: Homo sapiens

<400> SEQUENCE: 85

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Ala Leu His Trp Val Arg Gln Ala Pro Gly Gln Arg Leu Glu Trp Met
            35                  40                  45
Gly Trp Ile Asn Thr Gly Asn Gly Asn Thr Lys Tyr Ser Gln Lys Phe
        50                  55                  60
Gln Gly Arg Val Thr Leu Thr Ser Asp Thr Ser Ala Ser Thr Ala Tyr
65                  70                  75                  80
Met Glu Met Ser Ser Leu Arg Ser Glu Asp Thr Ala Val Tyr Tyr Cys
                85                  90                  95
Ala Arg Ser Ser Gly Trp Tyr Val Trp Phe Asp Pro Trp Gly Gln Gly
            100                 105                 110
Thr Leu Val Thr Val Ser Ser
        115
```

<210> SEQ ID NO 86
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 86

```
atg gaa gtc ctc gtg cag ctt ctc ttc ctc ctg cta ctc tgg ctc cca      48
Met Glu Val Leu Val Gln Leu Leu Phe Leu Leu Leu Leu Trp Leu Pro
1               5                   10                  15 gat acc acc gga gaa att gtg ttg aca cag tct cca gcc acc ctg tct      96
Asp Thr Thr Gly Glu Ile Val Leu Thr Gln Ser Pro Ala Thr Leu Ser
                20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
            35                  40                  45 gtt agc agc tac tta gcc tgg tat caa cag aaa cct ggc cag gct ccc     192
Val Ser Ser Tyr Leu Ala Trp Tyr Gln Gln Lys Pro Gly Gln Ala Pro
        50                  55                  60 agg ctc ctc atc tat gat gca tcc aac agg gcc act ggc atc cca gcc     240
Arg Leu Leu Ile Tyr Asp Ala Ser Asn Arg Ala Thr Gly Ile Pro Ala
65                  70                  75                  80 agg ttc agt ggc agt ggg tct ggg aca gac ttc act ctc acc atc agc     288
Arg Phe Ser Gly Ser Gly Ser Gly Thr Asp Phe Thr Leu Thr Ile Ser
                85                  90                  95 agc cta gag cct gaa gat ttt gca gtt tat tac tgt cag cag cgt agc     336
Ser Leu Glu Pro Glu Asp Phe Ala Val Tyr Tyr Cys Gln Gln Arg Ser
            100                 105                 110 aac tgg cct cgg tcg ttc ggc caa ggg acc aag gtg gaa atc aaa cga     384
Asn Trp Pro Arg Ser Phe Gly Gln Gly Thr Lys Val Glu Ile Lys Arg
        115                 120                 125
```

<210> SEQ ID NO 87
<211> LENGTH: 128
<212> TYPE: PRT
<213> ORGANISM: Homo sapiens

<400> SEQUENCE: 87

```
Met Glu Val Leu Val Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Arg Ser Phe Gly Gln Gly Thr Lys Val Glu Ile Lys Arg
        115                 120                 125
```

<210> SEQ ID NO 88
<211> LENGTH: 601
<212> TYPE: DNA
<213> ORGANISM: Homo sapiens
<220> FEATURE:
<221> NAME/KEY: CDS
<222> LOCATION: (112)..(477)

<400> SEQUENCE: 88

```
acccaaaaac cacacccctc cttgggagaa tccctagat cacagctcct caccatggac      60
tggacctgga gcatccttt cttggtggca gcagcaacag gtgcccactc c cag gtt     117
                                                        Gln Val
                                                        1 cag ctg gtg cag tct gga gct gag gtg aag aag cct ggg gcc tca gtg    165
Gln Leu Val Gln Ser Gly Ala Glu Val Lys Lys Pro Gly Ala Ser Val
        5                   10                  15 aag gtc tcc tgc aag gct tct ggt tac acc ttt acc agt tat ggt atc    213
Lys Val Ser Cys Lys Ala Ser Gly Tyr Thr Phe Thr Ser Tyr Gly Ile
    20                  25                  30 agt tgg gtg cgc cag gcc cct gga caa ggg ctt gag tgg atg gga ttg    261
Ser Trp Val Arg Gln Ala Pro Gly Gln Gly Leu Glu Trp Met Gly Leu
35                  40                  45                  50 atc agc gct tac aat ggt aac aca aac tat gca cag aag ctc cag ggc    309
Ile Ser Ala Tyr Asn Gly Asn Thr Asn Tyr Ala Gln Lys Leu Gln Gly
                55                  60                  65 aga gtc acc atg acc gta gac acg tct acg agc aca gcc tat atg gaa    357
Arg Val Thr Met Thr Val Asp Thr Ser Thr Ser Thr Ala Tyr Met Glu
            70                  75                  80 ctg agg agc ctg aga tct gac gac acg gcc gtc tat tac tgt gcg aga    405
Leu Arg Ser Leu Arg Ser Asp Asp Thr Ala Val Tyr Tyr Cys Ala Arg
        85                  90                  95 gat gga ata gca gtg gcg acc aaa gat gct ttt gat atc tgg ggc caa    453
Asp Gly Ile Ala Val Ala Thr Lys Asp Ala Phe Asp Ile Trp Gly Gln
    100                 105                 110 ggg aca atg gtc acc gtc tct tca gcacccacca aggctccgga tgtgttcccc   507
Gly Thr Met Val Thr Val Ser Ser
115                 120 atcatatcag ggtgcagaca cccaaaggat aacagccctg tggtcctggc atgcttgata   567
actgggtacc acccaacgtc cgtgactgtc acct                              601
```

<210> SEQ ID NO 89
<211> LENGTH: 122
<212> TYPE: PRT
<213> ORGANISM: Homo sapiens

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Leu Ile Ser Ala Tyr Asn Gly Asn Thr Asn Tyr Ala Gln Lys Leu
    50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Gly Ile Ala Val Ala Thr Lys Asp Ala Phe Asp Ile Trp
            100                 105                 110

Gly Gln Gly Thr Met Val Thr Val Ser Ser
        115                 120
```

<210> SEQ ID NO 90
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 90

```
gat att gtg atg act cag tct cca ctc tcc ctg ccc gtc acc cct gga        48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc agg gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa act ctg ggg ctc act ttc ggc gga ggg acc aag gtg gag atc       336
Leu Gln Thr Leu Gly Leu Thr Phe Gly Gly Gly Thr Lys Val Glu Ile
            100                 105                 110 aaa cga                                                                342
Lys Arg
```

<210> SEQ ID NO 91
<211> LENGTH: 114
<212> TYPE: PRT
<213> ORGANISM: Homo sapiens -continued

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Gly Leu Thr Phe Gly Gly Gly Thr Lys Val Glu Ile
            100                 105                 110

Lys Arg

<210> SEQ ID NO 92
<211> LENGTH: 115
<212> TYPE: PRT
<213> ORGANISM: Artificial
<220> FEATURE:
<223> OTHER INFORMATION: recombinant protein

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Ile Asn Trp Val Arg Gln Ala Pro Gly Gln Arg Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Ser Met Ala Asp Tyr Trp Gly Gln Gly Thr Leu Val Thr
            100                 105                 110

Val Ser Ser
        115

<210> SEQ ID NO 93
<211> LENGTH: 107
<212> TYPE: PRT
<213> ORGANISM: Artificial
<220> FEATURE:
<223> OTHER INFORMATION: recombinant protein

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Ile Pro Ala Arg Phe Ser Gly

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Asn Ser Trp Pro Phe
                    85                  90                  95

Thr Phe Gly Gln Gly Thr Lys Val Glu Ile Lys
                100                 105
```

<210> SEQ ID NO 94
<211> LENGTH: 122
<212> TYPE: PRT
<213> ORGANISM: Artificial
<220> FEATURE:
<223> OTHER INFORMATION: recombinant protein

<400> SEQUENCE: 94

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
                35                  40                  45

Gly Tyr Ile Tyr Pro Tyr Asn Gly Gly Thr Gly Tyr Asn Gln Arg Phe
            50                  55                  60

Lys Ser Arg Ala Thr Met Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Glu Asp Tyr Gly Ser Ser Pro Ser Tyr Ala Met Asp Tyr Trp
                100                 105                 110

Gly Gln Gly Thr Met Val Thr Val Ser Ser
                115                 120
```

<210> SEQ ID NO 95
<211> LENGTH: 122
<212> TYPE: PRT
<213> ORGANISM: Artificial
<220> FEATURE:
<223> OTHER INFORMATION: recombinant protein

<400> SEQUENCE: 95

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
                35                  40                  45

Gly Tyr Ile Tyr Pro Tyr Asn Gly Gly Thr Gly Tyr Asn Gln Arg Phe
            50                  55                  60

Lys Ser Arg Ala Thr Met Thr Val Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Glu Asp Tyr Gly Ser Ser Pro Ser Tyr Ala Met Asp Tyr Trp
                100                 105                 110

Gly Gln Gly Thr Met Val Thr Val Ser Ser
                115                 120
```

<210> SEQ ID NO 96
<211> LENGTH: 111
<212> TYPE: PRT
<213> ORGANISM: Artificial
<220> FEATURE:
<223> OTHER INFORMATION: recombinant protein

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Gly
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Val Pro Thr Phe Gly Gly Gly Thr Lys Val Glu Ile Lys
            100                 105                 110

<210> SEQ ID NO 97
<211> LENGTH: 134
<212> TYPE: PRT
<213> ORGANISM: Artificial
<220> FEATURE:
<223> OTHER INFORMATION: Synthetic Construct (recombinant protein)

<400> SEQUENCE: 97

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ile Tyr Trp Ile Asn Trp Val Arg Gln Ala Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Thr Ser Met Ala Asp Tyr Trp Gly Gln Gly Thr
        115                 120                 125

Leu Val Thr Val Ser Ser
    130

<210> SEQ ID NO 98
<211> LENGTH: 115
<212> TYPE: PRT
<213> ORGANISM: Artificial
<220> FEATURE:
<223> OTHER INFORMATION: recombinant protein

<400> SEQUENCE: 98

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Ile Tyr
                20                  25                  30

Trp Ile Asn Trp Val Arg Gln Ala Pro Gly Gln Gly Leu Glu Trp Ile
                35                  40                  45

Gly Asn Ile Tyr Pro Ser Asp Ser Tyr Thr Asn Tyr Asn Gln Lys Phe
            50                  55                  60

Lys Asp Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Ser Met Ala Asp Tyr Trp Gly Gln Gly Thr Leu Val Thr
                100                 105                 110

Val Ser Ser
        115

<210> SEQ ID NO 99
<211> LENGTH: 420
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (13)..(414)

<400> SEQUENCE: 99
gaattcacca cc atg gga tgg tcc tgc att att ctc ttt ctc gtc gcc acc      51
              Met Gly Trp Ser Cys Ile Ile Leu Phe Leu Val Ala Thr
                1               5                   10 gcc aca ggc gtg cac agc cag gtt caa ctg cag caa cct ggg gca gag       99
Ala Thr Gly Val His Ser Gln Val Gln Leu Gln Gln Pro Gly Ala Glu
        15                  20                  25 ctg gtt cgg cca ggg gcc tcc gtc aaa ctg tcc tgc aaa gct tct ggc      147
Leu Val Arg Pro Gly Ala Ser Val Lys Leu Ser Cys Lys Ala Ser Gly
30                  35                  40                  45 tac act ttc acc atc tac tgg atc aac tgg gtg aag cag agg ccc ggc      195
Tyr Thr Phe Thr Ile Tyr Trp Ile Asn Trp Val Lys Gln Arg Pro Gly
                50                  55                  60 cag ggc ctg gaa tgg atc gga aat atc tat cct agc gat tct tac aca      243
Gln Gly Leu Glu Trp Ile Gly Asn Ile Tyr Pro Ser Asp Ser Tyr Thr
            65                  70                  75 aat tac aac cag aag ttc aag gac aag gct acc ctg acc gtg gac aaa      291
Asn Tyr Asn Gln Lys Phe Lys Asp Lys Ala Thr Leu Thr Val Asp Lys
        80                  85                  90 tct agc tcc aca gcc tac atg cag ctg agc agc ccc act agc gag gat      339
Ser Ser Ser Thr Ala Tyr Met Gln Leu Ser Ser Pro Thr Ser Glu Asp
    95                  100                 105 agc gca gtg tat tat tgt acc aga acc agc atg gcc gac tat tgg gga      387
Ser Ala Val Tyr Tyr Cys Thr Arg Thr Ser Met Ala Asp Tyr Trp Gly
110                 115                 120                 125 cag ggc aca act ctg acc gtg agc agc gctagc                           420
Gln Gly Thr Thr Leu Thr Val Ser Ser
                130

<210> SEQ ID NO 100
<211> LENGTH: 399
<212> TYPE: DNA
<213> ORGANISM: Artificial
<220> FEATURE:
<223> OTHER INFORMATION: recombinant DNA
```

```
<220> FEATURE:
<221> NAME/KEY: CDS
<222> LOCATION: (13)..(393)

<400> SEQUENCE: 100
accggtacca cc atg gtt agc aca cct caa ttt ctg gtc ttc ctg ctc ttc      51
              Met Val Ser Thr Pro Gln Phe Leu Val Phe Leu Leu Phe
                1               5                  10 tgg att cct gcc agc aga gga gat atc ctc ctg aca caa agc ccc gca        99
Trp Ile Pro Ala Ser Arg Gly Asp Ile Leu Leu Thr Gln Ser Pro Ala
     15                  20                  25 atc ctg agc gtg tcc ccc gga gag cgc gtg agc ttt agc tgc cgg gcc       147
Ile Leu Ser Val Ser Pro Gly Glu Arg Val Ser Phe Ser Cys Arg Ala
 30                  35                  40                  45 agc cag agc att gga acc agc atc cac tgg tat cag cag aga acc aac       195
Ser Gln Ser Ile Gly Thr Ser Ile His Trp Tyr Gln Gln Arg Thr Asn
                 50                  55                  60 ggg tct ccc agg ctg ctg att aaa tac gct tct gag tct att tcc ggg       243
Gly Ser Pro Arg Leu Leu Ile Lys Tyr Ala Ser Glu Ser Ile Ser Gly
 65                  70                  75 atc cca agc aga ttc tcc ggc tct ggc agc ggc act gat ttt act ctg       291
Ile Pro Ser Arg Phe Ser Gly Ser Gly Ser Gly Thr Asp Phe Thr Leu
         80                  85                  90 tct atc aac agc gtg gag tcc gaa gac atc gcc gac tac tat tgt cag       339
Ser Ile Asn Ser Val Glu Ser Glu Asp Ile Ala Asp Tyr Tyr Cys Gln
 95                 100                 105 cag agc aat tcc tgg cca ttc acc ttt ggc agc ggc acc aag ctg gaa       387
Gln Ser Asn Ser Trp Pro Phe Thr Phe Gly Ser Gly Thr Lys Leu Glu
110                 115                 120                 125 atc aag cgtacg                                                        399
Ile Lys <210> SEQ ID NO 101
<211> LENGTH: 30
<212> TYPE: PRT
<213> ORGANISM: homo sapiens

<400> SEQUENCE: 101

Asn Lys Met Thr Val Cys Ser Pro Asp Gly Pro Gly Gly Arg Cys Gln
 1               5                  10                  15

Cys Arg Ala Leu Gly Ser Gly Met Ala Val Asp Cys Ser Thr
             20                  25                  30

<210> SEQ ID NO 102
<211> LENGTH: 30
<212> TYPE: PRT
<213> ORGANISM: homo sapiens

<400> SEQUENCE: 102

Thr Val Cys Ser Pro Asp Gly Pro Gly Gly Arg Cys Gln Cys Arg Ala
 1               5                  10                  15

Leu Gly Ser Gly Met Ala Val Asp Cys Ser Thr Leu Thr Ser
             20                  25                  30

<210> SEQ ID NO 103
<211> LENGTH: 30
<212> TYPE: PRT
<213> ORGANISM: homo sapiens

<400> SEQUENCE: 103

Thr Asn Lys Met Thr Val Cys Ser Pro Asp Gly Pro Gly Gly Arg Cys
 1               5                  10                  15
```

```
Gln Cys Arg Ala Leu Gly Ser Gly Met Ala Val Asp Cys Ser
         20                  25                  30
```

<210> SEQ ID NO 104
<211> LENGTH: 30
<212> TYPE: PRT
<213> ORGANISM: homo sapiens

<400> SEQUENCE: 104

```
Met Thr Val Cys Ser Pro Asp Gly Pro Gly Arg Cys Gln Cys Arg
1               5                   10                  15

Ala Leu Gly Ser Gly Met Ala Val Asp Cys Ser Thr Leu Thr
            20                  25                  30
```

<210> SEQ ID NO 105
<211> LENGTH: 30
<212> TYPE: PRT
<213> ORGANISM: homo sapiens

<400> SEQUENCE: 105

```
Lys Met Thr Val Cys Ser Pro Asp Gly Pro Gly Gly Arg Cys Gln Cys
1               5                   10                  15

Arg Ala Leu Gly Ser Gly Met Ala Val Asp Cys Ser Thr Leu
            20                  25                  30
```

<210> SEQ ID NO 106
<211> LENGTH: 30
<212> TYPE: PRT
<213> ORGANISM: homo sapiens

<400> SEQUENCE: 106

```
Pro Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Cys
            20                  25                  30
```

<210> SEQ ID NO 107
<211> LENGTH: 30
<212> TYPE: PRT
<213> ORGANISM: homo sapiens

<400> SEQUENCE: 107

```
Val Cys Ser Pro Asp Gly Pro Gly Gly Arg Cys Gln Cys Arg Ala Leu
1               5                   10                  15

Gly Ser Gly Met Ala Val Asp Cys Ser Thr Leu Thr Ser Lys
            20                  25                  30
```

<210> SEQ ID NO 108
<211> LENGTH: 33
<212> TYPE: PRT
<213> ORGANISM: homo sapiens

<400> SEQUENCE: 108

```
Cys Ala Ala Val His Tyr Glu Gln Pro Thr Ile Gln Ile Glu Leu Arg
1               5                   10                  15

Cys Ala Ala Val His Tyr Glu Gln Pro Thr Ile Gln Ile Glu Leu Arg
            20                  25                  30

Cys
```

<210> SEQ ID NO 109
<211> LENGTH: 30

```
<212> TYPE: PRT
<213> ORGANISM: homo sapiens

<400> SEQUENCE: 109

Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30

<210> SEQ ID NO 110
<211> LENGTH: 33
<212> TYPE: PRT
<213> ORGANISM: homo sapiens

<400> SEQUENCE: 110

Cys Val His Tyr Glu Gln Pro Thr Ile Gln Ile Glu Leu Arg Gln Asn
1               5                   10                  15

Cys Val His Tyr Glu Gln Pro Thr Ile Gln Ile Glu Leu Arg Gln Asn
            20                  25                  30

Cys

<210> SEQ ID NO 111
<211> LENGTH: 32
<212> TYPE: PRT
<213> ORGANISM: homo sapiens

<400> SEQUENCE: 111

His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
            20                  25                  30

<210> SEQ ID NO 112
<211> LENGTH: 30
<212> TYPE: PRT
<213> ORGANISM: homo sapiens

<400> SEQUENCE: 112

Arg Leu Phe Arg Glu Arg Tyr Arg Leu His Pro Lys Phe Val Ala Ala
1               5                   10                  15

Val His Tyr Glu Gln Pro Thr Ile Gln Ile Glu Leu Arg Gln
            20                  25                  30

<210> SEQ ID NO 113
<211> LENGTH: 15
<212> TYPE: PRT
<213> ORGANISM: homo sapiens

<400> SEQUENCE: 113

Ala Val His Tyr Glu Gln Pro Thr Ile Gln Ile Glu Leu Arg Gln
1               5                   10                  15

<210> SEQ ID NO 114
<211> LENGTH: 33
<212> TYPE: PRT
<213> ORGANISM: homo sapiens

<400> SEQUENCE: 114

Cys Ala Gly Ala Phe Asn His Ser Asp Leu Asp Ala Glu Leu Arg Arg
1               5                   10                  15

Cys His His Ile Leu Ile Asp Leu Arg His Arg Pro Thr Ala Gly Ala
            20                  25                  30
```

Cys

<210> SEQ ID NO 115
<211> LENGTH: 33
<212> TYPE: PRT
<213> ORGANISM: homo sapiens

<400> SEQUENCE: 115

Cys Pro Lys Phe Val Ala Ala Val His Tyr Glu Gln Pro Thr Ile Gln
1               5                   10                  15

Cys Gly Leu Asp Leu Arg Val Arg Gly Glu Pro Leu Gln Val Glu Arg
                20                  25                  30

Cys

<210> SEQ ID NO 116
<211> LENGTH: 23
<212> TYPE: PRT
<213> ORGANISM: homo sapiens

<400> SEQUENCE: 116

Cys His Ser Asp Leu Asp Ala Glu Leu Arg Arg Leu Phe Arg Glu Arg
1               5                   10                  15

Cys Gly Leu Asp Leu Arg Val
                20

<210> SEQ ID NO 117
<211> LENGTH: 15
<212> TYPE: PRT
<213> ORGANISM: homo sapiens

<400> SEQUENCE: 117

Phe Gln Gly Arg Gly Gly Leu Asp Leu Arg Val Arg Gly Glu Pro
1               5                   10                  15

<210> SEQ ID NO 118
<211> LENGTH: 33
<212> TYPE: PRT
<213> ORGANISM: homo sapiens

<400> SEQUENCE: 118

Cys Val His Tyr Glu Gln Pro Thr Ile Gln Ile Glu Leu Arg Gln Asn
1               5                   10                  15

Cys Asp Leu Asp Ala Glu Leu Arg Arg Leu Phe Arg Glu Arg Tyr Arg
                20                  25                  30

Cys

<210> SEQ ID NO 119
<211> LENGTH: 23
<212> TYPE: PRT
<213> ORGANISM: homo sapiens

<400> SEQUENCE: 119

Cys His Ser Asp Leu Asp Ala Glu Leu Arg Arg Leu Phe Arg Glu Arg
1               5                   10                  15

Cys Arg Gly Glu Pro Leu Gln
                20

<210> SEQ ID NO 120
<211> LENGTH: 33
<212> TYPE: PRT
<213> ORGANISM: homo sapiens

```
<400> SEQUENCE: 120

Cys Thr Ile Gln Ile Glu Leu Arg Gln Asn Thr Ser Gln Lys Ala Ala
1               5                   10                  15

Cys Val His Tyr Glu Gln Pro Thr Ile Gln Ile Glu Leu Arg Gln Asn
                20                  25                  30

Cys

<210> SEQ ID NO 121
<211> LENGTH: 33
<212> TYPE: PRT
<213> ORGANISM: homo sapiens

<400> SEQUENCE: 121

Cys Val His Tyr Glu Gln Pro Thr Ile Gln Ile Glu Leu Arg Gln Asn
1               5                   10                  15

Cys His Ser Asp Leu Asp Ala Glu Leu Arg Arg Leu Phe Arg Glu Arg
                20                  25                  30

Cys

<210> SEQ ID NO 122
<211> LENGTH: 33
<212> TYPE: PRT
<213> ORGANISM: homo sapiens

<400> SEQUENCE: 122

Cys His His Ile Leu Ile Asp Leu Arg His Arg Pro Thr Ala Gly Ala
1               5                   10                  15

Cys His Ser Asp Leu Asp Ala Glu Leu Arg Arg Leu Phe Arg Glu Arg
                20                  25                  30

Cys

<210> SEQ ID NO 123
<211> LENGTH: 33
<212> TYPE: PRT
<213> ORGANISM: homo sapiens

<400> SEQUENCE: 123

Cys His His Ile Leu Ile Asp Leu Arg His Arg Pro Thr Ala Gly Ala
1               5                   10                  15

Cys Val His Tyr Glu Gln Pro Thr Ile Gln Ile Glu Leu Arg Gln Asn
                20                  25                  30

Cys

<210> SEQ ID NO 124
<211> LENGTH: 33
<212> TYPE: PRT
<213> ORGANISM: homo sapiens

<400> SEQUENCE: 124

Cys His His Ile Leu Ile Asp Leu Arg His Arg Pro Thr Ala Gly Ala
1               5                   10                  15

Cys Gly Leu Asp Leu Arg Val Arg Gly Glu Pro Leu Gln Val Glu Arg
                20                  25                  30

Cys

<210> SEQ ID NO 125
<211> LENGTH: 33
<212> TYPE: PRT
```

```
<213> ORGANISM: homo sapiens

<400> SEQUENCE: 125

Cys Asp Ala Glu Leu Arg Arg Leu Phe Arg Glu Arg Tyr Arg Leu His
1               5                   10                  15
Cys Asp Glu Leu Val Arg Thr His His Ile Leu Ile Asp Leu Arg His
            20                  25                  30
Cys

<210> SEQ ID NO 126
<211> LENGTH: 17
<212> TYPE: PRT
<213> ORGANISM: homo sapiens

<400> SEQUENCE: 126

Cys Val His Tyr Glu Gln Pro Thr Ile Gln Ile Glu Leu Arg Gln Asn
1               5                   10                  15
Cys

<210> SEQ ID NO 127
<211> LENGTH: 33
<212> TYPE: PRT
<213> ORGANISM: homo sapiens

<400> SEQUENCE: 127

Cys Ala Phe Asn His Ser Asp Leu Asp Ala Glu Leu Arg Arg Leu Phe
1               5                   10                  15
Cys Val His Tyr Glu Gln Pro Thr Ile Gln Ile Glu Leu Arg Gln Asn
            20                  25                  30
Cys

<210> SEQ ID NO 128
<211> LENGTH: 33
<212> TYPE: PRT
<213> ORGANISM: homo sapiens

<400> SEQUENCE: 128

Cys Val His Tyr Glu Gln Pro Thr Ile Gln Ile Glu Leu Arg Gln Asn
1               5                   10                  15
Cys His His Ile Leu Ile Asp Leu Arg His Arg Pro Thr Ala Gly Ala
            20                  25                  30
Cys

<210> SEQ ID NO 129
<211> LENGTH: 33
<212> TYPE: PRT
<213> ORGANISM: homo sapiens

<400> SEQUENCE: 129

Cys Asp Leu Asp Ala Glu Leu Arg Arg Leu Phe Arg Glu Arg Tyr Arg
1               5                   10                  15
Cys Asp Glu Leu Val Arg Thr His His Ile Leu Ile Asp Leu Arg His
            20                  25                  30
Cys

<210> SEQ ID NO 130
<211> LENGTH: 32
<212> TYPE: PRT
<213> ORGANISM: homo sapiens
```

-continued

```
<400> SEQUENCE: 130

Val His Tyr Glu Gln Pro Thr Ile Gln Ile Glu Leu Arg Gln Asn Cys
1               5                   10                  15

Gly Leu Asp Leu Arg Val Arg Gly Glu Pro Leu Gln Val Glu Arg Cys
            20                  25                  30

<210> SEQ ID NO 131
<211> LENGTH: 33
<212> TYPE: PRT
<213> ORGANISM: homo sapiens

<400> SEQUENCE: 131

Cys Asp Glu Leu Val Arg Thr His His Ile Leu Ile Asp Leu Arg His
1               5                   10                  15

Cys Asp Leu Asp Ala Glu Leu Arg Arg Leu Phe Arg Glu Arg Tyr Arg
            20                  25                  30

Cys

<210> SEQ ID NO 132
<211> LENGTH: 32
<212> TYPE: PRT
<213> ORGANISM: homo sapiens

<400> SEQUENCE: 132

Ala Val His Tyr Glu Gln Pro Thr Ile Gln Ile Glu Leu Arg Gln Cys
1               5                   10                  15

Ala Val His Tyr Glu Gln Pro Thr Ile Gln Ile Glu Leu Arg Gln Cys
            20                  25                  30

<210> SEQ ID NO 133
<211> LENGTH: 33
<212> TYPE: PRT
<213> ORGANISM: homo sapiens

<400> SEQUENCE: 133

Cys His Ser Asp Leu Asp Ala Glu Leu Arg Arg Leu Phe Arg Glu Arg
1               5                   10                  15

Cys Asp Glu Leu Val Arg Thr His His Ile Leu Ile Asp Leu Arg His
            20                  25                  30

Cys

<210> SEQ ID NO 134
<211> LENGTH: 30
<212> TYPE: PRT
<213> ORGANISM: homo sapiens

<400> SEQUENCE: 134

Thr Asn Lys Met Thr Val Cys Ser Pro Asp Gly Pro Gly Gly Arg Cys
1               5                   10                  15

Gln Cys Arg Ala Leu Gly Ser Gly Met Ala Val Asp Cys Ser
            20                  25                  30

<210> SEQ ID NO 135
<211> LENGTH: 30
<212> TYPE: PRT
<213> ORGANISM: homo sapiens

<400> SEQUENCE: 135

Asn Lys Met Thr Val Cys Ser Pro Asp Gly Pro Gly Gly Arg Cys Gln
1               5                   10                  15
```

Cys Arg Ala Leu Gly Ser Gly Met Ala Val Asp Cys Ser Thr
            20                  25                  30

<210> SEQ ID NO 136
<211> LENGTH: 30
<212> TYPE: PRT
<213> ORGANISM: homo sapiens

<400> SEQUENCE: 136

Lys Met Thr Val Cys Ser Pro Asp Gly Pro Gly Gly Arg Cys Gln Cys
1               5                   10                  15

Arg Ala Leu Gly Ser Gly Met Ala Val Asp Cys Ser Thr Leu
            20                  25                  30

<210> SEQ ID NO 137
<211> LENGTH: 30
<212> TYPE: PRT
<213> ORGANISM: homo sapiens

<400> SEQUENCE: 137

Met Thr Val Cys Ser Pro Asp Gly Pro Gly Gly Arg Cys Gln Cys Arg
1               5                   10                  15

Ala Leu Gly Ser Gly Met Ala Val Asp Cys Ser Thr Leu Thr
            20                  25                  30

<210> SEQ ID NO 138
<211> LENGTH: 30
<212> TYPE: PRT
<213> ORGANISM: homo sapiens

<400> SEQUENCE: 138

Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30

<210> SEQ ID NO 139
<211> LENGTH: 30
<212> TYPE: PRT
<213> ORGANISM: homo sapiens

<400> SEQUENCE: 139

Thr Val Cys Ser Pro Asp Gly Pro Gly Gly Arg Cys Gln Cys Arg Ala
1               5                   10                  15

Leu Gly Ser Gly Met Ala Val Asp Cys Ser Thr Leu Thr Ser
            20                  25                  30

<210> SEQ ID NO 140
<211> LENGTH: 30
<212> TYPE: PRT
<213> ORGANISM: homo sapiens

<400> SEQUENCE: 140

Thr Cys Pro Thr Asn Lys Met Thr Val Cys Ser Pro Asp Gly Pro Gly
1               5                   10                  15

Gly Arg Cys Gln Cys Arg Ala Leu Gly Ser Gly Met Ala Val
            20                  25                  30

<210> SEQ ID NO 141
<211> LENGTH: 30
<212> TYPE: PRT
<213> ORGANISM: homo sapiens

```
<400> SEQUENCE: 141

Pro Thr Asn Lys Met Thr Val Cys Ser Pro Asp Gly Pro Gly Arg
1               5                   10                  15

Cys Gln Cys Arg Ala Leu Gly Ser Gly Met Ala Val Asp Cys
            20                  25                  30

<210> SEQ ID NO 142
<211> LENGTH: 30
<212> TYPE: PRT
<213> ORGANISM: homo sapiens

<400> SEQUENCE: 142

Val Cys Ser Pro Asp Gly Pro Gly Gly Arg Cys Gln Cys Arg Ala Leu
1               5                   10                  15

Gly Ser Gly Met Ala Val Asp Cys Ser Thr Leu Thr Ser Lys
            20                  25                  30

<210> SEQ ID NO 143
<211> LENGTH: 30
<212> TYPE: PRT
<213> ORGANISM: homo sapiens

<400> SEQUENCE: 143

Cys Ser Pro Asp Gly Pro Gly Gly Arg Cys Gln Cys Arg Ala Leu Gly
1               5                   10                  15

Ser Gly Met Ala Val Asp Cys Ser Thr Leu Thr Ser Lys Cys
            20                  25                  30

<210> SEQ ID NO 144
<211> LENGTH: 30
<212> TYPE: PRT
<213> ORGANISM: homo sapiens

<400> SEQUENCE: 144

Cys Thr Cys Pro Thr Asn Lys Met Thr Val Cys Ser Pro Asp Gly Pro
1               5                   10                  15

Gly Gly Arg Cys Gln Cys Arg Ala Leu Gly Ser Gly Met Ala
            20                  25                  30

<210> SEQ ID NO 145
<211> LENGTH: 30
<212> TYPE: PRT
<213> ORGANISM: homo sapiens

<400> SEQUENCE: 145

Asn Cys Thr Cys Pro Thr Asn Lys Met Thr Val Cys Ser Pro Asp Gly
1               5                   10                  15

Pro Gly Gly Arg Cys Gln Cys Arg Ala Leu Gly Ser Gly Met
            20                  25                  30

<210> SEQ ID NO 146
<211> LENGTH: 30
<212> TYPE: PRT
<213> ORGANISM: homo sapiens

<400> SEQUENCE: 146

Asp Asn Cys Thr Cys Pro Thr Asn Lys Met Thr Val Cys Ser Pro Asp
1               5                   10                  15

Gly Pro Gly Gly Arg Cys Gln Cys Arg Ala Leu Gly Ser Gly
            20                  25                  30
```

```
<210> SEQ ID NO 147
<211> LENGTH: 33
<212> TYPE: PRT
<213> ORGANISM: homo sapiens

<400> SEQUENCE: 147

Cys Thr Val Ala Ser Pro Asp Gly Pro Gly Gly Arg Ala Gln Ala Arg
1               5                   10                  15

Cys Leu Gly Ser Gly Met Ala Val Asp Ala Ser Thr Leu Thr Ser Lys
            20                  25                  30

Cys

<210> SEQ ID NO 148
<211> LENGTH: 30
<212> TYPE: PRT
<213> ORGANISM: homo sapiens

<400> SEQUENCE: 148

Gln Asp Asn Cys Thr Cys Pro Thr Asn Lys Met Thr Val Cys Ser Pro
1               5                   10                  15

Asp Gly Pro Gly Gly Arg Cys Gln Cys Arg Ala Leu Gly Ser
            20                  25                  30

<210> SEQ ID NO 149
<211> LENGTH: 30
<212> TYPE: PRT
<213> ORGANISM: homo sapiens

<400> SEQUENCE: 149

Ser Pro Asp Gly Pro Gly Gly Arg Cys Gln Cys Arg Ala Leu Gly Ser
1               5                   10                  15

Gly Met Ala Val Asp Cys Ser Thr Leu Thr Ser Lys Cys Leu
            20                  25                  30

<210> SEQ ID NO 150
<211> LENGTH: 33
<212> TYPE: PRT
<213> ORGANISM: homo sapiens

<400> SEQUENCE: 150

Cys Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Ala Ser Thr
            20                  25                  30

Cys

<210> SEQ ID NO 151
<211> LENGTH: 15
<212> TYPE: PRT
<213> ORGANISM: homo sapiens

<400> SEQUENCE: 151

Thr Val Cys Ser Pro Asp Gly Pro Gly Gly Arg Cys Gln Cys Arg
1               5                   10                  15

<210> SEQ ID NO 152
<211> LENGTH: 33
<212> TYPE: PRT
<213> ORGANISM: homo sapiens

<400> SEQUENCE: 152

Cys Ala Pro Lys Asn Ala Arg Thr Leu Val Arg Pro Ser Glu His Ala
```

-continued

```
                1               5                  10                  15
Cys Ala Arg Thr Leu Val Arg Pro Ser Glu His Ala Leu Val Asp Asn
                20                  25                  30
Cys

<210> SEQ ID NO 153
<211> LENGTH: 32
<212> TYPE: PRT
<213> ORGANISM: homo sapiens

<400> SEQUENCE: 153

His Ser Asp Leu Asp Ala Glu Leu Arg Arg Leu Phe Arg Glu Arg Cys
1               5                  10                  15

His Ser Asp Leu Asp Ala Glu Leu Arg Arg Leu Phe Arg Glu Arg Cys
                20                  25                  30

<210> SEQ ID NO 154
<211> LENGTH: 30
<212> TYPE: PRT
<213> ORGANISM: homo sapiens

<400> SEQUENCE: 154

Thr Val Cys Ser Pro Asp Gly Pro Gly Gly Arg Cys Gln Cys Arg Ala
1               5                  10                  15

Leu Gly Ser Gly Met Ala Val Asp Cys Ser Thr Leu Thr Ser
                20                  25                  30

<210> SEQ ID NO 155
<211> LENGTH: 30
<212> TYPE: PRT
<213> ORGANISM: homo sapiens

<400> SEQUENCE: 155

Asn Lys Met Thr Val Cys Ser Pro Asp Gly Pro Gly Gly Arg Cys Gln
1               5                  10                  15

Cys Arg Ala Leu Gly Ser Gly Met Ala Val Asp Cys Ser Thr
                20                  25                  30

<210> SEQ ID NO 156
<211> LENGTH: 30
<212> TYPE: PRT
<213> ORGANISM: homo sapiens

<400> SEQUENCE: 156

Thr Asn Lys Met Thr Val Cys Ser Pro Asp Gly Pro Gly Gly Arg Cys
1               5                  10                  15

Gln Cys Arg Ala Leu Gly Ser Gly Met Ala Val Asp Cys Ser
                20                  25                  30

<210> SEQ ID NO 157
<211> LENGTH: 30
<212> TYPE: PRT
<213> ORGANISM: homo sapiens

<400> SEQUENCE: 157

Met Thr Val Cys Ser Pro Asp Gly Pro Gly Gly Arg Cys Gln Cys Arg
1               5                  10                  15

Ala Leu Gly Ser Gly Met Ala Val Asp Cys Ser Thr Leu Thr
                20                  25                  30

<210> SEQ ID NO 158
```

```
<211> LENGTH: 30
<212> TYPE: PRT
<213> ORGANISM: homo sapiens

<400> SEQUENCE: 158

Lys Met Thr Val Cys Ser Pro Asp Gly Pro Gly Gly Arg Cys Gln Cys
1               5                   10                  15

Arg Ala Leu Gly Ser Gly Met Ala Val Asp Cys Ser Thr Leu
            20                  25                  30

<210> SEQ ID NO 159
<211> LENGTH: 30
<212> TYPE: PRT
<213> ORGANISM: homo sapiens

<400> SEQUENCE: 159

Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30

<210> SEQ ID NO 160
<211> LENGTH: 30
<212> TYPE: PRT
<213> ORGANISM: homo sapiens

<400> SEQUENCE: 160

Pro Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Cys
            20                  25                  30

<210> SEQ ID NO 161
<211> LENGTH: 33
<212> TYPE: PRT
<213> ORGANISM: homo sapiens

<400> SEQUENCE: 161

Cys Ala Gly Ala Phe Asn His Ser Asp Leu Asp Ala Glu Leu Arg Arg
1               5                   10                  15

Cys His His Ile Leu Ile Asp Leu Arg His Arg Pro Thr Ala Gly Ala
            20                  25                  30

Cys

<210> SEQ ID NO 162
<211> LENGTH: 17
<212> TYPE: PRT
<213> ORGANISM: homo sapiens

<400> SEQUENCE: 162

Cys Thr His His Ile Leu Ile Asp Leu Arg His Arg Pro Thr Ala Gly
1               5                   10                  15

Cys

<210> SEQ ID NO 163
<211> LENGTH: 33
<212> TYPE: PRT
<213> ORGANISM: homo sapiens

<400> SEQUENCE: 163

Cys Val His Tyr Glu Gln Pro Thr Ile Gln Ile Glu Leu Arg Gln Asn
1               5                   10                  15
```

```
Cys His His Ile Leu Ile Asp Leu Arg His Arg Pro Thr Ala Gly Ala
                20                  25                  30

Cys

<210> SEQ ID NO 164
<211> LENGTH: 33
<212> TYPE: PRT
<213> ORGANISM: homo sapiens

<400> SEQUENCE: 164

Cys His His Ile Leu Ile Asp Leu Arg His Arg Pro Thr Ala Gly Ala
1               5                   10                  15

Cys His Ser Asp Leu Asp Ala Glu Leu Arg Arg Leu Phe Arg Glu Arg
                20                  25                  30

Cys

<210> SEQ ID NO 165
<211> LENGTH: 32
<212> TYPE: PRT
<213> ORGANISM: homo sapiens

<400> SEQUENCE: 165

His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
                20                  25                  30

<210> SEQ ID NO 166
<211> LENGTH: 33
<212> TYPE: PRT
<213> ORGANISM: homo sapiens

<400> SEQUENCE: 166

Cys Asp Ala Glu Leu Arg Arg Leu Phe Arg Glu Arg Tyr Arg Leu His
1               5                   10                  15

Cys His Ser Asp Leu Asp Ala Glu Leu Arg Arg Leu Phe Arg Glu Arg
                20                  25                  30

Cys

<210> SEQ ID NO 167
<211> LENGTH: 19
<212> TYPE: PRT
<213> ORGANISM: homo sapiens

<400> SEQUENCE: 167

Cys Asp Ala Glu Leu Arg Arg Leu Phe Arg Glu Arg Tyr Arg Leu His
1               5                   10                  15

Cys Pro Lys

<210> SEQ ID NO 168
<211> LENGTH: 30
<212> TYPE: PRT
<213> ORGANISM: homo sapiens

<400> SEQUENCE: 168

Val Cys Ser Pro Asp Gly Pro Gly Gly Arg Cys Gln Cys Arg Ala Leu
1               5                   10                  15

Gly Ser Gly Met Ala Val Asp Cys Ser Thr Leu Thr Ser Lys
                20                  25                  30
```

```
<210> SEQ ID NO 169
<211> LENGTH: 30
<212> TYPE: PRT
<213> ORGANISM: homo sapiens

<400> SEQUENCE: 169

Asp Leu Ser Leu Arg Cys Asp Glu Leu Val Arg Thr His His Ile Leu
1               5                   10                  15

Ile Asp Leu Arg His Arg Pro Thr Ala Gly Ala Phe Asn His
            20                  25                  30

<210> SEQ ID NO 170
<211> LENGTH: 33
<212> TYPE: PRT
<213> ORGANISM: homo sapiens

<400> SEQUENCE: 170

Cys Asp Glu Leu Val Arg Thr His His Ile Leu Ile Asp Leu Arg His
1               5                   10                  15

Cys Asp Leu Asp Ala Glu Leu Arg Arg Leu Phe Arg Glu Arg Tyr Arg
            20                  25                  30

Cys

<210> SEQ ID NO 171
<211> LENGTH: 17
<212> TYPE: PRT
<213> ORGANISM: homo sapiens

<400> SEQUENCE: 171

Cys Phe Gln Gly Arg Gly Gly Leu Asp Leu Arg Val Arg Gly Glu Pro
1               5                   10                  15

Cys

<210> SEQ ID NO 172
<211> LENGTH: 33
<212> TYPE: PRT
<213> ORGANISM: homo sapiens

<400> SEQUENCE: 172

Cys Asp Ala Glu Leu Arg Arg Leu Phe Arg Glu Arg Tyr Arg Leu His
1               5                   10                  15

Cys Asp Glu Leu Val Arg Thr His His Ile Leu Ile Asp Leu Arg His
            20                  25                  30

Cys

<210> SEQ ID NO 173
<211> LENGTH: 33
<212> TYPE: PRT
<213> ORGANISM: homo sapiens

<400> SEQUENCE: 173

Cys Gly Leu Asp Leu Arg Val Arg Gly Glu Pro Leu Gln Val Glu Arg
1               5                   10                  15

Cys His His Ile Leu Ile Asp Leu Arg His Arg Pro Thr Ala Gly Ala
            20                  25                  30

Cys

<210> SEQ ID NO 174
<211> LENGTH: 33
<212> TYPE: PRT
```

<213> ORGANISM: homo sapiens

<400> SEQUENCE: 174

Cys His Ser Asp Leu Asp Ala Glu Leu Arg Leu Phe Arg Glu Arg
1               5                   10                  15
Cys His Ser Asp Leu Asp Ala Glu Leu Arg Arg Leu Phe Arg Glu Arg
            20                  25                  30
Cys

<210> SEQ ID NO 175
<211> LENGTH: 33
<212> TYPE: PRT
<213> ORGANISM: homo sapiens

<400> SEQUENCE: 175

Cys Asp Glu Leu Val Arg Thr His His Ile Leu Ile Asp Leu Arg His
1               5                   10                  15
Cys His His Ile Leu Ile Asp Leu Arg His Arg Pro Thr Ala Gly Ala
            20                  25                  30
Cys

<210> SEQ ID NO 176
<211> LENGTH: 33
<212> TYPE: PRT
<213> ORGANISM: homo sapiens

<400> SEQUENCE: 176

Cys Asp Ala Glu Leu Arg Arg Leu Phe Arg Glu Arg Tyr Arg Leu His
1               5                   10                  15
Cys Asp Glu Leu Val Arg Thr His His Ile Leu Ile Asp Leu Arg His
            20                  25                  30
Cys

<210> SEQ ID NO 177
<211> LENGTH: 33
<212> TYPE: PRT
<213> ORGANISM: homo sapiens

<400> SEQUENCE: 177

Cys His His Ile Leu Ile Asp Leu Arg His Arg Pro Thr Ala Gly Ala
1               5                   10                  15
Cys Arg Gly Glu Pro Leu Gln Val Glu Arg Thr Leu Ile Tyr Tyr Leu
            20                  25                  30
Cys

<210> SEQ ID NO 178
<211> LENGTH: 15
<212> TYPE: PRT
<213> ORGANISM: homo sapiens

<400> SEQUENCE: 178

Cys Ser Pro Asp Gly Pro Gly Gly Arg Cys Gln Cys Arg Ala Leu
1               5                   10                  15

<210> SEQ ID NO 179
<211> LENGTH: 33
<212> TYPE: PRT
<213> ORGANISM: homo sapiens

<400> SEQUENCE: 179

Cys Thr Val Ala Ser Pro Asp Gly Pro Gly Arg Ala Gln Ala Arg
1               5                   10                  15

Cys Val His Tyr Glu Gln Pro Thr Ile Gln Ile Glu Leu Arg Gln Asn
                20                  25                  30

Cys

<210> SEQ ID NO 180
<211> LENGTH: 33
<212> TYPE: PRT
<213> ORGANISM: homo sapiens

<400> SEQUENCE: 180

Cys His His Ile Leu Ile Asp Leu Arg His Arg Pro Thr Ala Gly Ala
1               5                   10                  15

Cys Val His Tyr Glu Gln Pro Thr Ile Gln Ile Glu Leu Arg Gln Asn
                20                  25                  30

Cys

<210> SEQ ID NO 181
<211> LENGTH: 30
<212> TYPE: PRT
<213> ORGANISM: homo sapiens

<400> SEQUENCE: 181

Leu Ser Leu Arg Cys Asp Glu Leu Val Arg Thr His His Ile Leu Ile
1               5                   10                  15

Asp Leu Arg His Arg Pro Thr Ala Gly Ala Phe Asn His Ser
                20                  25                  30

<210> SEQ ID NO 182
<211> LENGTH: 33
<212> TYPE: PRT
<213> ORGANISM: homo sapiens

<400> SEQUENCE: 182

Cys Asp Glu Leu Val Arg Thr His His Ile Leu Ile Asp Leu Arg His
1               5                   10                  15

Cys His Ser Asp Leu Asp Ala Glu Leu Arg Arg Leu Phe Arg Glu Arg
                20                  25                  30

Cys

<210> SEQ ID NO 183
<211> LENGTH: 33
<212> TYPE: PRT
<213> ORGANISM: homo sapiens

<400> SEQUENCE: 183

Cys Tyr Asp Pro Asp Ala Asp Pro Glu Gly Arg Phe Lys Ala Arg Gln
1               5                   10                  15

Cys Ala Asp Pro Glu Gly Arg Phe Lys Ala Arg Gln Ala Asn Gln Thr
                20                  25                  30

Cys

<210> SEQ ID NO 184
<211> LENGTH: 15
<212> TYPE: PRT
<213> ORGANISM: homo sapiens

<400> SEQUENCE: 184

Pro Asp Cys Asp Pro Glu Gly Arg Phe Lys Ala Arg Gln Cys Asn

```
1               5                   10                  15

<210> SEQ ID NO 185
<211> LENGTH: 31
<212> TYPE: PRT
<213> ORGANISM: homo sapiens

<400> SEQUENCE: 185

Cys Ala Asp Pro Glu Gly Arg Phe Lys Ala Arg Gln Ala Asn Cys Pro
1               5                   10                  15

Asp Ala Asp Pro Glu Gly Arg Phe Lys Ala Arg Gln Ala Asn Cys
            20                  25                  30

<210> SEQ ID NO 186
<211> LENGTH: 33
<212> TYPE: PRT
<213> ORGANISM: homo sapiens

<400> SEQUENCE: 186

Cys Pro Asp Ala Asp Pro Glu Gly Arg Phe Lys Ala Arg Gln Ala Asn
1               5                   10                  15

Cys Pro Asp Ala Asp Pro Glu Gly Arg Phe Lys Ala Arg Gln Ala Asn
            20                  25                  30

Cys

<210> SEQ ID NO 187
<211> LENGTH: 15
<212> TYPE: PRT
<213> ORGANISM: homo sapiens

<400> SEQUENCE: 187

Val Cys Ser Pro Asp Gly Pro Gly Gly Arg Cys Gln Cys Arg Ala
1               5                   10                  15

<210> SEQ ID NO 188
<211> LENGTH: 33
<212> TYPE: PRT
<213> ORGANISM: homo sapiens

<400> SEQUENCE: 188

Cys Tyr Asp Pro Asp Ala Asp Pro Glu Gly Arg Phe Lys Ala Arg Gln
1               5                   10                  15

Cys Pro Asp Ala Asp Pro Glu Gly Arg Phe Lys Ala Arg Gln Ala Asn
            20                  25                  30

Cys

<210> SEQ ID NO 189
<211> LENGTH: 33
<212> TYPE: PRT
<213> ORGANISM: homo sapiens

<400> SEQUENCE: 189

Cys Ala Asp Pro Glu Gly Arg Phe Lys Ala Arg Gln Ala Asn Gln Thr
1               5                   10                  15

Cys Tyr Asp Pro Asp Ala Asp Pro Glu Gly Arg Phe Lys Ala Arg Gln
            20                  25                  30

Cys

<210> SEQ ID NO 190
<211> LENGTH: 15
<212> TYPE: PRT
```

<213> ORGANISM: homo sapiens

<400> SEQUENCE: 190

Asp Cys Asp Pro Glu Gly Arg Phe Lys Ala Arg Gln Cys Asn Gln
1               5                   10                  15

<210> SEQ ID NO 191
<211> LENGTH: 33
<212> TYPE: PRT
<213> ORGANISM: homo sapiens

<400> SEQUENCE: 191

Cys Thr Val Ala Ser Pro Asp Gly Pro Gly Gly Arg Ala Gln Ala Arg
1               5                   10                  15

Cys His Ser Asp Leu Asp Ala Glu Leu Arg Arg Leu Phe Arg Glu Arg
                20                  25                  30

Cys

<210> SEQ ID NO 192
<211> LENGTH: 33
<212> TYPE: PRT
<213> ORGANISM: homo sapiens

<400> SEQUENCE: 192

Cys Asp Ala Asp Pro Glu Gly Arg Phe Lys Ala Arg Gln Ala Asn Gln
1               5                   10                  15

Cys Asp Ala Asp Pro Glu Gly Arg Phe Lys Ala Arg Gln Ala Asn Gln
                20                  25                  30

Cys

<210> SEQ ID NO 193
<211> LENGTH: 33
<212> TYPE: PRT
<213> ORGANISM: homo sapiens

<400> SEQUENCE: 193

Cys Gly Arg Phe Lys Ala Arg Gln Ala Asn Gln Thr Ser Val Ala Trp
1               5                   10                  15

Cys Ala Arg Thr Leu Val Arg Pro Ser Glu His Ala Leu Val Asp Asn
                20                  25                  30

Cys

<210> SEQ ID NO 194
<211> LENGTH: 33
<212> TYPE: PRT
<213> ORGANISM: homo sapiens

<400> SEQUENCE: 194

Cys Ala Asp Pro Glu Gly Arg Phe Lys Ala Arg Gln Ala Asn Gln Thr
1               5                   10                  15

Cys Pro Asp Ala Asp Pro Glu Gly Arg Phe Lys Ala Arg Gln Ala Asn
                20                  25                  30

Cys

<210> SEQ ID NO 195
<211> LENGTH: 33
<212> TYPE: PRT
<213> ORGANISM: homo sapiens

<400> SEQUENCE: 195

```
Cys Pro Asp Ala Asp Pro Glu Gly Arg Phe Lys Ala Arg Gln Ala Asn
1               5                   10                  15

Cys Pro Asp Ala Asp Pro Glu Gly Arg Phe Lys Ala Arg Gln Ala Asn
            20                  25                  30

Cys

<210> SEQ ID NO 196
<211> LENGTH: 15
<212> TYPE: PRT
<213> ORGANISM: homo sapiens

<400> SEQUENCE: 196

Cys Ser Pro Asp Gly Pro Gly Gly Arg Cys Gln Cys Arg Ala Leu
1               5                   10                  15

<210> SEQ ID NO 197
<211> LENGTH: 33
<212> TYPE: PRT
<213> ORGANISM: homo sapiens

<400> SEQUENCE: 197

Cys Glu Gly Arg Phe Lys Ala Arg Gln Ala Asn Gln Thr Ser Val Ala
1               5                   10                  15

Cys Glu Gly Arg Phe Lys Ala Arg Gln Ala Asn Gln Thr Ser Val Ala
            20                  25                  30

Cys

<210> SEQ ID NO 198
<211> LENGTH: 33
<212> TYPE: PRT
<213> ORGANISM: homo sapiens

<400> SEQUENCE: 198

Cys Thr Val Ala Ser Pro Asp Gly Pro Gly Gly Arg Ala Gln Ala Arg
1               5                   10                  15

Cys Pro Asp Ala Asp Pro Glu Gly Arg Phe Lys Ala Arg Gln Ala Asn
            20                  25                  30

Cys

<210> SEQ ID NO 199
<211> LENGTH: 33
<212> TYPE: PRT
<213> ORGANISM: homo sapiens

<400> SEQUENCE: 199

Cys Gly Leu Tyr Asp Pro Asp Ala Asp Pro Glu Gly Arg Phe Lys Ala
1               5                   10                  15

Cys Pro Asp Ala Asp Pro Glu Gly Arg Phe Lys Ala Arg Gln Ala Asn
            20                  25                  30

Cys

<210> SEQ ID NO 200
<211> LENGTH: 31
<212> TYPE: PRT
<213> ORGANISM: homo sapiens

<400> SEQUENCE: 200

Asp Pro Asp Cys Asp Pro Glu Gly Arg Phe Lys Ala Arg Gln Cys Asn
1               5                   10                  15

Cys Gln Thr Ser Val Cys Trp Cys Val Asn Ser Val Gly Val Arg
```

20                  25                  30

<210> SEQ ID NO 201
<211> LENGTH: 32
<212> TYPE: PRT
<213> ORGANISM: homo sapiens

<400> SEQUENCE: 201

Cys Pro Glu Gly Arg Phe Lys Ala Arg Gln Ala Asn Gln Thr Ser Val
1               5                   10                  15

Cys Asp Glu Leu Val Arg His His Ile Leu Ile Asp Leu Arg His Cys
                20                  25                  30

<210> SEQ ID NO 202
<211> LENGTH: 33
<212> TYPE: PRT
<213> ORGANISM: homo sapiens

<400> SEQUENCE: 202

Cys Pro Asp Gly Pro Gly Gly Arg Ala Gln Ala Arg Ala Leu Gly Ser
1               5                   10                  15

Cys His Ser Asp Leu Asp Ala Glu Leu Arg Arg Leu Phe Arg Glu Arg
                20                  25                  30

Cys

<210> SEQ ID NO 203
<211> LENGTH: 33
<212> TYPE: PRT
<213> ORGANISM: homo sapiens

<400> SEQUENCE: 203

Cys Thr Leu Val Arg Pro Ser Glu His Ala Leu Val Asp Asn Asp Gly
1               5                   10                  15

Cys Gly Arg Phe Lys Ala Arg Gln Ala Asn Gln Thr Ser Val Ala Trp
                20                  25                  30

Cys

<210> SEQ ID NO 204
<211> LENGTH: 33
<212> TYPE: PRT
<213> ORGANISM: homo sapiens

<400> SEQUENCE: 204

Cys Pro Asp Ala Asp Pro Glu Gly Arg Phe Lys Ala Arg Gln Ala Asn
1               5                   10                  15

Cys Tyr Asp Pro Asp Ala Asp Pro Glu Gly Arg Phe Lys Ala Arg Gln
                20                  25                  30

Cys

<210> SEQ ID NO 205
<211> LENGTH: 33
<212> TYPE: PRT
<213> ORGANISM: homo sapiens

<400> SEQUENCE: 205

Cys Gly Leu Tyr Asp Pro Asp Ala Asp Pro Glu Gly Arg Phe Lys Ala
1               5                   10                  15

Cys Pro Glu Gly Arg Phe Lys Ala Arg Gln Ala Asn Gln Thr Ser Val
                20                  25                  30

Cys

<210> SEQ ID NO 206
<211> LENGTH: 15
<212> TYPE: PRT
<213> ORGANISM: homo sapiens

<400> SEQUENCE: 206

Tyr Asp Pro Asp Cys Asp Pro Glu Gly Arg Phe Lys Ala Arg Gln
1               5                   10                  15

<210> SEQ ID NO 207
<211> LENGTH: 33
<212> TYPE: PRT
<213> ORGANISM: homo sapiens

<400> SEQUENCE: 207

Cys Pro Asp Ala Asp Pro Glu Gly Arg Phe Lys Ala Arg Gln Ala Asn
1               5                   10                  15

Cys Ala Asp Pro Glu Gly Arg Phe Lys Ala Arg Gln Ala Asn Gln Thr
            20                  25                  30

Cys

<210> SEQ ID NO 208
<211> LENGTH: 15
<212> TYPE: PRT
<213> ORGANISM: homo sapiens

<400> SEQUENCE: 208

Cys Asp Pro Glu Gly Arg Phe Lys Ala Arg Gln Cys Asn Gln Thr
1               5                   10                  15

<210> SEQ ID NO 209
<211> LENGTH: 33
<212> TYPE: PRT
<213> ORGANISM: homo sapiens

<400> SEQUENCE: 209

Cys Val Asn Ser Val Gly Val Arg Arg Thr Asp Lys Gly Asp Leu Ser
1               5                   10                  15

Cys Tyr Asp Pro Asp Ala Asp Pro Glu Gly Arg Phe Lys Ala Arg Gln
            20                  25                  30

Cys

<210> SEQ ID NO 210
<211> LENGTH: 33
<212> TYPE: PRT
<213> ORGANISM: homo sapiens

<400> SEQUENCE: 210

Cys Ser Val Gly Val Arg Arg Thr Asp Lys Gly Asp Leu Ser Leu Arg
1               5                   10                  15

Cys Tyr Asp Pro Asp Ala Asp Pro Glu Gly Arg Phe Lys Ala Arg Gln
            20                  25                  30

Cys

<210> SEQ ID NO 211
<211> LENGTH: 32
<212> TYPE: PRT
<213> ORGANISM: homo sapiens

<400> SEQUENCE: 211

His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
            20                  25                  30

<210> SEQ ID NO 212
<211> LENGTH: 33
<212> TYPE: PRT
<213> ORGANISM: homo sapiens

<400> SEQUENCE: 212

Cys Asp Glu Leu Val Arg Thr His His Ile Leu Ile Asp Leu Arg His
1               5                   10                  15

Cys Asp Leu Asp Ala Glu Leu Arg Arg Leu Phe Arg Glu Arg Tyr Arg
            20                  25                  30

Cys

<210> SEQ ID NO 213
<211> LENGTH: 30
<212> TYPE: PRT
<213> ORGANISM: homo sapiens

<400> SEQUENCE: 213

Cys Val Asn Ser Val Gly Val Arg Arg Thr Asp Lys Gly Asp Leu Ser
1               5                   10                  15

Leu Arg Cys Asp Glu Leu Val Arg Thr His His Ile Leu Ile
            20                  25                  30

<210> SEQ ID NO 214
<211> LENGTH: 30
<212> TYPE: PRT
<213> ORGANISM: homo sapiens

<400> SEQUENCE: 214

Val Arg Arg Thr Asp Lys Gly Asp Leu Ser Leu Arg Cys Asp Glu Leu
1               5                   10                  15

Val Arg Thr His His Ile Leu Ile Asp Leu Arg His Arg Pro
            20                  25                  30

<210> SEQ ID NO 215
<211> LENGTH: 33
<212> TYPE: PRT
<213> ORGANISM: homo sapiens

<400> SEQUENCE: 215

Cys Val Glu Arg Thr Leu Ile Tyr Tyr Leu Asp Glu Ile Pro Pro Lys
1               5                   10                  15

Cys His His Ile Leu Ile Asp Leu Arg His Arg Pro Thr Ala Gly Ala
            20                  25                  30

Cys

<210> SEQ ID NO 216
<211> LENGTH: 33
<212> TYPE: PRT
<213> ORGANISM: homo sapiens

<400> SEQUENCE: 216

Cys His His Ile Leu Ile Asp Leu Arg His Arg Pro Thr Ala Gly Ala
1               5                   10                  15

Cys His Ser Asp Leu Asp Ala Glu Leu Arg Arg Leu Phe Arg Glu Arg
            20                  25                  30

Cys

<210> SEQ ID NO 217
<211> LENGTH: 33
<212> TYPE: PRT
<213> ORGANISM: homo sapiens

<400> SEQUENCE: 217

Cys Val Asn Ser Val Gly Val Arg Arg Thr Asp Lys Gly Asp Leu Ser
1               5                   10                  15

Cys Pro Asp Ala Asp Pro Glu Gly Arg Phe Lys Ala Arg Gln Ala Asn
            20                  25                  30

Cys

<210> SEQ ID NO 218
<211> LENGTH: 33
<212> TYPE: PRT
<213> ORGANISM: homo sapiens

<400> SEQUENCE: 218

Cys Val His Tyr Glu Gln Pro Thr Ile Gln Ile Glu Leu Arg Gln Asn
1               5                   10                  15

Cys His His Ile Leu Ile Asp Leu Arg His Arg Pro Thr Ala Gly Ala
            20                  25                  30

Cys

<210> SEQ ID NO 219
<211> LENGTH: 30
<212> TYPE: PRT
<213> ORGANISM: homo sapiens

<400> SEQUENCE: 219

Val Gly Val Arg Arg Thr Asp Lys Gly Asp Leu Ser Leu Arg Cys Asp
1               5                   10                  15

Glu Leu Val Arg Thr His His Ile Leu Ile Asp Leu Arg His
            20                  25                  30

<210> SEQ ID NO 220
<211> LENGTH: 33
<212> TYPE: PRT
<213> ORGANISM: homo sapiens

<400> SEQUENCE: 220

Cys Ala Gly Ala Phe Asn His Ser Asp Leu Ala Glu Leu Arg Arg
1               5                   10                  15

Cys His His Ile Leu Ile Asp Leu Arg His Arg Pro Thr Ala Gly Ala
            20                  25                  30

Cys

<210> SEQ ID NO 221
<211> LENGTH: 33
<212> TYPE: PRT
<213> ORGANISM: homo sapiens

<400> SEQUENCE: 221

Cys Ser Val Gly Val Arg Arg Thr Asp Lys Gly Asp Leu Ser Leu Arg
1               5                   10                  15

Cys Pro Asp Ala Asp Pro Glu Gly Arg Phe Lys Ala Arg Gln Ala Asn
            20                  25                  30

Cys

<210> SEQ ID NO 222
<211> LENGTH: 33
<212> TYPE: PRT
<213> ORGANISM: homo sapiens

<400> SEQUENCE: 222

Cys Val Arg Pro Ser Glu His Ala Leu Val Asp Asn Asp Gly Leu Tyr
1               5                   10                  15

Cys Ser Val Gly Val Arg Arg Thr Asp Lys Gly Asp Leu Ser Leu Arg
                20                  25                  30

Cys

<210> SEQ ID NO 223
<211> LENGTH: 33
<212> TYPE: PRT
<213> ORGANISM: homo sapiens

<400> SEQUENCE: 223

Cys Asp Ala Glu Leu Arg Arg Leu Phe Arg Glu Arg Tyr Arg Leu His
1               5                   10                  15

Cys His Ser Asp Leu Asp Ala Glu Leu Arg Arg Leu Phe Arg Glu Arg
                20                  25                  30

Cys

<210> SEQ ID NO 224
<211> LENGTH: 33
<212> TYPE: PRT
<213> ORGANISM: homo sapiens

<400> SEQUENCE: 224

Cys Ser Val Gly Val Arg Arg Thr Asp Lys Gly Asp Leu Ser Leu Arg
1               5                   10                  15

Cys Asn Asp Gly Leu Tyr Asp Pro Asp Ala Asp Pro Glu Gly Arg Phe
                20                  25                  30

Cys

<210> SEQ ID NO 225
<211> LENGTH: 33
<212> TYPE: PRT
<213> ORGANISM: homo sapiens

<400> SEQUENCE: 225

Cys Val Asn Ser Val Gly Val Arg Arg Thr Asp Lys Gly Asp Leu Ser
1               5                   10                  15

Cys Gly Leu Tyr Asp Pro Asp Ala Asp Pro Glu Gly Arg Phe Lys Ala
                20                  25                  30

Cys

<210> SEQ ID NO 226
<211> LENGTH: 33
<212> TYPE: PRT
<213> ORGANISM: homo sapiens

<400> SEQUENCE: 226

Cys Asp Leu Asp Ala Glu Leu Arg Arg Leu Phe Arg Glu Arg Tyr Arg
1               5                   10                  15

Cys His Ser Asp Leu Asp Ala Glu Leu Arg Arg Leu Phe Arg Glu Arg
                20                  25                  30

Cys

```
<210> SEQ ID NO 227
<211> LENGTH: 33
<212> TYPE: PRT
<213> ORGANISM: homo sapiens

<400> SEQUENCE: 227
```

Cys Asp Glu Leu Val Arg Thr His His Ile Leu Ile Asp Leu Arg His
1               5                   10                  15

Cys His His Ile Leu Ile Asp Leu Arg His Arg Pro Thr Ala Gly Ala
            20                  25                  30

Cys

```
<210> SEQ ID NO 228
<211> LENGTH: 33
<212> TYPE: PRT
<213> ORGANISM: homo sapiens

<400> SEQUENCE: 228
```

Cys Ala Gly Ala Phe Asn His Ser Asp Leu Asp Ala Glu Leu Arg Arg
1               5                   10                  15

Cys Asp Leu Asp Ala Glu Leu Arg Arg Leu Phe Arg Glu Arg Tyr Arg
            20                  25                  30

Cys

```
<210> SEQ ID NO 229
<211> LENGTH: 33
<212> TYPE: PRT
<213> ORGANISM: homo sapiens

<400> SEQUENCE: 229
```

Cys Asp Ala Glu Leu Arg Arg Leu Phe Arg Glu Arg Tyr Arg Leu His
1               5                   10                  15

Cys Asp Glu Leu Val Arg Thr His His Ile Leu Ile Asp Leu Arg His
            20                  25                  30

Cys

```
<210> SEQ ID NO 230
<211> LENGTH: 33
<212> TYPE: PRT
<213> ORGANISM: homo sapiens

<400> SEQUENCE: 230
```

Cys Val His Tyr Glu Gln Pro Thr Ile Gln Ile Glu Leu Arg Gln Asn
1               5                   10                  15

Cys Asp Leu Asp Ala Glu Leu Arg Arg Leu Phe Arg Glu Arg Tyr Arg
            20                  25                  30

Cys

```
<210> SEQ ID NO 231
<211> LENGTH: 33
<212> TYPE: PRT
<213> ORGANISM: homo sapiens

<400> SEQUENCE: 231
```

Cys His His Ile Leu Ile Asp Leu Arg His Arg Pro Thr Ala Gly Ala
1               5                   10                  15

Cys Val His Tyr Glu Gln Pro Thr Ile Gln Ile Glu Leu Arg Gln Asn

```
                    20                  25                  30
Cys

<210> SEQ ID NO 232
<211> LENGTH: 33
<212> TYPE: PRT
<213> ORGANISM: homo sapiens

<400> SEQUENCE: 232

Cys Gly Val Arg Arg Thr Asp Lys Gly Asp Leu Ser Leu Arg Ala Asp
1               5                   10                  15

Cys Gly Val Arg Arg Thr Asp Lys Gly Asp Leu Ser Leu Arg Ala Asp
                20                  25                  30

Cys

<210> SEQ ID NO 233
<211> LENGTH: 33
<212> TYPE: PRT
<213> ORGANISM: homo sapiens

<400> SEQUENCE: 233

Cys Gly Leu Asp Leu Arg Val Arg Gly Glu Pro Leu Gln Val Glu Arg
1               5                   10                  15

Cys His His Ile Leu Ile Asp Leu Arg His Arg Pro Thr Ala Gly Ala
                20                  25                  30

Cys

<210> SEQ ID NO 234
<211> LENGTH: 33
<212> TYPE: PRT
<213> ORGANISM: homo sapiens

<400> SEQUENCE: 234

Cys Asp Leu Asp Ala Glu Leu Arg Arg Leu Phe Arg Glu Arg Tyr Arg
1               5                   10                  15

Cys Asp Glu Leu Val Arg Thr His His Ile Leu Ile Asp Leu Arg His
                20                  25                  30

Cys
```

ANTI-HUMAN TROP-2 ANTIBODY HAVING AN ANTITUMOR ACTIVITY IN VIVO

CROSS REFERENCE TO RELATED APPLICATIONS

The application is a Continuation of U.S. application Ser. No. 13/682,319, filed on Nov. 20, 2012, which claims priority under 35 U.S.C. § 119 to U.S. Provisional Patent Application No. 61/562,672, filed Nov. 22, 2011, the disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jan. 23, 2015, is named 086268-0136_SL.txt and is 130,893 bytes in size.

FIELD OF THE INVENTION

The present invention relates to an anti-human TROP-2 antibody having anti-tumor activity, and particularly, to an anti-human TROP-2 antibody having anti-tumor activity in vivo. In addition, the present invention relates to a hybridoma, which produces the aforementioned antibody, and a use of the aforementioned antibody.

BACKGROUND OF THE INVENTION

Human TROP-2 (Tacstd2, GA733-1 and EGP-1) (hereinafter also referred to as "hTROP-2") is a single transmembrane, type 1 cell membrane protein consisting of 323 amino acid residues (see SEQ ID NO: 2), and this protein has been known to be overexpressed in various types of epidermal cell carcinomas. The presence of a cell membrane protein associated with immunological resistance, which is commonly expressed in both human trophoblasts and cancer cells, had been long suggested (Non-Patent Document 1). An antigen molecule recognized by mouse monoclonal antibodies (162-25.3, 162-46.2) reacting with the cell membrane protein of a human choriocarcinoma cell line BeWo was identified. This antigen molecule was considered as one of the molecules expressed in human trophoblasts, and was named as Trop-2 (Non-Patent Document 2). Thereafter, the same molecule was discovered by other researchers. That is to say, a tumor antigen recognized by a mouse monoclonal antibody GA733 which is obtained by immunization with stomach cancer cells SW948 was named as GA733-1 (Non-Patent Document 3), and an epithelial glycoprotein recognized by a mouse monoclonal antibody RS7-3G11 which is obtained by immunization with non-small cell lung cancer cells was named as an epithelial/carcinoma antigen, EGP-1 (Non-Patent Document 4). In 1995, the Trop-2 gene was cloned, and as a result, it was confirmed that these are the same molecules (Non-Patent Document 5). Moreover, it was clarified that the molecule has a function to amplify intracellular calcium signals in cancer cells (Non-Patent Document 6), and therefore, it is also referred to as a tumor-associated calcium signal transducer 2 (TACSTD2).

The hTROP-2 gene is mapped on chromosome 1p32, and it constitutes a TACSTD gene family together with GA733-2 having a homology of approximately 50% therewith (which has been known as "TACSTD1," "epithelial glycoprotein EGP-2," "EpCAM" or "Trop-1") (Non-Patent Document 7). The hTROP-2 protein (323 amino acid residues; SEQ ID NO: 2) has a molecular weight of approximately 36K Dalton, and this protein consists of a hydrophilic signal peptide ($1^{st}$ to $26^{th}$ amino acids), an extracellular domain ($27^{th}$ to $274^{th}$ amino acids), a transmembrane domain ($275^{th}$ to $297^{th}$ amino acids) and an intracellular domain ($298^{th}$ to $323^{rd}$ amino acids). The extracellular domain has four heterogeneous N-linked glycosylation sites, and its apparent molecular weight is increased by 11 to 13K Dalton due to addition of sugar chains (Non-Patent Document 5). It is considered that TACSTD gene family has a characteristic thyroglobulin (TY) sequence in the extracellular domain and is associated with the proliferation, invasion and metastasis of cancer cells.

To date, a physiological ligand of hTROP-2 has not been identified, and the molecular function thereof has not been clarified. However, it has been described that hTROP-2 transmits a calcium signal in tumor cells (Non-Patent Document 6). In addition, from the facts that intracellular serine 303 is phosphorylated by protein kinase C (PKC) that is $Ca^{2+}$-dependent kinase (Non-Patent Document 4) and that hTROP-2 has a PIP2-binding sequence in its intracellular domain, it has been suggested that hTROP-2 has a signaling function in tumor cells (Non-Patent Document 8).

As a result of analyses such as immunohistochemistry (IHC) and flow cytometry, overexpression of hTROP-2 in many types of epithelium-derived carcinomas such as stomach cancer, lung cancer, colorectal cancer, ovarian cancer, breast cancer, prostate cancer, pancreatic cancer, liver cancer and esophagus cancer has been reported. In contrast, the expression of hTROP-2 in normal tissues is limited to cells in the epithelial region, and the expression level of hTROP-2 in normal cells is lower than that in cancer cells. Thus, the association of TROP-2 with tumor formation is suggested (Patent Documents 1-3 and 9).

Moreover, it has been demonstrated that the expression of hTROP-2 used as a biomarker in clinical samples correlates with the malignancy of colorectal cancer (Non-Patent Documents 10 and 11), pancreatic cancer (Non-Patent Document 12) or oral cancer (Non-Patent Document 13), and that when hTROP-2 is overexpressed, the possibility of metastasis or recurrence of such cancer is significantly high. Furthermore, in a large-scale gene expression analysis using a cDNA microarray technique, hTROP-2 has been identified as a gene cluster, which is overexpressed at the highest level in severe papillary adenocarcinoma of the ovary, in comparison with in normal ovary epithelium (Non-Patent Document 14).

Still further, in recent years, an important role of hTROP-2 in tumor formation has been demonstrated in the models by using colon cancer cells (Non-Patent Document 15). Since the expression of hTROP-2 promotes the anchorage-independent cell proliferation of tumor cells and is required for the tumor formation and proliferation of cancer cells subcutaneously transplanted in immunodeficient mice, it raised the possibility that hTROP-2 would act as a functional tumor antigen and would be used as a new therapeutic target.

To date, studies regarding the anti-tumor effects of several anti-hTROP-2 antibodies have been reported. An RS7 antibody (Patent Document 1) has been examined by employing in vivo models, in which radioactive substance-labeled antibodies were used, and anti-tumor activity was demonstrated in nude mouse xenograft models. However, the anti-tumor effects by antibody alone (a naked antibody) have not been reported.

In addition, the cytotoxicity of a cytotoxin-attached anti-hTROP-2 monoclonal antibody BR110 (Patent Document 2)

on human cancer cell lines H3619, H2987, MCF-7, H3396 and H2981 in in vitro experiments has been reported. However, the cytotoxicity of a naked antibody or an immunoconjugate of BR110 in vivo has not been disclosed.

In recent years, it has been reported that an isolated monoclonal antibody, which was produced from a hybridoma cell line AR47A6.4.2 or AR52A301.5 obtained by immunizing mice with human ovarian cancer tissues, bound to hTROP-2, and that, for the first time, it exhibited, as a naked antibody, anti-tumor activity on nude mouse xenograft models, as well as cytotoxicity in vitro (Patent Documents 3 and 4). In these patent documents, the aforementioned antibody exhibited anti-tumor effects by treatment with antibody alone in mouse xenograft models, into which pancreatic cancer cell lines BxPC-3 and PL45, a prostate cancer cell line PC-3, a breast cancer cell line MCF-7 and a colon cancer cell line Colo205 had been transplanted. The therapeutic effects of the antibody have appeared in the models, into which BxPC-3 cells had been transplanted. Other than this, tumor formation and proliferation were only partially (approximately 40% to 60%) suppressed by the preventive administration of the antibody, and an extremely large amount (approximately 20 mg/kg) of the antibody was necessary for such suppression of tumor formation and proliferation.

Based on the above-mentioned previous findings, the potential use of the anti-hTROP-2 antibody as an anti-tumor antibody has been suggested. However, not all of the anti-hTROP-2 antibodies exhibit anti-tumor effects by treatment with antibody alone as naked antibodies in vivo. The antibodies exhibit different actions on hTROP-2, depending on a binding site, affinity and the properties of a monoclonal antibody.

Patent Document 1: U.S. Pat. No. 6,653,104
Patent Document 2: U.S. Pat. No. 5,840,854
Patent Document 3: U.S. Pat. No. 7,420,040
Patent Document 4: U.S. Pat. No. 7,420,041
Non-Patent Document 1: Faulk W P, et al., Proc. Natl. Acad. Sci. U.S.A., 75(4), pp. 1947-1951 (1978)
Non-Patent Document 2: Lipinski M, et al., Proc. Natl. Acad. Sci. U.S.A., 78(8), pp. 5147-5150 (1981)
Non-Patent Document 3: Linnenbach A J, et al., Proc. Natl. Acad. Sci. U.S.A., 86(1), pp. 27-31 (1989)
Non-Patent Document 4: Basu A, et al., Int. J. Cancer, 62(4), pp. 472-479 (1995)
Non-Patent Document 5: Fornaro M, et al., Int. J. Cancer, 62(5), pp. 610-618 (1995)
Non-Patent Document 6: Ripani E, et al., Int. J. Cancer, 76(5), pp. 671-676 (1998)
Non-Patent Document 7: Calabrese G, et al., Cell Genet., 92(1-2), pp. 164-165 (2001)
Non-Patent Document 8: El Sewedy T et al., Int. J. Cancer, 75(2), pp. 324-330 (1998)
Non-Patent Document 9: Cubas R, et al., Biochim. Biophys. Acta., 1796(2), pp. 309-314 (2009)
Non-Patent Document 10: Ohmachi T et al., Clin. Cancer Res., 12(10), pp. 3057-3063 (2006)
Non-Patent Document 11: Fang Y J, et al., Int. J. Colorectal Dis., 24(8), pp. 875-884 (2009)
Non-Patent Document 12: Fong D, et al., Br. J. Cancer, 99(8), pp. 1290-1295 (2008)
Non-Patent Document 13: Fong D, et al., Mod. Pathol., 21(2), pp. 186-191 (2008)
Non-Patent Document 14: Santin A D, et al., Int. J. Cancer, 112(1), pp. 14-25 (2004)
Non-Patent Document 15: Wang J, et al., Mol. Cancer Ther., 7(2), pp. 280-285 (2008)

SUMMARY OF THE INVENTION

Under the aforementioned circumstances, it has been desired to develop an anti-hTROP-2 antibody (an anti-hTROP-2 monoclonal antibody) having high anti-tumor activity in vivo, and specifically, an anti-hTROP-2 antibody or the like, which has an anti-tumor effect as a naked antibody alone in vivo and further, which has the anti-tumor effect at a low dose, and particularly, such an anti-hTROP-2 antibody, which is a humanized antibody.

The present invention has been completed, while taking into consideration the aforementioned circumstances. The present invention provides an anti-hTROP-2 antibody (an anti-hTROP-2 monoclonal antibody), a hybridoma, which produces the antibody, a fragment of the antibody, a conjugate (an immunoconjugate) of the antibody or the like and a drug, a pharmaceutical composition for diagnosing or treating a tumor, a method for detecting a tumor, a kit for detecting or diagnosing a tumor, and the like, which will be described below.

(1) An antibody against human TROP-2 in which an H chain V region of the antibody consists of the amino acid sequence shown in SEQ ID NO: 92 or 98, and an L chain V region of the antibody consists of the amino acid sequence shown in SEQ ID NO: 93.

In the antibody according to (1) above, the amino acid sequences of CDR 1 to 3 of the H chain V region of the antibody are shown in SEQ ID NOS: 36 to 38, respectively, and/or the amino acid sequences of CDR 1 to 3 of the L chain V region of the antibody are shown in SEQ ID NOS: 41 to 43, respectively.

(2) An antibody against human TROP-2 in which an H chain V region of the antibody consists of the amino acid sequence shown in SEQ ID NO: 94 or 95, and an L chain V region of the antibody consists of the amino acid sequence shown in SEQ ID NO: 96.

In the antibody according to (2) above, the amino acid sequences of CDR 1 to 3 of the H chain V region of the antibody are shown in SEQ ID NOS: 66 to 68, respectively, and/or the amino acid sequences of CDR 1 to 3 of the L chain V region of the antibody are shown in SEQ ID NOS: 71 to 73, respectively.

An example of the antibody according to (1) and (2) above is a humanized antibody.

An example of the antibody according to (1) and (2) above is an antibody having anti-tumor activity in vivo.

An example of the antibody according to (1) and (2) above is an antibody exhibiting 50% or more of tumor growth inhibitory activity at a dosage of 5 to 20 mg/kg body weight. Herein, the frequency of administration for exhibiting the tumor growth inhibitory activity is, for example, at most once a week.

An example of the antibody according to (1) and (2) above is an antibody exhibiting 50% or more of the tumor growth inhibitory activity by a single administration of the antibody at a dosage of 10 mg/kg body weight.

An example of the antibody according to (1) and (2) above is an antibody having anti-tumor activity on two or more types of human tumor cell lines.

An example of the antibody according to (1) and (2) above is an antibody having a dissociation constant (Kd value) of $1.0 \times 10^{-10}$ M or less.

An example of the antibody according to (1) and (2) above is a monoclonal antibody.

Herein, the tumor is at least one type selected from the group consisting of human pancreatic cancer, human prostate cancer, human colorectal cancer, human breast cancer, human ovarian cancer, human lung cancer and human bile duct cancer. The tumor is preferably at least one type selected from the group consisting of human pancreatic cancer, human colorectal cancer, human breast cancer, human lung cancer and human ovarian cancer.

In addition, the tumor is, for example, a recurrent cancer or a metastatic cancer.

Moreover, the tumor cell lines are, for example, at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT116, a human breast cancer cell line JIMT-1, a human breast cancer cell line HCC1143, a human breast cancer cell line MCF-7, a human breast cancer cell line MDA-MB-468, a human prostate cancer cell line DU145, a human prostate cancer cell line PC-3, a human lung cancer cell line Calu-3, a human ovarian cancer cell line SK-OV-3 and a human bile duct cancer cell line TFK-1. Among others, the tumor cell lines are preferably at least two types selected from the group consisting of a human pancreatic cancer cell line PK-59, a human pancreatic cancer cell line BxPC-3, a human colon cancer cell line SW480, a human lung cancer cell line Calu-3, a human breast cancer cell line MDA-MB-468 and a human ovarian cancer cell line SK-OV-3.

(3) An antibody fragment derived from the antibody according to (1) and (2) above.

Examples of the antibody fragment according to (3) above include an antibody fragment comprising the amino acid sequence shown in SEQ ID NO: 92 or 98 and/or the amino acid sequence shown in SEQ ID NO: 93, or an antibody fragment comprising the amino acid sequence shown in SEQ ID NO: 94 or 95 and/or the amino acid sequence shown in SEQ ID NO: 96.

(4) An antibody-drug conjugate, which comprises the antibody according to (1) and (2) above and a substance having anti-tumor activity and/or cell-killing activity.

(5) An antibody fragment-drug conjugate, which comprises the antibody fragment according to (3) above and a substance having anti-tumor activity and/or cell-killing activity.

In the conjugate according to (4) and (5) above, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one type selected from the group consisting of human pancreatic cancer, human colorectal cancer, human breast cancer, human lung cancer and human ovarian cancer. Moreover, the tumor is, for example, a recurrent cancer or a metastatic cancer.

(6) A pharmaceutical composition, which comprises at least one type selected from the group consisting of the antibody according to (1) and (2) above, the antibody fragment according to (3) above and the conjugate according to (4) and (5) above.

Examples of the composition according to (6) above include a composition which is used in the treatment of tumor, a composition which does not cause weight reduction as a side effect and a composition which is used in the diagnosis of tumor. Herein, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one selected from the group consisting of human pancreatic cancer, human colorectal cancer, human breast cancer, human lung cancer and human ovarian cancer. Moreover, the tumor is, for example, a recurrent cancer or a metastatic cancer (7) A tumor therapeutic agent, which comprises at least one type selected from the group consisting of the antibody according to (1) and (2) above, the antibody fragment according to (3) above and the conjugate according to (4) and (5) above.

An example of the tumor therapeutic agent according to (7) above is a tumor therapeutic agent which does not cause weight reduction as a side effect. Herein, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one selected from the group consisting of human pancreatic cancer, human colorectal cancer, human breast cancer, human lung cancer and human ovarian cancer.

(8) A tumor diagnostic agent, which comprises at least one type selected from the group consisting of the antibody according to (1) and (2) above, the antibody fragment according to (3) above and the conjugate according to (4) and (5) above.

In the tumor diagnostic agent according to (8) above, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one selected from the group consisting of human pancreatic cancer, human colorectal cancer, human breast cancer, human lung cancer and human ovarian cancer.

(9) A method for detecting a tumor, which comprises: allowing at least one type selected from the group consisting of the antibody according to (1) and (2) above, the antibody fragment according to (3) above and the conjugate according to (4) and (5) above, to react with a sample collected from a living body; and then detecting a signal(s) of the reacted antibody and/or antibody fragment.

In the method for detecting a tumor according to (9) above, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one selected from the group consisting of human pancreatic cancer, human colorectal cancer, human breast cancer, human lung cancer and human ovarian cancer.

(10) A kit for treating, diagnosing or detecting a tumor, which comprises at least one type selected from the group consisting of the antibody according to (1) and (2) above, the antibody fragment according to (3) above and the conjugate according to (4) and (5) above.

In the kit for treating, diagnosing or detecting a tumor according to (10) above, the tumor is, for example, at least one type selected from the group consisting of human pancreatic cancer, human prostate cancer, human colorectal cancer, human breast cancer, human ovarian cancer, human lung cancer and human bile duct cancer. Among others, the tumor is preferably at least one selected from the group consisting of human pancreatic cancer, human colorectal cancer, human breast cancer, human lung cancer and human ovarian cancer.

(11) A polynucleotide encoding the antibody according to (1) and (2) above.

(12) A polynucleotide encoding the antibody fragment according to (3) above.

(13) A recombinant vector comprising the polynucleotide according to (11) or (12) above.

(14) A transformant comprising the recombinant vector according to (13) above.

BRIEF DESCRIPTION OF THE DRAWINGS

FIG. 10 shows a scratch assay of a human pancreatic cancer cell line (PK-59 cells) in the presence of anti-hTROP-2 antibodies (T6-16 and K5-70).

FIG. 11 is a view illustrating FACS showing the expression of a stem cell marker in a human pancreatic cancer cell line PK-59.

FIG. 12 shows the evaluation of the anti-tumor activity of a novel anti-hTROP-2 monoclonal antibody clone K5-70 (mouse IgG2a) on xenograft treatment models using PK-59 cells.

FIG. 15 shows the evaluation of the anti-tumor activity of a clone K5-70 on xenograft prevention and treatment models using BxPC-3 cells.

FIG. 16 shows the dose-dependent anti-tumor activity of a clone K5-70 on xenograft prevention models using PK-59 cells. The volume of a tumor is expressed as a mean value±standard deviation.

FIG. 17 is a schematic view of a human/mouse chimeric TROP-2 protein used in the experiment. SP: signal sequence; TY domain: thyroglobulin type 1 region; TM: transmembrane region; C: intracellular region, wherein the filled region is a polypeptide derived from hTROP-2, whereas the open region is a polypeptide derived from mouse TROP-2. The number in the upper position of the schematic view of the chimeric protein indicates the amino acid number of a mouse TROP-2 protein, and the number in the lower position thereof indicates the amino acid number of an hTROP-2 protein.

FIG. 18 shows the results obtained by identifying an anti-hTROP-2 monoclonal antibody-binding region, using human/mouse chimeric TROP-2. Using HEK293 cells, which constantly express either human/mouse chimeric TROP-2-C (hmTROP-2-C) or mouse/human chimeric TROP-2-D (mhTROP-2-D) proteins, the reactivity with the anti-hTROP-2 monoclonal antibodies shown in the figure was studied. As a negative control, mouse IgG2b was used.

FIG. 19 shows the results obtained by identifying the antibody-binding region of an anti-hTROP-2 monoclonal antibody.

An hTROP-2 gene and each human/mouse chimeric TROP-2 gene were introduced into HEK293 cells, and FACS analysis was then carried out using the cells, in which the genes were transiently expressed.

FIG. 22 shows the anti-tumor activity of a clone K5-70 by a single administration on xenograft prevention models using PK-59 cells.

FIG. 22A shows the time course of tumor formation in a control group (●: mouse IgG) and in a K5-70 antibody (10 mg/kg body weight) administration group (○) (a mean value±standard deviation). The arrow indicates antibody administration. * P<0.05 (by Student's t-test), ** P<0.01 (by Student's t-test).

FIG. 22B shows the plotted tumor weight of each mouse at the time of the 28$^{th}$ day (Day 28) (the final day of experiment) in the test of FIG. 22A. ** P<0.01 (by Student's t-test).

FIG. 22C shows the time course of tumor formation in each mouse in a control group (●: mouse IgG) and in a K5-70 antibody (10 mg/kg body weight) administration group (○). The arrow indicates antibody administration.

FIG. 23 shows the anti-tumor activity of a clone K5-70 on xenograft treatment models using human colon cancer SW480 cells.

FIG. 23A shows the time course of tumor formation in a control group (●: mouse IgG) and in a K5-70 antibody (10 mg/kg body weight) administration group (○) (a mean value±standard deviation). The arrow indicates an antibody administration period. ** P<0.01 (by Student's t-test).

FIG. 23B shows the plotted tumor weight of each mouse at the time of the 44$^{th}$ day (Day 44) (the final day of experiment) in the test of FIG. 23A. ** P<0.01 (by Student's t-test).

FIG. 24 shows the anti-tumor activity of a clone K5-116-2-1 on xenograft treatment models using SW480 cells.

FIG. 24A shows the time course of tumor formation in a control group (●: mouse IgG) and in a K5-116-2-1 antibody (10 mg/kg body weight) administration group (○) (a mean value±standard deviation). The arrow indicates an antibody administration period. ** P<0.01 (by Student's t-test).

FIG. 24B shows the plotted tumor weight of each mouse at the time of the 42$^{nd}$ day (Day 42) (the final day of experiment) in the test of FIG. 24A. ** P<0.01 (by Student's t-test).

FIG. 25 shows the anti-tumor activity of a clone T6-16 on xenograft treatment models using SW480 cells.

FIG. 25A shows the time course of tumor formation in a control group (●: mouse IgG) and in a T6-16 antibody (10 mg/kg body weight) administration group (○) (a mean value±standard deviation). The arrow indicates an antibody administration period. * P<0.05 (by Student's t-test).

FIG. 25B shows the plotted tumor weight of each mouse at the time of the 42$^{nd}$ day (Day 42) (the final day of experiment) in the test of FIG. 25A. * P<0.05 (by Student's t-test).

FIG. 26 shows the dose-dependent anti-tumor activity of a clone K5-70 on xenograft treatment models using SW480 cells.

FIG. 26A shows the time course of tumor formation in a control group (●: mouse IgG) and in a K5-70 antibody administration group (○: 1 mg/kg body weight, Δ: 5 mg/kg body weight, □: 10 mg/kg body weight) (a mean value±standard deviation). The arrow indicates an antibody administration period. * P<0.05 (by Student's t-test).

FIG. 26B shows the plotted tumor weight of each mouse at the time of the 42$^{nd}$ day (Day 42) (the final day of experiment) in the test of FIG. 26A. * P<0.05 (by Student's t-test).

FIG. 27 shows the anti-tumor activity of a clone K5-70 on xenograft treatment models using SW480 cells.

FIG. 28 shows the dose-dependent anti-tumor activity of a clone T6-16 on xenograft treatment models using SW480 cells.

FIG. 30 shows the anti-tumor activity of a clone K5-70 on xenograft prevention models using human prostate DU-145 cells.

FIG. 31 shows the metastasis-inhibitory activity of a clone K5-70 on liver metastatic models using PK-59 cells.

FIG. 33 shows the cDNA nucleotide sequence of a clone K5-70 H chain variable region (VH) (SEQ ID NO: 34) and the deduced amino acid sequence (SEQ ID NO: 35). A signal peptide is shown in italics. The double-underlined glutamine (Q) indicates the N-terminal amino acid residue of a mature peptide. The CDR sequences (underlined; IYWIN (SEQ ID NO: 36), NIYPSDSYTNYNQKFKD (SEQ ID NO: 37), and TSMADY (SEQ ID NO: 38)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-70 VH are shown in SEQ ID NOS: 36 to 38, respectively.

FIG. 34 shows the cDNA nucleotide sequence of a clone K5-70 L chain variable region (VL) (SEQ ID NO: 39) and the deduced amino acid sequence (SEQ ID NO: 40). A signal peptide is shown in italics. The double-underlined aspartic acid (D) indicates the N-terminal amino acid residue of a mature peptide. The CDR sequences (underlined; RASQSIGTSIH (SEQ ID NO: 41), YASESIS (SEQ ID NO: 42), and QQSNSWPFT (SEQ ID NO: 43)) were determined in accordance with the definitions of Kabat et al. (as described above; U.S. Department of Health and Human Services, 1991). The amino acid sequences of CDR 1 to 3 of the clone K5-70 VL are shown in SEQ ID NOS: 41 to 43, respectively.

FIG. 35 shows the cDNA nucleotide sequence of a clone K5-107 H chain variable region (VH) (SEQ ID NO: 44) and the deuced amino acid sequence (SEQ ID NO: 45). A signal peptide is shown in italics. The double-underlined glutamine (Q) indicates the N-terminal amino acid residue of a mature peptide. The CDR sequences (underlined; SYWMH (SEQ ID NO: 46), NIYPGGGYTNYDEKFKS (SEQ ID NO: 47), and SSVFDY (SEQ ID NO: 48)) were determined in accordance with the definitions of Kabat et al. (as described above; U.S. Department of Health and Human Services, 1991). The amino acid sequences of CDR 1 to 3 of the clone K5-107 VH are shown in SEQ ID NOS: 46 to 48, respectively.

FIG. 36 shows the cDNA nucleotide sequence of a clone K5-107 L chain variable region (VL) (SEQ ID NO: 49) and the deduced amino acid sequence (SEQ ID NO: 50). A signal peptide is shown in italics. The double-underlined aspartic acid (D) indicates the N-terminal amino acid residue of a mature peptide. The CDR sequences (underlined; RASQNIGTSIH (SEQ ID NO: 51), YASESIS (SEQ ID NO: 52), and QQSNSWPFT (SEQ ID NO: 53)) were determined in accordance with the definitions of Kabat et al. (as described above; U.S. Department of Health and Human Services, 1991). The amino acid sequences of CDR 1 to 3 of the clone K5-107 VL are shown in SEQ ID NOS: 51 to 53, respectively.

FIG. 37 shows the cDNA nucleotide sequence of a clone K5-116-2-1 H chain variable region (VH) (SEQ ID NO: 54) and the deduced amino acid sequence (SEQ ID NO: 55). A signal peptide is shown in italics. The double-underlined glutamine (Q) indicates the N-terminal amino acid residue of a mature peptide. The CDR sequences (underlined; SYWIT (SEQ ID NO: 56), NIYPSDSYTNYNQKFRD (SEQ ID NO: 57), and LFDY (SEQ ID NO: 58)) were determined in accordance with the definitions of Kabat et al. (as described above; U.S. Department of Health and Human Services, 1991). The amino acid sequences of CDR 1 to 3 of the clone K5-116-2-1 VH are shown in SEQ ID NOS: 56 to 58, respectively.

FIG. 38 shows the cDNA nucleotide sequence of a clone K5-116-2-1 L chain variable region (VL) (SEQ ID NO: 59) and the deduced amino acid sequence (SEQ ID NO: 60). A signal peptide is shown in italics. The double-underlined aspartic acid (D) indicates the N-terminal amino acid residue of a mature peptide. The CDR sequences (underlined; RASQSIGTSIH (SEQ ID NO: 61), YASESIS (SEQ ID NO: 62), and QQSNSWPFT (SEQ ID NO: 63)) were determined in accordance with the definitions of Kabat et al. (as described above; U.S. Department of Health and Human Services, 1991). The amino acid sequences of CDR 1 to 3 of the clone K5-116-2-1 VL are shown in SEQ ID NOS: 61 to 63, respectively.

FIG. 39 shows the cDNA nucleotide sequence of a clone T6-16 H chain variable region (VH) (SEQ ID NO: 64) and the deduced amino acid sequence (SEQ ID NO: 65). A signal peptide is shown in italics. The double-underlined glutamic acid (E) indicates the N-terminal amino acid residue of a mature peptide. The CDR sequences (underlined; DYNMH (SEQ ID NO: 66), YIYPYNGGTGYNQRFKS (SEQ ID NO: 67), and EDYGSSPSYAMDY (SEQ ID NO: 68)) were determined in accordance with the definitions of Kabat et al. (as described above; U.S. Department of Health and Human Services, 1991). The amino acid sequences of CDR 1 to 3 of the clone T6-16 VH are shown in SEQ ID NOS: 66 to 68, respectively.

FIG. 40 shows the cDNA nucleotide sequence of a clone T6-16 L chain variable region (VL) (SEQ ID NO: 69) and the deduced amino acid sequence (SEQ ID NO: 70). A signal peptide is shown in italics. The double-underlined aspartic acid (D) indicates the N-terminal amino acid residue of a mature peptide. The CDR sequences (underlined; RSSQSLVHGNGNTYLH (SEQ ID NO: 71), KVSNRFS (SEQ ID NO: 72), and SQTTHVPT (SEQ ID NO: 73)) were determined in accordance with the definitions of Kabat et al. (as described above; U.S. Department of Health and Human Services, 1991). The amino acid sequences of CDR 1 to 3 of the clone T6-16 VL are shown in SEQ ID NOS: 71 to 73, respectively.

FIG. 41 shows an alignment of the amino acid sequence (SEQ ID NO: 35) of the H chain variable region of a clone K5-70 (K5-70 VH), the amino acid sequence (SEQ ID NO: 75) of the H chain variable region of a humanized K5-70 (HuK5-70 VH), and the amino acid sequence (SEQ ID NO: 85) of the H chain variable region of an acceptor (Genbank accession No. DA980102; SEQ ID NO: 84) used for the production of the humanized antibody (DA980102 VH). (It is to be noted that each of the amino acid sequences shown in the figure indicates a portion of the amino acid sequence of each H chain variable region (specifically, the amino acid sequence of a mature protein portion from which a signal peptide portion is removed)).

Figure 1:
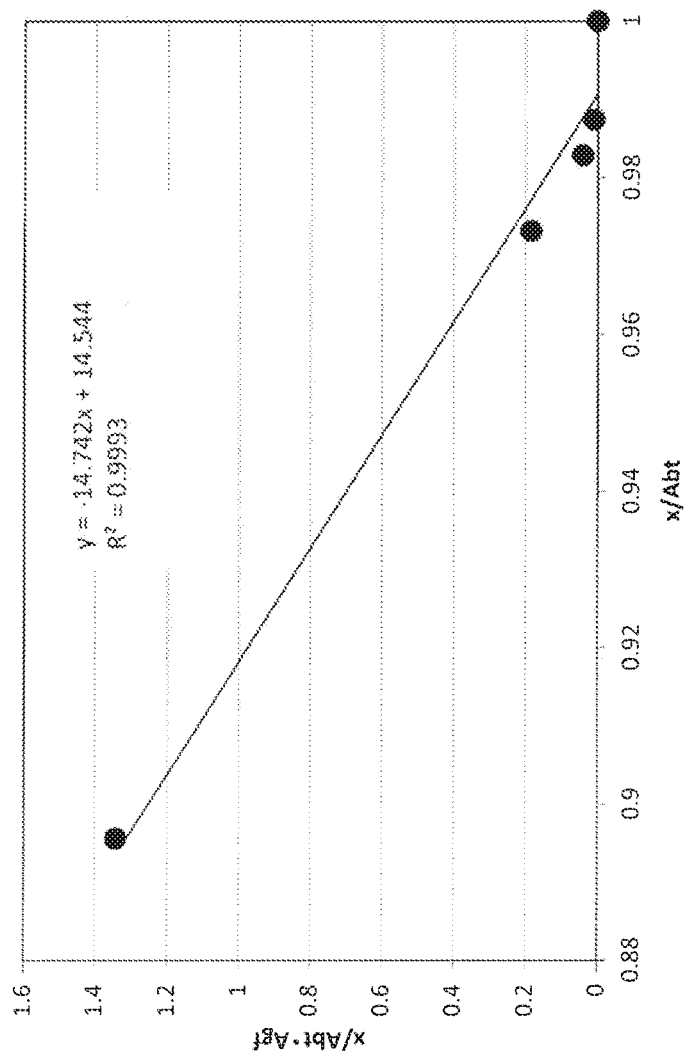
FIG. 1 shows the measurement of the antigen binding affinity (Kd: dissociation constant) of an anti-hTROP-2 monoclonal antibody (K5-70). Abt: Antibody (total); Agf: Antigen (free).

The amino acid sequence underlined in the K5-70 VH indicates a CDR sequence determined in accordance with the definitions of Kabat et al. (as described above; U.S. Department of Health and Human Services, 1991). In addition, the number in the upper position of the amino acid sequence indicates the position number of an amino acid determined in accordance with the aforementioned definitions of Kabat et al. Each CDR sequence in the DA980102 VH is expressed with the symbol "---," and thus the description is omitted. Since the amino acid underlined in the HuK5-70 VH was assumed to be important for the maintenance of the structure of CDR, the sequence of the K5-70 VH was maintained. In addition, with regard to the amino acid double-underlined in the HuK5-70 VH, the amino acid of the corresponding DA980102 VH (methionine (M)) is rarely found at this position. Hence, for the purpose of decreasing antigenicity, the amino acid double-underlined in the HuK5-70 VH was substituted with leucine (L) as a representative amino acid belonging to the same subgroup.

FIG. 42 shows an alignment of the amino acid sequence (SEQ ID NO: 40) of the L chain variable region of a clone K5-70 (K5-70 VL), the amino acid sequence (SEQ ID NO: 77) of the L chain variable region of a humanized K5-70 (HuK5-70 VL), and the amino acid sequence (SEQ ID NO: 87; Genbank accession No. AAA64877) of the L chain variable region of an acceptor (Genbank accession No. L41174; SEQ ID NO: 86) used for the production of the humanized antibody (L41174 VL). (It is to be noted that each of the amino acid sequences shown in the figure indicates a portion of the amino acid sequence of each L chain variable region (specifically, the amino acid sequence of a mature protein portion from which a signal peptide portion is removed)).

The amino acid sequence underlined in the K5-70 VL indicates a CDR sequence determined in accordance with the definitions of Kabat et al. (as described above; U.S. Department of Health and Human Services, 1991). In addition, the number in the upper position of the amino acid sequence indicates the position number of an amino acid determined in accordance with the aforementioned definitions of Kabat et al. Each CDR sequence in the L41174 VL is expressed with the symbol "---," and thus the description is omitted. Since the amino acid underlined in the HuK5-70 VL was assumed to be important for the maintenance of the structure of CDR, the sequence of the K5-70 VL was maintained.

FIG. 43 shows an alignment of the amino acid sequence (SEQ ID NO: 65) of the H chain variable region of a clone T6-16 (T6-16 VH), the amino acid sequences (SEQ ID NOS: 79 and 81, respectively) of the H chain variable regions of two types of humanized T6-16 (HuT6-16 VH1 and HuT6-16 VH2), and the amino acid sequence (SEQ ID NO: 89) of the H chain variable region of an acceptor (Genbank accession No. DA935238; SEQ ID NO: 88) used for the production of the humanized antibody (DA935238 VH). (It is to be noted that each of the amino acid sequences shown in the figure indicates a portion of the amino acid sequence of each H chain variable region (specifically, the amino acid sequence of a mature protein portion from which a signal peptide portion is removed)).

The amino acid sequence underlined in the HuT6-16 VH indicates a CDR sequence determined in accordance with the definitions of Kabat et al. (as described above; U.S. Department of Health and Human Services, 1991). In addition, the number in the upper position of the amino acid sequence indicates the position number of an amino acid determined in accordance with the aforementioned definitions of Kabat et al. Each CDR sequence in the DA935238 VH is expressed with the symbol "---," and thus the description is omitted. Since the amino acids underlined in the HuT6-16 VH1 and HuT6-16 VH2 were assumed to be important for the maintenance of the structure of CDR, the sequence of the T6-16 VH was maintained. In addition, the lysine (K) at position 73 in the HuT6-16 VH1 was substituted with a threonine (T) derived from DA935238 as an acceptor sequence in the HuT6-16 VH2.

FIG. 44 shows an alignment of the amino acid sequence (SEQ ID NO: 70) of the L chain variable region of a clone T6-16 (T6-16 VL), the amino acid sequence (SEQ ID NO: 83) of the L chain variable region of a humanized T6-16 (HuT6-16 VL), and the amino acid sequence (SEQ ID NO: 91; Genbank accession No. AAA60341) of the L chain variable region of an acceptor (Genbank accession No. M99608; SEQ ID NO: 90) used for the production of the humanized antibody (M99608 VL). (It is to be noted that each of the amino acid sequences shown in the figure indicates a portion of the amino acid sequence of each L chain variable region (specifically, the amino acid sequence of a mature protein portion from which a signal peptide portion is removed)).

The amino acid sequence underlined in the T6-16 VL indicates a CDR sequence determined in accordance with the definitions of Kabat et al. (as described above; U.S. Department of Health and Human Services, 1991). In addition, the number in the upper position of the amino acid sequence indicates the position number of an amino acid determined in accordance with the aforementioned definitions of Kabat et al. Each CDR sequence in the M99608 VL is expressed with the symbol "---," and thus the description is omitted.

FIG. 45 shows the gene sequence (SEQ ID NO: 74) and amino acid sequence (SEQ ID NO: 75) of HuK5-70 VH.

The upper position of each line indicates the gene sequence (cDNA sequence) and the lower position thereof indicates the amino acid sequence. In the amino acid sequence, a signal peptide portion is underlined with a dashed line and each CDR sequence (CDR 1 to 3) is underlined with a solid line (the amino acid sequence of only the mature protein portion, from which the signal peptide portion is removed, is shown in SEQ ID NO: 92). An EcoRI site (GAA TTC) and a Kozak sequence (ACC ACC) were added to the 5' end of the HuK5-70 VH gene, and an NheI site (GCT AGC) was added to the 3' end thereof.

FIG. 46 shows the gene sequence (SEQ ID NO: 76) and amino acid sequence (SEQ ID NO: 77) of HuK5-70 VL.

The upper position of each line indicates the gene sequence (cDNA sequence) and the lower position thereof indicates the amino acid sequence. In the amino acid sequence, a signal peptide portion is underlined with a dashed line and each CDR sequence (CDR 1 to 3) is underlined with a solid line (the amino acid sequence of only the mature protein portion, from which the signal peptide portion is removed, is shown in SEQ ID NO: 93). An AgeI site (ACC GGT) and a Kozak sequence (ACC ACC) were added to the 5' end of the HuK5-70 VL gene, and a BsiWI site (CGT ACG) was added to the 3' end thereof.

FIG. 47 shows the gene sequence (SEQ ID NO: 78) and amino acid sequence (SEQ ID NO: 79) of HuT6-16 VH1.

The upper position of each line indicates the gene sequence (cDNA sequence) and the lower position thereof indicates the amino acid sequence. In the amino acid sequence, a signal peptide portion is underlined with a dashed line and each CDR sequence (CDR 1 to 3) is underlined with a solid line (the amino acid sequence of only the mature protein portion, from which the signal peptide portion is removed, is shown in SEQ ID NO: 94). An EcoRI site (GAA TTC) and a Kozak sequence (ACC ACC) were added to the 5' end of the HuT6-16 VH1 gene, and an NheI site (GCT AGC) was added to the 3' end thereof.

Figure 48:
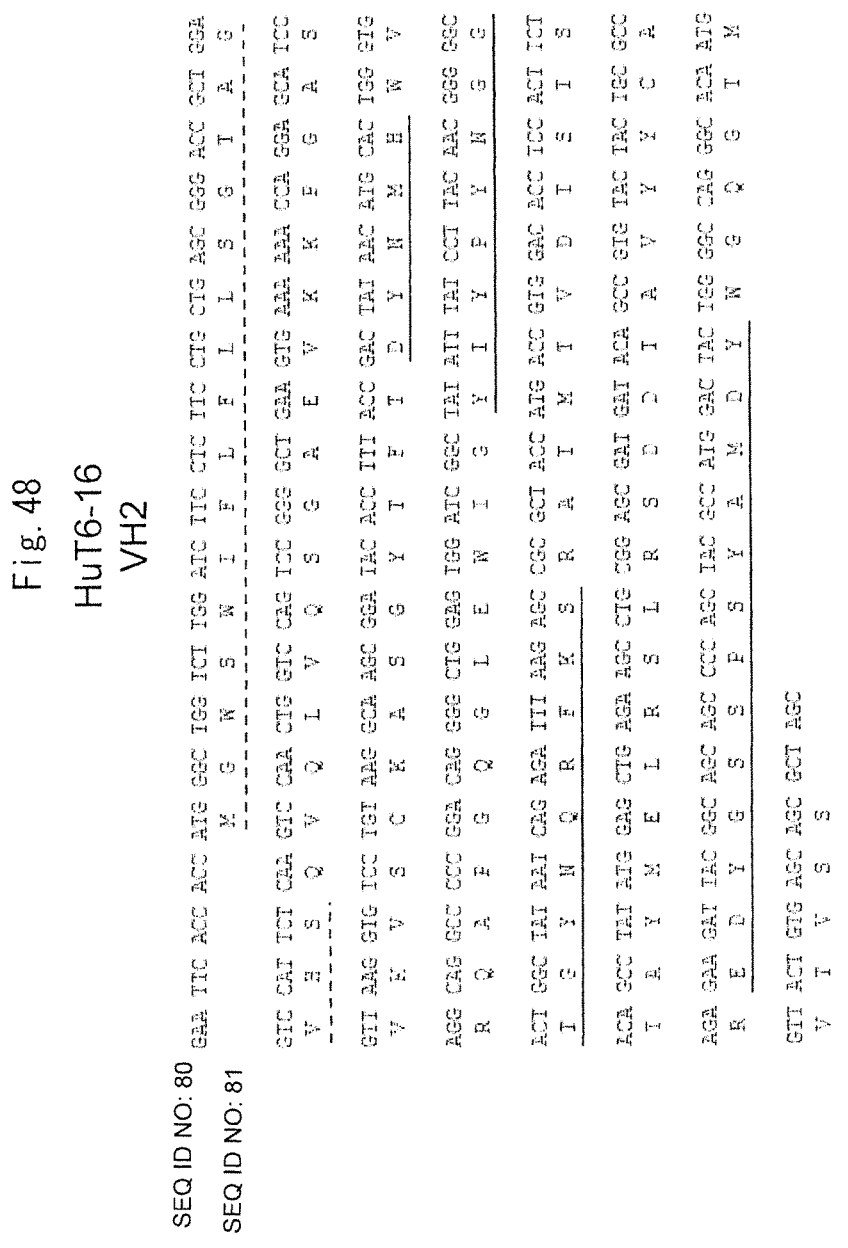

FIG. 48 shows the gene sequence (SEQ ID NO: 80) and amino acid sequence (SEQ ID NO: 81) of HuT6-16 VH2.

The upper position of each line indicates the gene sequence (cDNA sequence) and the lower position thereof indicates the amino acid sequence. In the amino acid sequence, a signal peptide portion is underlined with a dashed line and each CDR sequence (CDR 1 to 3) is underlined with a solid line (the amino acid sequence of only the mature protein portion, from which the signal peptide portion is removed, is shown in SEQ ID NO: 95). An EcoRI site (GAA TTC) and a Kozak sequence (ACC ACC) were added to the 5' end of the HuT6-16 VH2 gene, and an NheI site (GCT AGC) was added to the 3' end thereof.

FIG. 49 shows the gene sequence (SEQ ID NO: 82) and amino acid sequence (SEQ ID NO: 83) of HuT6-16 VL.

The upper position of each line indicates the gene sequence (cDNA sequence) and the lower position thereof indicates the amino acid sequence. In the amino acid sequence, a signal peptide portion is underlined with a dashed line and each CDR sequence (CDR 1 to 3) is underlined with a solid line (the amino acid sequence of only the mature protein portion, from which the signal peptide portion is removed, is shown in SEQ ID NO: 96). An AgeI site (ACC GGT) and a Kozak sequence (ACC ACC) were added to the 5' end of the HuT6-16 VL gene, and a BsiWI site (CGT ACG) was added to the 3' end thereof.

FIG. 50 shows the results obtained by confirming the expression of the HuK5-70 antibody, HuT6-16-1 antibody and HuT6-16-2 antibody.

FIG. 50(A) The expression vectors pFUSE-CHIg-HuK5-70 and pFUSE2-CLIg-HuK5-70 were introduced into 293F cells, and the expression of the HuK5-70 antibody in the culture supernatant was analyzed by Western blotting. Lane 1 indicates the culture supernatant of 293F cells into which no genes were introduced (negative control), and lane 2 indicates the culture supernatant of 293F cells into which the aforementioned expression vectors were introduced. The heavy chain and light chain proteins of the HuK5-70 antibody were detected with a biotin-labeled anti-human IgG F(ab')$^2$ antibody.

FIG. 50(B) The expression vectors pFUSE-CHIg-HuT6-16-1 and pFUSE2-CLIg-HuT6-16 (lane 3), and the expression vectors pFUSE-CHIg-HuT6-16-2 and pFUSE2-CLIg-HuT6-16 (lane 4), were introduced into 293F cells in these combinations. Then, the expression of the HuT6-16-1 antibody and HuT6-16-2 antibody was analyzed by Western blotting. The heavy chain proteins of the HuT6-16-1 antibody and HuT6-16-2 antibody were detected with a biotin-labeled anti-human IgG Fc antibody, and the light chain proteins of the HuT6-16-1 antibody and HuT6-16-2 antibody were detected with a biotin-labeled anti-human IgG F(ab')$^2$ antibody.

FIG. 51 shows the results obtained by staining the purified HuK5-70 antibody, HuT6-16-1 antibody and HuT6-16-2 antibody with Coomassie.

The purified HuK5-70 antibody (lane 1), HuT6-16-1 antibody (lane 2) and HuT6-16-2 antibody (lane 3) were loaded in amounts of 1 μg each on SDS-PAGE, and were then stained with Coomassie.

FIG. 52 shows the results obtained by analyzing the antigen-binding ability of the HuK5-70 antibody, HuT6-16-1 antibody and HuT6-16-2 antibody, using a flow cytometer.

The reactivity of each antibody shown in the figure with HEK293-hTROP-2 cells (FIG. 52A) and PK-59 cells (FIG. 52B) was analyzed by FACS. Secondary antibody alone was used as a negative control (filled), and the reactivity of each antibody was indicated with a gray line.

Figure 53:
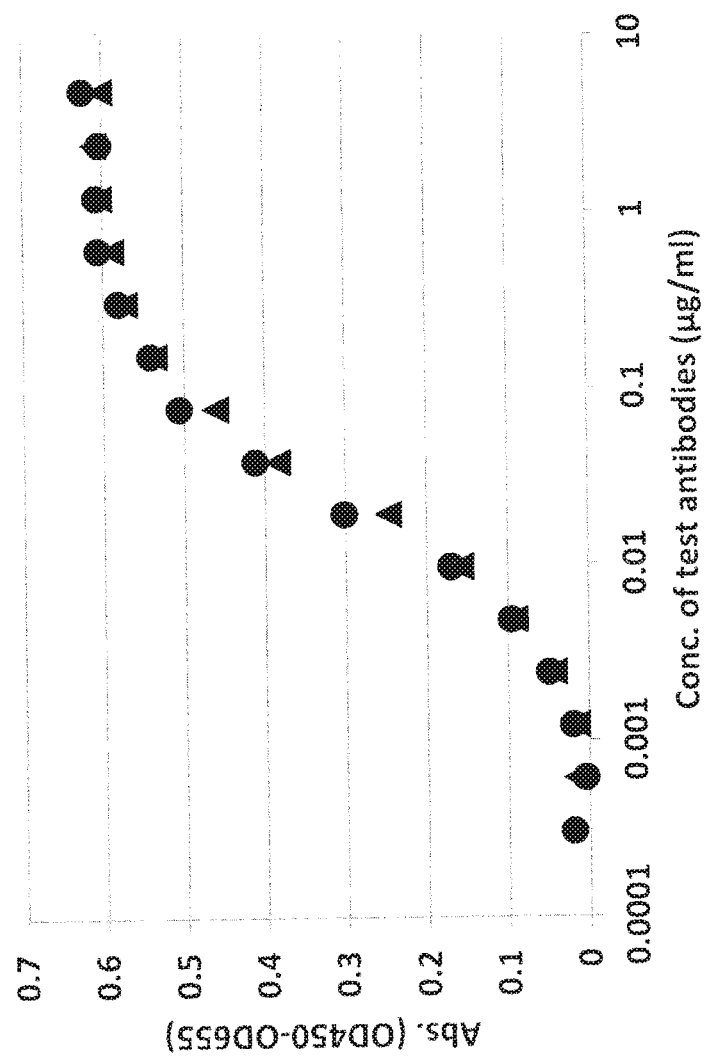

FIG. 53 shows the results obtained by measuring the antigen-binding ability of the HuK5-70 antibody according to an ELISA method.

The antigen-binding ability of the K5-70 antibody and HuK5-70 antibody was analyzed according to an antigen-coated ELISA method. The symbol ▲ indicates the measurement results of the K5-70 antibody, and the symbol ● indicates the measurement results of the HuK5-70 antibody.

Figure 54:
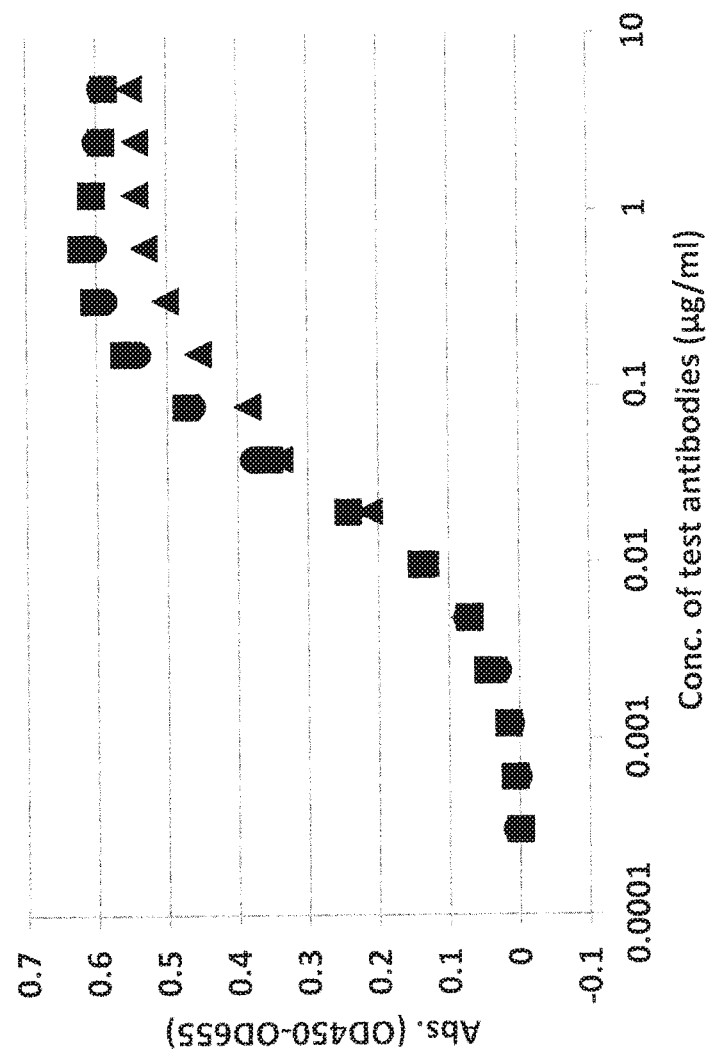

FIG. 54 shows the results obtained by measuring the antigen-binding ability of the HuT6-16-1 antibody and HuT6-16-2 antibody according to an ELISA method.

The antigen-binding ability of the T6-16 antibody, HuT6-16-1 antibody and HuT6-16-2 was analyzed according to an antigen-coated ELISA method. The symbol ▲ indicates the measurement results of the T6-16 antibody, the symbol ● indicates the measurement results of the HuT6-16-1 antibody, and the symbol ■ indicates the measurement results of the HuT6-16-2 antibody.

FIG. 55 shows the anti-tumor activity of a humanized anti-hTROP-2 antibody (HuK5-70 antibody) on xenograft treatment models using human colon cancer SW480 cells.

FIG. 55A shows the time course of tumor formation in a control group (●: PBS) and in a HuK5-70 antibody (10 mg/kg body weight) administration group (○) (a mean value±standard deviation). The arrow indicates an antibody administration period. * P<0.05, ** P<0.01 (by Student's t-test).

FIG. 55B shows the plotted tumor weight of each mouse at the time of the 39$^{th}$ day (Day 39) (the final day of experiment) in the test of FIG. 55A. * P<0.05 (by Student's t-test).

FIG. 56 shows the dose-dependent anti-tumor activity of a humanized anti-hTROP-2 antibody (HuK5-70) on xenograft treatment models using human colon cancer SW480 cells.

FIG. 56A shows the time course of tumor formation in a control group (●: PBS) and in a HuK5-70 antibody administration groups (○: 1 mg/kg body weight, Δ: 5 mg/kg body weight, □: 10 mg/kg body weight) (a mean value±standard deviation). The arrow indicates an antibody administration period. ** P<0.01 (by Student's t-test).

FIG. 56B shows the plotted tumor weight of each mouse at the time of the 48$^{th}$ day (Day 48) (the final day of experiment) after cancer cell transplantation in the test of FIG. 56A. ** P<0.01 (by Student's t-test).

FIG. 57 shows the dose-dependent anti-tumor activity of a humanized anti-hTROP-2 antibody (HuT6-16-2) on xenograft treatment models using human colon cancer SW480 cells.

Figure 57B:
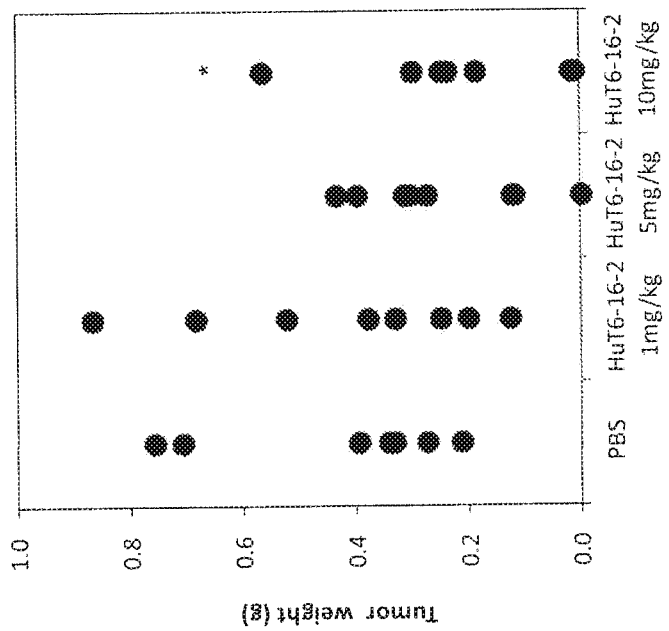
Figure 57A:
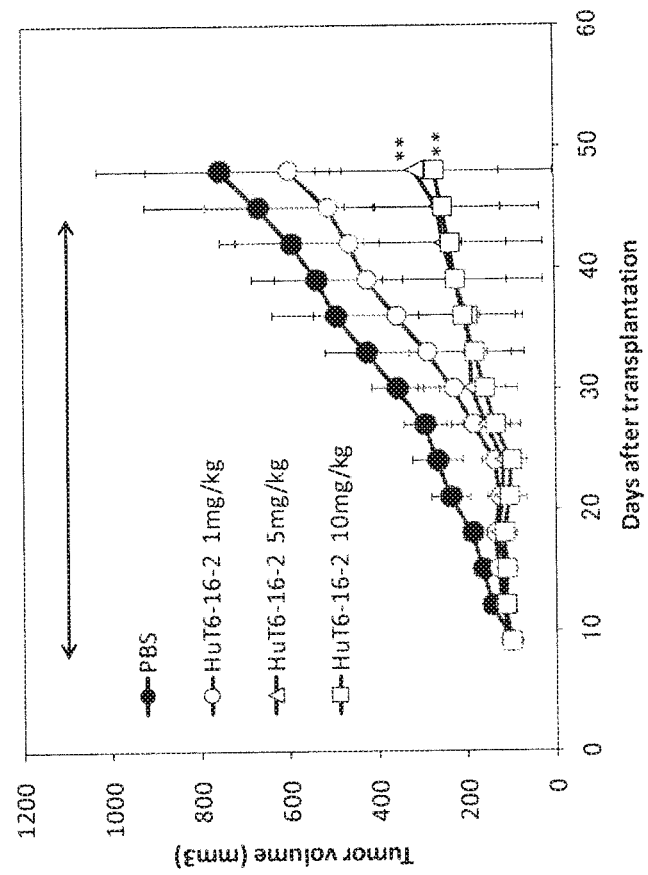

FIG. 57A shows the time course of tumor formation in a control group (●: PBS) and in a HuT6-16-2 antibody administration groups (○: 1 mg/kg body weight, Δ: 5 mg/kg body weight, □: 10 mg/kg body weight) (a mean value±standard deviation). The arrow indicates an antibody administration period. ** P<0.01 (by Student's t-test).

FIG. 57B shows the plotted tumor weight of each mouse at the time of the 48$^{th}$ day (Day 48) (the final day of experiment) after cancer cell transplantation in the test of FIG. 57A. * P<0.05 (by Student's t-test).

FIG. 58 shows the anti-tumor activity of mouse anti-hTROP-2 antibodies (K5-70 and T6-16) on xenograft treatment models using human ovarian cancer SK-OV-3 cells.

Figure 58B:
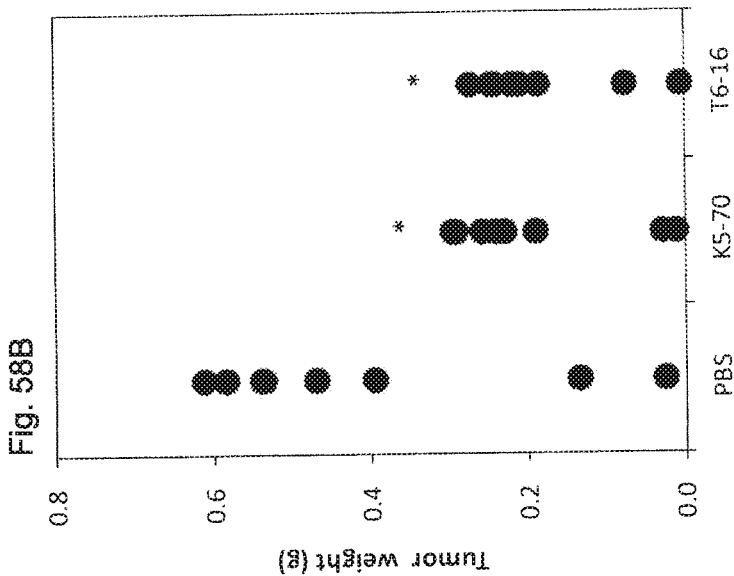
Figure 58A:
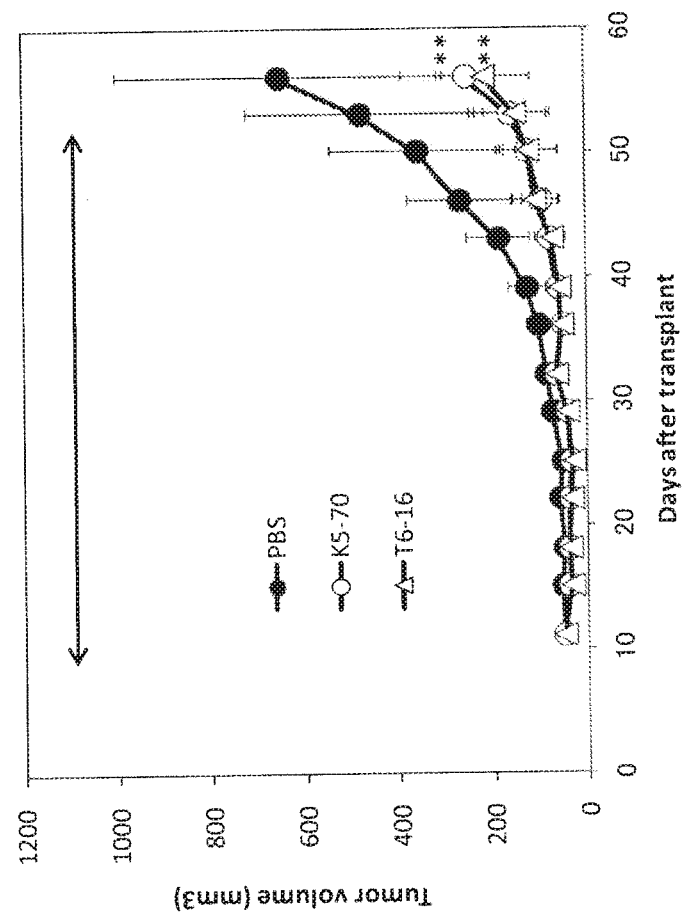

FIG. 58A shows the time course of tumor formation in a control group (●: PBS), in a K5-70 antibody (10 mg/kg body weight) administration group (○), and in a T6-16 antibody (10 mg/kg body weight) administration group (Δ) (a mean value±standard deviation). The arrow indicates an antibody administration period. * P<0.01 (by Student's t-test).

FIG. 58B shows the plotted tumor weight of each mouse at the time of the 56$^{th}$ day (Day 56) (the final day of experiment) after cancer cell transplantation in the test of FIG. 58A. * P<0.05 (by Student's t-test).

FIG. 59 shows the anti-tumor activity of mouse anti-hTROP-2 antibodies (K5-70 and T6-16) on xenograft treatment models using human breast cancer MDA-MB-468 cells.

Figure 59B:
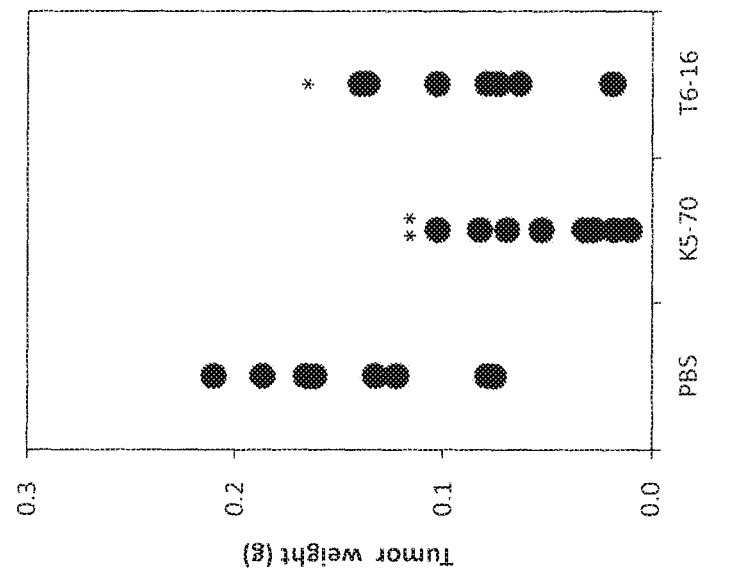
Figure 59A:
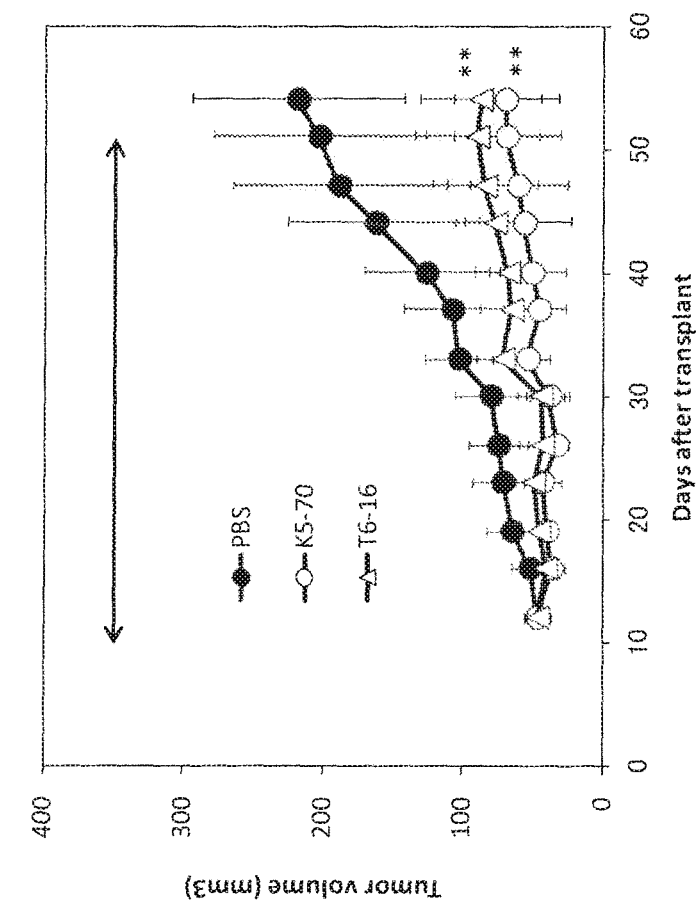

FIG. 59A shows the time course of tumor formation in a control group (●: PBS), in a K5-70 antibody (10 mg/kg body weight) administration group (○), and in a T6-16 antibody (10 mg/kg body weight) administration group (Δ) (a mean value±standard deviation). The arrow indicates an antibody administration period. ** P<0.01 (by Student's t-test).

FIG. 59B shows the plotted tumor weight of each mouse at the time of the 54$^{th}$ day (Day 54) (the final day of experiment) after cancer cell transplantation in the test of FIG. 59A. * P<0.05, ** P<0.01 (by Student's t-test).

FIG. 60 shows the anti-tumor activity of mouse anti-hTROP-2 antibodies (K5-70 and T6-16) on xenograft treatment models using human lung cancer Calu-3 cells.

Figure 60B:
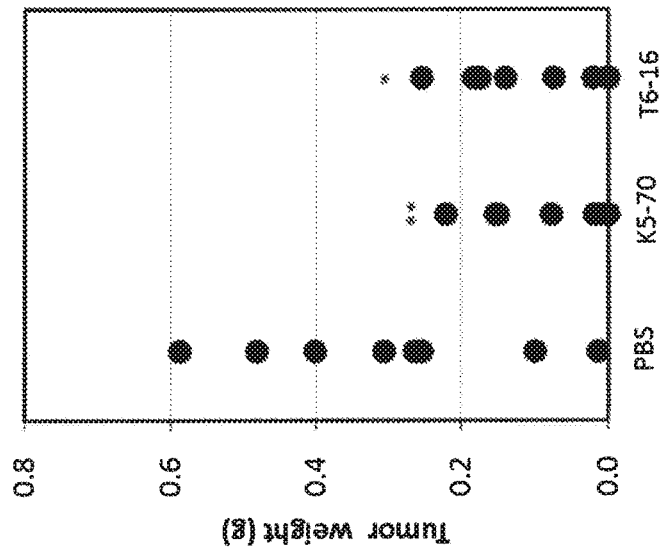
Figure 60A:
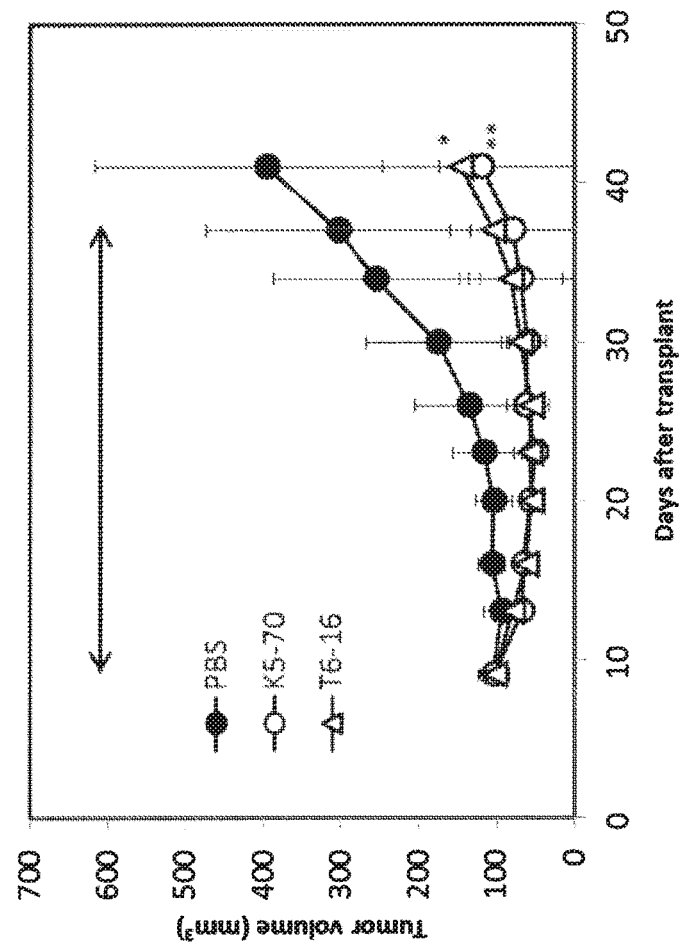

FIG. 60A shows the time course of tumor formation in a control group (●: PBS), in a K5-70 antibody (10 mg/kg body weight) administration group (○), and in a T6-16 antibody (10 mg/kg body weight) administration group (Δ) (a mean value±standard deviation). The arrow indicates an antibody administration period. * P<0.05, ** P<0.01 (by Student's t-test).

FIG. 60B shows the plotted tumor weight of each mouse at the time of the 41st day (Day 41) (the final day of experiment) after cancer cell transplantation in the test of FIG. 60A. * P<0.05, ** P<0.01 (by Student's t-test).

FIG. 61 shows the anti-tumor activity of a mouse anti-hTROP-2 antibody K5-70 on xenograft prevention models using human bile duct cancer TFK-1 cells.

Figure 61B:
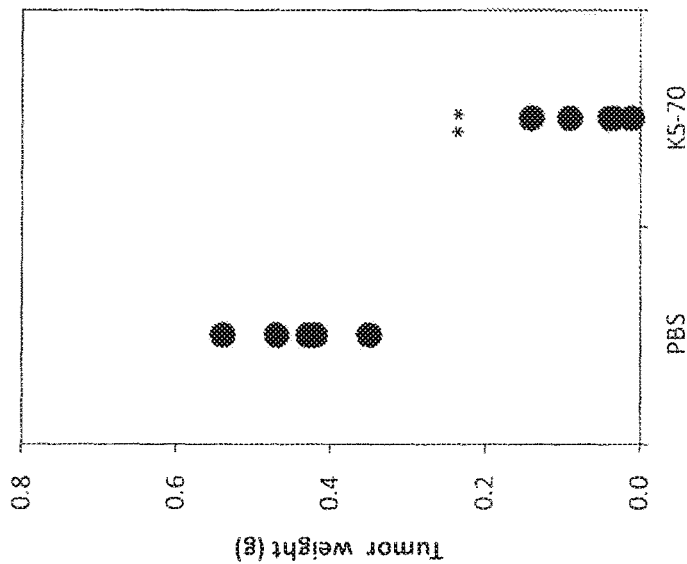
Figure 61A:
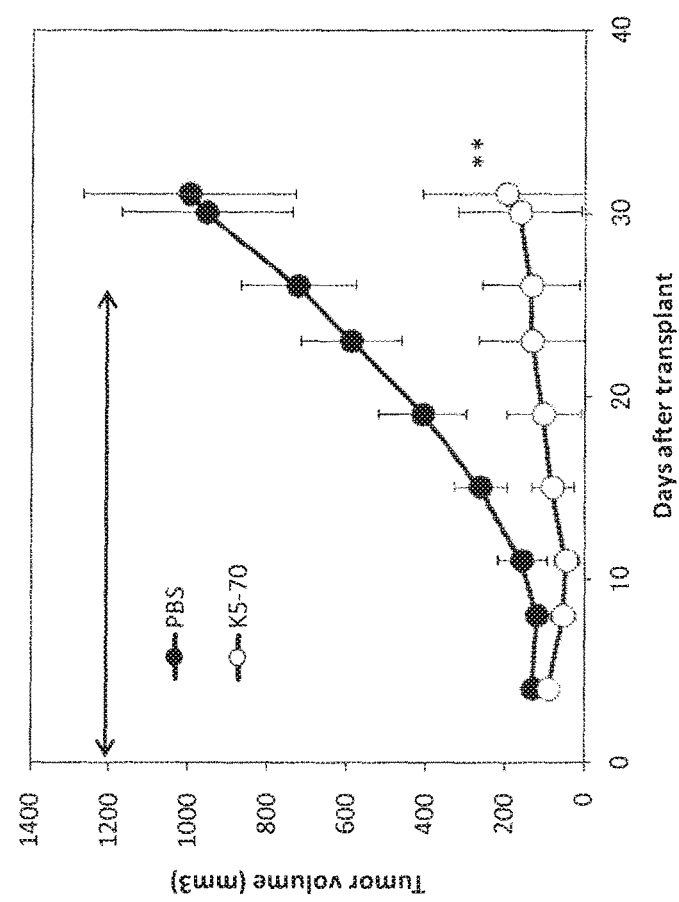

FIG. 61A shows the time course of tumor formation in a control group (●: PBS) and in a K5-70 antibody (10 mg/kg body weight) administration group (○) (a mean value±standard deviation). The arrow indicates an antibody administration period. ** P<0.01 (by Student's t-test).

FIG. 61B shows the plotted tumor weight of each mouse at the time of the 31st day (Day 31) (the final day of experiment) after cancer cell transplantation in the test of FIG. 61A. ** P<0.01 (by Student's t-test).

FIG. 62 shows the results obtained by analyzing the binding activity of the HuK5-70 and HuT6-16-2 antibodies according to low-density antigen-coated ELISA. A 96-well plate was coated with a 0.1 μg/mL recombinant hTACSTD2-Fc-His protein, and thereafter, test antibodies (K5-70, HuK5-70, T6-16 and HuT6-16-2 antibodies), which had been prepared in concentrations from 20 μg/mL to a series of two-fold dilutions, were allowed to react with the protein. In FIG. 62(A), K5-70 (▲) and HuK5-70 (●) antibodies were used as test antibodies, and in FIG. 62(B), T6-16 (▲) and HuT6-16-2 antibody (●) were used as test antibodies.

Figure 63:
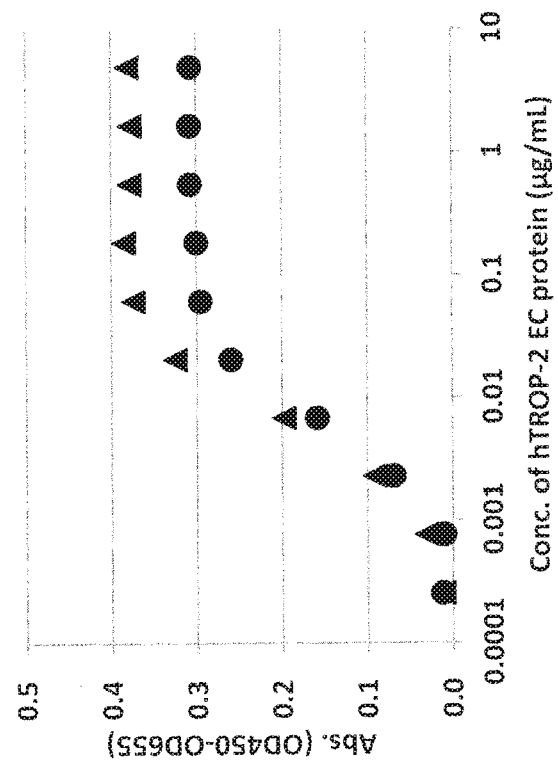

FIG. 63 shows the results obtained by analyzing the binding activity of hTROP-2 to K5-70 and HuK5-70 antibodies by ELISA. A 96-well plate was coated with the K5-70 and HuK5-70 antibodies via anti-mouse IgG (γ chain specific) and anti-human IgG1 (Fcγ specific), and thereafter, these antibodies were allowed to react with hTROP-2-EC-His proteins, which had been prepared in concentrations from 5 μg/mL to a series of two-fold dilutions. The binding of such a hTROP-2-EC-His protein was detected using an anti-His tag antibody. (▲) K5-70 antibody and (●) HuK5-70 antibody.

FIG. 64 shows the nucleotide sequence (upper case; SEQ ID NO: 99) and amino acid sequence (lower case; SEQ ID NO: 35) of a K5-70 VH gene that was prepared by gene synthesis. With regard to this nucleotide sequence, an EcoRI site (GAA TTC) and a Kozak sequence (ACC ACC) were added to the 5' end, and an NheI site (GCT AGC) was added to the 3' end. The amino acid sequence is shown by single letter code. A signal peptide on the N-terminal side is shown in italics. The double-underlined glutamine (Q) indicates the N-terminal amino acid residue of a mature peptide. The CDR sequences (underlined; IYWIN (SEQ ID NO: 36), NIYPSDSYTNYNQKFKD (SEQ ID NO: 37), and TSMADY (SEQ ID NO: 38)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-70 VH are shown in SEQ ID NOS: 36 to 38, respectively.

FIG. 65 shows the nucleotide sequence (upper case; SEQ ID NO: 100) and amino acid sequence (lower case; SEQ ID NO: 40) of a K5-70 VL gene that was prepared by gene synthesis. With regard to this nucleotide sequence, an AgeI site (ACC GGT) and a Kozak sequence (ACC ACC) were added to the 5' end, and a BsiWI site (CGT ACG) was added to the 3' end. The amino acid sequence is shown by single letter code. A signal peptide on the N-terminal side is shown in italics. The double-underlined aspartic acid (D) indicates the N-terminal amino acid residue of a mature peptide. The CDR sequences (underlined; RASQSIGTSIH (SEQ ID NO: 41), YASESIS (SEQ ID NO: 42), and QQSNSWPFT (SEQ ID NO: 43)) were determined in accordance with the definitions of Kabat et al. (as described above, U.S. Department of Health and Human Services, 1991). The amino acid sequences of CDR 1 to 3 of the clone K5-70 VL are shown in SEQ ID NOS: 41 to 43, respectively.

FIG. 66 shows the binding activity of ChK5-70, HuK5-70, HuVH/MuVL (in which the VL of the HuK5-70 antibody is substituted with the VL of the K5-70 antibody) and MuVH/HuVL (in which the VH of the HuK5-70 antibody is substituted with the VH of the K5-70 antibody) antibodies to hTROP-2. A 96-well plate was coated with a 0.1 μg/mL recombinant hTACSTD2-Fc-His protein. A culture supernatant of cells, in which test antibodies (ChK5-70, HuK5-70, HuVH/MuVL and MuVH/HuVL antibodies) had been transiently expressed, was diluted to result in antibody concentrations of 1, 0.1, 0.01 and 0.001 μg/mL. Thus, the diluted test antibodies were allowed to react with the antigen. (▲) ChK5-70 antibody, (Δ) MuVH/HuVL antibody, (○) HuVH/MuVL antibody and (●) HuK5-70 antibody.

FIG. 67 shows the amino acid sequences of HuK5-70 VH (SEQ ID NO: 75) and its amino acid substitution mutants. Amino acids are shown by single letter code. The amino acid of each amino acid substitution mutant, which is the same as that of the HuK5-70 VH, is indicated with the symbol "-," and only the substituted amino acids are shown by single letter code. The number in the upper position of the sequence indicates an amino acid number (Kabat et al., 1991).

Figure 68:
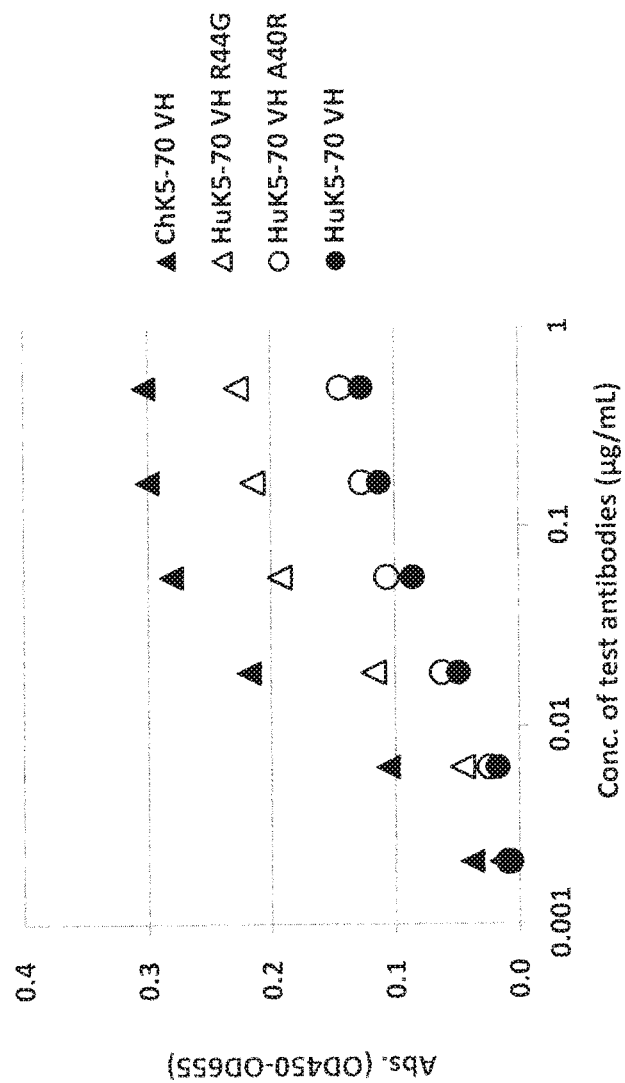

FIG. 68 shows the binding activity of ChK5-70, HuK5-70, HuK5-70 VH A40R (a mutant in which the alanine at position 40 of the VH of the HuK5-70 antibody is substituted with an arginine) and HuK5-70 VH R44G (a mutant in which the arginine at position 44 of the VH of the HuK5-70 antibody is substituted with a glycine) antibodies to hTROP-2. A 96-well plate was coated with a 0.1 μg/mL recombinant hTACSTD2-Fc-His protein. A culture supernatant of cells, in which test antibodies (ChK5-70, HuK5-70, HuK5-70 VH A40R and HuK5-70 VH R44G antibodies) had been transiently expressed, was diluted to result in concentrations from 0.5 μg/mL to a series of two-fold dilutions (six samples). Thus, the diluted test antibodies were allowed to react with the antigen. (▲) ChK5-70 antibody, (Δ) HuK5-70 VH R44G antibody, (○) HuK5-70 VH A40R antibody and (●) HuK5-70 antibody.

FIG. 69 shows the nucleotide sequence (upper case) and amino acid sequence (lower case) of a HuK5-70 VH R44G gene (a mutant in which the arginine at position 44 of the VH of the HuK5-70 antibody, SEQ ID NO: 75, is substituted with a glycine that was prepared by gene synthesis. With regard to this nucleotide sequence (SEQ ID NO: 74), an EcoRI site (GAA TTC) and a Kozak sequence (ACC ACC) were added to the 5' end, and an NheI site (GCT AGC) was added to the 3' end. The amino acid sequence is shown by single letter code. A signal peptide on the N-terminal side is shown in italics. The amino acid (Q: glutamine) on the N-terminal side of mature VH is double-underlined, and the CDR sequence (Kabat et al., 1991) is underlined.

Figure 70:
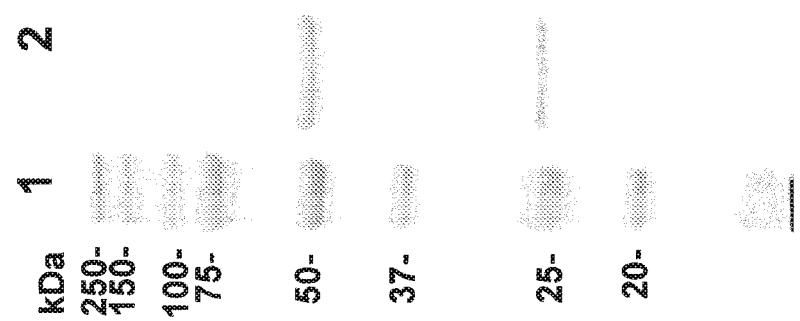

FIG. 70 shows SDS-PAGE performed on a purified HuK5-70-2 antibody. The HuK5-70-2 antibody (1 μg) was loaded on a 11% SDS-PAGE gel under reducing conditions. Lane 1: a molecular weight marker (Precision Plus Dual Standard (BIO-RAD)), lane 2: a HuK5-70-2 antibody. The numerical value on the left side of the figure indicates a molecular weight.

Figure 71:
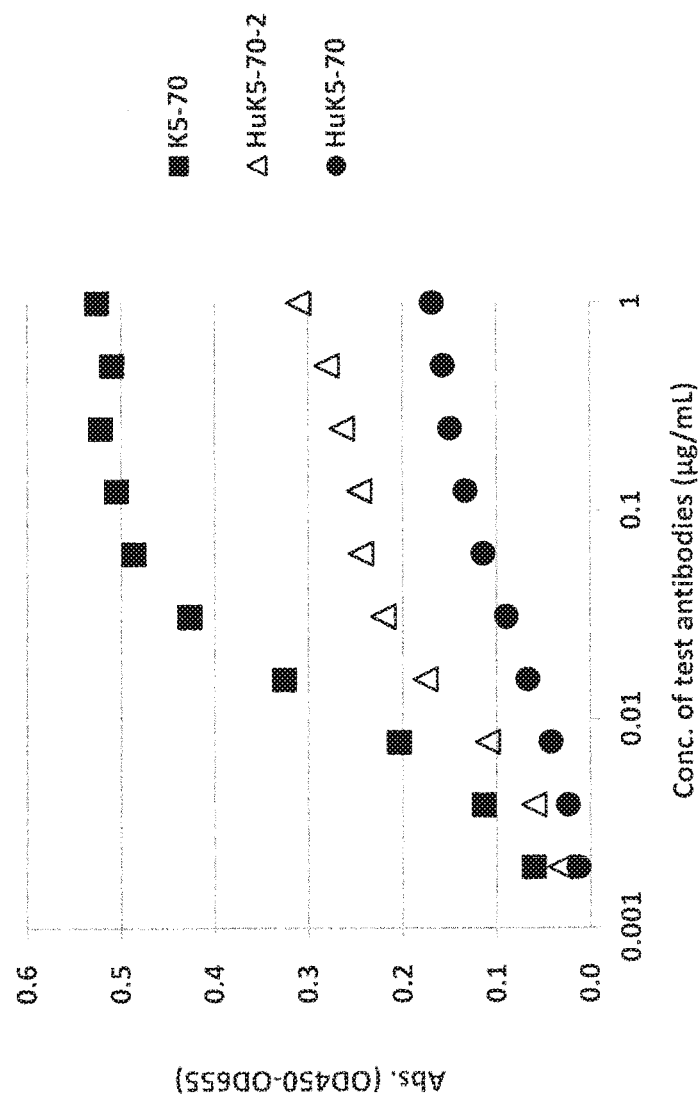

FIG. 71 shows the binding activity of K5-70, HuK5-70 and HuK5-70-2 antibodies to hTROP-2. A 96-well plate was coated with a 0.1 μg/mL recombinant hTACSTD2-Fc-His protein. The purified test antibodies (K5-70, HuK5-70 and HuK5-70-2 antibodies) were diluted to result in concentrations from 1 μg/mL to a series of two-fold dilutions (ten samples). Thus, the diluted test antibodies were allowed to react with the antigen. (■) K5-70 antibody, (Δ) HuK5-70-2 antibody, and (●) HuK5-70 antibody.

Figure 72A:
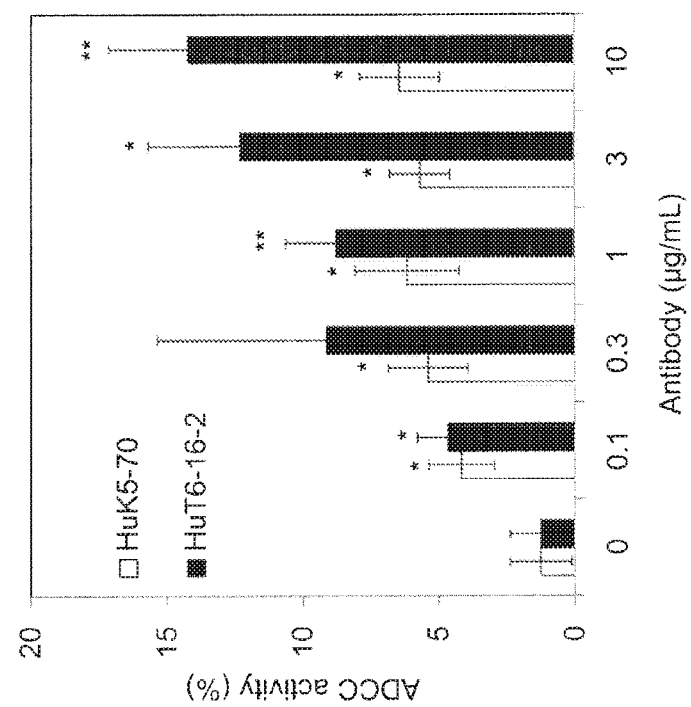

FIG. 72A shows the ADCC activity of humanized anti-hTROP-2 antibodies (open column: HuK5-70, and filled column: HuT6-16-2). More specifically, a HuK5-70 antibody and a HuT6-16-2 antibody (all of which were in concentrations of 0, 0.1, 0.3, 1, 3, and 10 μg/mL) and healthy human peripheral blood monocytes were added to a human colon cancer cell line SW480, and they were then cultured for 6 hours. Thereafter, the activity of LDH released into the culture supernatant was measured, so that the ADCC activity could be measured (a mean value±standard deviation (N=3), effector/target (E/T)=40). The antibody concentration that is 0 indicates non-addition of the antibody. *$P<0.05$, **$P<0.01$ (by Student's t-test).

FIG. 72B shows the ADCC activity of humanized anti-hTROP-2 antibodies (open column: HuK5-70, gray column: HuK5-70-2, and filled column: HuT6-16-2). More specifically, a HuK5-70 antibody, a HuK5-70-2 antibody and a HuT6-16-2 antibody (all of which were in concentrations of 0, 0.3, 1, 3, 10 and 30 μg/mL) and healthy human peripheral blood monocytes were added to a human pancreatic cancer cell line (PK-59), and they were then cultured for 6 hours. Thereafter, the activity of LDH released into the culture supernatant was measured, so that the ADCC activity could be measured (a mean value±standard deviation (N=3), effector/target (E/T)=40). The antibody concentration that is 0 indicates non-addition of the antibody. **$P<0.01$ (by Student's t-test).

FIG. 72C shows the ADCC activity of humanized anti-hTROP-2 antibodies (open column: HuK5-70, gray column: HuK5-70-2, and filled column: HuT6-16-2). More specifically, a HuK5-70 antibody, a HuK5-70-2 antibody and a HuT6-16-2 antibody (all of which were in concentrations of 0, 0.3, 1, 3, 10 and 30 μg/mL) and healthy human peripheral blood monocytes were added to a human prostate cancer cell line (PC-3), and they were then cultured for 6 hours. Thereafter, the activity of LDH released into the culture supernatant was measured, so that the ADCC activity could be measured (a mean value±standard deviation (N=3), effector/target (E/T)=40). The antibody concentration that is 0 indicates non-addition of the antibody. **$P<0.01$ (by Student's t-test).

DETAILED DESCRIPTION OF THE INVENTION

Hereinafter, the present invention will be described in detail. The following descriptions are not intended to limit the scope of the present invention. Other than the following examples, the present invention may be modified and may be carried out, as appropriate, within a range that does not impair the intention of the present invention The present specification includes all of the contents as disclosed in the specification of U.S. Provisional Patent Application No. 61/562,672 (filed on Nov. 22, 2011), which is a priority document of the present application.

In addition, all publications cited in the present specification, which include prior art documents and patent documents such as laid-open application publications and patent publications, are incorporated herein by reference in their entirety.

1. Summary of the Present Invention

As mentioned above, human TROP-2 (hTROP-2) is a single transmembrane, type 1 membrane protein having a full length of 323 amino acid residues. It has been known that an hTROP-2 gene and a gene product thereof are expressed in various types of cancer cells.

As mentioned above, it has been desired to develop an anti-hTROP-2 antibody (an anti-hTROP-2 monoclonal antibody) or the like having high anti-tumor activity in vivo. Under such circumstances, the present inventor performed a screening through an extremely large number of clones, and as a result, the inventor succeeded in obtaining a clone having high anti-tumor activity in vivo. Specifically, the present invention provides a monoclonal antibody, which specifically recognizes the extracellular region of hTROP-2 in vivo, and particularly, a monoclonal antibody exhibiting high affinity at a picomole (pM) order. The antibody of the present invention is extremely useful in that it is an anti-hTROP-2 monoclonal antibody (particularly, a humanized antibody), which exhibits significant tumor growth inhibitory activity at a lower dose than that of the existing anti-hTROP-2 antibody (for example, at a dosage of ¹/₂₀) when it is administered singly as a naked antibody, and which also exhibits significant tumor growth inhibitory activity on tumor-bearing mouse treatment models, in which multiple types of human cancer cells are used.

2. Production of Anti-hTROP-2 Antibody (1) Preparation of Antigen

Information regarding the amino acid sequence (SEQ ID NO: 2) of hTROP-2 is disclosed under "Accession number NP_002344" in the website of, for example, NCBI (GenBank). Information regarding a nucleotide sequence (SEQ ID NO: 1) encoding the amino acid sequence of hTROP-2 is disclosed under "Accession number NM_002353" in the same website as described above.

As an antigen, a polypeptide or peptide (which is also simply referred to as a peptide) comprising at least a portion (the entire or a part) of the amino acid sequence of hTROP-2 can be used, and preferably, a peptide comprising at least a portion (the entire or a part) of the amino acid sequence of the extracellular region of hTROP-2 can be used. The extracellular region (including a signal peptide) of hTROP-2 indicates a region comprising the amino acids at positions 1 to 274 from the amino acid sequence shown in SEQ ID NO: 2 (the signal peptide: the amino acids at positions 1 to 26). Herein, with regard to a peptide used as an antigen, the above description "at least a portion of the amino acid sequence" is not particularly limited in terms of length. For example, a region comprising the amino acids at positions 1 to 145 from the amino acid sequence shown in SEQ ID NO: 2, a region comprising the amino acids at positions 146 to 274 from the same amino acid sequence as described above, and the like are preferable.

A peptide used as an antigen may be produced either by chemical synthesis, or by synthesis according to a genetic engineering method using *Escherichia coli* or the like. A method well known to persons skilled in the art may be applied.

When a peptide is produced by chemical synthesis, it can be synthesized by a well known peptide synthesis method. In addition, either a solid-phase synthesis method or a liquid-phase synthesis method can be applied to the peptide synthesis. A commercially available peptide synthesizer (for example, PSSM-8 manufactured by Shimadzu Corporation, etc.) may also be used.

When a peptide is synthesized by a genetic engineering method, first, DNA encoding the peptide is designed and synthesized. The design and synthesis of such DNA can be carried out according to a PCR method, using a vector comprising an entire-length hTROP-2 gene or the like as a template, and also using primers designed to be able to synthesize a desired DNA region. Thereafter, the DNA is ligated to a suitable vector to obtain a recombinant vector used for protein expression, and this recombinant vector is then introduced into a host so that a gene of interest can be expressed therein, thereby obtaining a transformant (Sambrook J. et al., Molecular Cloning, A Laboratory Manual, 3rd edition, Cold Spring Harbor Laboratory Press, 2001).

As a vector, a phage or a plasmid capable of autonomously replicating in a host microorganism is used. Further, an animal virus or an insect virus vector can also be used. To produce a recombinant vector, a purified DNA may be cleaved with suitable restriction enzymes, and the thus cleaved DNA portion may be then inserted into the restriction enzyme site or the like of a suitable vector DNA, so as to ligate it to the vector. The type of a host used in transformation is not particularly limited, as long as it is able to express a gene of interest. Examples of such a host include bacteria (*Escherichia coli, Bacillus subtilis*, etc.), yeasts, animal cells (COS cells, CHO cells, etc.), insect cells, and insects. A mammal such as a goat may also be used as such a host. A method of introducing a recombinant vector into a host is publicly known.

The above-described transformant is cultured, and a peptide used as an antigen is then collected from the culture. The term "culture" is used herein to mean both (a) a culture supernatant, and (b) cultured cells, a cultured cell mass or a disintegrated product thereof.

After completion of the culture, when a peptide of interest is produced in a cell mass or in cells, the peptide is extracted by disintegrating the cell mass or the cells. On the other hand, when a peptide of interest is produced outside a cell mass or outside cells, a culture solution is directly used, or the cell mass or the cells are removed from the culture solution by centrifugation or the like. Thereafter, the peptide of interest can be isolated and purified by a single use of biochemical methods commonly used in the isolation and purification of peptides, such as ammonium sulfate precipitation, gel filtration, ion exchange chromatography and affinity chromatography, or by appropriately combining the aforementioned biochemical methods.

In the present invention, a peptide used as an antigen can also be obtained by in vitro translation using a cell-free synthesis system. In this case, two methods, namely, a method using RNA as a template and a method using DNA as a template (transcription/translation) can be applied. As such a cell-free synthesis system, a commercially available system, such as EXPRESSWAY™ system (Invitrogen), PURESYSTEM® (Post Genome Institute) or TNT® system (Promega) can be used.

The thus obtained peptide may bind to a suitable carrier protein such as bovine serum albumin (BSA), keyhole limpet hemocyanin (KLH), human thyroglobulin or chicken γ-globulin.

Moreover, the antigen may be a peptide consisting of an amino acid sequence comprising a deletion, substitution or addition of one or more amino acids with respect to the amino acid sequence of hTROP-2 (SEQ ID NO: 2) or a partial sequence thereof as described above. There can be used, for example, a peptide consisting of an amino acid sequence, in which one or more (preferably one or several (for example, 1 to 10, and more preferably 1 to 5)) amino acids are deleted, or one or more (preferably one or several (for example, 1 to 10, and more preferably 1 to 5)) amino acids are substituted with other amino acids, or one or more (preferably one or several (for example, 1 to 10, and more preferably 1 to 5)) other amino acids are added, with respect to the amino acid sequence of hTROP-2 or a partial sequence thereof.

In the present invention, a gene to be introduced into a cell or the like is a gene encoding an hTROP-2 protein or a partial fragment thereof, or a mutant protein thereof or a fragment thereof. As such a gene, a gene having the nucleotide sequence shown in SEQ ID NO: 1 or a partial sequence thereof can be used, for example.

Furthermore, as a gene to be introduced into a cell or the like, there may also be used a nucleotide sequence hybridizing under stringent conditions with a sequence complementary to the nucleotide sequence shown in SEQ ID NO: 1 and encoding a protein having hTROP-2 activity, or a partial sequence thereof.

The description "stringent conditions" is used herein to mean washing conditions after completion of the hybridization. As such stringent conditions, a salt (sodium) concentration in buffer is 10 to 500 mM and a temperature is 42° C. to 72° C., and preferably, the aforementioned salt condition is 50 to 300 mM and a temperature is 55° C. to 68° C.

Mutation can be introduced into a gene according to a known method such as a Kunkel method or a Gapped duplex method, using, for example, a mutation introduction kit which utilizes site-directed mutagenesis, such as GeneTailor™ Site-Directed Mutagenesis System (manufactured by Invitrogen) or TaKaRa Site-Directed Mutagenesis System (Mutan-K, Mutan-Super Express Km, etc.; manufactured by Takara Bio Inc.).

(2) Production of Polyclonal Antibody

The prepared antigen is administered to a mammal for immunization. The type of such a mammal is not particularly limited. For example, a rat, a mouse and a rabbit can be used, and among them, a mouse is preferable.

The dosage of the antigen per animal can be determined, as appropriate, depending on the presence or absence of an adjuvant. Examples of such an adjuvant include a Freund's complete adjuvant (FCA), a Freund's incomplete adjuvant (FIA) and an aluminum hydroxide adjuvant. Immunization can be carried out mainly by injecting the antigen into the vein, footpad, subcutis or abdominal cavity of an animal. In addition, immunization interval is not particularly limited, and immunization is carried out at intervals of several days to several weeks, preferably at intervals of 1 week, 1 to 10 times, and preferably 2 or 3 times. Three to seven days after the final immunization day, an antibody titer is measured by enzyme immunoassay (ELISA or EIA), radioimmunoassay (RIA) or other methods. On the date at which a desired antibody titer is obtained, blood can be collected to obtain antiserum. In the above-described method of collecting an antibody, if it is necessary to purify the antibody, the antibody can be purified by selecting a suitable method from known methods such as ammonium sulfate precipitation, ion exchange chromatography, gel filtration chromatography and affinity chromatography, or by combining the above-mentioned methods, as appropriate. Thereafter, the reactivity of a polyclonal antibody in the antiserum is measured by the ELISA method or the like.

(3) Production of Monoclonal Antibody (3-1) Collection of Antibody-Producing Cells The anti-hTROP-2 antibody of the present invention is not limited, but it is preferably a monoclonal antibody.

The prepared antigen is administered to a mammal, such as a rat, a mouse or a rabbit, for immunization. The dosage of the antigen per animal can be determined, as appropriate, depending on the presence or absence of an adjuvant. The same adjuvants as described above can be used herein. Also, the same immunization methods as described above can be applied herein. One to sixty days, and preferably, one to fourteen days after the final immunization day, antibody-producing cells are collected. Examples of such antibody-producing cells include splenic cells, lymph node cells and peripheral blood cells. Of these, lymph node cells and splenic cells are preferable.

(3-2) Cell Fusion

In order to obtain hybridomas (an antibody-producing cell line), the cell fusion of antibody-producing cells with myeloma cells is carried out. As myeloma cells to be fused with antibody-producing cells, commonly available established cells from animals such as mice can be used. The cell line used herein is preferably a cell line, which has drug selectivity, cannot survive in an unfused state in a HAT selective medium (containing hypoxanthine, aminopterin and thymidine), and can survive only in a state fused with antibody-producing cells.

Examples of myeloma cells include mouse myeloma cell lines such as P3-X63-Ag8.653, P3-X63-Ag8(X63), P3-X63-Ag8.U1(P3U1), P3/NS I/1-Ag4-1(NS1) and Sp2/0-Ag14 (Sp2/0). Myeloma cells can be selected, while taking into consideration the compatibility with antibody-producing cells, as appropriate.

Subsequently, myeloma cells are fused with antibody-producing cells. For such cell fusion, antibody-producing cells ($1 \times 10^6$ to $1 \times 10^7$ cells/mL) are mixed with myeloma cells ($2 \times 10^5$ to $2 \times 10^6$ cells/mL) in a medium for animal cells, such as DMEM or an RPMI-1640 medium containing no serum. The cell ratio between the antibody-producing cells and the myeloma cells (antibody-producing cells:myeloma cells) is not limited. In general, the cell ratio is preferably 1:1 to 10:1, and more preferably 3:1. Thereafter, a fusion reaction is carried out in the presence of a cell fusion promoter. As such a cell fusion promoter, polyethylene glycol having a mean molecular weight of 1,000 to 6,000 Dalton (D) or the like can be used. In addition, it is also possible to fuse antibody-producing cells with myeloma cells, employing a commercially available cell fusion apparatus which utilizes electrical stimulation (for example, electroporation).

(3-3) Selection and Cloning of Hybridomas

Hybridomas of interest are selected from the cells after the cell fusion treatment. As a method of selecting hybridomas, the cell suspension is appropriately diluted with, for example, a fetal bovine serum-containing RPMI-1640 medium, and the diluted solution is then dispersed on a microtiter plate. Thereafter, a selective medium is added to each well. While the selective medium is appropriately exchanged with a fresh one, culture is carried out. As a result, approximately 14 days after initiation of the culture on the selective medium, cells growing from the selective medium can be obtained as hybridomas.

Subsequently, screening is carried out to examine whether or not an antibody reacting with hTROP-2 is present in a culture supernatant of the growing hybridomas. The screening of hybridomas may be carried out according to an ordinary method, and thus, the screening method is not particularly limited. For example, an aliquot is collected from the culture supernatant of the growing hybridomas contained in the well, and screening is then carried out by ELISA, EIA, RIA or the like.

The cloning of the fused cells can be carried out by a limiting dilution method or the like. An antibody showing high reactivity with hTROP-2 is determined by flow cytometry or the like, and a hybridoma producing this antibody is then selected. The selected hybridoma is established as a clone.

(3-4) Collection of Monoclonal Antibody

As a method of culturing the established hybridoma and then collecting a monoclonal antibody from the obtained culture, a common cell culture method, an ascites formation method or the like can be adopted. The term "culture" is used herein to mean allowing hybridomas to grow in a culture dish or a culture bottle, or allowing hybridomas to grow in the abdominal cavity of an animal, as described below.

In the case of the cell culture method, hybridomas are cultured in a medium for animal cells, such as a 10% fetal bovine serum-containing RPMI-1640 medium, an MEM medium or a serum-free medium, under common culture conditions (for example, 37° C., 5% $CO_2$ concentration) for 7 to 14 days, and thereafter, an antibody can be obtained from the culture supernatant.

In the case of the ascites formation method, approximately $1 \times 10^7$ hybridomas are administered into the abdominal cavity of an animal of the same species as the mammal from which myeloma cells are derived, so that large quantities of hybridomas are allowed to proliferate. Thereafter, 2 to 3 weeks later, ascites is preferably collected.

In the above-described antibody collection methods, if it is necessary to purify the antibody, the antibody can be purified by appropriately selecting a suitable method from known methods such as ammonium sulfate precipitation, ion exchange chromatography, gel filtration and affinity chromatography, or by combining the above-mentioned methods.

(3-5) Selection of Clone Having Anti-Tumor Activity

The anti-hTROP-2 antibody of the present invention is an antibody having anti-tumor activity in vivo.

The term "anti-tumor activity" is used herein to mean activity of killing tumor cells (cancer cells) or activity of inhibiting tumor growth. Preferred examples of such anti-tumor activity include activity of inhibiting the growth of cancer cells and activity of inhibiting tumor angiogenesis. The type of human tumor (tumor cells), on which the antibody of the present invention is able to exhibit anti-tumor activity, includes various types of known human tumors, in which the expression of hTROP-2 has been confirmed. The type of such human tumor is not particularly limited. For example, one or two or more types selected from various human tumors such as human pancreatic cancer, human prostate cancer, human colorectal cancer, human breast cancer, human ovarian cancer, human lung cancer and human bile duct cancer are preferable; and one or two or more types selected from human pancreatic cancer, human colorectal cancer, human prostate cancer, human colorectal cancer, human breast cancer, human ovarian cancer and human lung cancer are more preferable. Human pancreatic cancer and/or human colorectal cancer are further preferable.

Moreover, the above-described tumor may be a recurrent cancer or a metastatic cancer. The antibody of the present invention is also able to exhibit excellent anti-tumor activity on these types of tumors.

The presence of anti-tumor activity in vivo can be confirmed, for example, by employing a tumor-bearing mouse (a mouse xenograft model), into the subcutis of which desired tumor cells have been transplanted, and then by administering the antibody as obtained above to the mouse. In this case, the antibody may be administered immediately after the transplantation of tumor cells (prevention models). Alternatively, it may be administered after confirming that the transplanted tumor has reached a predetermined volume (treatment models). The administration method is not limited. For example, the antibody may be administered once every three days, every one week, every ten days, or every two weeks, or by a single administration (only one time), at a dosage of 5 to 20 mg/kg body weight, via intraperitoneal administration or the like. In the case of prevention models, the presence or absence of anti-tumor activity and the level thereof can be evaluated based on tumor formation frequency and tumor volume. In the case of treatment models, the presence or absence of anti-tumor activity and the level thereof can be evaluated based on tumor volume.

In the present invention, a preferred example of the anti-hTROP-2 antibody having anti-tumor activity in vivo is an antibody in which the amino acid sequences of CDR 1 to 3 of the H chain V region thereof are shown in SEQ ID NOS: 36 to 38, respectively, and/or the amino acid sequences of CDR 1 to 3 of the L chain V region thereof are shown in SEQ ID NOS: 41 to 43, respectively. A preferred example of the H chain V region is an H chain V region consisting of the amino acid sequence shown in SEQ ID NO: 35. A preferred example of the L chain V region is an L chain V region consisting of the amino acid sequence shown in SEQ ID NO: 40.

As another embodiment of the anti-hTROP-2 antibody of the present invention, a preferred example is an antibody in which the amino acid sequences of CDR 1 to 3 of the H chain V region thereof are shown in SEQ ID NOS: 46 to 48, respectively, and/or the amino acid sequences of CDR 1 to 3 of the L chain V region thereof are shown in SEQ ID NOS: 51 to 53, respectively. A preferred example of the H chain V region is an H chain V region consisting of the amino acid sequence shown in SEQ ID NO: 45. A preferred example of the L chain V region is an L chain V region consisting of the amino acid sequence shown in SEQ ID NO: 50.

Likewise, as a further embodiment of the anti-hTROP-2 antibody of the present invention, a preferred example is an antibody in which the amino acid sequences of CDR 1 to 3 of the H chain V region thereof are shown in SEQ ID NOS: 56 to 58, respectively, and/or the amino acid sequences of CDR 1 to 3 of the L chain V region thereof are shown in SEQ ID NOS: 61 to 63, respectively. A preferred example of the H chain V region is an H chain V region consisting of the amino acid sequence shown in SEQ ID NO: 55. A preferred example of the L chain V region is an L chain V region consisting of the amino acid sequence shown in SEQ ID NO: 60.

Likewise, as a further embodiment of the anti-hTROP-2 antibody of the present invention, a preferred example is an antibody in which the amino acid sequences of CDR 1 to 3 of the H chain V region thereof are shown in SEQ ID NOS: 66 to 68, respectively, and/or the amino acid sequences of CDR 1 to 3 of the L chain V region thereof are shown in SEQ ID NOS: 71 to 73, respectively. A preferred example of the H chain V region is an H chain V region consisting of the amino acid sequence shown in SEQ ID NO: 65. A preferred example of the L chain V region is an L chain V region consisting of the amino acid sequence shown in SEQ ID NO: 70.

In the present invention, more specifically, preferred examples of an anti-hTROP-2 antibody having anti-tumor activity in vivo include: an anti-hTROP-2 monoclonal antibody (clone name: K5-70) produced by a hybridoma with Accession number FERM BP-11251; an anti-hTROP-2 monoclonal antibody (clone name: K5-107) produced by a hybridoma with Accession number FERM BP-11252; an anti-hTROP-2 monoclonal antibody (clone name: K5-116-2-1) produced by a hybridoma with Accession number FERM BP-11253; an anti-hTROP-2 monoclonal antibody (clone name: T6-16) produced by a hybridoma with Accession number FERM BP-11346; and an anti-hTROP-2 monoclonal antibody (clone name: T5-86) produced by a hybridoma with Accession number FERM BP-11254.

Herein, the hybridoma with Accession number FERM BP-11251 was named as "Mouse-Mouse Hybridoma K5-70" and was deposited on May 12, 2010; the hybridoma with Accession number FERM BP-11252 was named as "Mouse-Mouse Hybridoma K5-107" and was deposited on May 12, 2010; the hybridoma with Accession number FERM BP-11253 was named as "Mouse-Mouse Hybridoma K5-116-2-1" and was deposited on May 12, 2010; the hybridoma with Accession number FERM BP-11346 was named as "Mouse-Mouse Hybridoma T6-16" and was deposited on Mar. 1, 2011; and the hybridoma with Accession number FERM BP-11254 was named as "Mouse-Mouse Hybridoma T5-86" and was deposited on May 12, 2010. All of these hybridomas were deposited with the International Patent Organism Depositary (IPOD), the National Institute of Advanced Industrial Science and Technology, an Independent Administrative Institution under the Ministry of Economy, Trade and Industry (the AIST, Tsukuba Central 6, Higashi 1-1-1, Tsukuba, Ibaraki, Japan, postal code: 305-8566).

Still further, another preferred example of the anti-hTROP-2 antibody of the present invention is an anti-hTROP-2 antibody that binds to a site (e.g. an epitope), to which a monoclonal antibody produced by the hybridoma having accession No. FERM BP-11251, FERM BP-11252, FERM BP-11253, FERM BP-11346 or FERM BP-11254 binds (recognizes).

Preferred examples of such an epitope will be given in (3-6) below.

(3-6) Epitope of Anti-hTROP-2 Antibody

The type of an epitope (an antigenic determinant) of the anti-hTROP-2 antibody of the present invention is not limited, as long as it is at least a portion of hTROP-2 as an antigen. For example, such an epitope is preferably at least a portion of a region formed by removing a region consisting of amino acids at positions 252 to 260 from the amino acid sequence of hTROP-2 shown in SEQ ID NO: 2, more preferably at least a portion of a region consisting of amino acids at positions 1 to 69 or at least a portion of a region consisting of amino acids at positions 100 to 274 (except for a region consisting of amino acids at position 252 to 260), and further preferably at least a portion of a region consisting of amino acids at positions 27 to 69 or a region consisting of amino acids at positions 109 to 206. Particularly preferred examples of the above-described epitope include a region consisting of amino acids at positions 43 to 65, a region consisting of amino acids at positions 152 to 165, a region consisting of amino acids at positions 171 to 183, a region consisting of amino acids at positions 109 to 120, a region consisting of amino acids at positions 194 to 207, a region consisting of amino acids at positions 43 to 56, and a portion comprising such a region, in the amino acid sequence of hTROP-2 shown in SEQ ID NO: 2. Further particularly preferred examples include a region consisting of amino acids at positions 43 to 65, a region consisting of amino acids at positions 152 to 165, a region consisting of amino acids at positions 171 to 183, a region consisting of amino acids at positions 109 to 120, and a portion comprising such a region. An anti-hTROP-2 antibody, which recognizes the above-described regions (binds to the above-described regions or portions comprising such regions), has high internalization activity into tumor cells, for example, and thus it is extremely useful as an immunoconjugate as described later.

(3-7) Characteristics of Anti-hTROP-2 Antibody

As described above, the anti-hTROP-2 antibody of the present invention is an antibody having high anti-tumor activity in vivo at a low dose. Specifically, it is preferable that the present anti-hTROP-2 antibody exhibits tumor growth inhibitory activity of 50% or more (preferably 80% or more, more preferably 90% or more, further preferably 95% or more, and particularly preferably almost 100% (for example, 98% or more, or 99% or more)) at a dose (as a naked antibody) of 20 mg/kg body weight or less (preferably 10 mg/kg body weight or less, more preferably 5 mg/kg body weight or less, and further preferably 1 mg/kg body weight or less) with respect to a tumor-bearing animal model.

Herein, the tumor growth inhibitory activity (%) can be calculated, for example, by the following formula:

Tumor growth inhibitory activity (%)=100−[(tumor volume or tumor weight of antibody administration group)/(tumor volume or tumor weight of control group)]×100

In addition, the anti-hTROP-2 antibody of the present invention preferably has anti-tumor activity on two or more types of human tumor cell lines. The type of such a human tumor cell line is not limited. For example, such human tumor cell lines are at least two types selected from the group consisting of various types of human pancreatic cancer cell lines, human prostate cancer cell lines, human colorectal cancer cell lines, human breast cancer cell lines, human ovarian cancer cell lines, human lung cancer cell lines and human bile duct cancer cell lines. Specifically, preferred examples of such human tumor cell lines include at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT 116, a human breast cancer cell line JIMT-1, a human breast cancer cell line HCC1143, a human breast cancer cell line MCF-7, a human breast cancer cell line MDA-MB-468, a human prostate cancer cell line DU145, a human prostate cancer cell line PC-3, a human ovarian cancer cell line SK-OV-3, a human lung cancer cell line Calu-3 and a human bile duct cancer cell line TFK-1. Of these, as the above-described two or more types of human tumor cell lines, at least two types selected from the group consisting of the human pancreatic cancer cell line PK-59, the human pancreatic cancer cell line BxPC-3, the human colon cancer cell line SW480, the human lung cancer cell line Calu-3, the human breast cancer cell line MDA-MB-468 and the human ovarian cancer cell line SK-OV-3 are more preferable.

Moreover, the anti-hTROP-2 antibody of the present invention has a dissociation constant (Kd value) of preferably $1.0 \times 10^{-10}$ M or less, more preferably $1.0 \times 10^{-11}$ M or less, and further preferably $1.0 \times 10^{-12}$ M or less. Herein, the binding ability (affinity) of the antibody can be measured in the form of a dissociation constant (Kd value), a dissociation rate constant (Kdiss [1/Sec]) or an association rate constant (Kass [1/M.Sec]), for example, by Scatchard analysis or surface plasmon resonance sensor called Biacore. As such Biacore apparatuses, Biacore 3000, Biacore 2000, Biacore X, Biacore J and Biacore Q (all of which were manufactured by Biacore) may be used, for example. It is preferable that the antibody have a dissociation constant (Kd value) that is as small as possible because it could have high binding ability (affinity). The Kd value is determined based on the two parameters of Kdiss and Kass, and it can be expressed in the formula: Kd[M]=Kdiss/Kass. As a method of calculating the Kd value, the method described in the Examples as described later (specifically, Example 10) can be preferably adopted.

(4) Genetically Recombinant Antibody and Antibody Fragment (4-1) Genetically Recombinant Antibody In a preferred embodiment of the anti-hTROP-2 antibody of the present invention, there is provided a genetically recombinant antibody. The type of such a genetically recombinant antibody is not limited. Examples include a chimeric antibody, a humanized antibody, and a human antibody.

A chimeric antibody (that is, a humanized chimeric antibody) is an antibody formed by ligating (conjugating) the variable region of a mouse-derived antibody to the constant region of a human-derived antibody (please refer to Proc. Natl. Acad. Sci. U.S.A. 81, 6851-6855, (1984), etc.). When such a chimeric antibody is produced, the thus ligated antibody can be easily constructed by a genetic recombination technique.

When a humanized antibody is produced, a complementarity determining region (CDR) is transplanted from the variable region of a mouse antibody into the variable region of a human antibody, so as to produce a reconstructed variable region, in which a framework region (FR) is derived from the human and CDR is derived from the mouse (what is called CDR grafting (CDR transplantation)). Subsequently, the thus humanized, reconstructed human variable region is ligated to a human constant region. Such a method for producing a humanized antibody is well known in the present technical field (please refer to see Nature, 321, 522-525 (1986); J. Mol. Biol., 196, 901-917 (1987); Queen C et al., Proc. Natl. Acad. Sci. USA, 86: 10029-10033 (1989); J P Patent Publication (Kohyo) No. 4-502408 A (1992) (Japanese Patent No. 2828340; Queen et al.), etc.).

Herein, the type of a CDR sequence derived from the mouse, which can be used in the humanized anti-hTROP-2 antibody of the present invention, is not particularly limited. For example, the amino acid sequences shown in SEQ ID NOS: 36 to 38 or the amino acid sequences shown in SEQ ID NO: 66 to 68 are preferably used as the CDR 1 to 3 of the H chain V region (VH), respectively. The amino acid sequences shown in SEQ ID NOS: 41 to 43 or the amino acid sequences shown in SEQ ID NO: 71 to 73 are preferably used as the CDR 1 to 3 of the L chain V region (VL), respectively.

In addition, preferred examples of the amino acid sequence of an H chain V region in a humanized reconstructed human variable region include: the amino acid sequence shown in SEQ ID NO: 92 (comprising CDR 1 to 3 consisting of the amino acid sequences shown in SEQ ID NOS: 36 to 38; the amino acid sequence further comprising a signal peptide is shown in SEQ ID NO: 75); the amino acid sequence shown in SEQ ID NO: 98 (comprising CDR 1 to 3 consisting of the amino acid sequences shown in SEQ ID NOS: 36 to 38; the amino acid sequence further comprising a signal peptide is shown in SEQ ID NO: 97); the amino acid sequence shown in SEQ ID NO: 94 (comprising CDR 1 to 3 consisting of the amino acid sequences shown in SEQ ID NOS: 66 to 68; the amino acid sequence further comprising a signal peptide is shown in SEQ ID NO: 79); and the amino acid sequence shown in SEQ ID NO: 95 (comprising CDR 1 to 3 consisting of the amino acid sequences shown in SEQ ID NOS: 66 to 68; the amino acid sequence further comprising a signal peptide is shown in SEQ ID NO: 81). Herein, the above-mentioned amino acid sequence of the H chain V region shown in SEQ ID NO: 98 is a modified amino acid sequence in which the arginine (R) at position 44 of the above-mentioned amino acid sequence of the H chain V region shown in SEQ ID NO: 92 is substituted with a glycine (G).

Likewise, preferred examples of the amino acid sequence of an L chain V region in a humanized reconstructed human variable region include: the amino acid sequence shown in SEQ ID NO: 93 (comprising CDR 1 to 3 consisting of the amino acid sequences shown in SEQ ID NOS: 41 to 43; and the amino acid sequence further comprising a signal peptide is shown in SEQ ID NO: 77); and the amino acid sequence shown in SEQ ID NO: 96 (comprising CDR 1 to 3 consisting of the amino acid sequences shown in SEQ ID NOS: 71 to 73; the amino acid sequence further comprising a signal peptide is shown in SEQ ID NO: 83).

Herein, preferred examples of the humanized anti-hTROP-2 antibody of the present invention include: (i) a humanized anti-hTROP-2 antibody, in which the amino acid sequence of the H chain V region is shown in SEQ ID NO: 92 and the amino acid sequence of the L chain V region is shown in SEQ ID NO: 93; and (ii) a humanized anti-hTROP-2 antibody, in which the amino acid sequence of the H chain V region is shown in SEQ ID NO: 98 and the amino acid sequence of the L chain V region is shown in SEQ ID NO: 93. In particular, the humanized anti-hTROP-2 antibody described in (ii) above, in which the amino acid sequence of the H chain V region is shown in SEQ ID NO: 98, has an improved avidity (that is flexibility of the movement of two antigen-binding arms) and has high antigen-binding activity, and thus, this antibody is particularly preferable.

Also, other preferred examples of the humanized anti-hTROP-2 antibody of the present invention include: (iii) a humanized anti-hTROP-2 antibody, in which the amino acid sequence of the H chain V region is shown in SEQ ID NO: 94 and the amino acid sequence of the L chain V region is shown in SEQ ID NO: 96; and (ii) a humanized anti-hTROP-2 antibody, in which the amino acid sequence of the H chain V region is shown in SEQ ID NO: 95 and the amino acid sequence of the L chain V region is shown in SEQ ID NO: 96.

In general, in the case of a human antibody (a complete human antibody), its structure comprising a Hyper Variable region that is the antigen-binding site of a V region, other parts of the V region, and a constant region is the same as the structure of the antibody of a human. However, such a Hyper Variable site may also be derived from other animals. A technique of producing a human antibody is publicly known, and a method for producing gene sequences that are common in humans by genetic engineering has been established. A human antibody can be obtained, for example, by a method using a human antibody-producing mouse that has human chromosomal fragments comprising the genes of the H chain and L chain of the human antibody (please refer to Tomizuka, K. et al., Nature Genetics, (1977) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y., Matsuda, T. and Iijima, S. eds.), Kluwer Academic Publishers; Tomizuka, K. et. al., Proc. Natl. Acad. Sci. USA, (2000) 97, 722-727, etc.), or by a method of obtaining a phage display-derived human antibody selected from a human antibody library (please refer to Wormstone, I. M. et. al, Investigative Ophthalmology & Visual Science., (2002) 43 (7), 2301-8; Carmen, S. et. al., Briefings in Functional Genomics and Proteomics, (2002) 1 (2), 189-203; Siriwardena, D. et. al., Opthalmology, (2002) 109 (3), 427-431, etc.).

In the case of the aforementioned chimeric antibody, humanized antibody and human antibody, the N-glycoside-linked sugar chain in the antibody Fc region is preferably a sugar chain, in which fucose does not bind to N-acetylglucosamine at the reducing terminal thereof. A specific example is an antibody consisting of genetically recombinant antibody molecules, which has, in the Fc region of the antibody molecules, a sugar chain in which the position 1 of the fucose does not bind to the position 6 of the N-acetylglucosamine at the reducing terminal of the N-glycoside-linked sugar chain via an a bond. Such an antibody is able to significantly improve ADCC activity. This point (the characteristics of the N-glycoside-linked sugar chain in the antibody Fc region) is preferable also for the aforementioned polyclonal antibody and monoclonal antibody.

(4-2) Antibody Fragment

The anti-hTROP-2 antibody fragment (partial fragment) of the present invention is included in the antibody of the present invention. Herein, the antibody fragment of the present invention has binding activity to hTROP-2 (namely, it is able to bind to hTROP-2) and also has anti-tumor activity in vivo, as in the case of the anti-hTROP-2 antibody of the present invention.

The fragment of the antibody means a region of a portion of an anti-hTROP-2 polyclonal antibody or anti-hTROP-2 monoclonal antibody (namely, an antibody fragment derived from the anti-hTROP-2 antibody of the present invention). Examples of such an antibody fragment include peptides comprising, as at least a portion thereof, Fab, Fab', F(ab')$_2$, Fv (variable fragment of antibody), a single-stranded antibody (an H chain, an L chain, an H chain V region, and an L chain V region, etc.), scFv, diabody (scFv dimer), dsFv (a disulfide-stabilized V region), and a complementarity determining region (CDR).

Fab is an antibody fragment with a molecular weight of approximately 50,000 having antigen-binding activity, which is formed by binding about a half on the N-terminal side of the H chain to the entire L chain via a disulfide bond, among fragments obtained by treating antibody molecules with a protease, papain. In addition, it is also possible to produce such Fab by inserting DNA encoding the Fab of an antibody into a prokaryote expression vector or a eukaryote expression vector, and then introducing the vector into a prokaryote or a eukaryote so as to allow the DNA to express therein.

F(ab')$_2$ is an antibody fragment with a molecular weight of approximately 100,000 having antigen-binding activity, whose size is slightly greater than Fab that binds to Fab via disulfide bond in the hinge region, among fragments obtained by treating antibody molecules with a protease, pepsin. In addition, it is also possible to produce such F(ab')$_2$ by the thioether bond or disulfide bond of Fab, as described later.

Fab' is an antibody fragment with a molecular weight of approximately 50,000 having antigen-binding activity, which is formed by cleaving the disulfide bond in the hinge region of the aforementioned F(ab')$_2$. In addition, it is also possible to produce such Fab' by inserting DNA encoding the Fab' fragment of an antibody into a prokaryote expression vector or a eukaryote expression vector, and then introducing the vector into a prokaryote or a eukaryote so as to allow the DNA to express therein.

scFv is an antibody fragment having antigen-binding activity, which is a VH-P-VL or VL-P-VH polypeptide formed by ligating a single H chain V region (VH) to a single L chain V region (VL) using a suitable peptide linker (P). Such scFv can be produced by obtaining cDNA encoding the VH and VL of an antibody, constructing DNA encoding scFv, inserting the DNA into a prokaryote expression vector or a eukaryote expression vector, and then introducing the vector into a prokaryote or a eukaryote so as to allow the DNA to express therein.

Diabody is an antibody fragment formed by dimerization of scFv, which has divalent antigen-binding activities. Such divalent antigen-binding activities may be identical to each other, or they may also be different from each other. Such diabody can be produced by obtaining cDNA encoding the VH and VL of an antibody, constructing DNA encoding scFv such that the length of the amino acid sequence of P is 8 residues or less, inserting the DNA into a prokaryote expression vector or a eukaryote expression vector, and then introducing the vector into a prokaryote or a eukaryote so as to allow the DNA to express therein.

dsFv is an antibody fragment formed by binding polypeptides, in which one amino acid residue in each of VH and VL has been substituted with a cysteine residue, to each other via a disulfide bond between the cysteine residues. The amino acid residue to be substituted with cysteine residues can be selected based on estimation of the three-dimensional structure of the antibody according to the method of Reiter et al. (Protein Engineering, 7, 697-704, 1994). Such dsFv can be produced by obtaining cDNA encoding the VH and VL of an antibody, constructing DNA encoding dsFv, inserting the DNA into a prokaryote expression vector or a eukaryote expression vector, and then introducing the vector into a prokaryote or a eukaryote so as to allow the DNA to express therein.

A peptide comprising a CDR comprises at least one region of CDRs of VH (CDR 1 to 3) and CDRs of VL (CDR 1 to 3). More preferred examples of such a peptide include a peptide comprising all of the CDRs of VH and a peptide comprising all of the CDRs of VL. A particularly preferred example of the peptide is a peptide comprising all of the CDRs of VH and VL (total 6 regions). Preferred examples of the amino acid sequence of such a CDR include the amino acid sequences shown in SEQ ID NOS: 36 to 38, 41 to 43, 46 to 48, 51 to 53, 56 to 58, 61 to 63, 66 to 68, and 71 to 73, as described above. A peptide comprising multiple CDRs can be bound to one another, directly or via a suitable peptide linker. Such a peptide comprising CDR can be produced by constructing DNA encoding the VH and VL of an antibody, inserting the DNA into a prokaryote expression vector or a eukaryote expression vector, and then introducing the expression vector into a prokaryote or a eukaryote so as to allow the DNA to express therein. Moreover, such a peptide comprising CDR can also be produced by chemical synthesis methods such as a Fmoc method (a fluorenylmethyloxycarbonyl method) and a tBoc method (a t-butyloxycarbonyl method).

The antibody fragment of the present invention, as is, may be an antibody fragment, which comprises a part of or the entire antibody Fc region in which fucose does not bind to N-acetylglucosamine at the reducing terminal of an N-glycoside-linked sugar chain. Otherwise, the antibody fragment of the present invention may also be a fusion protein, in which the aforementioned antibody fragment is fused with a part of or the entire antibody Fc region in which fucose does not bind to N-acetylglucosamine at the reducing terminal of an N-glycoside-linked sugar chain. Such an antibody fragment is able to significantly improve ADCC activity, and thus it is preferable.

Hereinafter, in the descriptions of the present specification, the aforementioned antibody fragments are also included in the anti-hTROP-2 antibody of the present invention.

3. Polynucleotide, Recombinant Vector and Transformant

In the present invention, a polynucleotide (a gene, DNA) encoding the above-described anti-hTROP-2 antibody of the present invention or an antibody fragment thereof can also be provided. Specifically, the present polynucleotide is preferably a polynucleotide which comprises a nucleotide sequence encoding each amino acid sequence exemplified as the above-described anti-hTROP-2 antibody of the present invention or an antibody fragment thereof. Moreover, the polynucleotide of the present invention may be either a polynucleotide consisting of a polynucleotide alone encoding the anti-hTROP-2 antibody of the present invention or an antibody fragment thereof, or a polynucleotide which comprises the present polynucleotide as a portion thereof and also comprises known nucleotide sequences necessary for gene expression (e.g. a transcriptional promoter, an SD sequence, a Kozak sequence, a terminator, etc.). Thus, the type of the present polynucleotide is not limited.

With regard to the polynucleotide encoding the anti-hTROP-2 antibody of the present invention or an antibody fragment thereof, the codon corresponding to individual amino acids after translation is not particularly limited. The polynucleotide may comprise nucleotide DNA showing a codon commonly used in mammals such as a human (preferably, a frequently-used codon), or may also comprise nucleotide DNA showing a codon commonly used in microorganisms such as *Escherichia coli* or yeast, plants and the like (preferably, a frequently-used codon).

In the present invention, a recombinant vector comprising the above-described polynucleotide of the present invention, or a transformant comprising the recombinant vector, can also be provided.

A transcriptional promoter, an SD sequence (in a case in which the host is a prokaryotic cell) and a Kozak sequence (in a case in which the host is a eukaryotic cell) may previously be ligated to the upstream of a polynucleotide (a gene, DNA) to be incorporated into an expression vector used as a recombinant vector. Moreover, a terminator may be ligated to the downstream of the polynucleotide. Furthermore, an enhancer, a splicing signal, a poly(A) additional signal, a selective marker and the like may also be ligated to the polynucleotide. Individual elements necessary for gene expression, such as the above-described transcriptional promoter, may be comprised in the present polynucleotide from the beginning. When these elements are originally comprised in an expression vector, they may be used. Thus, the usage of individual elements is not particularly limited.

As methods of incorporating the present polynucleotide into an expression vector, various types of methods utilizing known genetic recombination techniques, such as a method using restriction enzymes or a method using topoisomerase, can be adopted. The type of an expression vector is not limited, as long as it is able to retain a polynucleotide (a gene, DNA) encoding the anti-hTROP-2 antibody of the present invention or an antibody fragment thereof, and a vector suitable for host cells to be used can be selected, as appropriate, and can be used. Examples of such an expression vector include plasmid DNA, bacteriophage DNA, retrotransposon DNA, a retrovirus vector and artificial chromosomal DNA.

Subsequently, the thus constructed recombinant vector is introduced into a host to obtain a transformant, and the obtained transformant is then cultured, so that the anti-hTROP-2 antibody of the present invention or an antibody fragment thereof can be expressed. It is to be noted that the term "transformant" is used in the present invention to mean a host into which a foreign gene has been introduced. Examples of such a transformant include: a host into which a foreign gene has been introduced by introduction of plasmid DNA or the like (transformation); and a host into which a foreign gene has been introduced by infecting the host with various types of viruses and phages (transduction).

The type of a host is not limited, as long as it is able to express the anti-hTROP-2 antibody of the present invention or an antibody fragment thereof, after the above-described recombinant vector has been introduced into the host. Thus, a host can be selected, as appropriate. Examples of such a host include known hosts such as various types of animal cells such as a human or a mouse, and various types of plant cells, bacteria, yeasts and plant cells.

When animal cells are used as host cells, examples of such animal cells include: human fibroblasts, human embryonic kidney cells, HEK293 cells, 293F cells, CHO cells, monkey COS-7 cells, Vero, mouse L cells, rat GH3 and human FL cells. Moreover, insect cells such as Sf9 cells or Sf21 cells may also be used as host cells.

When bacteria are used as hosts, examples of such bacteria include *Escherichia coli* and *Bacillus subtilis*.

When yeast is used as a host, examples of such yeast include *Saccharomyces cerevisiae* and *Schizosaccharomyces pombe*.

When plant cells are used as host cells, tobacco BY-2 cells are used for example.

The method of obtaining a transformant is not limited, and it can be selected, as appropriate, while taking into consideration a combination of the type of a host and the type of an expression vector. Preferred examples of the method of obtaining a transformant include electroporation, lipofection, a heat shock method, PEG, a calcium phosphate method, a DEAE dextran method, and a method of infecting a host with various types of viruses such as DNA virus or RNA virus.

In the obtained transformant, the codon type of a polynucleotide contained in a recombinant vector comprised may be identical to or different from the codon type of a host used. Thus, the codon type is not limited.

4. Preparation of Antibody-Drug Conjugate

As an immunoconjugate prepared using the aforementioned anti-hTROP-2 antibody of the present invention, there can be provided an antibody-drug conjugate, which comprises the aforementioned antibody and a substance (a compound, etc.) having anti-tumor activity and/or cell-killing activity. It is to be noted that a conjugate formed by previously preparing each of the aforementioned antibody molecule and the aforementioned substance having anti-tumor activity and/or cell-killing activity, separately, and then combining them, is generally referred to as an immunoconjugate. On the other hand, a conjugate obtained by ligating a protein toxin used as such a substance having anti-tumor activity and/or cell-killing activity to an antibody gene on a gene according to a genetic recombination technique, so as to allow it to express as a single protein (a fusion protein), is generally referred to as an immunotoxin.

Examples of a substance having anti-tumor activity include doxorubicin, calicheamicin, mitomycin C, Auristatin E and radioactive isotope (RI). Examples of a substance having cell-killing activity include saporin, lysine, *pseudomonas* exotoxin, diphtheria toxin and radioactive isotope (RI). Of these, saporin and *pseudomonas* exotoxin are preferably used. The type of RI having anti-tumor activity and/or cell-killing activity is not particularly limited, and examples of such RI include $^{90}$Y, $^{111}$In, $^{125}$I, $^{3}$H, $^{35}$S, $^{14}$C, $^{186}$Re, $^{188}$Re, $^{189}$Re, $^{177}$Lu, $^{67}$Cu, $^{212}$Bi, $^{213}$Bi, $^{211}$At, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{94m}$Tc, $^{121m}$Te, $^{122m}$Te, $^{125m}$Te, $^{165}$Tm, $^{167}$Tm, $^{168}$Tm, $^{111}$Ag, $^{197}$Pt, $^{109}$Pd, $^{32}$P, $^{33}$P, $^{47}$Sc, $^{153}$Sm, $^{177}$Lu, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{18}$F, $^{75}$Se, $^{201}$Tl, $^{225}$Ac, $^{76}$Br, $^{86}$Y, $^{169}$Yb, $^{166}$Dy, $^{212}$Pb and $^{223}$Ra.

A method for producing an antibody-drug conjugate is not limited. For example, a method of coupling an antibody with a drug via a disulfide bond or a hydrazone bond is applied.

The aforementioned anti-hTROP-2 antibody of the present invention is excellent in terms of internalization activity into target tumor cells that express hTROP-2. Thus, by previously combining a substance having anti-tumor activity and cell-killing activity with the anti-hTROP-2 antibody, it becomes possible to allow such a substance to directly and highly selectively act on the tumor cells. The antibody-drug conjugate of the present invention is extremely excellent in terms of ability to deliver the agent to the target tumor cells.

The internalization activity into cells can be evaluated by fluorescently labeling an antibody with rhodamine or the like and then observing the migratory behavior and localization of the antibody using a fluorescence microscope or the like.

Moreover, in the present invention, in addition to the aforementioned antibody-drug conjugate, there can also be provided an antibody fragment-drug conjugate, in which the aforementioned antibody fragment is used instead of an antibody. With regard to the details of such an antibody fragment-drug conjugate, the descriptions of the aforementioned antibody-drug conjugate can be applied, as appropriate.

Hereinafter, in the descriptions of the present specification, such an antibody fragment-drug conjugate is also included in the antibody-drug conjugate of the present invention.

5. Pharmaceutical Composition

The anti-hTROP-2 antibody and antibody-drug conjugate of the present invention are useful as active ingredients contained in a pharmaceutical composition.

The pharmaceutical composition is useful as a pharmaceutical composition for treating and/or diagnosing a tumor. In particular, since the anti-hTROP-2 antibody of the present invention and an antibody-drug conjugate comprising the aforementioned antibody have excellent tumor growth inhibitory activity as such anti-tumor activity, they are preferably used in the treatment of tumor. That is to say, the anti-hTROP-2 antibody and antibody-drug conjugate of the present invention are useful as active ingredients contained in a tumor therapeutic agent and a tumor diagnostic agent. It is to be noted that the above-described treatment of tumor includes inhibition of tumor growth and suppression of tumor growth. Specifically, if it is a tumor therapeutic agent, examples of the tumor therapeutic agent include a tumor growth inhibitor and a tumor growth suppressor.

It is preferable to provide the pharmaceutical composition of the present invention in the form of a pharmaceutical composition comprising the anti-hTROP-2 antibody and/or antibody-drug conjugate of the present invention as active ingredient(s), and further comprising a pharmacologically acceptable carrier. In addition, the pharmaceutical composition of the present invention can be used in combination with known anti-tumor agents. By such a combined use, a higher anti-tumor effect can be obtained.

Target diseases (tumors), to which the pharmaceutical composition of the present invention is applied, include: the aforementioned various types of known human tumors, in which the expression of hTROP-2 has previously been confirmed. Among others, one or two or more types selected from various types of human tumors such as human pancreatic cancer, human prostate cancer, human colorectal cancer, human breast cancer, human ovarian cancer, human lung cancer and human bile duct cancer are particularly preferable. Such target disease may be a single disease, or two or more diseases may be developed in combination. Moreover, the target tumor may be a recurrent cancer or a metastatic cancer. The pharmaceutical composition of the present invention (further, the anti-hTROP-2 antibody and/or antibody-drug conjugate of the present invention) can be effectively used as a therapeutic agent and a diagnostic agent for a recurrent cancer or a metastatic cancer.

Examples of the "pharmacologically acceptable carrier" include an excipient, a diluent, an extender, a disintegrator, a stabilizer, a preservative, a buffer, an emulsifier, an aromatic, a coloring agent, a sweetener, a thickener, a corrigent, a solubilizer and other additives. Using one or more types of such carriers, a pharmaceutical composition can be prepared in the form of an injection, a liquid agent, a capsule, a suspension, an emulsion, a syrup, etc. These pharmaceutical compositions can be administered orally or parenterally. Another form for parenteral administration is, for example, an injection comprising one or more active ingredients, which is prepared by an ordinary method. Such an injection can be produced by dissolving or suspending the present antibody in a pharmacologically acceptable carrier such as a normal saline solution or a commercially available distilled water used for injection.

In particular, when an antibody fragment derived from the anti-hTROP-2 antibody of the present invention (particularly, an antibody fragment with a low molecular weight) is administered into a living body, a colloidal dispersion system can be used in addition to the aforementioned components. Such a colloidal dispersion system is anticipated to have an effect of enhancing the stability of a compound (an antibody fragment) in a living body or an effect of efficiently transporting such a compound to a specific organ, tissue, or cell. The type of such a colloidal dispersion system is not limited, as long as it is commonly used. Examples of such a colloidal dispersion system include dispersion systems comprising, as bases, polyethylene glycol, a macromolecular conjugate, a macromolecular aggregate, a nanocapsule, microsphere, beads, and lipids including an oil in water emulsifier, micelle, mixed micelle and liposome. Preferred examples of such a colloidal dispersion system include multiple liposomes and the vesicles of artificial membrane, which have an effect of efficiently transporting such a compound to a specific organ, tissue, or cell (Mannino et al., Biotechniques, 1988, 6, 682; Blume and Cevc, Biochem. et Biophys. Acta, 1990, 1029, 91; Lappalainen et al., Antiviral Res., 1994, 23, 119; Chonn and Cullis, Current Op. Biotech., 1995, 6, 698).

The dosage of the pharmaceutical composition of the present invention differs depending on the age, sex, body weight and symptoms of a patient, therapeutic effects, an administration method, a treatment time, the types of the anti-hTROP-2 antibody and antibody-drug conjugate of the present invention contained in the pharmaceutical composition, etc. In general, the present pharmaceutical composition may be administered within the range between 600 μg and 6,000 mg per adult per administration. However, the dose is not limited to the aforementioned range.

In a case in which the pharmaceutical composition is administered in the form of an injection, for example, it may be administered at a dosage of 100 μg to 100 mg, per administration, per body weight of a human patient, once or divided over several administrations, as an average daily dose. Preferably, the pharmaceutical composition may be administered once every three days, once a week, once every ten days, or once every two weeks, or by a single administration (wherein the total number of administrations is 1). Examples of the dosage form include intravenous injection, subcutaneous injection, intradermal injection, intramuscular injection and intraperitoneal injection. Of these, intravenous injection is preferable. In addition, such an injection may be prepared in the form of a nonaqueous diluent (e.g. polyethylene glycol, vegetable oil such as olive oil, alcohols such as ethanol, etc.), a suspension, or an emulsion. Such an injection can be sterilized by mechanical sterilization using a filter, the mixing of a microbicide, etc. The injection can be produced in the form of an injection to be prepared before using. That is, a sterilized solid composition is prepared by a freeze-drying method or the like, and the composition is then dissolved in sterilized distilled water used for injection or other solvents before it is used, so that it can be then used.

The present invention provides a use of the aforementioned anti-hTROP-2 antibody and/or antibody-drug conjugate of the present invention in the production of a pharmaceutical agent (a drug) for treating and/or diagnosing a tumor. In addition, the present invention provides the aforementioned anti-hTROP-2 antibody and/or antibody-drug conjugate of the present invention, which are used for treating and/or diagnosing a tumor.

Moreover, the present invention provides a method for treating and/or diagnosing a tumor, which is characterized in that it comprises using (namely, administering to patients) the aforementioned anti-hTROP-2 antibody and/or antibody-drug conjugate of the present invention. Furthermore, the present invention also provides the use of the aforementioned anti-hTROP-2 antibody and/or antibody-drug conjugate of the present invention in the treatment and/or diagnosis of tumor.

6. Method for Detecting Tumor

The method for detecting a tumor of the present invention is characterized in that it comprises allowing the aforementioned anti-hTROP-2 antibody of the present invention to react with a sample collected from a living body (hereinafter referred to as a biological sample), and detecting a signal(s) of the reacted antibody.

As described above, hTROP-2 has been confirmed to be specifically expressed in various types of tumor cells. Thus, hTROP-2, and particularly, free hTROP-2 (an extracellular region portion of hTROP-2) can be used as a marker for various types of tumors. In particular, such hTROP-2 can be preferably used as a marker for human pancreatic cancer, human prostate cancer, human colorectal cancer and human breast cancer.

Hence, the anti-hTROP-2 antibody of the present invention is allowed to react with a biological sample, and a signal of the reacted antibody is then detected, so as to detect a tumor. The obtained antibody signal can be used as an indicator of the amount of an antigen in the biological sample (that is, an hTROP-2 amount or a free hTROP-2 amount). In detection of a tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flow cytometry and the like can be used. In radioimmunoassay, a labeled antibody is used, and thus an antibody signal is expressed as the amount of the labeled antibody that is directly detected. Otherwise, an antibody whose concentration or antibody titer has been known may be used as a standard solution, and thus a signal of the target antibody may be expressed as a relative value. That is, both the standard solution and the analyte may be measured using a measurement device, and an antibody signal in a biological sample may be expressed as a value relative to the value of the standard solution used as a criterion. Examples of such radioimmunoassay include the ELISA method, the EI method, the RIA method, fluorescence immunoassay (FIA), and luminescence immunoassay. Of these, the ELISA method is particularly preferable in that it is simple and highly sensitive.

In the present invention, the state of a tumor can be evaluated or diagnosed, using the detection result obtained by the aforementioned detection method as an indicator. For example, when the detection result exceeds a predetermined standard value, the state of a tumor is defined as tumor positive, and when the detection result is less than the predetermined standard value, it is defined as tumor negative. In the case of tumor positive, it is determined that a certain type of tumor could have been developed, and thus the tumor state can be evaluated. The term "the state of a tumor" is used herein to mean the presence or absence of the development of a tumor, or the progression degree thereof. Thus, specific examples of the state of a tumor include the presence or absence of the development of a tumor, the progression degree thereof, the degree of malignancy, the presence or absence of metastasis, and the presence or absence of recurrence.

In the aforementioned evaluation, as a state of a tumor to be evaluated, only one state may be selected from the aforementioned examples, or multiple examples may be combined and selected. The presence or absence of a tumor can be evaluated by determining whether or not the tumor has been developed, with reference to the predetermined standard value used as a boundary, based on the obtained detection result. The degree of malignancy is used as an indicator that indicates the progression degree of a cancer. Based on the detection result, the target tumor can be classified into a certain disease stage and it can be evaluated. Otherwise, an early cancer and an advanced cancer can be distinguished from each other, and then they can be evaluated. For example, it is also possible to determine the target tumor as an early cancer or an advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

7. Kit for Detecting or Diagnosing Tumor

The anti-hTROP-2 antibody of the present invention can be provided in the form of a kit for detecting or diagnosing a tumor. The kit of the present invention comprises a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an Eppendorf tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc.

The kit of the present invention can be effectively used to carry out the aforementioned detection method of the present invention, and thus it is extremely useful.

Hereinafter, the present invention will be more specifically described in the following examples. However, these examples are not intended to limit the scope of the present invention.

Example 1

[Cloning of hTROP-2 Gene]

A full-length hTROP-2 gene was isolated from human fetal liver (10-week-old embryo) according to an RT-PCR method. First, the following PCR primers were designed based on the sequence of an hTROP-2 gene (Genbank accession No. NM_002353).

Forward primer: 5'-ttcctccgccccaccatggc-3' (SEQ ID NO: 3)
Reverse primer: 5'-ctcgagcaagctcggttcctttctc-3' (SEQ ID NO: 4)

When these primers were designed, a XhoI restriction enzyme-digested sequence except for a stop codon was added to the reverse primer. cDNA was synthesized from total RNA (TAKARA) prepared from human fetal liver (10-week-old embryo). Using this cDNA as a template, a PCR reaction was carried out with the aforementioned primers. Thereafter, development by agarose gel electrophoresis and extraction of a band of interest were carried out, and it was then cloned into a pCRII vector (Invitrogen) (pCRII-hTROP-2). The cloned hTROP-2 cDNA was confirmed by sequencing.

An expression vector was constructed by cleaving a EcoRI/XhoI fragment comprising an hTROP-2 gene from pCRII-hTROP-2, and then inserting the fragment into the EcoRI/XhoI site of a pcDNA4/myc-His© A vector (Invitrogen) (pcDNA4-hTROP-2-myc/His). Moreover, a HindIII/PmeI fragment comprising an hTROP-2 gene was cut out of pcDNA4-hTROP-2-myc/His (wherein the HindIII cleavage portion was blunt-ended), and the fragment was then inserted into a PmeI site of a pcDNA3.1(+) vector (Invitrogen), so as to construct an expression vector comprising a neomycin resistance gene (pcDNA3.1-hTROP-2-myc/His).

Example 2

[Construction of Cell Line Capable of Stably Expressing hTROP-2 Gene]

The expression vector (pcDNA3.1-hTROP-2-myc/His) encoding the full-length cDNA of hTROP-2, which had been produced by the above-described method, was introduced into HEK293 cells (RIKEN), HuH-7 cells (HSRRB), 7E2-C cells (described in WO 2005/052156) and CHO-K1 cells (HSRRB), using a lipofectamine 2000 reagent (Invitrogen), and selection was then carried out using an antibiotic G418 (geneticin; GIBCO BRL). Thereafter, a cell line, which stably expressed hTROP-2, was established and obtained.

Example 3

[Production of Recombinant Protein of hTROP-2 Extracellular Region]

A gene fragment encoding a portion of the extracellular region of hTROP-2 (specifically, a region consisting of amino acids at positions 1 to 263 from the amino acid sequence shown in SEQ ID NO: 2) was amplified by a PCR method. The following primers were used in the amplification.
Forward primer: 5'-ttcctccgccccaccatggc-3' (SEQ ID NO: 3)
Reverse primer: 5'-ctcgagctcgtccaggtaatagatgagcg-3' (SEQ ID NO: 5)

In this operation, a XhoI restriction enzyme-digested sequence was added to the reverse primer. The DNA fragment amplified by the PCR method was developed by agarose gel electrophoresis, and it was then purified using QIAquick® Gel Extraction Kit (QIAGEN®). The purified DNA fragment was subcloned into a pCR®-Blunt vector (Invitrogen) (pCRB-hTROP-2 EC), and the gene sequence was confirmed. Subsequently, a EcoRI/XhoI fragment comprising the gene fragment encoding the extracellular region of hTROP-2 was cut out of the pCRB-hTROP-2 EC, and it was then inserted into the EcoRI/XhoI site of a pcDNA4/myc-His© A vector (Invitrogen) (pcDNA4mH-hTROP-2 EC). Further, in order to produce a NruI restriction enzyme cleavage site, the following oligonucleotides were associated and inserted into the BamHI/EcoRI site of the pcDNA4mH-hTROP-2 EC.
Oligonucleotide 1: 5'-gatccactagtcgcgagtggtgg-3' (SEQ ID NO: 6)
Oligonucleotide 2: 5'-aattccaccactcgcgactagtg-3' (SEQ ID NO: 7)

Likewise, a pBgl II linker (TAKARA) was inserted into the PmeI site of the pcDNA4mH-hTROP-2 EC (pcDNA4mH-NB-hTROP-2 EC). In order to produce a recombinant protein using baculovirus, a NruI/BglII fragment comprising the gene fragment encoding the extracellular region of hTROP-2 was cut out of the pcDNA4mH-NB-hTROP-2 EC, and it was then inserted into the NruI/BglII site of a pPSC8 vector (Nosan Corporation) (pPSC8-hTROP-2 EC). The production of the recombinant protein of the extracellular region of hTROP-2 using baculovirus was delegated to Nosan Corporation.

The recombinant protein of the extracellular region of hTROP-2 was purified as follows. Ni Sepharose 6 Fast Flow (GE Healthcare Biosciences) was added to a culture supernatant comprising the recombinant protein, so that they were allowed to bind to each other at 4° C. for 2 hours. Thereafter, the resultant was washed with a phosphate buffer containing 20 mM imidazole, employing EconoColumn (BIO RAD), and it was then eluted with a phosphate buffer containing 300 mM imidazole, so that it was purified.

Example 4

[Isolation of Human EpCAM cDNA and Construction of Expression Vector]

A full-length human EpCAM gene was isolated from human fetal liver (10-week-old embryo) according to an RT-PCR method. First, the following PCR primers were designed based on the sequence of a human EpCAM gene (Genbank accession No. NM_002354).
Forward primer: 5'-tcctcgtgtcccactcccgg-3' (SEQ ID NO: 8)
Reverse primer: 5'-ctcgagtgcattgagttccctatgc-3' (SEQ ID NO: 9)

When these primers were designed, a XhoI restriction enzyme-digested sequence except for a stop codon was added to the reverse primer. cDNA was synthesized from total RNA (TAKARA) from human fetal liver (10-week-old embryo). Using this cDNA as a template, a PCR reaction was carried out with the aforementioned primers. Thereafter, development by agarose gel electrophoresis and extraction of a band of interest were carried out, and it was then cloned into a pCRII vector (Invitrogen) (pCRII-hEpCAM). The cloned human EpCAM cDNA was confirmed by sequencing.

An expression vector was constructed by cleaving a EcoRI/XhoI fragment comprising a human EpCAM gene from pCRII-hEpCAM, and then inserting the fragment into the EcoRI/XhoI site of a pcDNA4/myc-His© A vector (Invitrogen) (pcDNA4-hEpCAM-myc/His). Moreover, a HindIII/PmeI fragment comprising a human EpCAM gene was cut out of pcDNA4-hEpCAM-myc/His (wherein the HindIII cleavage portion was blunt-ended), and the fragment was then inserted into the PmeI site of a pcDNA3.1(+) vector (Invitrogen), so as to construct an expression vector comprising a neomycin resistance gene (pcDNA3.1-hEpCAM-myc/His).

Example 5

[Production of Anti-hTROP-2 Monoclonal Antibody]

As immunogens, there were used cell lines capable of stably expressing hTROP-2 (HEK293-hTROP-2 cells, CHO-K1-hTROP-2 cells and 7E2-C-hTROP-2 cells); human pancreatic cancer cell line endogenously expressing an hTROP-2 protein on the cell surface (PK-59, RCB1901; purchased from RIKEN cell bank); and the recombinant protein of the extracellular region of hTROP-2 produced by the above-described method.

In the case of the cell lines capable of stably expressing hTROP-2, $1 \times 10^7$ cells were used, and in the case of the recombinant hTROP-2 protein, 20 µg of the protein was used. The cell lines or the recombinant hTROP-2 protein was mixed with an adjuvant TiterMax Gold (Funakoshi Corporation) at a mixing ratio of 1:1, so as to prepare an emulsion. The emulsion was then injected into the two footpads or abdominal cavity of a mouse (C57/BL6, Balb/c) (initial immunization). When immunization was carried out by injection into the two footpads for a short period of time, booster was carried out three to ten days after the initial immunization. On the day following the final immunization, lymph nodes were collected from both knees, and lymphocytes were then prepared. When immunization was carried out by injection into the abdominal cavity for a long period of time, boosters were carried out at intervals of once a week after the initial immunization (wherein boosters were carried out for 1 to 2 months). Thereafter, B cells were isolated from the spleen according to an ordinary method. In the case of immunization using cells as immunogens, a cell suspension which was PBS containing $5 \times 10^6$ cells was used for boosters. In the case of using a protein as an immunogen, 5 μg of a PBS solution was used.

The prepared lymphocytes were mixed with a mouse myeloma cell line (P3-X63-Ag8.653) at a mixing ratio of 3:1, and cell fusion was then carried out according to a polyethylene glycol method. Thereafter, the fused cells were cultured for 7 to 28 days in a methyl cellulose medium (trade name: ClonaCell-HY Cloning Medium D; Stem Cell), which contained HAT (hypoxanthine, aminopterin and thymidine). Single colonies of growing hybridomas were each picked up and placed on a 96-well flat-bottom plate, and using a liquid selective medium containing HAT, the hybridomas were cultured in a 5% $CO_2$ incubator. A culture supernatant of growing hybridomas from single colonies was subjected to a primary screening via Cell ELISA (described later) and then to a secondary screening via FACS analysis using HuH-7-hTROP-2 cells, PK-59, thereby establishing 300 types of hybridomas, which produce anti-hTROP-2 monoclonal antibodies recognizing hTROP-2 proteins expressed on the cell surface of living cells.

Example 6

[Primary Screening Using Cell ELISA]

CHO-K1 cells (hTROP-2 negative control; purchased from Japan Health Sciences Foundation) and CHO-K1-hTROP-2 cells (or HUH-7 cells (hTROP-2 negative control; purchased from Japan Health Sciences Foundation) and HuH-7-hTROP-2 cells) were alternately inoculated on a 96-well culture plate (BD Falcon) at a cell density of $3 \times 10^4$ cells/well, and the cells were then cultured in a 5% $CO^2$ atmosphere at 37° C. for 1 to 2 days. The cell culture medium was removed by decantation. Thereafter, the cells were washed with ice-cold PBS, and were then treated with 4% paraformaldehyde-PBS for 5 minutes, so that the cells were immobilized. The cells were washed with PBS which had been cooled on ice, and an ELISA plate was then prepared. Thereafter, ELISA was carried out according to an ordinary method. Specific procedures will be described below.

First, blocking with a 2% skim milk-PBS solution was carried out at room temperature for 30 minutes to 1 hour. Subsequently, the hybridoma culture supernatant was added thereto, and they were then reacted at room temperature for 1 hour. Thereafter, the resultant was washed with a 0.1% TWEEN20 (polyoxyethylenesorbitan monolaurate)-PBS solution three times. As a secondary antibody, Horseradish peroxidase (HRP)-labeled anti-mouse IgG (GE Healthcare Biosciences), which had been 1000 times diluted with a blocking solution, was added to the resultant, and they were then reacted at room temperature for 1 hour. Thereafter, the resultant was washed with a 0.1% TWEEN20-PBS solution three times. A TMB (3,3',5,5'-tetramethylbenzidine: SIGMA) substrate solution was added to the reaction solution to carry out a color reaction, and the reaction was then terminated by adding 1 M sulfuric acid. Thereafter, absorbance (405 nm) was measured using Microplate reader Model 550 (BIO RAD). Hybridomas corresponding to a hybridoma culture supernatant exhibiting a high absorbance value to the negative control were subjected to a large-scale culture on a 24-well flat-bottom plate, and were then subjected to a secondary screening using FACS analysis.

Example 7

[Secondary Screening Using FACS Analysis]

Hybridomas, which were found positive in the above-described primary screening using Cell ELISA, were subjected to a secondary screening using FACS analysis. In the evaluation of Hybridoma cells, HuH-7 cells, which were human liver cancer cells which did not express hTROP-2, were used as negative control cells and the reactivity with HuH-7-hTROP-2 cells, which were stably expressing hTROP-2, was used as an indicator. Then, the evaluation was carried out based on the reactivity with PK-59 cells (RCB1901; purchased from RIKEN cell bank), which were human pancreatic cancer cells endogenously expressing an hTROP-2 protein on the cell surface.

The cells were removed from the culture dish by a trypsin treatment, and a cell suspension was then prepared (cell density: $2 \times 10^6$ cells/mL). The hybridoma culture supernatant, which exhibited positive in the primary screening using Cell ELISA, was reacted with 100 μL of the cell suspension at 4° C. for 20 minutes. The reaction mixture was washed with PBS, and it was then reacted with PE-labeled mouse IgG (BD Pharmingen) (0.1 μg) (4° C., 30 minutes). Thereafter, the reaction mixture was analyzed using FACSCalibur (Becton, Dickinson and Company).

Eventually, approximately 300 types of hybridomas, which produce an anti-hTROP-2 monoclonal antibody recognizing an hTROP-2 protein expressed on the cell surface of living cells, were established.

Example 8

[Identification of Isotype]

The isotype of the produced anti-hTROP-2 monoclonal antibody was identified using MOUSE MONOCLONAL ANTIBODY ISOTYPING TEST KIT (Serotec) in accordance with a method included with the above-mentioned kit.

Example 9

[Ascites Formation and Purification of TROP-2 Antibody]

The hybridoma clones produced by the above-described method were administered at a density of $3 \times 10^6$ clones into the abdominal cavity of a BALB/c nude mouse, to which 2,6,10,14-tetramethylpentadecane (pristane) had previously (seven days before) been administered. Two weeks later, ascites was collected. Moreover, this ascites was subjected to caprylic acid precipitation, and then to affinity purification using a protein G column (HiTrap protein G; GE Healthcare Biosciences) or a protein A column (HiTrap protein A; GE Healthcare Biosciences), so as to obtain anti-hTROP-2 monoclonal antibodies from individual hybridoma clones.

Example 10

[Measurement of Antigen Binding Affinity (Measurement of Kd Value)]

The antigen binding affinity (Kd value) of the generated anti-hTROP-2 monoclonal antibody was calculated by a method using ELISA (Djavadi-Ohaniance L. et al (1996), In Antibody Engineering, Chapter 4, pp. 77-97. IRL Press, Oxford).

Specifically, the purified recombinant hTROP-2 protein (0.1 µg/mL) was added to a 96-well culture plate (Corning) so that the plate was coated with the antigen (at room temperature for 1 hour, or at 4° C. overnight). Subsequently, the resultant was washed with PBS three times, and 2% skim milk (PBS solution) was then added thereto to block it (at room temperature for 1 hour). The resultant was washed with PBS twice. Thereafter, an antigen-antibody complex which had previously been formed by mixing an antigen solution (a purified hTROP-2 protein; 50, 25, 12.5, 6.25, or 3.125 nM) with each clone (0.5 nM) of the anti-hTROP-2 monoclonal antibody and then equilibrating the mixture, was added to the above-described ELISA plate, and they were reacted (at room temperature for 1 hour). The reaction product was washed with PBS three times, and it was then reacted with HRP-labeled anti-mouse IgG (final concentration: 1 µg/mL) (GE Healthcare Biosciences) diluted with a blocking solution (at room temperature for 1 hour). Subsequently, the reaction product was washed with a 0.1% TWEEN20-PBS solution three times, and a TMB (3,3',5,5'-tetramethylbenzidine: SIGMA) substrate solution was then added to the resultant to carry out a color reaction. Then, 1 M sulfuric acid was added to the reaction product to terminate the reaction. Using Microplate reader Model 550 (BIO RAD), absorbance was measured.

The following calculation expressions were used to measure dissociation constant (Kd).

In accordance with the law of mass action, an antigen-antibody reaction is represented by the following expressions.

$$Ag(\text{Antigen}) + Ab(\text{Antibody}) \underset{k2}{\overset{k1}{\rightleftharpoons}} Ag-Ab(\text{Antigen}-\text{Antibody complex}) \quad (1)$$

$$Kd = k2/k1 = Agf \times Abf / Ag-Ab = Agf \times Abf / x \quad (2)$$

In the expression (2), Agf represents the concentration of a free antigen, Abf represents the concentration of a free antibody, and Ag–Ab represents the concentration of an antigen-antibody complex. If Ag–Ab=x, the free antibody concentration is represented by the following expression.

$$Abf = Abt - x \quad (3)$$

The above expression (2) therefore can be $$Kd = Agf \times (Abt - x)/x \quad (4)$$

If both terms of the expression (4) are multiplied by x/Kd×Abt, $$x/Abt = Agf \times (1 - x/Abt) \times 1/Kd$$

$$x/Abt \times 1/Agf = (1 - x/Abt) \times 1/Kd \quad (5)$$

If X=x/Abt and Y=x/Abt×Agf in the expression (5), $$Y = (1-X) \times 1/Kd \quad (6)$$

Based on the expression (6), the Kd value was calculated.

The Kd values of the generated 300 anti-hTROP-2 monoclonal antibody clones were measured by the above-described method. As a result, there were 133 clones exhibiting a Kd value of $1 \times 10^{-10}$ (M) or less, 59 clones exhibiting a Kd value of $1 \times 10^{-11}$ (M) or less, and 2 clones exhibiting a Kd value of $1 \times 10^{-12}$ (M) or less.

Among the anti-hTROP-2 monoclonal antibodies, which exhibited tumor growth inhibitory activity in vivo, the Kd values of K5-70 (mouse IgG2a), T6-16 (mouse IgG2a) K5-107 (mouse IgG1), K5-116-2-1 (mouse IgG2a) and T5-86 (mouse IgG1) were found to be $6.8 \times 10^{-12}$ (M), $4.3 \times 10^{-12}$ (M), $4.7 \times 10^{-12}$ (M), $2.69 \times 10^{-11}$ (M) and $8.49 \times 10^{-11}$ (M), respectively (FIG. 1 and Table 1).

TABLE 1

| Kd values of anti-hTROP-2 monoclonal antibodies | | | | | |
|---|---|---|---|---|---|
| | Clone No. | | | | |
| | K5-70 | T6-16 | K5-107 | K5-116-2-1 | T5-86 |
| Kd ($\times 10^{-12}$ M) | 6.8 | 4.3 | 4.7 | 26.9 | 84.9 |

Example 11

[Reactivity of Anti-hTROP-2 Monoclonal Antibodies with Human Cancer Cell Lines]

The human cancer cell lines (human tumor cell lines) used in this studies were acquired from Health Science Research Resources Bank (HSRRB), RIKEN cell bank (RIKEN), ATCC (American Type Culture Collection), ECACC (European Collection of Cell Cultures) and DSMZ (German Collection of Microorganisms and Cell Cultures). Specifically, the following cancer cell lines were used.

huH-1 (HSRRB), HUH-6 (HSRRB), HuH-7 (HSRRB), JHH-5 (HSRRB), JHH-6 (HSRRB), JHH-7(HSRRB), HLE (HSRRB), HLF (HSRRB), HepG2 (HSRRB), Alexander (HSRRB), KP-1N (HSRRB), KP-1NL (HSRRB), KP-2 (HSRRB), KP-3 (HSRRB), KP-3L (HSRRB), PK-1 (RIKEN), PANC-1 (RIKEN), MIA PaCa-2 (HSRRB), PK-59 (RIKEN), PK-45H (RIKEN), PK-45P (RIKEN), BxPC-3 (ATCC), SUIT-2 (HSRRB), TCC-PAN2 (HSRRB), SW480 (ATCC), DLD-1 (HSRRB), LoVo (HSRRB), COLO-320 (RIKEN), CACO-2 (RIKEN), CW-2 (RIKEN), HCT 116 (ATCC), HCC-56 (HSRRB), MCF-7 (HSRRB), JIMT-1 (DSMZ), HCC1143 (ATCC), A549 (HSRRB), DU145 (RIKEN) and PC-3 (HSRRB).

Cancer cells were removed from a culture dish by a trypsin treatment, and a cell suspension was then prepared (cell density: $2 \times 10^6$ cells/mL). An anti-hTROP-2 monoclonal antibody (0.1 µg) was added to 100 µL of the cell suspension, and they were then reacted at 4° C. for 20 minutes. The reaction solution was washed with PBS, and it was then reacted with PE-labeled anti-mouse IgG (BD Biosciences Pharmingen) (0.1 µg) (at 4° C. for 30 minutes). Thereafter, the resultant was analyzed by FACSCalibur (Becton, Dickinson and Company).

Figure 2:
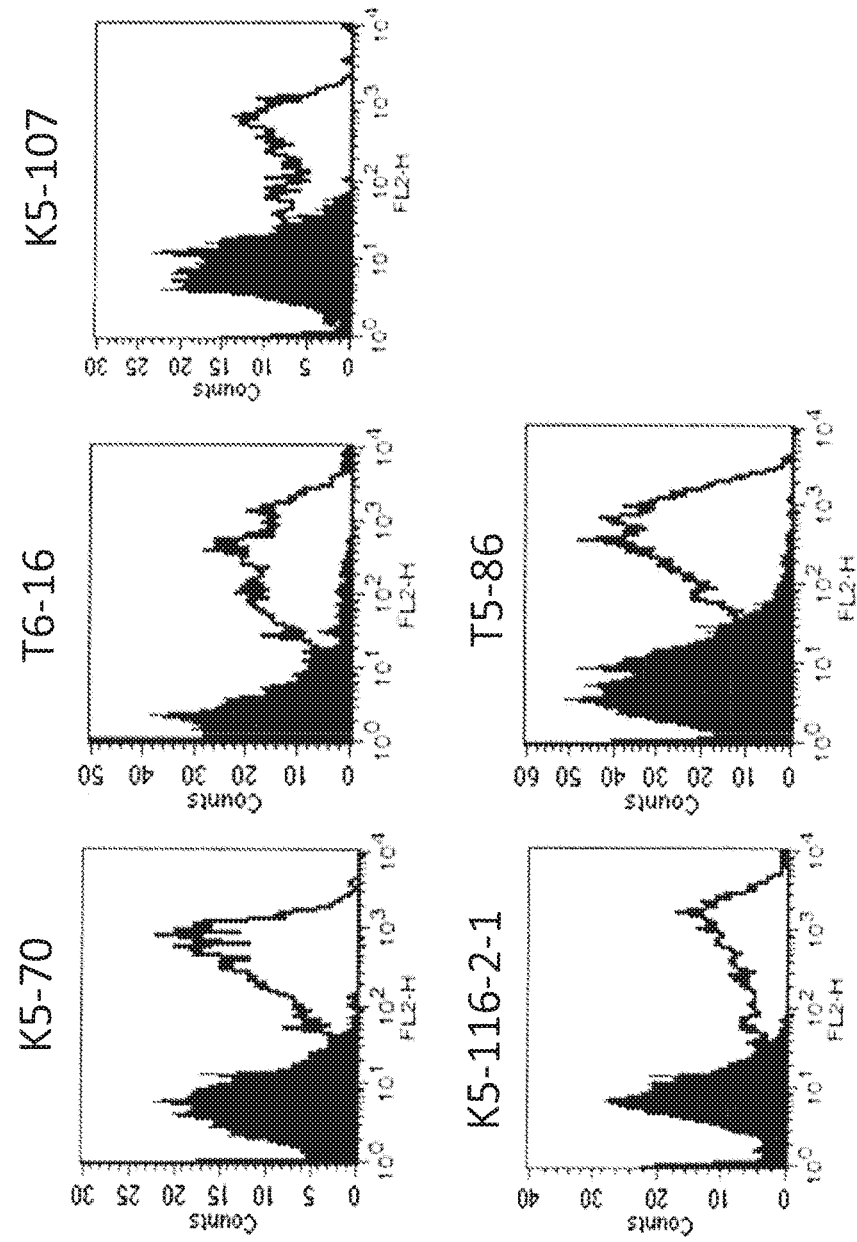
FIG. 2 shows the reactivity of a culture supernatant of hybridoma producing an anti-hTROP-2 monoclonal antibody, with HuH-7 cells (hTROP-2-negative) and HuH-7-hTROP-2 cells. The filled histogram indicates HuH-7 cells, and the open histogram indicates HuH-7-hTROP-2 cells.
Figure 3:
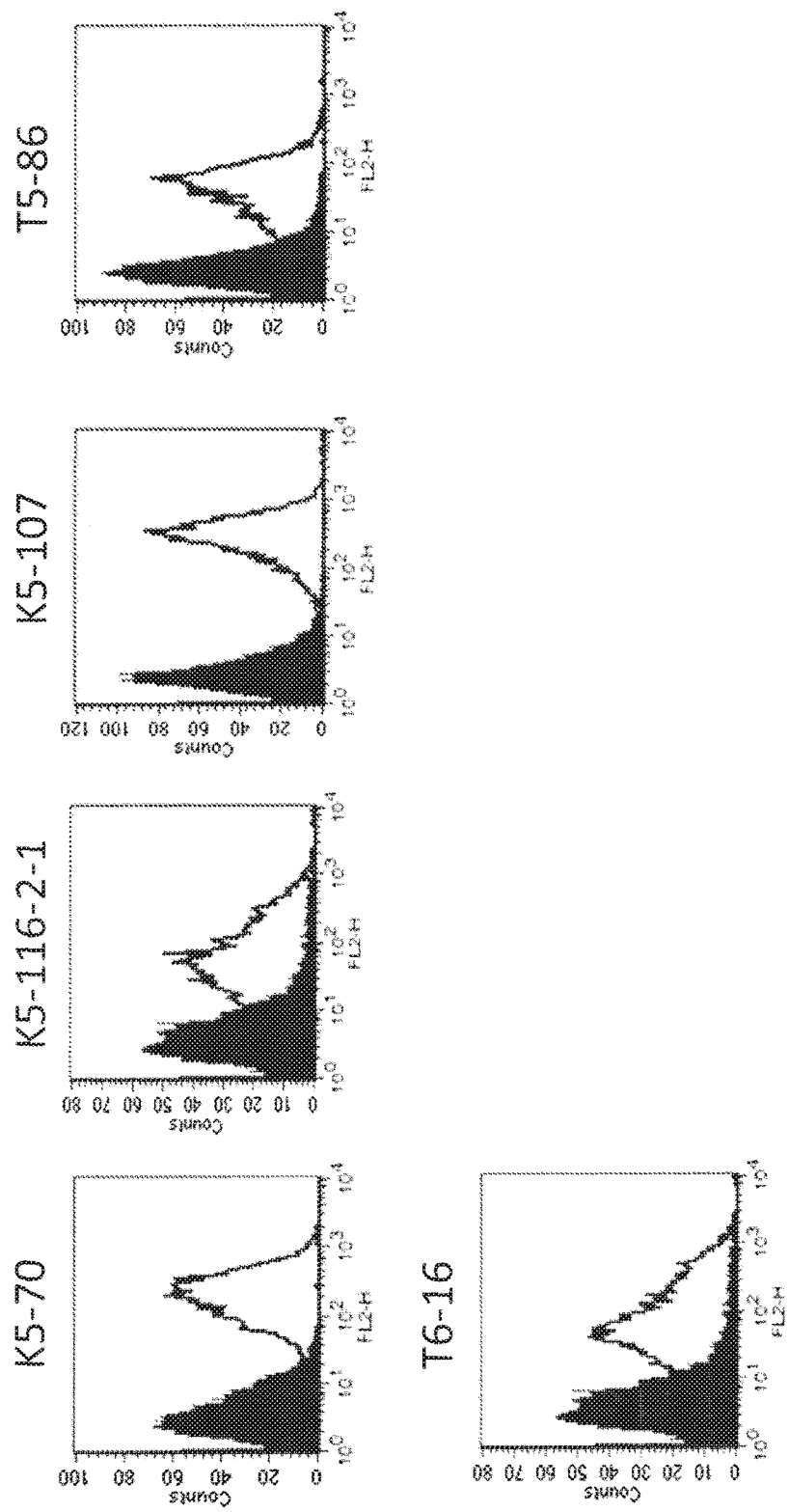
FIG. 3 shows the reactivity of an anti-hTROP-2 monoclonal antibody with a human pancreatic cancer cell line (PK-59 cells), which endogenously expresses hTROP-2 on the cell surface. The filled histogram indicates the reaction of the cell line only with a secondary antibody (PE-labeled anti-mouse IgG), and the open histogram indicates the reaction of the cell line with each anti-hTROP-2 monoclonal antibody.
Figure 4:
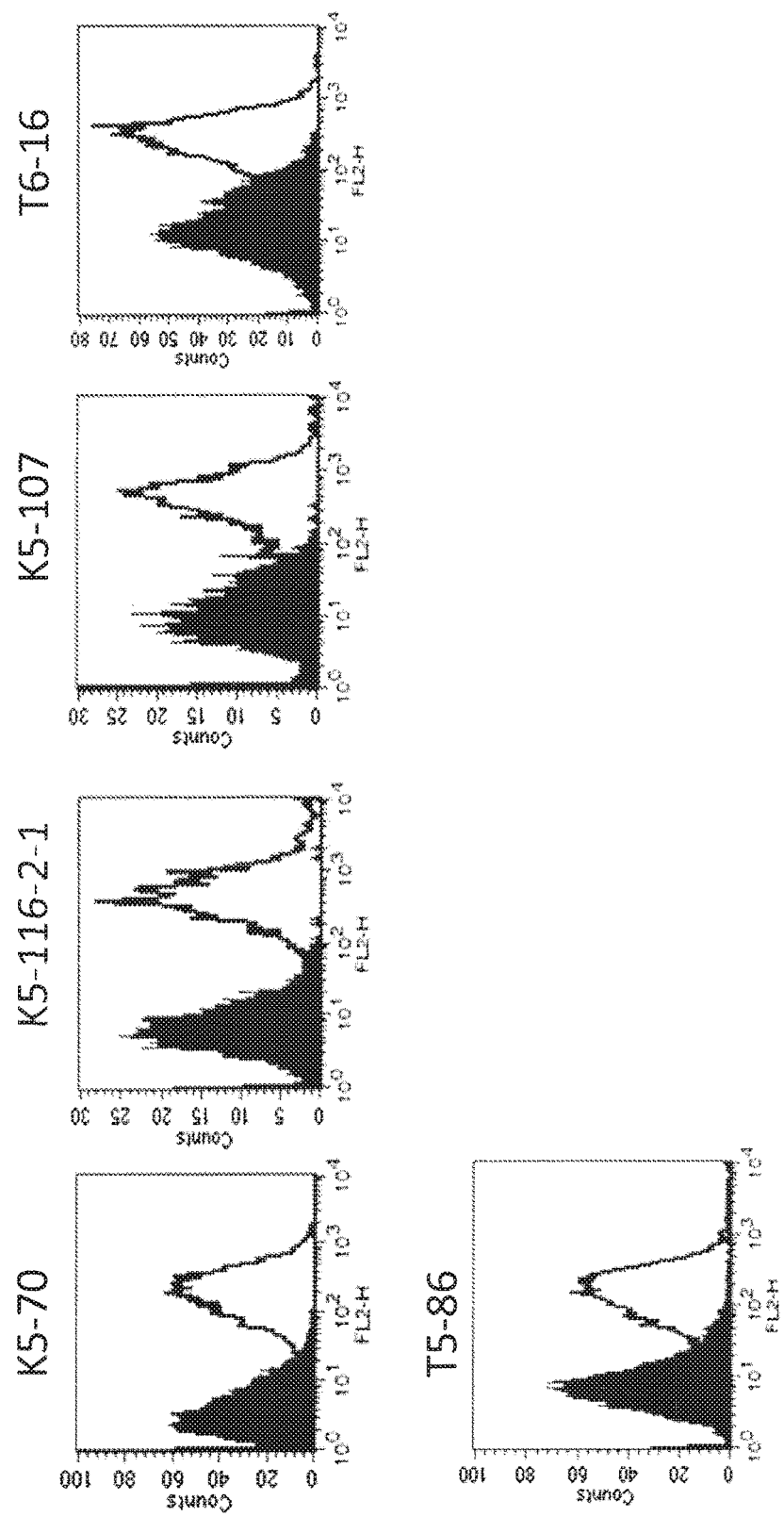
FIG. 4 shows the reactivity of an anti-hTROP-2 monoclonal antibody with a human pancreatic cancer cell line (BxPC-3 cells), which endogenously expresses hTROP-2 on the cell surface. The filled histogram indicates the reaction of the cell line only with a secondary antibody (PE-labeled anti-mouse IgG), and the open histogram indicates the reaction of the cell line with each anti-hTROP-2 monoclonal antibody.

All of the generated anti-hTROP-2 antibodies did not bind to a human liver cancer cell line HuH-7, which did not endogenously express hTROP-2. On the other hand, the anti-hTROP-2 antibodies bound to HuH-7-hTROP-2 cells, in which an hTROP-2 gene was stably expressed (FIG. 2). Subsequently, the reactivity of the generated anti-hTROP-2 monoclonal antibodies with human cancer cell lines (in which an hTROP-2 protein was endogenously expressed on the cell surface) was examined by FACS analysis. As a result, the generated 300 types of anti-hTROP-2 monoclonal antibodies all bound to human pancreatic cancer cell lines (PK-59 and BxPC-3). In particular, K5-70, T6-16, K5-107, K5-116-2-1 and T5-86 antibodies, which exhibited tumor growth inhibitory activity in vivo, all bound to human cancer cell lines at high levels. For example, when compared with a case in which cancer cell lines were reacted with only PE-labeled anti-mouse IgG (BD Biosciences Pharmingen), the aforementioned antibodies exhibited the following binding ability to PK-59 cells and to BxPC-3 cells at mean fluorescence intensity: K5-70 (44 times), T6-16 (59 times), K5-107 (89 times), K5-116-2-1 (122 times) and T5-86 (15 times) (to PK-59 cells; FIG. 3); and K5-70 (45 times), T6-16 (25 times), K5-107 (90 times), K5-116-2-1 (121 times) and T5-86 (10 times) (to BxPC-3 cells; FIG. 4).

Figure 5:
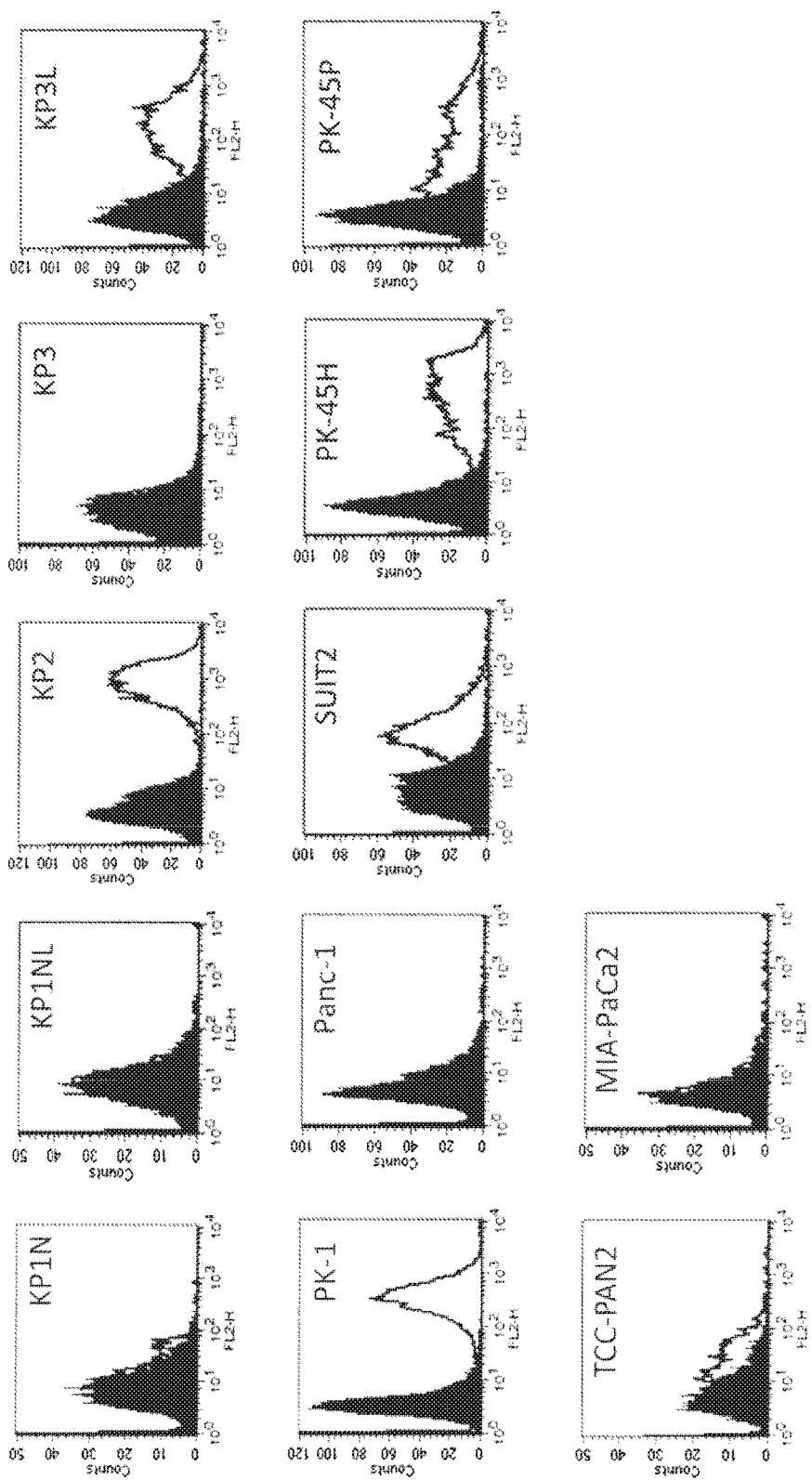
FIG. 5 shows the reactivity of an anti-hTROP-2 monoclonal antibody (K5-70) with human pancreatic cancer cell lines. The filled histogram indicates the reaction of the cell line only with a secondary antibody (PE-labeled anti-mouse IgG), and the open histogram indicates the reaction of the cell line with each anti-hTROP-2 monoclonal antibody.
Figure 6:
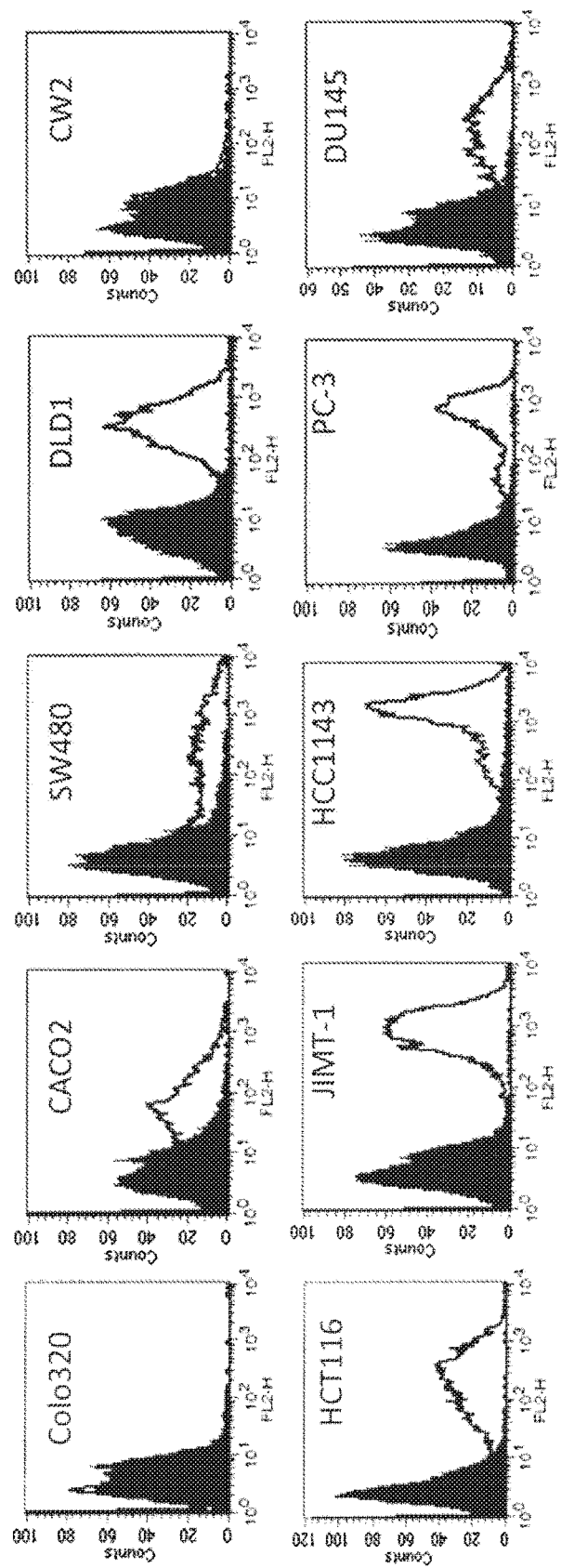
FIG. 6 shows the reactivity of an anti-hTROP-2 monoclonal antibody (K5-70) with human colon cancer cell lines (Colo320, CACO2, SW480, DLD1, CW2 and HCT 116), human breast cancer cell lines (JIMT-1 and HCC1143) and human prostate cancer cell lines (PC-3 and DU145). The filled histogram indicates the reaction of the cell line only with a secondary antibody (PE-labeled anti-mouse IgG), and the open histogram indicates the reaction of the cell line with the anti-hTROP-2 monoclonal antibody.

With regard to human cancer cell lines other than PK-59 and BxPC-3, among 12 types of pancreatic cancer cell lines, the anti-hTROP-2 monoclonal antibodies bound to KP-2, KP-3L, PK-1, PK-45H, SUIT-2 and TCC-PAN2, and did not bind to KP-1N, KP-1NL, KP-3, PANC-1 and MIA-PaCa2 (FIG. 5). Among human colon cancer cell lines, the anti-hTROP-2 monoclonal antibodies bound to CACO-2, SW480, DLD-1 and HCT 116, and did not bind to COLO-320 and CW-2 (FIG. 6). Furthermore, the anti-hTROP-2 monoclonal antibodies bound to JIMT-1 and HCC1143 (which were both human breast cancer cell lines) and to PC-3 and DU145 (which were both human prostate cancer cell lines). Thus, they recognized hTROP-2 proteins endogenously expressing on the cell surface of many types of human cancer cell lines (FIG. 6).

Example 12

[Cross-Reactivity with Mouse TROP-2 Protein and Human Trop-1/EpCAM Protein]

For the purpose of examining the specificity of the generated anti-hTROP-2 monoclonal antibodies, the reactivity of the antibodies with a mouse TROP-2 protein showing homology of 80% at the amino acid sequence level with the hTROP-2 protein, and with a human TROP-1/EpCAM protein showing homology of 50% at the amino acid sequence level with the hTROP-2 protein, was examined by FACS analysis.

Specifically, each of an expression vector (mouse TROP-2-pcDNA3.1(+), furnished by the Institute of Molecular and Cellular Biosciences, the University of Tokyo) comprising the full-length cDNA of a mouse TROP-2 gene (GenBank accession No. NM_020047, Y08830), and an expression vector (pcDNA3.1-hEpCAM-myc/His) comprising the full-length cDNA of a human TROP-1/EpCAM gene (GenBank accession No. NM_002354), was transiently introduced into CHO-K1 cells, using Lipofectamine2000 reagent (Invitrogen). Thereafter, 24 to 48 hours later, the cells were removed from a culture dish by treating them with trypsin, and a cell suspension was then prepared. The thus prepared cell suspension was successively reacted with the produced anti-hTROP-2 monoclonal antibody (0.1 µg) and with PE-labeled anti-mouse IgG, and it was then analyzed by FACSCalibur.

Figure 7:
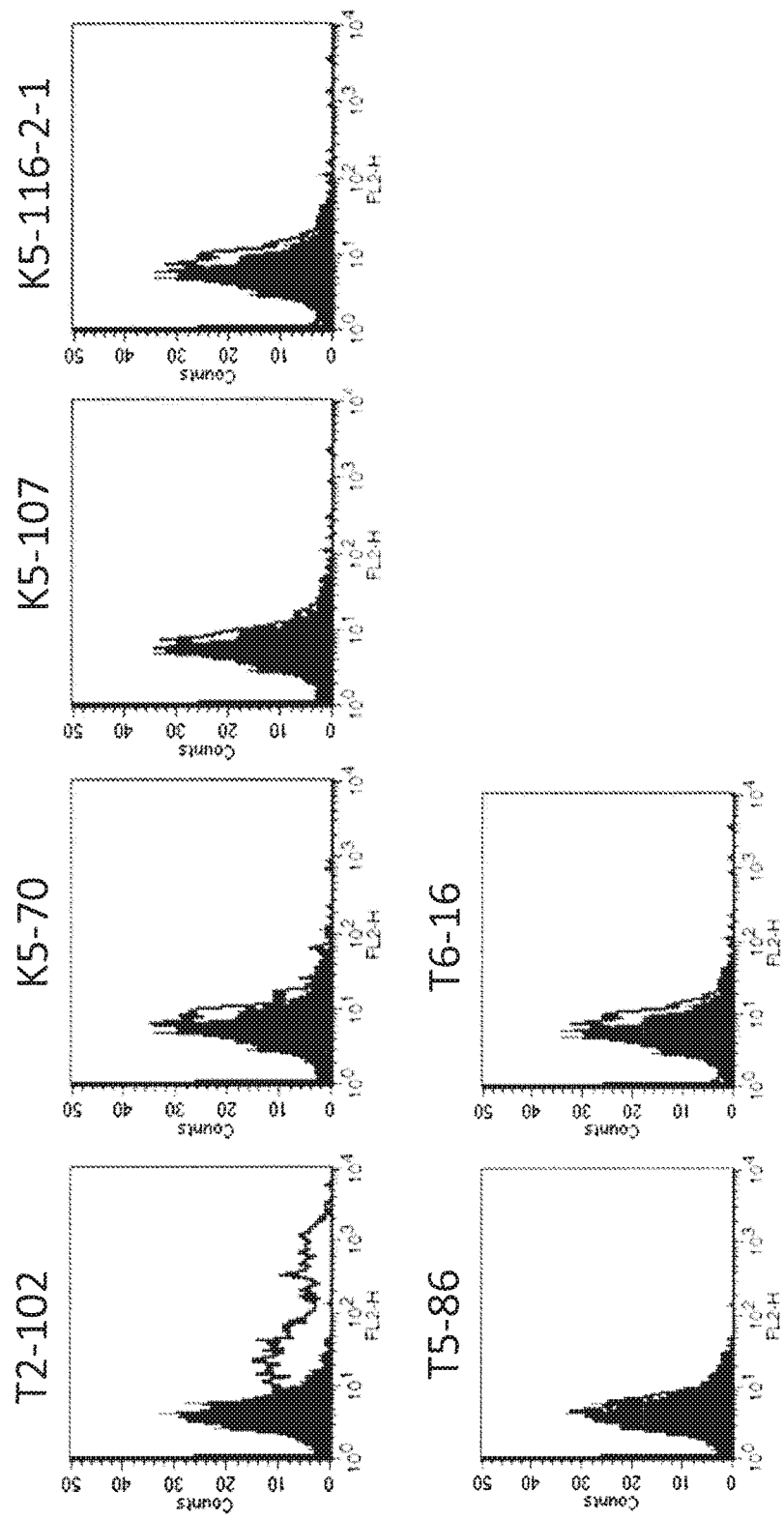
FIG. 7 shows the cross-reactivity of anti-hTROP-2 monoclonal antibodies with mouse TROP-2. Cells prepared by allowing a mouse TROP-2 gene to be transiently expressed in CHO-K1 cells were used, and a T2-102 antibody (mouse IgG1) exhibiting cross-reactivity with mouse TROP-2 was used as a positive control antibody. The filled histogram indicates the reaction of the cells only with a secondary antibody (PE-labeled anti-mouse IgG), and the open histogram indicates the reaction of the cells with each anti-hTROP-2 monoclonal antibody.

A T2-102 antibody (mouse IgG1) used as a positive control, which showed cross-reactivity with mouse TROP-2, exhibited high binding ability to the CHO-K1 cells in which the mouse TROP-2 gene was transiently expressed. On the other hand, K5-70, T6-16, K5-107, K5-116-2-1 and T5-86 antibodies did not show such cross-reactivity with mouse TROP-2 (FIG. 7).

Figure 8:
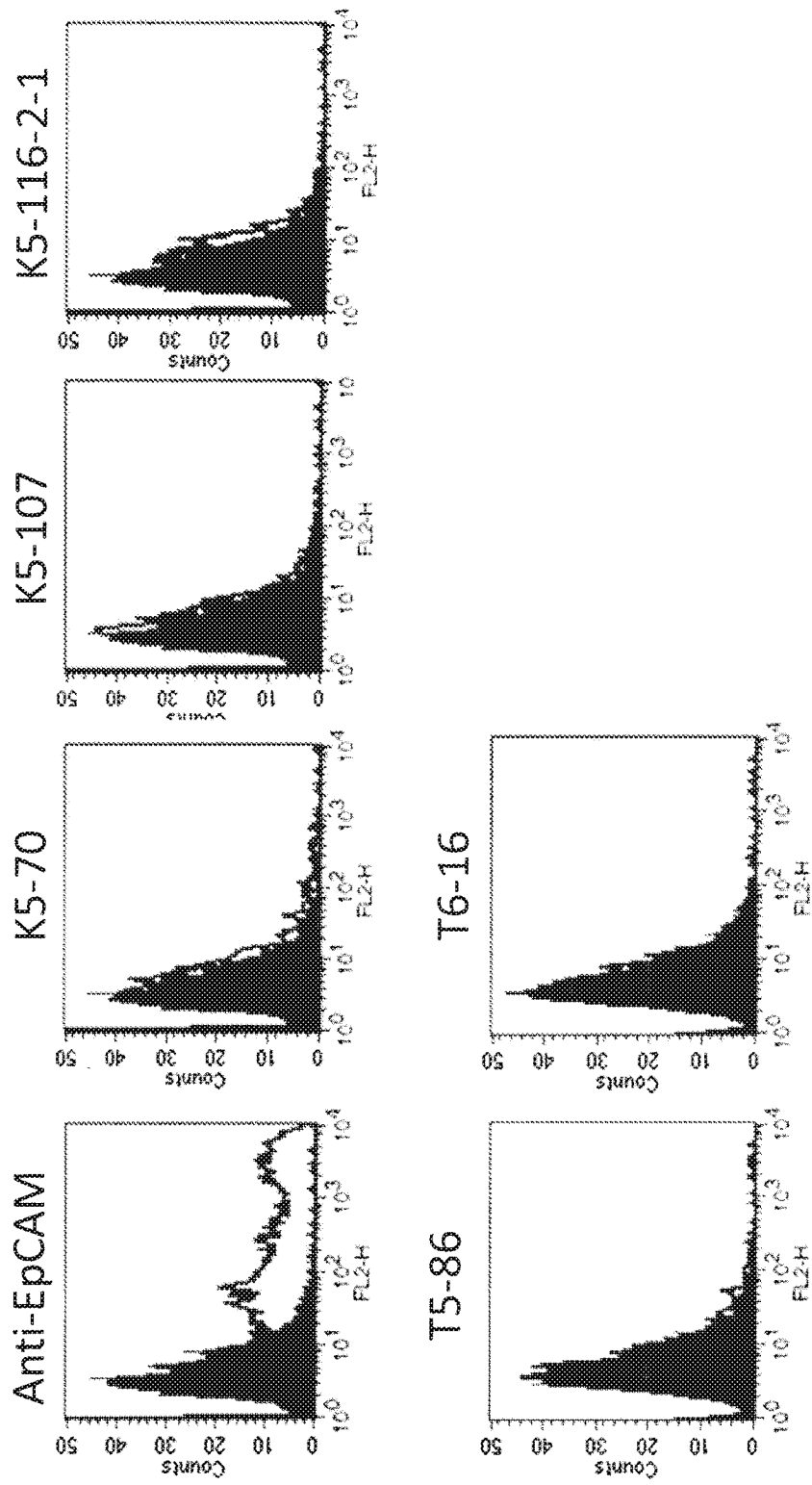
FIG. 8 shows the cross-reactivity of anti-hTROP-2 monoclonal antibodies with human EpCAM/TROP-1. Cells prepared by allowing a human EpCAM/TROP-1 gene to be transiently expressed in CHO-K1 cells were used, and a PE-labeled anti-human EpCAM monoclonal antibody (Becton, Dickinson and Company) was used as a positive control antibody. The filled histogram indicates the reaction of the cells only with a secondary antibody (PE-labeled anti-mouse IgG), and the open histogram indicates the reaction of the cells with each anti-hTROP-2 monoclonal antibody.

Similarly, an anti-human EpCAM monoclonal antibody (BD Biosciences Pharmingen) used as a positive control exhibited high binding ability to the CHO-K1 cells in which the human EpCAM/TROP-1 was transiently expressed. On the other hand, K5-70, T6-16, K5-107, K5-116-2-1 and T5-86 antibodies did not show such cross-reactivity with human EpCAM/TROP-1 (FIG. 8).

The aforementioned results demonstrated that the generated anti-hTROP-2 monoclonal antibodies, and in particular, K5-70, T6-16, K5-107, K5-116-2-1 and T5-86 antibodies, which exhibited anti-tumor activity in vivo, specifically bound to hTROP-2.

Example 13

[Measurement of Cell Growth Inhibitory Activity]

As a method of examining the activity of the anti-hTROP-2 monoclonal antibody to inhibit the function of hTROP-2, the influence of the antibody on the cell growth of human cancer cells, which endogenously express hTROP-2 on the cell surface, was evaluated by measuring the number of living cells using TetraColor ONE (Seikagaku Corporation). Specifically, PK-59 cells were suspended in an RPMI1640 medium containing 0.5% fetal bovine serum (manufactured by BioWest) at a cell concentration of $2\times10^5$ cells/mL, and 100 µL of the prepared cell suspension was then added to each well of a 96-well culture plate. Subsequently, mouse IgG (negative control) and anti-hTROP-2 monoclonal antibodies (final concentrations: 0.1 and 1 µg/mL) were added to the wells, and the mixtures were then cultured at 37° C. in a 5% $CO_2$ incubator for 72 hours. As a control, a commercially available anti-hTROP-2 monoclonal antibody (clone YY01, Santa Cruz) was used. TetraColor ONE (Seikagaku Corporation) was added to the wells, and they were then reacted in a 5% $CO_2$ incubator for 1 to 2 hours. After completion of the reaction, the 96-well culture plate was directly subjected to the measurement of absorbance at a wavelength of 490 nm (control wavelength: 655 nm), using Microplate Reader. The experiment was carried out using 3 wells for each group. A significant difference test was carried out according to Student's t-test, and $P<0.05$ was determined to be statistically significant.

Figure 9:
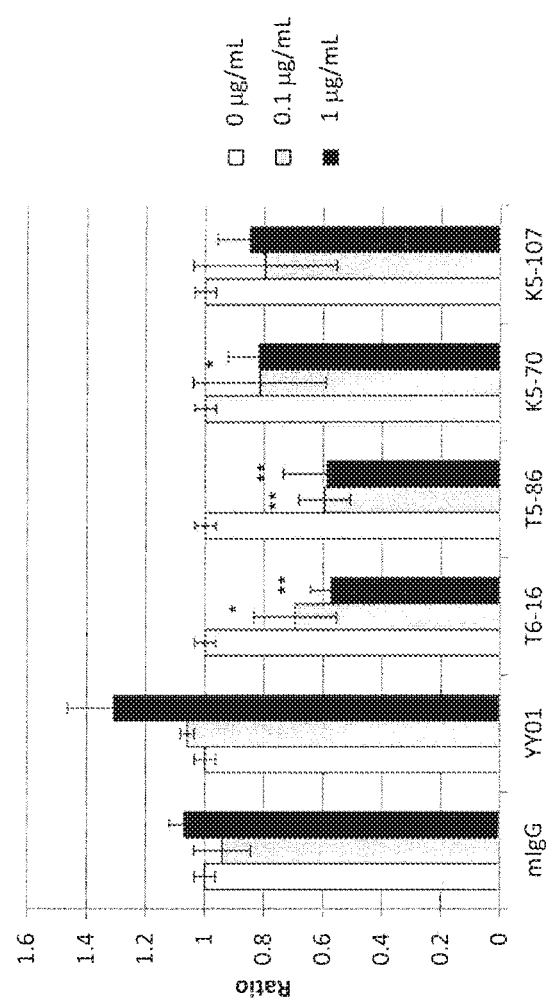
FIG. 9 shows the cell growth inhibitory activity of anti-hTROP-2 antibodies (T6-16, T5-86, K5-70 and K5-107) on a human pancreatic cancer cell line (PK-59 cells). mIgG indicates a control antibody (mouse IgG), and YY01 indicates a commercially available anti-hTROP-2 antibody (Santa Cruz). White column: 0 µg/mL; gray column: 0.1 µg/mL; black column: 1 µg/mL. The activity level was expressed as a ratio of the actual value to the value obtained when an antibody had not been added (0 µg/mL). The error bar indicates a standard deviation. *P<0.05, **P<0.01 (by Student's t-test).

Among anti-hTROP-2 monoclonal antibodies, which had been generated by our own company so far, approximately 160 clones were examined by the above-described method, in terms of their effect on the cell growth of PK-59 cells. As a result, T6-16, T5-86, K5-70 and K5-107, which had exhibited tumor growth inhibitory activity in vivo, were confirmed to have cell growth inhibitory activity of 20% to 40%, when compared with mouse IgG (negative control). It became clear that these anti-hTROP-2 antibodies have activity to bind to hTROP-2 proteins, which were expressed on the surface of human cancer cells, to neutralize the hTROP-2 proteins, and to inhibit the growth of the cancer cells (FIG. 9).

Example 14

[Scratch Assay]

The effect of an anti-hTROP-2 monoclonal antibody on the migratory ability of human cancer cells was evaluated by a scratch assay. PK-59 cells were suspended in an RPMI1640 medium containing 10% fetal bovine serum at a cell concentration of $3\times10^5$ cells/mL, and 100 µL of the prepared cell suspension was then added to each well of a 96-well culture plate. When the cells became confluent, a portion of the monolayer-cultured cells was peeled, such that the plate was scratched in a longitudinal direction with the end of a tip. An anti-hTROP-2 monoclonal antibody and mouse IgG used as a negative control were added to the medium to final concentrations of 0.1 and 1 µg/mL, respectively, and culture was then carried out for 24 hours. Before addition of the antibody (Day 0) and 24 hours after the culture (Day 1), the cell peeled region was photographed, and the distance between the cells was then measured. Moreover, the area of such a peeled region was quantified using Scion Image software. The experiment was carried out using 8 wells for each group. A significant difference test was carried out according to Student's t-test, and $P<0.05$ was determined to be statistically significant.

Figure 10B:
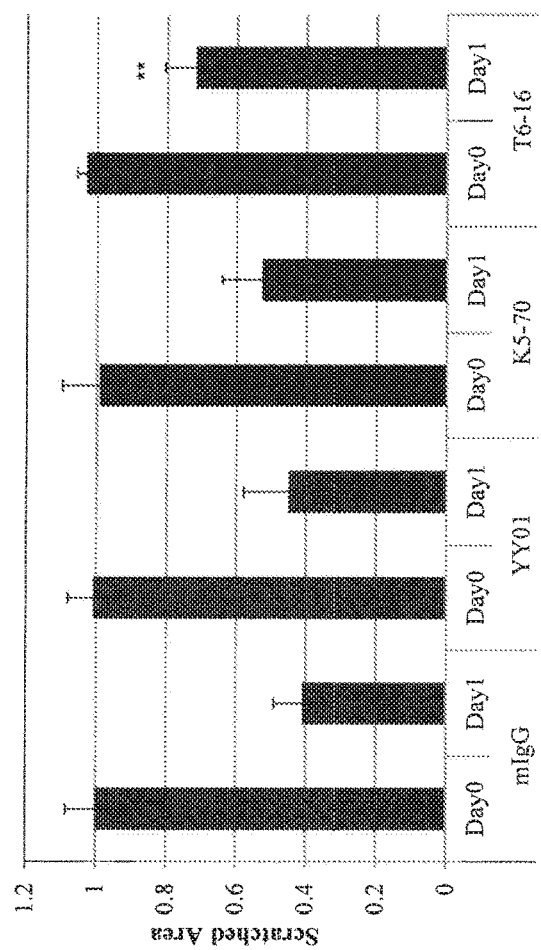
FIG. 10B. The area of a scratch region was analyzed using image analysis software (Scion Image), and based on the obtained value, the value of each test antibody was calculated using the value obtained on Day 0 of the control antibody (mIgG) addition group as a standard value of 1. *P<0.05, **P<0.01 (by Student's t-Test).
Figure 10A:
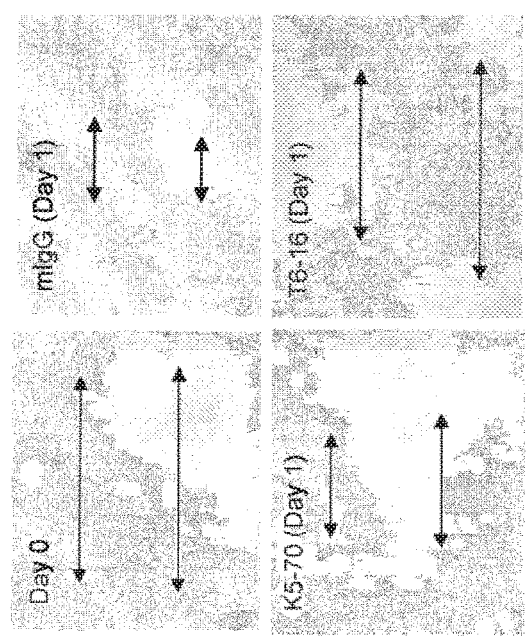
FIG. 10A shows representative examples of photographs of the scratch regions of PK-59 cells. Day 0 shows a representative example immediately after scratching. mIgG (Day 1) shows a photograph taken 1 day (24 hours) after scratching and then adding a control antibody (mouse IgG, 1 µg/mL) to the medium. K5-70 (Day 1) shows a photograph taken 1 day (24 hours) after scratching and then adding a K5-70 antibody (1 µg/mL) to the medium. T6-16 (Day 1) shows a photograph taken 1 day (24 hours) after scratching and then adding a T6-16 antibody (1 µg/mL) to the medium. Each arrow in each photograph indicates the width of a scratch region.

The effect of an hTROP-2 antibody on the migratory ability of the cells invading the scratch region was examined. As with the cell growth inhibition assay, antibodies having beneficial effects were evaluated. As an evaluation method, the cells were photographed on Day 0 (when the antibody was added) and on Day 1 (24 hours after the addition of the antibody), and the migratory distance (µm) and the area of a scratch region were determined by image analysis. As a result, as shown in FIG. 10, clear differences were observed in terms of the migratory ability of the cells. The antibodies T6-16 and K5-70, which were used in the present test, had significant cell growth inhibitory activity, when compared with the control. Even in a reproducibility test, the same tendency was observed. Particularly, T6-16 had a result of $P<0.01$ (by Student's t-test), and there was found correlation with the in vivo test.

Example 15

[Evaluation of Beneficial Effects of Anti-hTROP-2 Monoclonal Antibody on Tumor-Bearing Mice]
Prevention Model Pancreatic cancer cell lines (PK-59 and BxPC-3), which expressed hTROP-2, were harvested by treatment with trypsin, and PBS was added to them to prepare a cell suspension having a concentration of $1\times10^8$ cells/mL. The thus prepared cell suspension was mixed with an equal amount of Matrigel (BD Biosciences Pharmingen) on ice. Using a 26 G syringe, 100 µL of the obtained mixture ($5\times10^6$ cells) was injected into the subcutis of the right flank of each of 6-week-old female nude mouse (Balb/c, nu/nu). On the day of the transplantation of the cancer cells (Day 1), the mice were divided into groups, and administration of the antibody (1, 5 or 10 mg/kg body weight, intraperitoneal administration) was initiated. Thereafter, administration of the antibody was continued at intervals of once every three days. Anti-tumor activity was evaluated based on tumor formation frequency and tumor volume. The tumor volume was calculated by the following formula.

Tumor volume (mm$^3$)=(minor axis)$^2$×(major axis)×π/6

Treatment Model

Pancreatic cancer cell lines (PK-59 and BxPC-3), which expressed hTROP-2, were harvested by treatment with trypsin, and PBS was added to them to prepare a cell suspension having a concentration of $1\times10^8$ cells/mL. The thus prepared cell suspension was mixed with an equal amount of Matrigel (BD Biosciences Pharmingen) on ice. Using a 26 G syringe, 100 µL of the obtained mixture ($5\times10^6$ cells) was injected into the subcutis of the right flank of each of 6-week-old female nude mouse (Balb/c, nu/nu). Five to six days after the transplantation of the cancer cells, mice whose tumor volume had increased to 50 to 150 mm$^3$ (mean value: approximately 100 mm$^3$) were divided into groups. The day on which the mice were divided into groups was defined as a first day (Day 1), and administration of the antibody was initiated. The antibody was intraperitoneally administered at intervals of once every three days (10 mg/kg body weight). Anti-tumor activity was evaluated by measuring tumor volume. A significant difference test was carried out according to Student's t-test, and $P<0.05$ was determined to be statistically significant.

Example 16

[Analysis of In Vivo Anti-Tumor Activity of Anti-hTROP-2 Monoclonal Antibody on Human Pancreatic Cancer Cell Xenograft Model]

It is essential for an antibody used for the treatment of cancer, which targets hTROP-2, to have the activity of specifically killing tumor tissues expressing hTROP-2 or inhibiting the growth of tumor in a xenograft model.

Figures 11A, 11B, 11C, 11D:
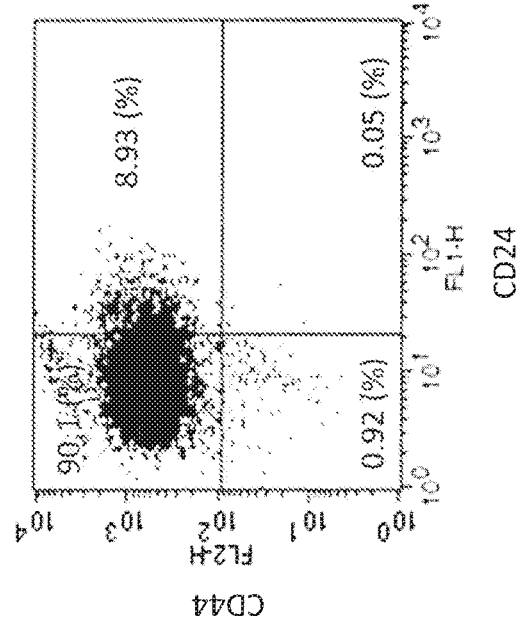
FIG. 11A is a view illustrating FACS showing the expression of EpCAM in the PK-59 cells. The filled histogram indicates the reaction of the cells only with a secondary antibody (PE-labeled anti-mouse IgG), and the open histogram indicates the reaction of the cells with an anti-human EpCAM antibody (Becton, Dickinson and Company).
FIGS. 11B and C are views illustrating FACS showing the expression of P-glycoprotein/MCR1 in the PK-59 cells (FIG. 11B), and the expression of ABCG2 in the PK-59 cells (FIG. 11C). The blue histogram indicates the reaction of the cells only with a secondary antibody, and the red histogram indicates the reaction of the cells with an anti-human P-glycoprotein/MDR1 antibody (BD Biosciences Pharmingen) (FIG. 11B), or with an anti-human ABCG2 antibody (BD Biosciences Pharmingen) (FIG. 11C).
FIG. 11D shows FACS analysis, in which the PK-59 cells were double stained with pancreatic cancer stem cell markers, an FITC-labeled anti-human CD24 antibody (BD Biosciences Pharmingen) and a PE-labeled anti-human CD44 antibody (BD Biosciences Pharmingen). Each number in FIG. 11D indicates the existing ratio of the cells in each fraction.

Anti-hTROP-2 monoclonal antibodies (approximately 160 clones), which were newly produced in the present invention, were evaluated using the xenograft treatment models of a pancreatic cancer cell line PK-59. The PK-59 cells express, on the surface thereof, EpCAM (FIG. 11A) acting as a pancreatic cancer stem cell marker (Chenwei Li, et al. Cancer Res 2007; 67: (3). 1030-1037), and also express P-glycoprotein/MDR1 (FIG. 11B) and ABCG2/CDw338 (FIG. 11C) (Chen, C. J. et al. Cell 47 (3), 381-389 (1986), Allikmets, R., et al. Hum. Mol. Genet. 5 (10), 1649-1655 (1996)), which are ABC transporters associated with drug resistance. In addition, the PK-59 cells contain a cell fraction (8.93%) (FIG. 11D) positive for both CD24 and CD44, which is characteristic for pancreatic cancer stem cells, and they are assumed to be a highly malignant human pancreatic cancer cell line (Chenwei Li, et al. Cancer Res 2007; 67: (3). 1030-1037, Jane E. Visvader and Geoffrey J. Lindeman. Nat Rev Cancer. Vol. 8(10):755-68, 2008).

Most of the newly generated approximately 160 clones did not exhibit beneficial effects on the xenograft treatment models of PK-59 cells. Among such clones, clones exhibiting significant tumor growth inhibitory activity, namely clones K5-70, T6-16, K5-107, T5-86 and K5-116-2-1 could be obtained.

Figure 12A:
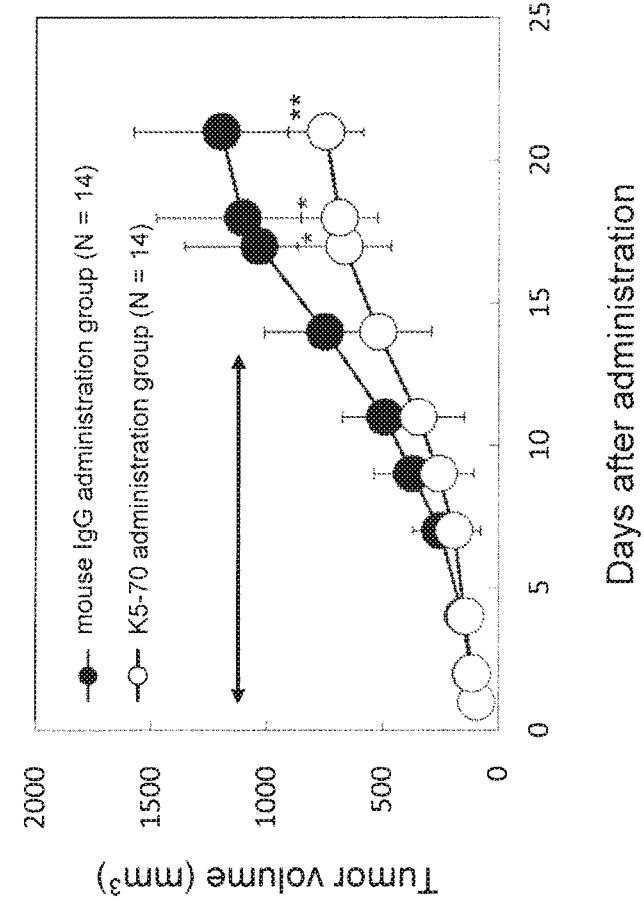
FIG. 12A shows the time course of tumor growth of a control group (●: mouse IgG) and a K5-70 antibody (10 mg/kg body weight) administration group (○) (a mean value±standard deviation). The arrow indicates an antibody administration period. * P<0.05, ** P<0.01 (by Student's t-test).
Figure 12B:
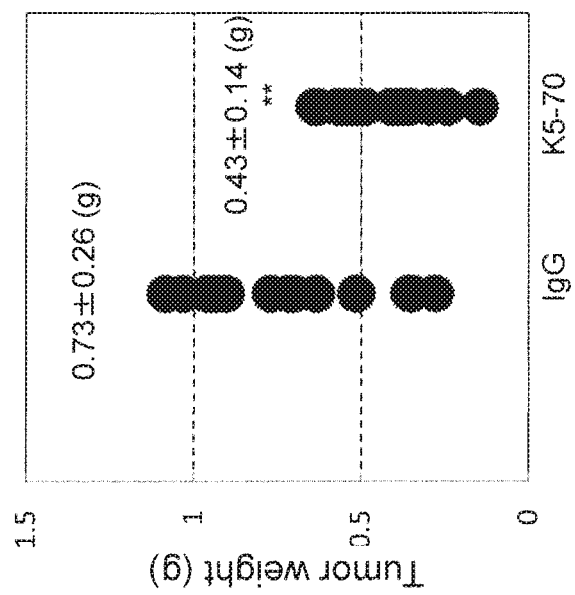
FIG. 12B shows the plotted tumor weight of each mouse at the time of the 21$^{st}$ day (Day 21) (the final day of experiment) in the test of FIG. 12A. The numerical value on each plot indicates a mean value±standard deviation. ** P<0.01 (by Student's t-test).

In a clone K5-70 (mouse IgG2a) administration group, tumor growth rate is statistically significantly inhibited. On the 21$^{st}$ day after initiation of the administration (day 21), the tumor volume of a control group (N=14) was 1200.8±377.3 mm$^3$, whereas the tumor volume of the clone K5-70 administration group was 748.7±175.0 mm$^3$ ($P<0.01$ by Student's t-test) (FIG. 12A). When the tumor volume at the time of initiation of the administration of the antibody was defined as 1.0, the tumor volume on the 21$^{st}$ day (Day 21) was 7.8 in the clone K5-70 administration group, whereas the tumor volume of the control group was 12.5 (FIG. 12A). The weight of the tumor excised was 0.43±0.14 g ($P<0.01$ by Student's t-test) in the clone K5-70 administration group, whereas that of the control group was 0.73±0.26 g. Thus, the clone K5-70 exhibited inhibitory activity of approximately 60% (FIG. 12B).

Figure 13A:
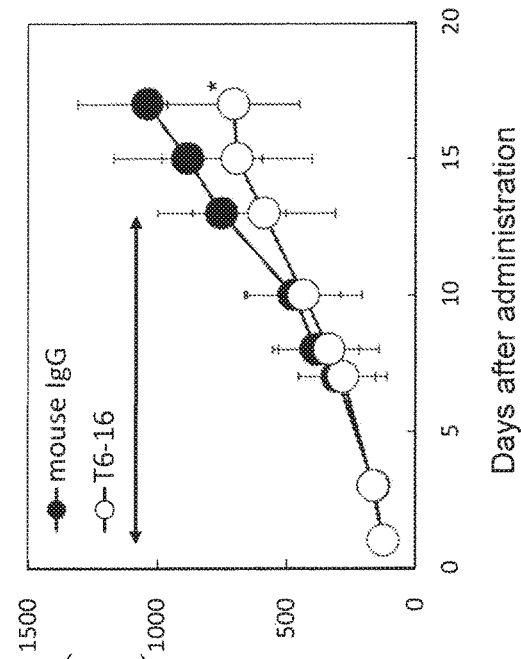
FIG. 13 shows the evaluation of the anti-tumor activity of a clone K5-107 (A), a clone T6-16 (B) and a clone K5-116-2-1 (C) on xenograft treatment models using PK-59 cells. The symbol "●" indicates a control group (mouse IgG), and the symbol "○" indicates an anti-hTROP-2 antibody (10 mg/kg body weight) administration group. The arrow in the graph indicates an antibody administration period, and the numerical value on each plot indicates a mean value±standard deviation. * P<0.05 (by Student's t-test).
Figure 13B:
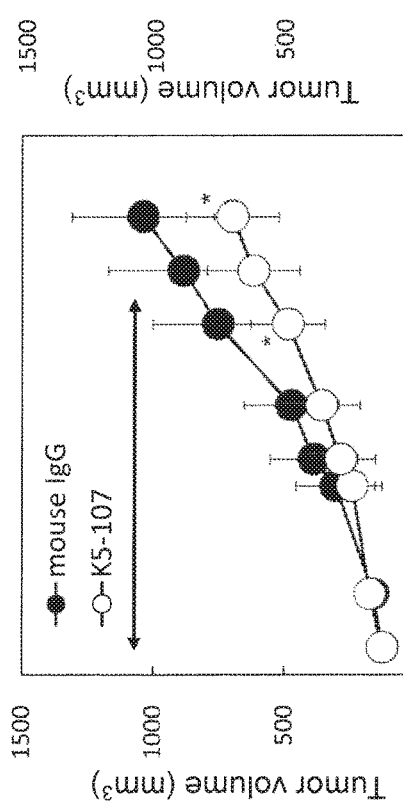
Figure 13C:
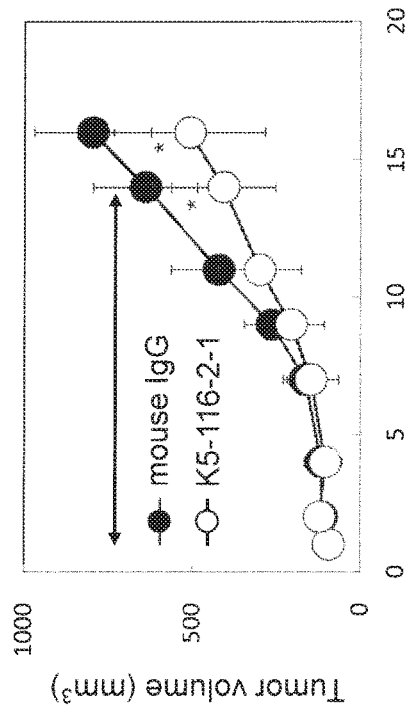

Similarly, tumor growth rate was statistically significantly inhibited even in a clone K5-107 (mouse IgG1) administration group (N=8), a clone T6-16 (mouse IgG2a) administration group (N=8), a clone T5-86 (mouse IgG1) administration group and a clone K5-116-2-1 (mouse IgG2a) administration group (N=8). On the 17$^{th}$ day after initiation of the administration (Day 17), the tumor volumes of the clone K5-107 administration group (N=8) and the clone T6-16 administration group (N=8) were 698.2±175.9 mm³ (P<0.05 by Student's t-test) and 707.2±254.5 mm³ (P<0.05 by Student's t-test), respectively, whereas the tumor volume of the control group was 1039.3±271.6 mm³. Likewise, on the 16$^{th}$ day after initiation of the administration (Day 16), the tumor volume of the clone K5-116-2-1 administration group (N=8) was 508.5±225.2 mm³ (P<0.05 by Student's t-test), whereas the tumor volume of the control group (N=8) was 797.0±172.9 mm³ (FIG. 13).

On the other hand, in the case of the clone T5-86, on the 15$^{th}$ day after initiation of the administration (Day 15), the tumor of the clone T5-86 administration group (N=8) was 744.1±289.1 mm³, whereas the tumor volume of the control group (N=8) was 1033.2±319.4 mm³. Thus, there was found no significant difference in terms of tumor volume. However, in the comparison of tumor weight, which was performed on the same day, the tumor weight of the clone T5-86 administration group was 0.44±0.13 g (P<0.05 by Student's t-test), whereas the tumor weight of the control group was 0.62±0.14 g. Thus, the clone T5-86 exhibited significant inhibitory activity.

Moreover, in terms of both tumor volume and tumor weight, the ratio (T/C) of each clone antibody administration group to the control group on the final day of experiment is shown in Table 2 below. As shown in Table 2, each clone antibody exhibited significant inhibitory activity (T/C=62% to 72%) on each clone antibody administration group.

TABLE 2

| Group | N (number of mice) | Tumor volume T/C (%) | Tumor weight T/C (%) |
|---|---|---|---|
| K5-70 | 14 | 62.3** | 58.8** |
| K5-107 | 8 | 67.2* | 65.0* |
| T6-16 | 8 | 68.0* | 64.7* |
| T5-86 | 8 | 72.0 | 70.5* |
| K5-116-2-1 | 8 | 63.8* | 60.5* |

*P < 0.05,
**P < 0.01 (by Student's t-test)

Figure 14B:
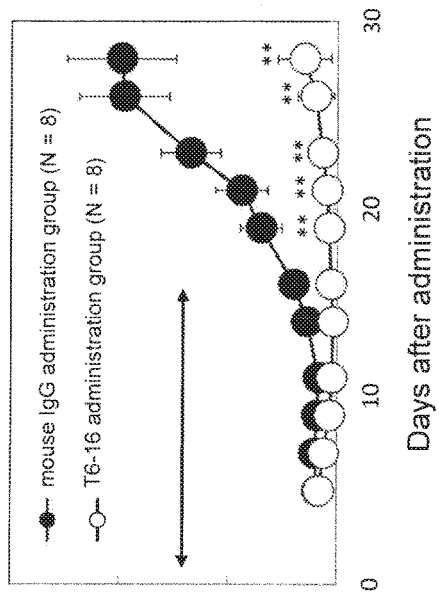
FIG. 14 shows the evaluation of the anti-tumor activity of a clone K5-70 (FIG. 14A), a clone T6-16 (FIG. 14B) and a clone K5-116-2-1 (FIG. 14C) in xenograft prevention models using PK-59 cells. The symbol "●" indicates a control group (mouse IgG), and the symbol "○" indicates an anti-hTROP-2 antibody (10 mg/kg body weight) administration group. The arrow in the graph indicates an antibody administration period, and the numerical value on each plot indicates a mean value±standard deviation. ** P<0.01 (by Student's t-test).
Figure 14A:
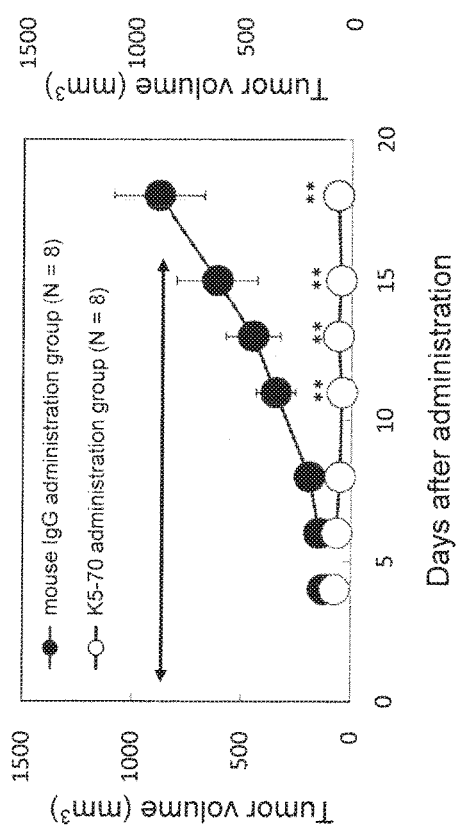
Figure 14C:
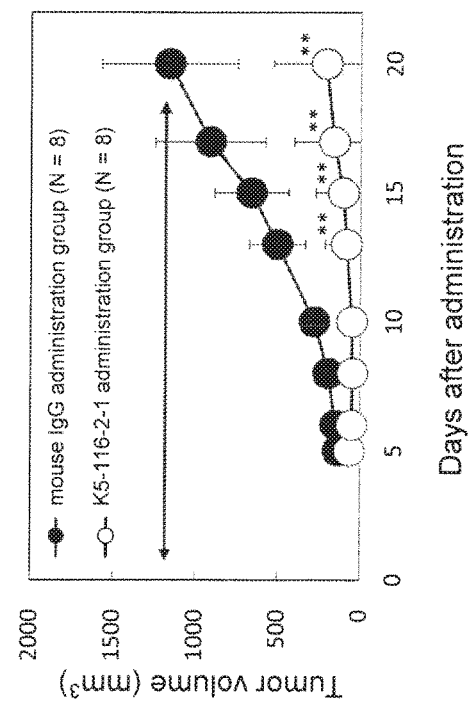

Furthermore, the anti-tumor activity of each of the clones K5-70, T6-16 and K5-116-2-1 on the xenograft prevention models of the pancreatic cancer cell line PK-59 was analyzed. After completion of the administration of each antibody clone, tumor growth was inhibited in all individuals (N=8). On the 18$^{th}$ day after initiation of the administration (Day 18), the tumor volume of the clone K5-70 administration group (10 mg/kg body weight) was 62.4±80.4 mm³ (P<0.01 by Student's t-test), whereas the tumor volume of the control group (N=8) was 880.8±206.4 mm³. Thus, the clone K5-70 exhibited tumor growth inhibitory activity of 92.9%. On the 28$^{th}$ day after initiation of the administration (Day 28), the tumor volume of the clone T6-16 administration group (10 mg/kg body weight) was 152.14±122.3 mm³ (P<0.01 by Student's t-test), whereas the tumor volume of the control group (N=8) was 992.3±250.8 mm³. Thus, the clone T6-16 exhibited tumor growth inhibitory activity of 84.6%. On the 20$^{th}$ day after initiation of the administration (Day 20), the tumor volume of the clone K5-116-2-1 administration group (10 mg/kg body weight) was 207.7±319 2 mm³ (P<0.01 by Student's t-test), whereas the tumor volume of the control group (N=8) was 1159.4±413.3 mm³. Thus, the clone K5-116-2-1 exhibited tumor growth inhibitory activity of 82.1% (FIG. 14 and Table 3). Moreover, in all of the experiments, there was no significant difference between the control group and each anti-hTROP-2 antibody administration group in terms of a change in mean body weight throughout the test period.

In terms of both tumor volume and tumor weight, the ratio (T/C) of each clone antibody administration group to the control group on the final day of experiment is shown in Table 3 below. As shown in Table 3, significant tumor growth inhibition was observed in each clone antibody administration group, and in particular, a significant effect such as T/C=10% or less was confirmed in the clone K5-70 administration group.

TABLE 3

| Group | N (number of mice) | Tumor volume T/C (%) | Tumor weight T/C (%) |
|---|---|---|---|
| K5-70 | 8 | 7.1** | 5.8** |
| T6-16 | 8 | 15.3** | 10.5** |
| K5-116-2-1 | 8 | 23.2** | 21.5** |

**P < 0.01 (by Student's t-test)

The known anti-TROP-2 antibody AR47A6.4.2 (U.S. Pat. No. 7,420,041) has exhibited the effect of inhibiting tumor growth, at a dosage of 20 mg/kg, on xenograft prevention models using various human cancer cell lines. This anti-TROP-2 antibody AR47A6.4.2 has inhibited the tumor growth of a human pancreatic cancer cell line PL45 at a percentage of almost 100%. However, this antibody has had the effect of inhibiting tumor on a pancreatic cancer cell line BxPC-3 at a percentage of approximately 50%, on a prostate cancer cell line PC-3 at a percentage of approximately 40%, on a breast cancer cell line MCF-7 at a percentage of approximately 60%, and on a colon cancer cell line Colo205 at a percentage of approximately 40%. In contrast, the anti-hTROP-2 antibody of the invention of the present application has exhibited a higher tumor growth inhibitory effect at a dosage of half the aforementioned dose (10 mg/kg body weight).

Example 17

[Analysis of Anti-Tumor Activity on Xenograft Models (Prevention Models and Treatment Models) of Human Pancreatic Cancer Cell Line BxPC-3]

As in the case of using the above-described xenograft treatment models of the human pancreatic cancer cell line PK-59, the anti-tumor activity of the clone K5-70 on xenograft prevention models and xenograft treatment models of a human pancreatic cancer cell line BxPC-3 was analyzed.

Figure 15A:
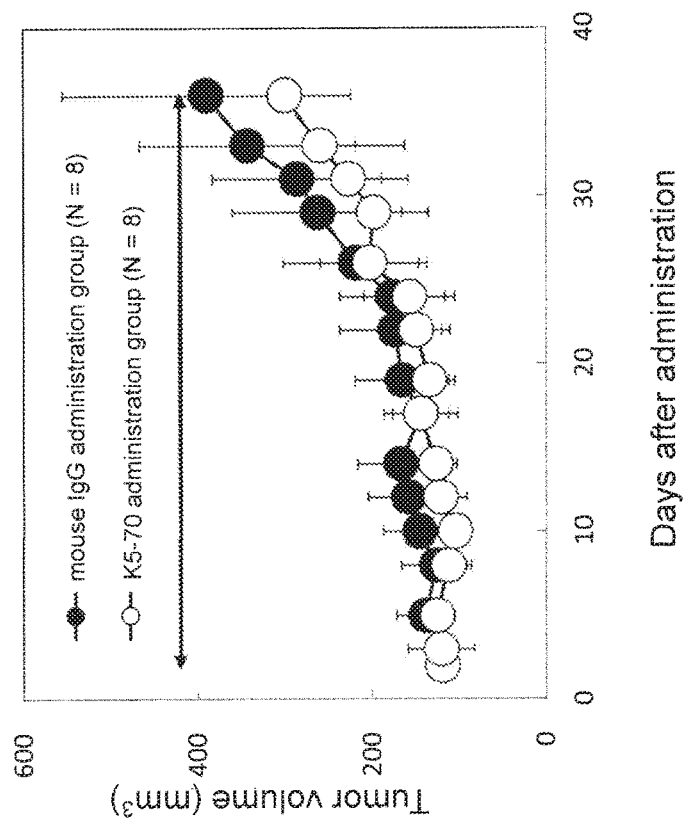
FIG. 15A shows the time course of tumor growth of a control group (●: mouse IgG) and a K5-70 antibody (10 mg/kg body weight) administration group (○) in prevention models (a mean value±standard deviation). The arrow indicates an antibody administration period. ** P<0.01 (by Student's t-test).
Figure 15B:
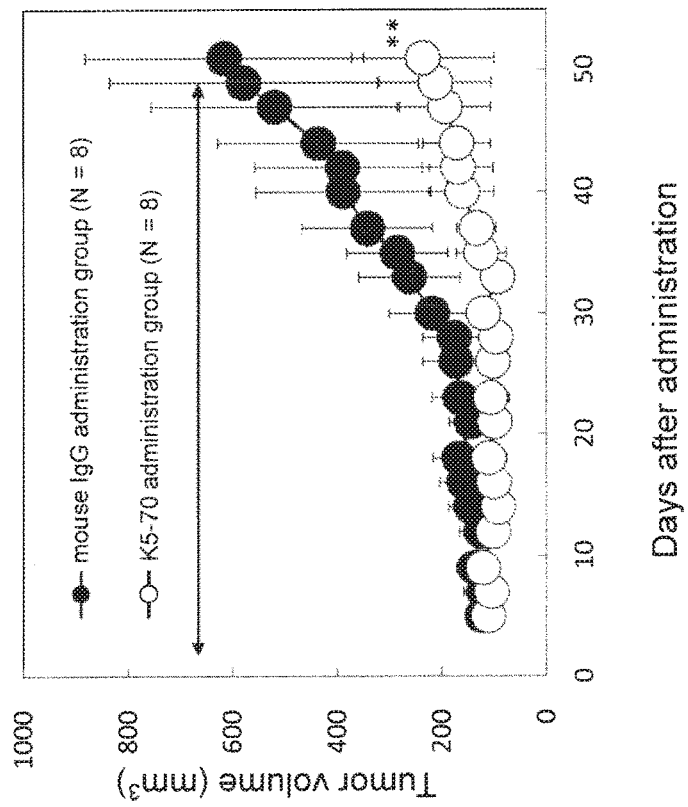
FIG. 15B shows the time course of tumor growth of a control group (●: mouse IgG) and a K5-70 antibody (10 mg/kg body weight) administration group (○) in treatment models (a mean value±standard deviation). The arrow indicates an antibody administration period. * P<0.05 (by Student's t-test).

When compared with a control group (N=8), the tumor growth of the clone K-70 administration group was significantly inhibited. On the 52$^{nd}$ day (Day 52), the tumor volume of the clone K5-70 administration group (N=8) was 236.0±136 4 mm³, whereas the tumor volume of the control group (N=8) was 616.3±266.8 mm³. Thus, the clone K-70 exhibited a tumor growth inhibitory effect of 61.7% (P<0.01 by Student's t-test) (FIG. 15).

From the aforementioned results, it became clear that the anti-hTROP-2 monoclonal antibody exhibits significant tumor growth inhibitory activity in vivo on at least two cancer cell species.

Example 18

[Dose-Dependent Anti-Tumor Activity of Anti-hTROP-2 Antibody (Clone K5-70) on Xenograft Prevention Models of hTROP-2-Expressing Pancreatic Cancer Cell Line (PK-59 Cells)]

Figure 16B:
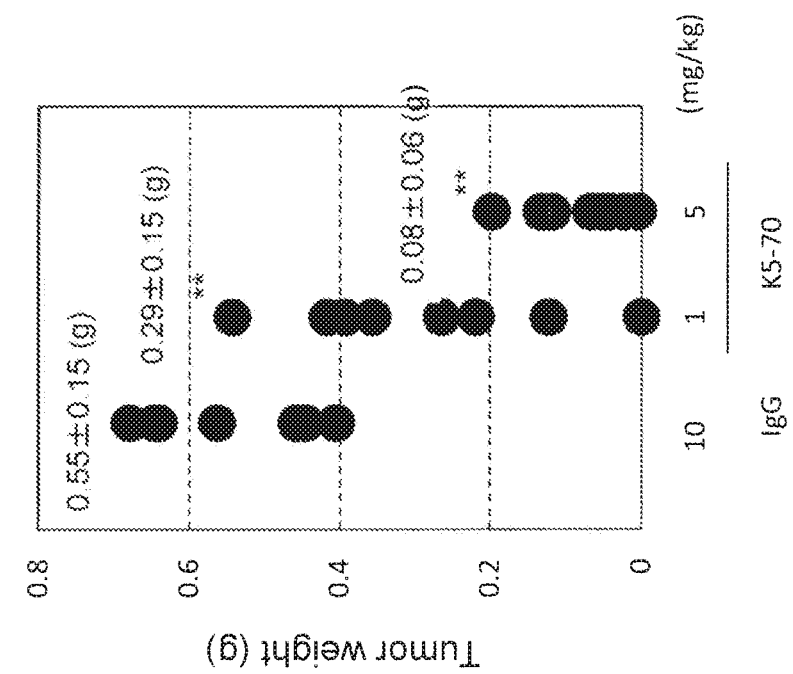
FIG. 16B shows the plotted tumor weight of each mouse at the time of the 17$^{th}$ day (Day 17) (the final day of experiment) in the test of FIG. 16A. The numerical number on each plot indicates a mean value±standard deviation. ** P<0.01 (by Student's t-test).
Figure 16A:
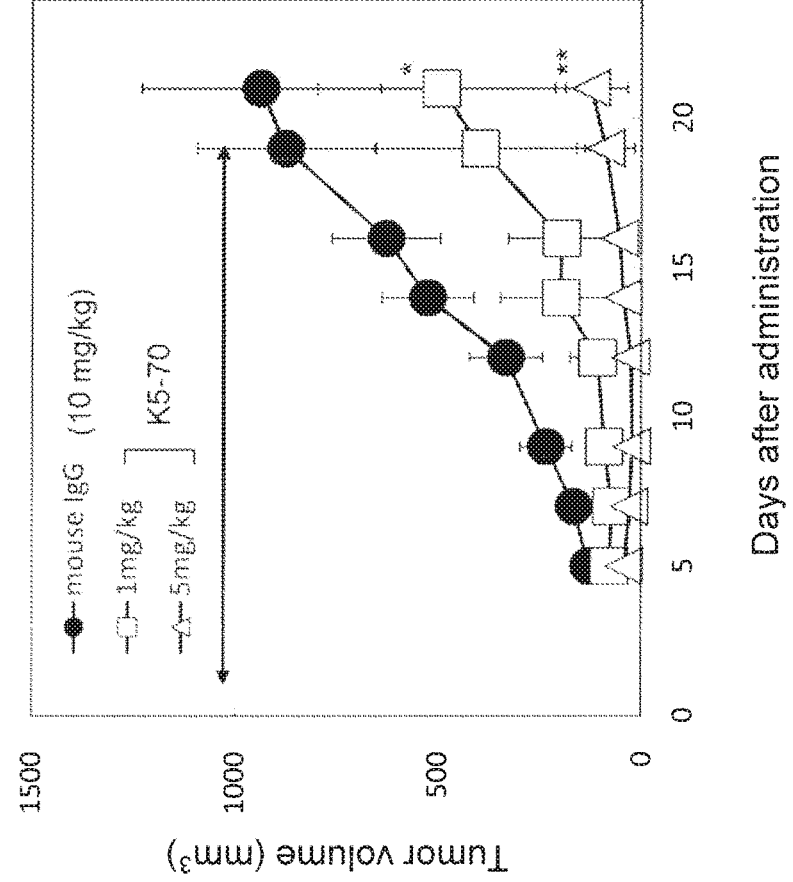
FIG. 16A shows the time course of tumor growth of a control group (●: mouse IgG) and K5-70 antibody administration groups (□: 1 mg/kg body weight, ∆: 5 mg/kg body weight) at different doses (a mean value±standard deviation). The arrow indicates an antibody administration period. * P<0.05 (by Student's t-test), ** P<0.01 (by Student's t-test).

For the purpose of analyzing more in detail the tumor growth inhibitory activity in vivo of the anti-hTROP-2 antibody, a dose-dependent test was carried out. As shown in FIG. 16, the tumor growth of PK-59 cells was dose-dependently inhibited by administration of the K5-70 antibody. On the 21$^{st}$ day after administration of the antibody (Day 21), the tumor volume of the control group (N=8) was 937.8±295.3 mm$^3$. On the other hand, the tumor volume of the K5-70 antibody (1 mg/kg body weight) administration group (N=8) was 493.5±305.1 mm$^3$, showing an inhibitory rate of 50%, and the tumor volume of the K5-70 antibody (5 mg/kg body weight) administration group (N=8) was 124.7±89.0 mm$^3$, showing an inhibitory rate of 90%. Thus, it became clear that, when compared with the known anti-TROP-2 antibody AR47A6.4.2 (U.S. Pat. No. 7,420,041), the anti-hTROP-2 antibody of the present invention exhibits in vivo a tumor growth inhibitory effect equivalent to that of the anti-TROP-2 antibody AR47A6.4.2 at a dosage of one-twentieth the anti-TROP-2 antibody AR47A6.4.2, and that it exhibits a higher inhibitory effect of 90% at a dosage of one-fourth thereof.

Example 19

[Epitope Assay]
Preparation of Human/Mouse Chimeric TROP-2 Protein

A human/mouse TROP-2 gene was prepared according to a PCR method. PCR primers as shown below were designed based on a human TROP-2 gene sequence and a mouse TROP-2 gene sequence (Genbank accession No. NM_020047).

```
Human/mouse TROP-2-C primers
Y606 (forward side):
                                       (SEQ ID NO: 10)
5'-cctgagcctacgctgcgacgaagtggtgcg-3'

Y607 (reverse side):
                                       (SEQ ID NO: 11)
5'-cgcaccacttcgtcgcagcgtaggctcagg-3'

Human/mouse TROP-2-A primers
Y612 (forward side):
                                       (SEQ ID NO: 12)
5'-gactgctccacgctgacttccaagtgcctg-3'

Y613 (reverse side):
                                       SEQ ID NO: 13)
5'-caggcacttggaagtcagcgtggagcagtc-3'

Human/mouse TROP-2-B primers
Y614 (forward side):
                                       (SEQ ID NO: 14)
5'-ctcgtggacaacgatggcctctacgacccg-3'

Y615 (reverse side):
                                       (SEQ ID NO: 15)
5'-cgggtcgtagaggccatcgttgtccacgag-3'

Mouse/human TROP-2-D primers
Y608 (forward side):
                                       (SEQ ID NO: 16)
5'-ccaaagcctgcgctgcgatgagctggtgcgc-3'

Y609 (reverse side):
                                       (SEQ ID NO: 17)
5'-gcgcaccagctcatcgcagcgcaggctttgg-3'

Mouse/human TROP-2-E primers
Y616 (forward side):
                                       (SEQ ID NO: 18)
5'-agcttcctatccgcggtgcactacgagcag-3'

Y617 (reverse side):
                                       (SEQ ID NO: 19)
5'-ctgctcgtagtgcaccgcggataggaagct-3'

Mouse/human TROP-2-F primers
Y618 (forward side):
                                       (SEQ ID NO: 20)
5'-gacattaaaggcgagtctctattccagggc-3'

Y619 (reverse side):
                                       (SEQ ID NO: 21)
5'-gccctggaatagagactcgcctttaatgtc-3'

Mouse TROP-2 primers
Forward primer:
                                       (SEQ ID NO: 22)
5-ctactccaccccaccctggcg-3'

Reverse primer:
                                       (SEQ ID NO: 23)
5'-ctcgagcaagctaggttcgcttctc-3'
```

To the mouse TROP-2 reverse primer, a XhoI restriction enzyme-digested sequence except for a stop codon was added. A schematic view of the prepared human/mouse chimeric TROP-2 proteins is shown in FIG. 17.

The hmTROP-2-A chimeric protein is a chimeric protein, which consists of a polypeptide ranging from the N-terminus to the amino acid at position 69 of the hTROP-2 protein and a polypeptide ranging from the amino acid at position 64 to the C-terminus of the mouse TROP-2 protein. The hmTROP-2-B chimeric protein is a chimeric protein, which consists of a polypeptide ranging from the N-terminus to the amino acid at position 101 of the hTROP-2 protein and a polypeptide ranging from the amino acid at position 96 to the C-terminus of the mouse TROP-2 protein. The hmTROP-2-C chimeric protein is a chimeric protein, which consists of a polypeptide ranging from the N-terminus to the amino acid at position 145 of the hTROP-2 protein and a polypeptide ranging from the amino acid at position 140 to the C-terminus of the mouse TROP-2 protein. The mhTROP-2-D chimeric protein is a chimeric protein, which consists of a polypeptide ranging from the N-terminus to the amino acid at position 139 of the mouse TROP-2 protein and a polypeptide ranging from the amino acid at position 146 to the C-terminus of the hTROP-2 protein. The mhTROP-2-E chimeric protein is a chimeric protein, which consists of a polypeptide ranging from the N-terminus to the amino acid at position 187 of the mouse TROP-2 protein and a polypeptide ranging from the amino acid at position 194 to the C-terminus of the hTROP-2 protein. The mhTROP-2-F chimeric protein is a chimeric protein, which consists of a polypeptide ranging from the N-terminus to the amino acid at position 227 of the mouse TROP-2 protein and a polypeptide ranging from the amino acid at position 234 to the C-terminus of the hTROP-2 protein.

Expression vectors used in the preparation of the above-described chimeric proteins were specifically constructed by the following methods. In order to prepare an hmTROP-2-A chimeric gene, the hTROP-2 gene was used as a template, and PCR was carried out using the hTROP-2 forward primer and the human/mouse TROP-2-A primer Y613. Likewise, the mouse TROP-2 gene was used as a template, and PCR was carried out using the human/mouse TROP-2-A primer Y612 and the mouse TROP-2 reverse primer. A DNA fragment amplified by the PCR was developed using acrylamide gel, and a band of interest was then recovered by extraction. Subsequently, the extracted two types of DNA fragments were mixed to prepare a template, and PCR was then carried out using the hTROP-2 forward primer and the mouse TROP-2 reverse primer. A PCR product was developed by agarose gel electrophoresis, and a DNA fragment of interest was then extracted. The extracted DNA fragment was cloned into a pCR®-Blunt vector (Invitrogen) (pCRB-hmTROP-2-A), and a gene sequence was then confirmed. An expression vector for animal cells was produced by removing the hTROP-2 gene from pcDNA3.1-hTROP-2-myc/His by EcoRI/XhoI digestion, and then inserting therein an EcoRI/XhoI fragment containing an hmTROP-2-A chimeric gene prepared from pCRB-hmTROP-2-A (pcDNA3.1-hmTROP-2-A-myc/His). Additionally, the following chimeric genes were prepared by the same method as described above, and expression vectors were constructed: hmTROP-2-B (using a human TROP-2 forward primer, a human/mouse TROP-2-B primer Y615, a human/mouse TROP-2-B primer Y614 and a mouse TROP-2 reverse primer), hmTROP-2-C (using a human TROP-2 forward primer, a human/mouse TROP-2-C primer Y607, a human/mouse TROP-2-C primer Y606 and a mouse TROP-2 reverse primer), mhTROP-2-D (using a mouse TROP-2 forward primer, a mouse/human TROP-2-D primer Y609, a mouse/human TROP-2-D primer Y608 and a human TROP-2 reverse primer), mhTROP-2-E (using a mouse TROP-2 forward primer, a mouse/human TROP-2-E primer Y617, a mouse/human TROP-2-E primer Y616 and a human TROP-2 reverse primer), mhTROP-2-F (using a mouse TROP-2 forward primer, a mouse/human TROP-2-F primer Y619, a mouse/human TROP-2-F primer Y618 and a human TROP-2 reverse primer) (pcDNA3.1-hmTROP-2-B-myc/His, pcDNA3.1-hmTROP-2-C-myc/His, pcDNA3.1-mhTROP-2-D-myc/His, pcDNA3.1-mhTROP-2-E-myc/His, and pcDNA3.1-mhTROP-2-F-myc/His).

Establishment of HEK293 Cell Lines, which Constitutively Express hTROP-2, Human/Mouse TROP-2-C and Mouse/Human TROP-2-D Chimeric Proteins The above-described expression vectors pcDNA3.1-hTROP-2-myc/His, pcDNA3.1-hmTROP-2-C-myc/His and pcDNA3.1-mhTROP-2-D-myc/His were each introduced into HEK293 cells. Selection was carried out using an antibiotic G418 (Calbiochem), and HEK293 cell lines constitutively expressing the hTROP-2 protein, the hmTROP-2-C chimeric protein and the mhTROP-2-D chimeric protein were established.

The binding regions of the anti-hTROP-2 monoclonal antibodies K5-70, T5-86, K5-107, T6-4, T6-16 and K5-116-2-1, which had exhibited beneficial effects on the xenograft treatment models of the pancreatic cancer cell line PK-59, were identified. First, the reactivity of the anti-hTROP-2 monoclonal antibodies exhibiting beneficial effects with HEK293 cells, which constantly express the chimeric proteins hmTROP-2-C and mhTROP-2-D, was examined by FACS analysis (FIG. 18). As a result, it was found that the K5-70, K5-107, T5-86 and K5-116-2-1 antibodies reacted with hmTROP-2-C, but that these antibodies did not react with mhTROP-2-D. On the other hand, the T6-4 and T6-16 antibodies reacted with mhTROP-2-D, but they did not react with hmTROP-2-C. From these results, the binding region of each of the K5-70, K5-107, T5-84 and K5-116-2-1 antibodies was limited to a region ranging from the N-terminus to the amino acid at position 145 of hTROP-2, and the binding region of each of the T6-4 and T6-16 antibodies was limited to a region ranging from the amino acid at position 146 to the C-terminal region of hTROP-2 (FIG. 18).

Figures 19A, 19B:
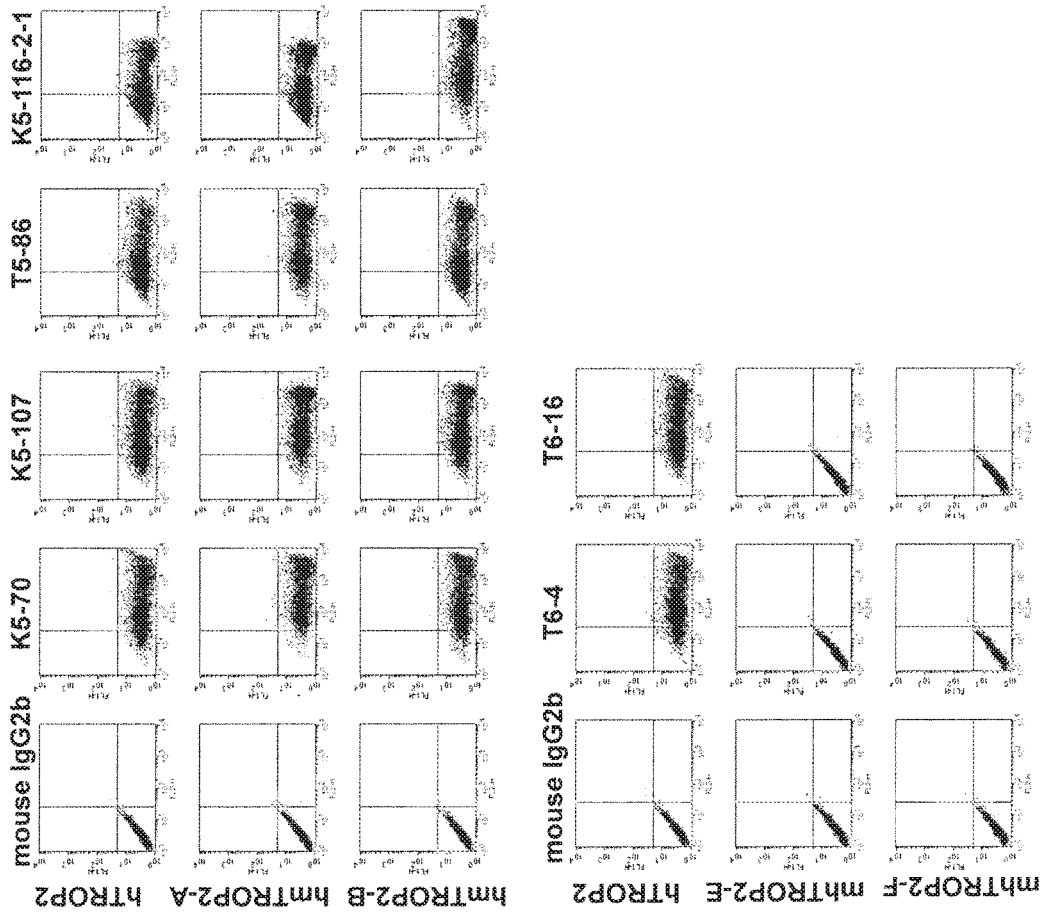
In FIG. 19(A), the reactivity of K5-70, K5-107, T5-86 and K5-116-2-1 antibodies with hTROP-2 (upper case), with hmTROP-2-A (middle case) and with hmTROP-2-B (lower case) was studied. As a negative control, mouse IgG2b was used.
In FIG. 19(B), the reactivity of T6-4 and T6-16 antibodies with hTROP-2 (upper case), with mhTROP-2-E (middle case) and with mhTROP-2-F (lower case) was studied. As a negative control, mouse IgG2b was used.

In order to analyze the binding regions more in detail, vectors used in the expression of hmTROP-2-A, hmTROP-2-B, mhTROP-2-E and mhTROP-2-F chimeric proteins were prepared, and the reactivity of the chimeric proteins with the anti-hTROP-2 monoclonal antibodies exhibiting beneficial effects was analyzed (FIG. 19). The newly prepared expression vectors, which were to be used in the expression of the chimeric proteins, were each introduced into HEK293 cells, and FACS analysis was then carried out, using the cells which transiently expressed the chimeric proteins. The K5-70, K5-107, T5-86 and K5-116-2-1 antibodies reacted with hmTROP-2-A, but did not react with mhTROP-2-B. The examined 6 types of monoclonal antibodies all reacted with hTROP-2. These results clearly showed that the binding region of the K5-70, K5-107, T5-86 and K5-116-2-1 antibodies is present in a region ranging from the N-terminus to the amino acid at position 69 of hTROP-2. Moreover, the T6-4 and T6-16 antibodies reacted with neither mhTROP-2-E nor mhTROP-2-F. This suggested that these antibodies recognize a region ranging from the amino acid at position 146 to the amino acid at position 193 of hTROP-2.

Example 20

[Immunohistochemistry]
<Materials/Method>

The following normal and cancer tissue arrays were used in immunohistostaining.

Human Normal Tissue Arrays:
  Human, normal organs in duplicates (Catalog No.: AB1, Super Bio Chips)
  Normal tissues more than single spots (Catalog No.: A103(VI), ISU ABXIS)

Lung Cancer Tissue Arrays:
  Human lung cancer-metastasis-normal (Catalog No.: CCA3, Super Bio Chips)
  Human lung carcinoma tissue with margin tissue, 2 location cores (Catalog No.: OD-CT-RsLug03-002, Shanghai Outdo Biotech)

Pancreatic Cancer Tissue Array:
  Human pancreas carcinoma tissue with mono-pathological type from 60 cases, 2 location cores (Catalog No.: OD-CT-DgPan03-001, Shanghai Outdo Biotech)

Liver Cancer Tissue Arrays:
  Hepatocellular carcinoma, grades I to III with normal tissue controls, 63 cases tissue arrays (Catalog No.: CS03-01-002U, Cybrdi)
  Human liver carcinoma tissue with mono-pathological type from 30 cases, 2 location cores (Catalog No.: OD-CT-DgLiv02-002, Shanghai Outdo Biotech)

Colorectal Cancer Tissue Arrays:
  Human, colorectal cancer (Catalog No.: CD3, Super Bio Chips)
  Human colon carcinoma with margin tissue, 2 location cores (Catalog No.: OD-CT-DgCo103-002, Shanghai Outdo Biotech)

Colorectal Cancer Lymph Node Metastasis and Liver Metastasis Tissue Arrays:
  Colorectal (colon and rectum) cancer with matched lymph node metastasis tissue array, 44 cases/99 cores, trial slide (Catalog No.: C0991t, Biomax us)
  Colorectal (colon and rectum) cancer with matched lymph node metastasis and normal adjacent tissue array, 43 cases/99 cores (Catalog No.: C0992, Biomax us)
  Colon cancer tissues liver metastasis (Catalog No.: A203 (IV), ISU ABXIS)

Breast Cancer Tissue Arrays:
  Human, breast cancer-metastasis-normal (Catalog No.: CBA3, Super Bio Chips)
  Human breast carcinoma with margin tissue, 2 location cores (Catalog No.: OD-CT-RpBre03-002, Shanghai Outdo Biotech)

Stomach Cancer Tissue Arrays:
Human, stomach cancer (Catalog No.: CQ1, Super Bio Chips)
Human gastric carcinoma with margin tissue, 2 location cores (Catalog No.: OD-CT-DgStm03-002, Shanghai Outdo Biotech)
Esophagus Cancer Tissue Array:
Human, esophagus cancer (Catalog No.: CR1, Super Bio Chips)
Human esophagus carcinoma with margin tissue, 2 location cores (Catalog No.: OD-CT-DgEso03-002, Shanghai Outdo Biotech)
Ovarian Cancer Tissue Array:
Human, ovary cancer (Catalog No.: CJ1, Super Bio Chips)
Prostate Cancer Tissue Array:
Human, prostate cancer-normal (Catalog No.: CA3, Super Bio Chips)
Bladder Cancer Tissue Array:
Bladder carcinoma/transitional cell carcinoma, grades I to III with normal tissue arrays (Catalog No.: CC12-01-001U, Cybrdi)
Patient information and clinical information regarding the above-described tissue arrays were obtained from data sheets attached herewith and the homepages of individual companies.

Immunohistostaining Method

After completion of a deparaffinization treatment, the tissue array slides of human normal tissues and cancer tissues were subjected to a protease treatment with pepsin at 37° C. for 5 minutes. Thereafter, the sections were used in immunostaining using an anti-hTROP-2 monoclonal antibody. A color reaction was carried out using DAB(3,3'-diaminobenzidine) as a substrate, and as a counter staining, nuclear staining was then carried out using hematoxylin.

More specifically, these operations were carried out as follows. A paraffin-embedded section was subjected to a deparaffinization treatment, and was then subjected to a protease treatment with pepsin (DAKO) at 37° C. for 5 minutes. After activation of the antigen, the section was treated at room temperature for 20 minutes using a solution prepared by adding a hydrogen peroxide solution to methanol to a final concentration of 0.3%, so that endogenous peroxidase activity was eliminated. The resultant was washed with PBS at room temperature for 5 minutes twice, and it was then blocked at room temperature for 30 minutes using a PBS solution containing 1.5% normal horse serum (DAKO), so as to carry out an operation to block non-specific binding in the tissues. Subsequently, the resultant was reacted with anti-hTROP-2 monoclonal antibody clone K5-63-17 (final concentration: 10 µg/ml), which had been diluted with a PBS solution containing 1.5% normal horse serum, at room temperature for 1 hour, and was then washed with PBS at room temperature for 5 minutes three times. Thereafter, a biotinylated anti-mouse IgG antibody (Vector), which had been 200 times diluted with a PBS solution containing 1.5% normal horse serum, was reacted at room temperature for 30 minutes. The reaction product was washed with PBS at room temperature for 5 minutes three times, and a reagent of Vectastain ABC kit (Vector) was mixed in accordance with the instruction manual included therewith, so as to prepare an ABC complex. This ABC complex was reacted at room temperature for 30 minutes. The reaction product was washed with PBS at room temperature for 5 minutes three times, and color development was then carried out using Histofine Peroxidase Substrate Simple Stain DAB solution (Nichirei Biosciences). After completion of the color development, the reaction product was washed with deionized water for 5 minutes, and the nucleus was stained with Mayer's hematoxylin solution (Wako Pure Chemical Industries, Ltd.). Thereafter, dehydration was carried out with alcohol, followed by penetration with xylene and mounting in Entellan New (Merck Japan).

<Results>

Expression of hTROP-2 in Human Normal Tissues

Figure 20:
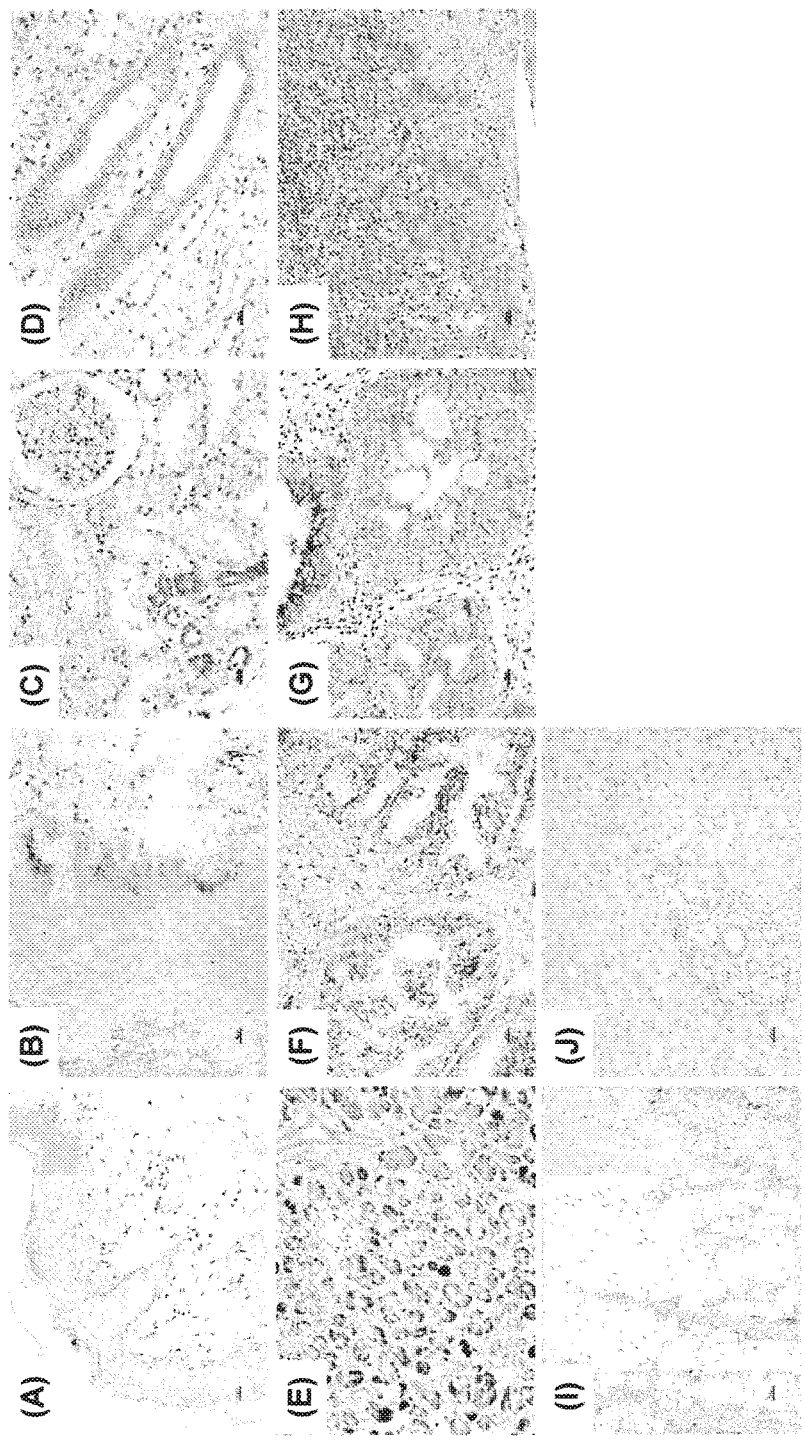
FIG. 20 shows the expression of hTROP-2 in human normal tissues. Human normal tissue arrays were immunostained with an anti-hTROP-2 monoclonal antibody clone K5-63-17. (A) skin, (B) esophagus, (C) kidney (cortex), (D) kidney (medulla), (E) pancreas, (F) prostate, (G) bladder, (H) tonsil, (I) heart, (J) liver (magnification: ×200)

The expression pattern of hTROP-2 in human normal tissues was analyzed using the anti-hTROP-2 monoclonal antibody clone K5-63-17. A human normal tissue array (Catalog No.: AB1, Super Bio Chips) was deparaffinized, and was then subjected to a hydrophilic treatment. Thereafter, the antigen was activated with a protease, pepsin, and immunostaining was then carried out using the anti-hTROP-2 monoclonal antibody clone K5-63-17 (FIG. 20). As a result, staining was observed in the skin, esophagus, kidney (cortex and medulla), pancreas, prostate, bladder and tonsil. A majority of stained images localized in the cell membrane (FIGS. 20A, B, C, D, F, G and H), but hTROP-2 expression was partially observed even in the cytoplasm (FIGS. 20E and H). On the other hand, such staining was not observed in the heart, liver, stomach, small intestine, large intestine, skeletal muscle, lung, spleen, thymus gland and the like (FIGS. 20I and J).

Expression of hTROP-2 in Human Cancer Tissues

In order to examine the expression of hTROP-2 (hTROP-2-positive rate) in human cancer tissues, the cancer tissue arrays of various human cancer species were immunostained using the anti-hTROP-2 monoclonal antibody clone K5-63-17. A tissue section, in which 10% or more of cancer cells were stained, was defined as hTROP-2-positive. The staining results are shown in Table 4.

TABLE 4

| Cancer tissues | number of TROP-2-positive cases/ total number of cases | TROP-2-positive rate (%) |
| --- | --- | --- |
| Breast cancer | 32/80 | 40 |
| Lung cancer | 53/81 | 65.4 |
| Esophagus cancer | 69/90 | 76.7 |
| Stomach cancer | 25/90 | 27.8 |
| Colon cancer | 29/178 | 16.3 |
| Pancreatic cancer | 26/62 | 41.9 |
| Liver cancer | 7/92 | 7.61 |
| Bladder cancer | 42/59 | 71.2 |
| Prostate cancer | 35/38 | 92.1 |
| Ovary cancer | 14/58 | 24.1 |

Figure 21:
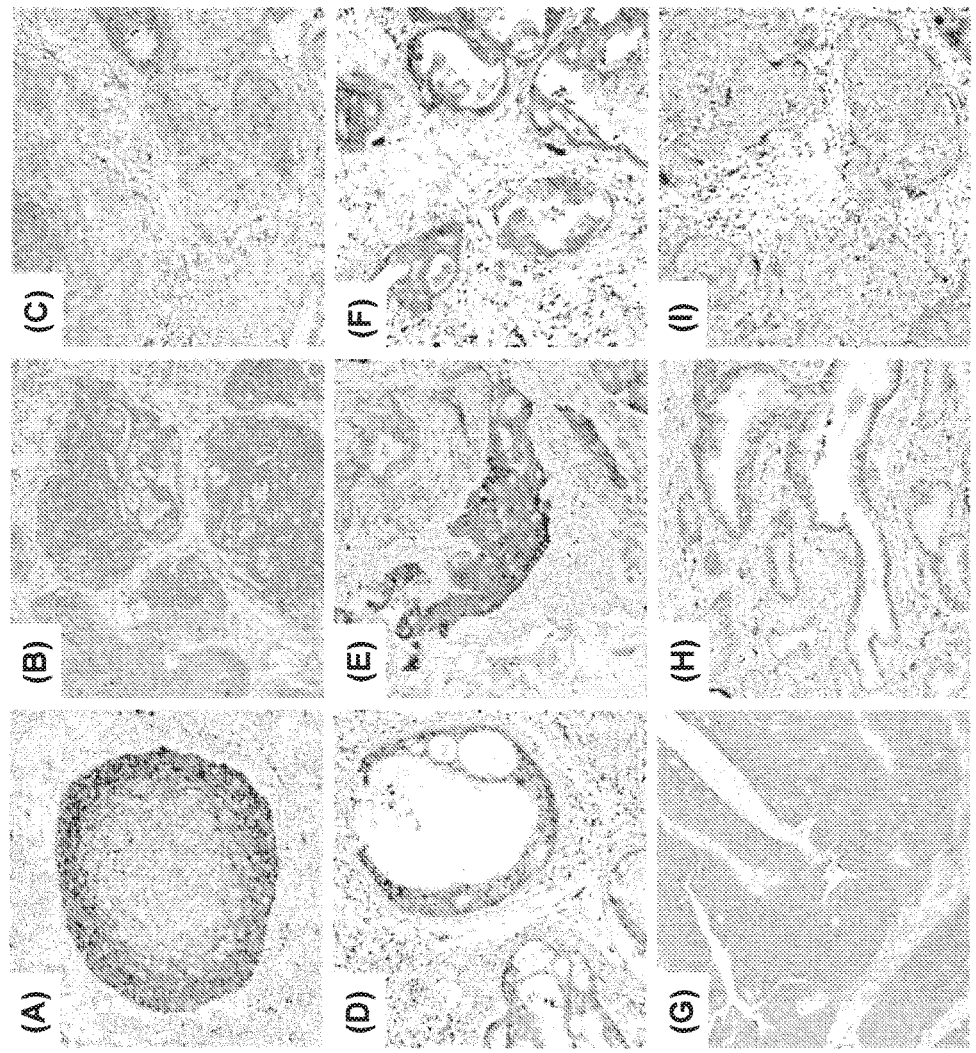
FIG. 21 shows the expression of hTROP-2 in cancer tissues. Human cancer tissue arrays were immunostained with an anti-hTROP-2 monoclonal antibody clone K5-63-17. (A) breast cancer, (B) lung cancer, (C) esophagus cancer, (D) stomach cancer, (E) pancreatic cancer, (F) colorectal cancer, (G) bladder cancer, (H) prostate cancer, (I) ovarian cancer (magnification: ×100)

Representative stained images are shown in FIG. 21. Among cancer species, regarding which the expression of hTROP-2 had been analyzed, prostate cancer had the highest positive rate (92.1%), and also, lung cancer (65.4%), esophagus cancer (76.7%), bladder cancer (71.2%) and the like had high positive rates. Liver cancer had the lowest positive rate (7.61%). It was observed from stained images that, as with in normal cells, hTROP-2 was highly localized in the cell membrane even in the case of cancer cells (FIGS. 21 A to F, H and I). In addition, hTROP-2 was also localized in the cytoplasm in some cases (FIGS. 21A, B, E and G).

The hTROP-2-positive rate in pancreatic cancer was 41.9%. The relationship between this hTROP-2-positive rate and the grade (degree of differentiation) of pancreatic cancer was analyzed. As a result, hTROP-2 was expressed at high frequency in pancreatic cancer with a high grade, namely, with a low degree of differentiation (Table 5).

TABLE 5

| Pancreatic cancer hTROP-2-positive spots 26/62 (41.94%) | | | | |
|---|---|---|---|---|
| Grade | − | + | Positive rate | |
| I | 8 | 0 | 0% | |
| I-II | 5 | 0 | 0% | |
| II | 19 | 21 | 52.5% | |
| II-III | 4 | 5 | 55.6% | p < 0.01 |
| total | 36 | 26 | | |

Example 21

[Anti-Tumor Activity of K5-70 Antibody by Single Administration on Xenograft Prevention Models of Human Pancreatic Cancer Cell Line PK-59]

Strong anti-tumor activity in vivo of a clone K5-70 (mouse IgG2a) was exhibited even by a single administration of K5-70 at a dosage of 10 mg/kg body weight to xenograft prevention models using a human pancreatic cancer cell line PK-59. In a control group (mouse IgG, 10 mg/kg body weight, N=3), tumor formation was observed in all of the individuals, and the tumor volume on the $28^{th}$ day after cell transplantation (Day 28) was 781.7±74.5 mm$^3$. On the other hand, in a group in which the K5-70 antibody was administered only once on the day of transplantation of the cancer cells (Day 1) (10 mg/kg body weight, N=3), the tumor volume on Day 28 was 144.4±176.9 mm$^3$ (P<0.05 by Student's t-test), showing tumor growth inhibitory activity of 81.5% (FIG. 22A). With regard to tumor weight, the tumor weight of the control group on Day 28 was 0.59±0.06 g. In contrast, the tumor weight of the clone K5-70 antibody administration group was 0.07±0.10 g (P<0.01 by Student's t-test), showing an inhibitory activity of 88% (FIG. 22B). With regard to both tumor volume and tumor weight, tumor formation was completely inhibited in 2 out of 3 individuals in the K5-70 antibody administration group at a dosage of 10 mg/kg body weight per administration (FIG. 22C).

Example 22

[Anti-Tumor Activity of Anti-hTROP-2 Monoclonal Antibody on Xenograft Treatment Models of Human Colon Cancer Cell Line SW480]

The anti-tumor activity of each of anti-hTROP-2 monoclonal antibodies (clones K5-70, K5-116-2-1, and T6-16) was examined with xenograft treatment models using a human colon cancer cell line SW480. SW480 cells (5×10$^6$ cells) were subcutaneously transplanted into the right flank of each of 6-week-old female NOD-scid mouse (Day 1). When the mean tumor volume reached 100 mm$^3$, grouping was carried out (Day 7 or Day 10). From Day 7 or Day 10, intraperitoneal administration of the antibody was carried out at administration intervals of once every three days. The anti-tumor activity of the clone K5-70 antibody and the anti-tumor activities of the clone K5-116-2-1 antibody and the clone T6-16 antibody were evaluated by independent studies, separately. In the study of evaluating the anti-tumor activity of the K5-70 antibody, the tumor volume of a control group (mouse IgG (10 mg/kg body weight), N=8) on the $44^{th}$ day after cancer cell transplantation (Day 44) was 365.4±214.6 mm$^3$. On the other hand, the tumor volume of a K5-70 antibody (10 mg/kg body weight) administration group was 27.4±29.4 mm$^3$ (P<0.01 by Student's t-test), and thus, tumor formation was significantly inhibited in the K5-70 administration group (inhibitory rate: 92.5%) (FIG. 23A). With regard to tumor weight, the tumor weight of the control group was 0.11±0.07 g, whereas the tumor weight of the K5-70 antibody administration group was 0.005±0.007 (g) (P<0.01 by Student's t-test), showing an inhibitory rate of 95.5% (FIG. 23B). In particular, in two out of the eight individual mice in the K5-70 antibody administration group, tumor formation was completely inhibited, and the presence of tumor could not be confirmed.

In the study of evaluating the anti-tumor activities of the K5-116-2-1 antibody and the T6-16 antibody, which was carried out separately, the tumor volume of the control group on Day 42 was 713.8±354.5 mm$^3$ (N=8). In contrast, the tumor volume of the K5-116-2-1 antibody administration group (10 mg/kg body weight) was 188.9±97.4 mm$^3$ (N=8, P<0.01 by Student's t-test) (FIG. 24A), and the tumor volume of the T6-16 antibody administration group (10 mg/kg body weight) was 292.8±199.7 mm$^3$ (N=8, P<0.05 by Student's t-test) (FIG. 25A). Thus, the two above administration groups showed inhibitory rates of 73.5% and 59.0%, respectively. With regard to tumor weight as well, the tumor weight of the control group was 0.39±0.19 g. In contrast, the tumor weight of the K5-116-2-1 antibody administration group was 0.10±0.07 g (P<0.01 by Student's t-test), and the tumor weight of the T6-16 antibody administration group was 0.17±0.14 g (P<0.05 by Student's t-test). Thus, the two above administration groups showed inhibitory rates of 72.2% and 56.4%, respectively (FIG. 24B and FIG. 25B).

Example 23

[Dose-Dependent Anti-Tumor Activity of Clone K5-70 on Xenograft Treatment Models Using Human Colon Cancer Cell Line SW480]

Subsequently, the dose-dependent anti-tumor activity of the K5-70 antibody was examined with xenograft treatment models using a human colon cancer cell line SW480. SW480 cells (5×10$^6$ cells) were subcutaneously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight administration group, N=8, 104.4±17.6 mm$^3$), a K5-70 antibody (1 mg/kg body weight) administration group (N=8, 104.3±16.1 mm$^3$), a K5-70 antibody (5 mg/kg body weight) administration group (N=8, 104.6±15.9 mm$^3$), and a K5-70 antibody (10 mg/kg body weight) administration group (N=8, 104.8±14.9 mm$^3$) Then, intraperitoneal administration was carried out at administration intervals of once every three days. On Day 42, the tumor volume of the control group was 713.8±354.5 mm$^3$. On the other hand, in the K5-70 antibody administration groups, dose-dependent tumor formation inhibitory activity was observed. That is, the tumor volume of the 1 mg/kg body weight administration group was 485.0±207.3 mm$^3$ (inhibitory rate: 32.1%), the tumor volume of the 5 mg/kg body weight administration group was 339.5±253.2 mm$^3$ (inhibitory rate: 52.4%), and the tumor volume of the 10 mg/kg body weight administration group was 355.4±202.8 mm$^3$ (inhibitory rate: 50.2%, P<0.05 by Student's t-test) (FIG. 26A). Likewise, with regard to tumor weight on Day 42, the tumor weight of the control group was 0.39±0.19 g. On the other hand, the tumor weight of the K5-70 antibody (1 mg/kg body weight) administration group was 0.24±0.11 g (inhibitory rate: 37.8%), the tumor weight of the 5 mg/kg body weight administration group was 0.17±0.14 g (inhibitory rate: 55.8%, P<0.05 by Student's t-test), and the tumor weight of the 10 mg/kg body weight administration group was 0.20±0.13 g (inhibitory rate: 47.1%). Thus, dose-dependent anti-tumor activity was confirmed (FIG. 26B).

Example 24

[Analysis of Administration Intervals of K5-70 Antibody to Xenograft Treatment Models Using Human Colon Cancer Cell Line SW480]

Figure 27B:
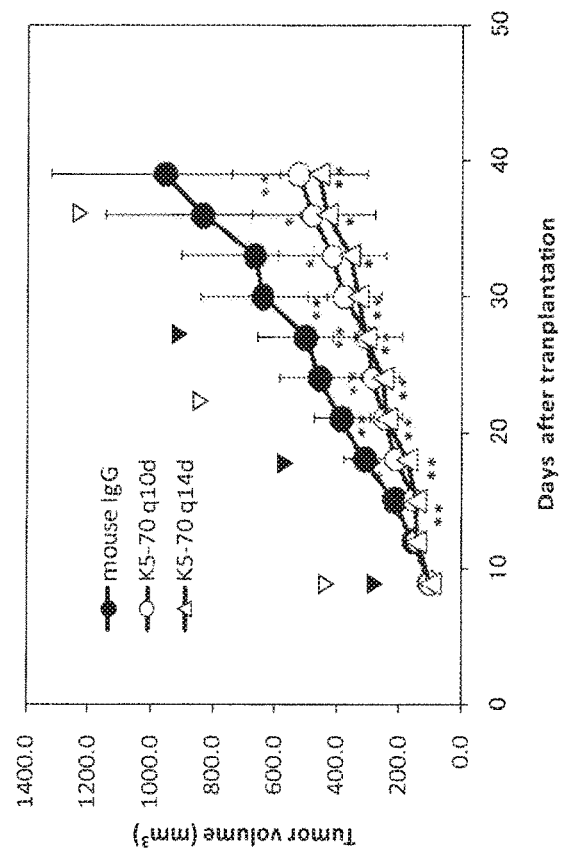
FIG. 27B is a view showing the anti-tumor activity of a K5-70 antibody at administration intervals of once every ten days (q10d) or once every two weeks (q14d). The figure shows the time course of tumor formation in a control group (●: mouse IgG, 10 mg/kg) and in a K5-70 antibody administration group (○: q10d, 10 mg/kg, Δ: q14d, 10 mg/kg) (a mean value±standard deviation). The filled arrowheads (▼: Days 9, 19, and 29) and the open arrowheads (▽: Days 9, 23, and 37) indicate administration of a K5-70 antibody. * P<0.05, ** P<0.01 by Student's t-test.
Figure 27A:
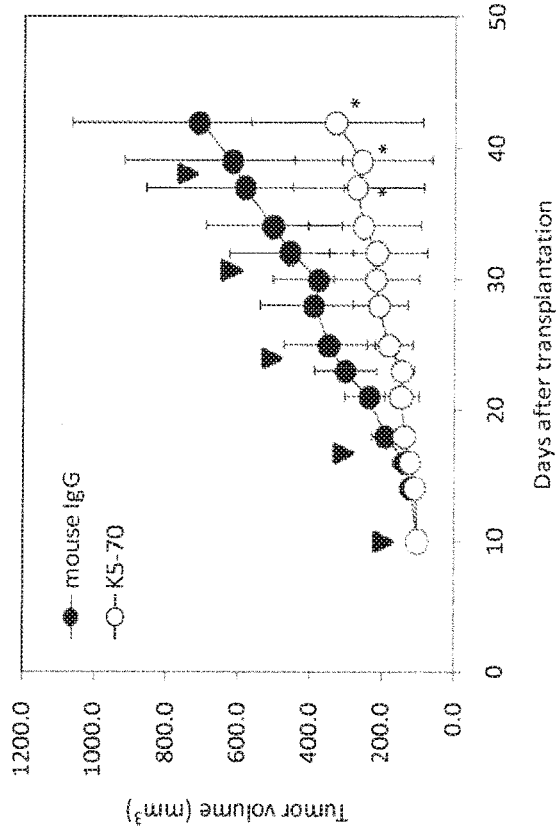
FIG. 27A shows the anti-tumor activity of a K5-70 antibody at administration intervals of once a week. Time course of tumor formation in a control group (●: mouse IgG) and in a K5-70 antibody (10 mg/kg body weight) administration group (○: 10 mg/kg) is shown (a mean value±standard deviation). The arrow heads (Days 10, 17, 24, 31, and 38) indicate administration of a K5-70 antibody. * P<0.05 by Student's t-test.

Subsequently, in order to analyze optimal administration intervals of the K5-70 antibody, the anti-tumor activity of the clone K5-70 when it was administered once a week (once every 7 days) was examined with xenograft treatment models using a human colon cancer cell line SW480. SW480 cells ($5 \times 10^6$ cells) were subcutaneously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight, N=8, 104.42±15.1 mm$^3$) and a K5-70 antibody administration group (10 mg/kg body weight, N=8, 104.3±16.1 mm$^3$) Then, intraperitoneal administration was carried out once every 7 days. On Day 42, the tumor volume of the control group was 713.8±354.5 mm$^3$, whereas the tumor volume of the K5-70 antibody administration group (administered once a week) was 332.3±239.9 mm$^3$ (inhibitory rate: 55%, P<0.05 by Student's t-test) (FIG. 27A). Moreover, when the administration interval was increased to once every 10 days and to once every two weeks, the tumor volume of the control group on Day 39 was 956.9±367.8 mm$^3$. On the other hand, the tumor volume of the K5-70 antibody administration group (administered once every 10 days) on Day 39 was 525.4±180.6 mm$^3$ (inhibitory rate: 45.1%, P<0.01 by Student's t-test), and the tumor volume of the K5-70 antibody administration group (administered once every 2 weeks) was 459.4±217.6 mm$^3$ (inhibitory rate: 52.0%, P<0.01 by Student's t-test) (FIG. 27B). In the prior arts (U.S. Pat. No. 7,420,040 and U.S. Pat. No. 7,420,041), when antibodies were administered to xenograft treatment models using a pancreatic cancer cell line (BxPC-3) at a dosage of 20 mg/kg body weight, three times a week (at administration intervals of 2 days), the antibodies exhibited anti-tumor activity at an inhibitory rate of 50% to 60%. In contrast, the K5-70 antibody exhibited anti-tumor activity equivalent to those of the prior arts, at a dosage of half of the prior arts (10 mg/kg body weight), once every 2 weeks (at administration intervals of 13 days). Accordingly, it became clear that that the K5-70 antibody exhibited significant anti-tumor activity at a total dosage of at least one twelfth of those of the prior-arts.

Example 251

[Dose-Dependent Anti-Tumor Activity of T6-16 Antibody on Xenograft Treatment Models Using Human Colon Cancer Cell Line SW480]

Figure 28B:
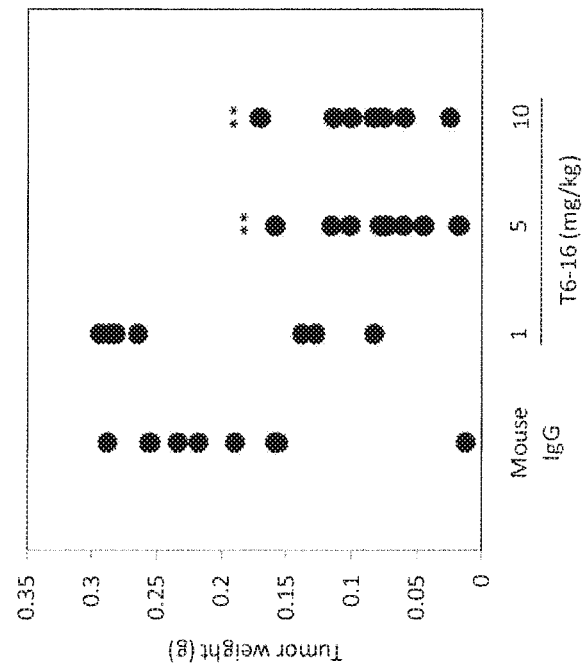
FIG. 28B shows the plotted tumor weight of each mouse at the time of the 43$^{rd}$ day (Day 43) (the final day of experiment) in the test of FIG. 28A. ** P<0.01 (by Student's t-test).
Figure 28A:
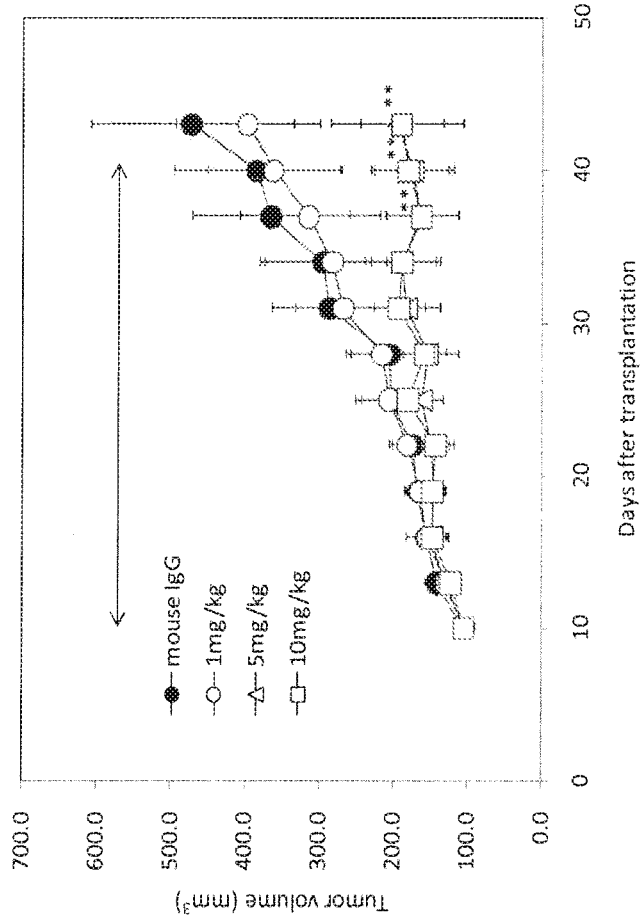
FIG. 28A shows the time course of tumor formation in a control group (●: mouse IgG) and in a T6-16 antibody administration group (○: 1 mg/kg body weight, Δ: 5 mg/kg body weight, □: 10 mg/kg body weight) (a mean value±standard deviation). The arrow indicates an antibody administration period. ** P<0.01 (by Student's t-test).

Subsequently, the dose-dependent anti-tumor activity of the T6-16 antibody was examined with xenograft treatment models using a human colon cancer cell line SW480. SW480 cells ($5 \times 10^6$ cells) were subcutaneously transplanted into the right flank of each of 6-week-old female NOD-scid mice. Ten days after the transplantation (Day 10) at which the mean tumor volume reached 100 mm$^3$, the mice were divided into a control group (mouse IgG, 10 mg/kg body weight, N=8, 105.8±9.9 mm$^3$), a T6-16 antibody administration group (1 mg/kg body weight, N=8, 104.4±13.3 mm$^3$), a T6-16 antibody administration group (5 mg/kg body weight, N=8, 104.7±13.0 mm$^3$), and a T6-16 antibody administration group (10 mg/kg body weight, N=8, 104.8±12.4 mm$^3$) Then, intraperitoneal administration was carried out at administration intervals of once every three days. On Day 43, the tumor volume of the control group was 473.5±137.0 mm$^3$. On the other hand, in the T6-16 antibody administration groups, dose-dependent tumor formation inhibitory activity was observed. That is, the tumor volume of the 1 mg/kg body weight administration group was 397.9±97.5 mm$^3$ (inhibitory rate: 16.0%), the tumor volume of the 5 mg/kg body weight administration group was 195.9±89.7 mm$^3$ (inhibitory rate: 58.7%, P<0.01 by Student's t-test), and the tumor volume of the 10 mg/kg body weight administration group was 190.2±56.5 mm$^3$ (inhibitory rate: 59.8%, P<0.01 by Student's t-test) (FIG. 28A). Likewise, with regard to tumor weight on Day 43, the tumor weight of the control group was 0.19±0.07 g. On the other hand, the tumor weight of the T6-16 antibody (1 mg/kg body weight) administration group was 0.20±0.08 g, the tumor weight of the T6-16 antibody (5 mg/kg body weight) administration group was 0.08±0.04 g (inhibitory rate: 57.9%, P<0.01 by Student's t-test), and the tumor weight of the T6-16 antibody (10 mg/kg body weight) administration group was 0.09±0.04 g (inhibitory rate: 52.6%, P<0.01 by Student's t-test). Thus, dose-dependent anti-tumor activity was confirmed (FIG. 28B).

Example 26

[Analysis of Administration Intervals of T6-16 Antibody to Xenograft Treatment Models Using Human Colon Cancer Cell Line SW480]

Figure 29:
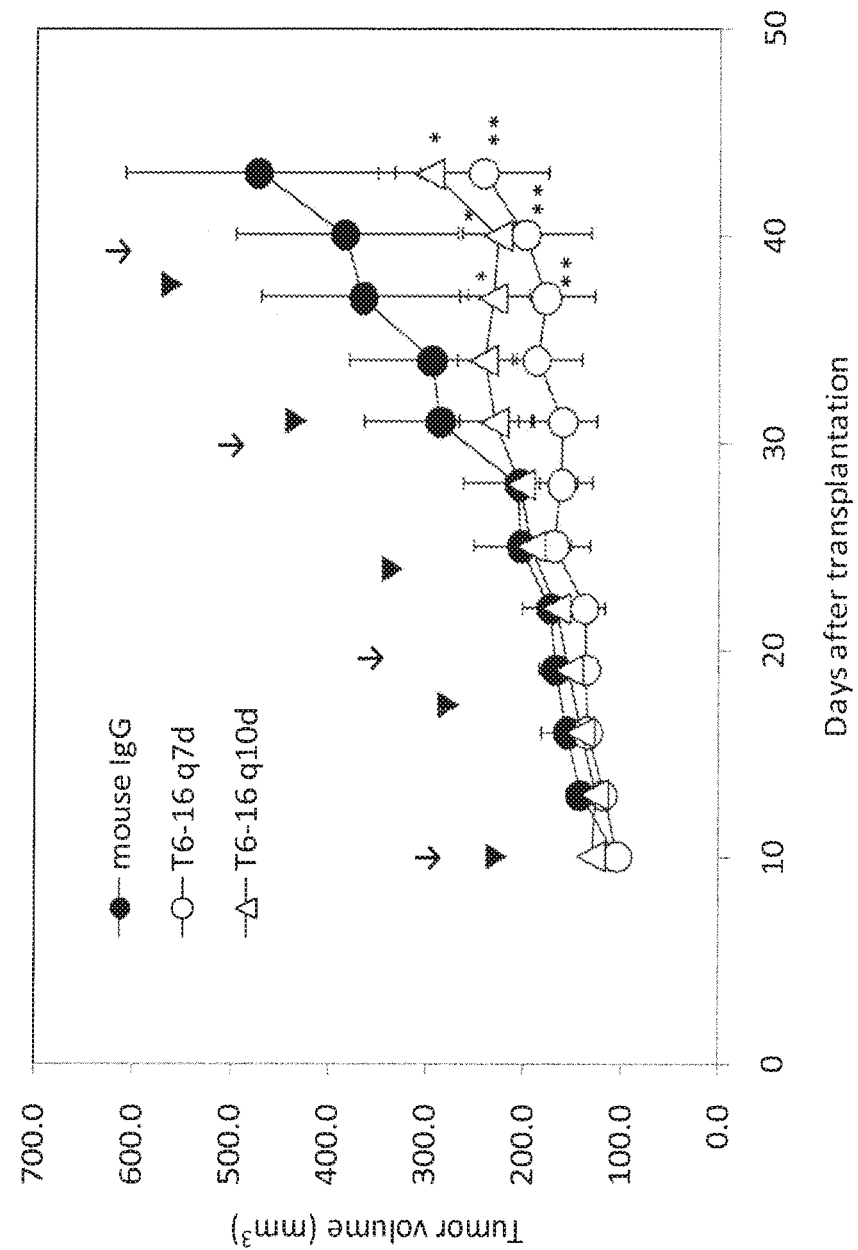
FIG. 29 shows the anti-tumor activity of a clone T6-16 on xenograft treatment models using SW480 cells. Time course of tumor formation in a control group (●: mouse IgG, 10 mg/kg body weight) and in a T6-16 antibody (10 mg/kg body weight) administration group (○: q7d, Δ: q10d) is shown (a mean value±standard deviation). The arrowheads (Days 10, 17, 24, 31, and 38) and the arrows (Days 10, 20, 30, and 40) indicate administration of a T6-16 antibody. Administration was carried out once every three days to the control group. * P<0.05, ** P<0.01 by Student's t-test.

Subsequently, in order to analyze optimal administration intervals of the T6-16 antibody, the anti-tumor activity of the clone T6-16 when it was administered at administration intervals of once a week (once every 7 days) and once every 10 days was examined with xenograft treatment models using a human colon cancer cell line SW480. SW480 cells ($5 \times 10^6$ cells) were subcutaneously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight, N=8, 105.8±9 9 mm$^3$), a T6-16 antibody (once a week) administration group (10 mg/kg body weight, N=8, 105.0±11.6 mm$^3$), and a T6-16 antibody (once every 10 days) administration group (10 mg/kg body weight, N=5, 130.8±2.4 mm$^3$) Then, administration was initiated. On Day 43, the tumor volume of the control group was 473.5±137.0 mm$^3$. On the other hand, the tumor volume of the T6-16 antibody (once a week) administration group was 243.7±65.3 mm$^3$ (inhibitory rate: 48.5%, P<0.01 by Student's t-test), and the tumor volume of the T6-16 antibody (once every 10 days) administration group was 297.8±54 4 mm$^3$ (inhibitory rate: 37.1%, P<0.05 by Student's t-test) (FIG. 29). In the prior arts (U.S. Pat. No. 7,420,040 and U.S. Pat. No. 7,420,041), when antibodies were administered to xenograft treatment models using a pancreatic cancer cell line (BxPC-3) at a dosage of 20 mg/kg body weight, three times a week (at administration intervals of 2 days), the antibodies exhibited anti-tumor activity at an inhibitory rate of 50% to 60%. In contrast, the T6-16 antibody exhibited significant anti-tumor activity, when it was administered at a dosage of half of the prior arts and at a frequency of once every 10 day (at administration intervals of 9 days). Accordingly, it became clear that that the T6-16 antibody exhibited significant anti-tumor activity at a total dosage of at least one eighth of those of the prior-arts.

Example 27

[Analysis of Anti-Tumor Activity of Clone K5-70 on Xenograft Prevention Models Using Human Prostate Cancer Cell Line DU-145]

Figure 30B:
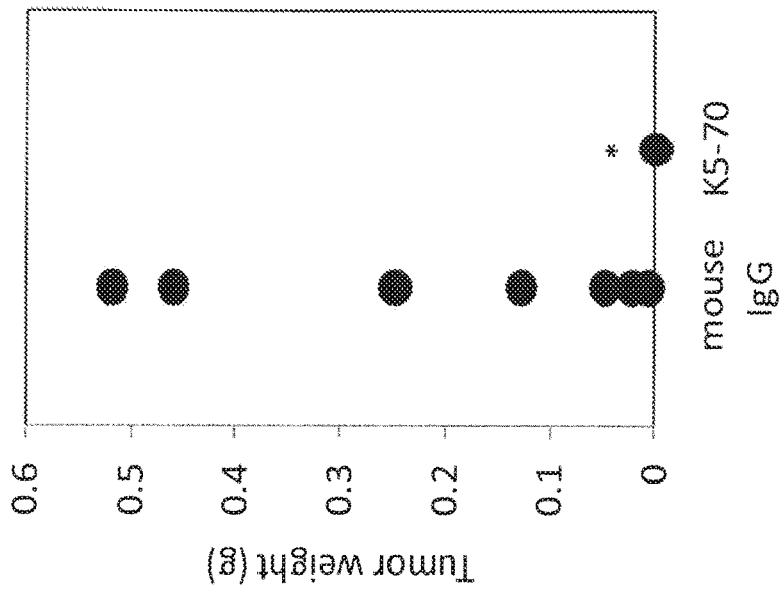
FIG. 30B shows the plotted tumor weight of each mouse at the time of the 40$^{th}$ day (Day 40) (the final day of experiment) in the test of FIG. 30A. * P<0.05 (by Student's t-test).
Figure 30A:
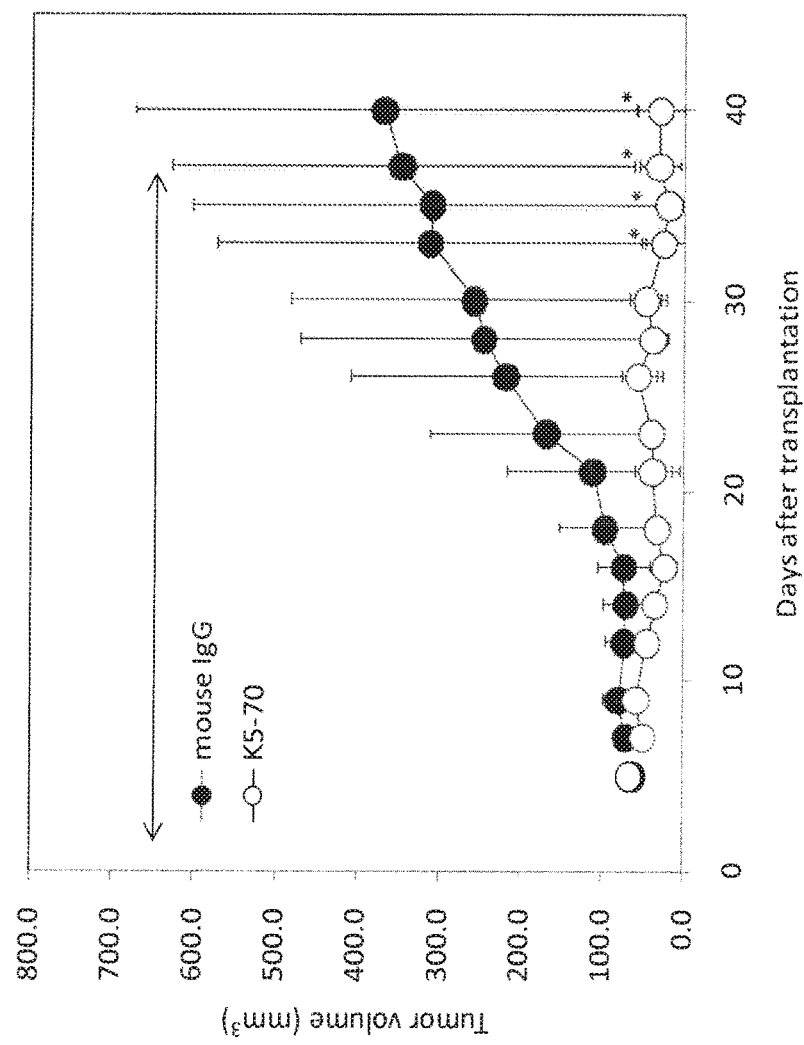
FIG. 30A shows the time course of tumor formation in a control group (●: mouse IgG) and in a K5-70 antibody (10 mg/kg body weight) administration group (○) (a mean value±standard deviation). The arrow indicates an antibody administration period. * P<0.05 (by Student's t-test).

The anti-tumor activity of clone K5-70 on human prostate cancer was evaluated with xenograft prevention models using DU-145 cells (RIKEN Cell Bank, RCB2143). DU-145 cells ($5 \times 10^6$ cells) were subcutaneously transplanted into each of 6-week-old female nude mouse (Balb/c, nu/nu). The day on which the transplantation was carried out was defined as Day 1. The mice were divided into a control group (mouse IgG) (N=8) and a K5-70 antibody administration group (N=8). From Day 1, the K-70 antibody and the control antibody were intraperitoneally administered to the mice at a frequency of once every 3 days at a dosage of 10 mg/kg body weight. On Day 40, the tumor volume of the control group was $368.2 \pm 307.8$ mm$^3$. On the other hand, the tumor volume of the K5-70 antibody administration group was $30.6 \pm 29$ 6 mm$^3$ ($P<0.05$ by Student's t-test), showing a tumor formation inhibitory activity of approximately 90% (FIG. 30A). With regard to tumor weight, further significant anti-tumor activity was observed. The tumor weight of the control group on Day 40 was $0.18 \pm 0.18$ g. In contrast, in the K5-70 antibody administration group, tumors disappeared from all of the 8 individual mice, and thus, tumor formation was completely inhibited (FIG. 30B). From the above-mentioned results, it became clear that the anti-human TROP-2 monoclonal antibody clone K5-70 shows strong anti-tumor activity even on human prostate cancer cells.

Example 28

[Metastasis-Inhibitory Activity of K5-70 Antibody on Liver Metastasis Models Using Human Pancreatic Cancer Cell Line PK-59]

Cancer metastasis is an important factor that influences clinical prognosis in the treatment of gastrointestinal cancer. The control of metastasis is therapeutically significantly important. If not only tumor formation but also the metastasis of cancer to other organs could be suppressed by administering an antibody for use in cancer therapy that targets to TROP-2, high clinical usefulness would be anticipated. Thus, this is a desired property as a cancer therapeutic antibody.

The expression of TROP-2 was confirmed in many types of carcinomas. It was reported that TROP-2 was expressed at a high level particularly in metastatic foci (Br. J. Cancer (2008); 99: 1290-1295, Clin. Cancer Res. (2006); 12: 3057-3063, Mod. Pathol. (2008); 21: 186-191). Moreover, it was also reported that, when Trop-2-gene-introduced cancer cells were transplanted into nude mice via transsplenic or transpancreastic administration, the incidence of liver metastasis increased (WO 2010/089782, Molecular Cancer (2010); 9: 253), and thus, the report suggested the importance of TROP-2 in the cancer metastasis process. However, to date, there have been no reports specifically describing that an antibody that targets TROP-2 has metastasis-inhibitory action in vivo.

The anti-hTROP-2 mouse monoclonal antibody K5-70, which was discovered by the present invention, exhibits high therapeutic effects on xenograft models, into the subcutis of which human pancreatic cancer cells had been transplanted. It was demonstrated by a scratch assay performed in vitro that the antibody K5-70 is able to suppress the migration ability of a human pancreatic cancer cell line PK-59, in addition to the effect of suppressing the growth of cancer cells. Thus, it was considered that the antibody K5-70 could inhibit cancer metastasis in vivo. Hence, the metastasis-inhibitory effect of an anti-hTROP-2 mouse monoclonal antibody was examined, using models in which the PK-59 cells were injected into the spleen of nude mice so that liver metastasis was developed.

On the day before cancer cell transplantation, the mice were divided into groups. Then, an anti-hTROP-2 monoclonal antibody (K5-70) or a control antibody (purified mouse IgG) was intraperitoneally administered to the mice at a dosage of 10 mg/kg body weight. On the following day, a human pancreatic cancer cell line (PK-59) endogenously expressing hTROP-2 was harvested by treatment with trypsin, and a $2 \times 10^7$ cells/mL cell suspension was then prepared with PBS. The cell suspension was preserved on ice until transplantation. Each of 6- or 7-week-old female nude mouse (Balb/c, nu/nu) was anesthetized by intraperitoneal administration of pentobarbital, and 10 to 15 mm of the left flank thereof was excised under anesthesia. The spleen was taken out of the abdominal cavity, and 50 μL of the cell suspension ($1 \times 10^6$ cells) was then injected into the spleen using a 27G syringe. Four minutes after injection of the cells, the hilum of spleen was ligated with 5-0 silk sutures, and the spleen was then excised. The cut peritoneum was closed with 4-0 silk sutures, and the surgical site was then closed with Wound Clips (AUTOCLIP 9 mm, Becton Dickinson). In addition, seven days after the cancer cell transplantation, the K-70 antibody and the control antibody were administered to the mice at a dosage of 10 mg/kg body weight. Four to six weeks after the cancer cell transplantation, the mice were subjected to euthanasia by cervical dislocation. Then, the liver was excised from each mouse, and the presence or absence of metastatic foci was confirmed.

Figure 31A:
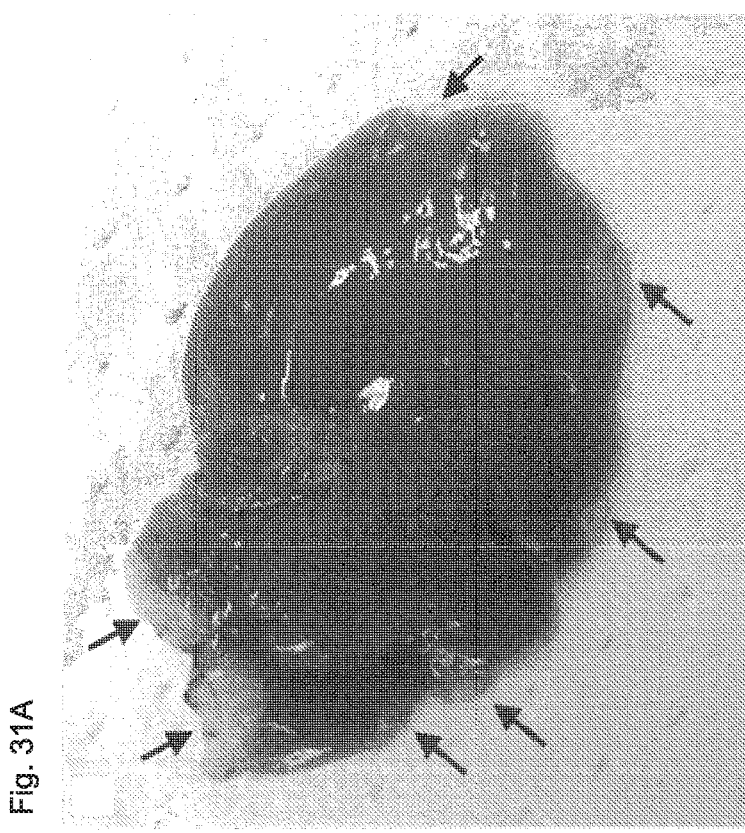
FIGS. 31A and 31B show the excised liver image of a control group (●: mouse IgG) (A) and a K5-70 antibody (10 mg/kg body weight) administration group (B), which were taken 6 weeks after the cell transplantation. The arrows indicate liver metastatic foci.
Figure 31B:
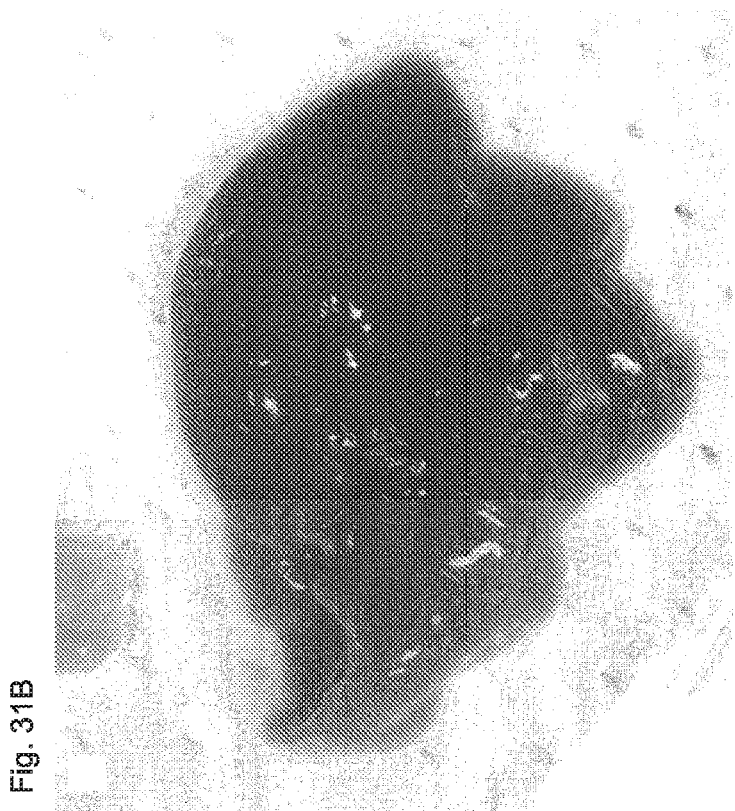

In the control group in which the mouse IgG was administered to the mice, in 4 out of the 6 mice into which PK-59 cells had been transplanted, apparent metastatic foci (2 to 7 foci) were observed around the liver lobe four to six weeks after the transplantation (FIG. 31A, incidence of metastasis: 67%, Table 6). In contrast, in four mice in the K5-70 antibody administration group, into which the PK-59 cells had also been transplanted, such metastatic foci were not observed in the liver of all of the mice, and thus, an incidence of metastasis was 0% (FIG. 31B, Table 6).

TABLE 6

Metastasis-suppressing effect of clone K5-70 on liver metastasis models produced by transsplenic transplantation of PK-59 cells into nude mice

| Administration group | Weeks after transplantation | Individual No. | Number of metastatic foci | Determination of metastasis |
|---|---|---|---|---|
| Control group | 4 W | C-1 | 0 | − |
| | 4 W | C-2 | 5 | ++ |
| | 6 W | C-3 | 7 | ++ |

TABLE 6-continued

Metastasis-suppressing effect of clone K5-70 on liver metastasis models produced by transsplenic transplantation of PK-59 cells into nude mice

| Administration group | Weeks after transplantation | Individual No. | Number of metastatic foci | Determination of metastasis | |
|---|---|---|---|---|---|
| | 6 W | C-4 | 7 | ++ | |
| | 6 W | C-5 | 2 | + | |
| | 6 W | C-6 | 0 | − | |
| | | Average number of metastatic foci | 3.5 | Incidence of metastasis | 67% |
| K5-70 administration group | 4 W | K-1 | 0 | − | |
| | 6 W | K-2 | 0 | − | |
| | 6 W | K-3 | 0 | − | |
| | 6 W | K-4 | 0 | − | |
| | | Average number of metastatic foci | 0 | Incidence of metastasis | 0% |

From these results, it became clear that the anti-hTROP-2 antibody K5-70 has extremely strong inhibitory action on the liver metastasis of the human pancreatic cancer cell line PK-59.

Example 29

[Anti-Tumor Activity of K5-70 Antibody on Xenograft Models Using Human Colon Cancer Cell Line SW480, which are Recurrent Cancer Models after Administration of Irinotecan Hydrochloride]

In recent years, many chemotherapeutical drugs for suppressing the growth of cancer cells have been developed as cancer therapeutic drugs. These drugs have achieved certain treatment results. However, these chemotherapeutical drugs have been problematic in terms of side effects associated with the growth suppressive action thereof on normal cells other than cancer cells and the recurrence of cancer after suspension of the treatment. Accordingly, if tumor recurrence after completion of the treatment with chemotherapeutical drugs could be suppressed by administration of a cancer therapeutic antibody targeting to TROP-2, high clinical usefulness would be anticipated. Thus, this is a desired property as a cancer therapeutic antibody.

Figure 32:
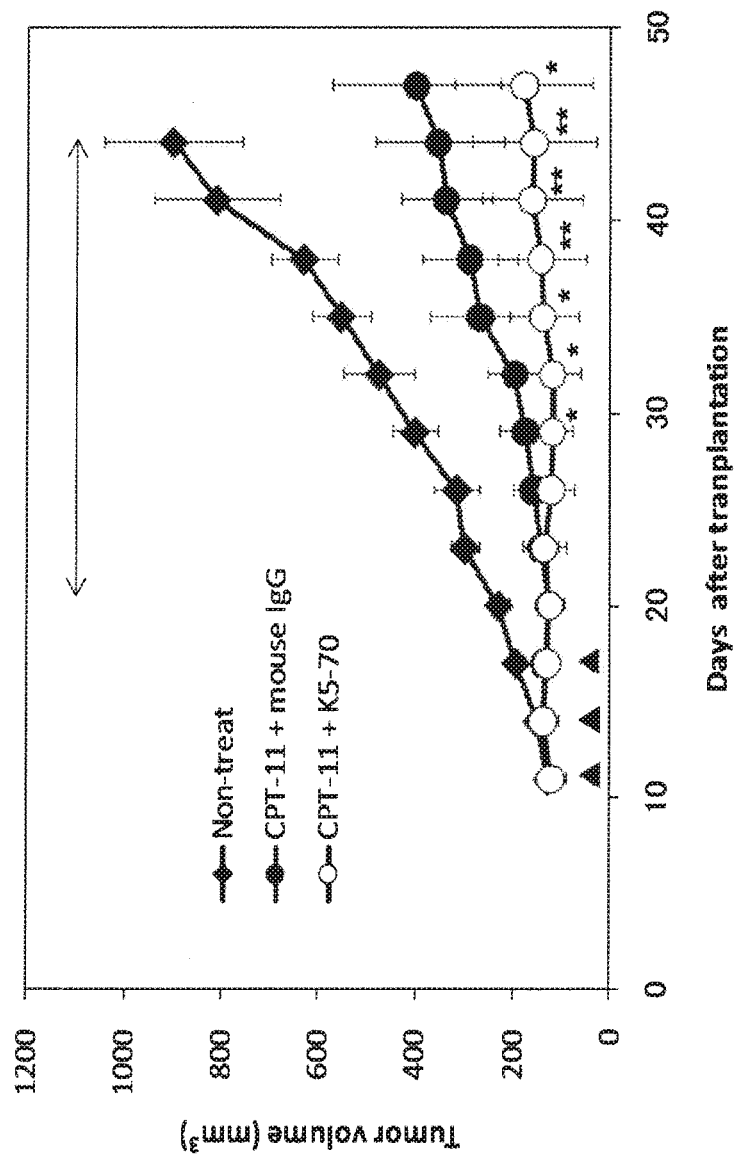
FIG. 32 shows the anti-tumor activity of K5-70 on xenograft models using SW480 cells, which are recurrent cancer models after administration of irinotecan hydrochloride. This figure shows the time course of tumor formation in a non-treat group (♦), in an irinotecan hydrochloride (40 mg/kg body weight)+K5-70 antibody (○: 10 mg/kg body weight) administration group, and in an irinotecan hydrochloride (40 mg/kg body weight)+mouse IgG (●: 10 mg/kg body weight) administration group (a mean value±standard deviation). The arrowheads (Days 11, 14, and 17) indicate administration of irinotecan hydrochloride. The K-70 antibody or the mouse IgG was administered once every three days from Day 20. The arrow indicates an antibody administration period. *P<0.05, **P<0.01 by Student's t-test.

As therapeutic agents for colorectal cancer, in addition to 5-FU and platinum-containing drugs, irinotecan hydrochloride (Topotecin, Daiichi Sankyo Co., Ltd.) having a topoisomerase inhibitory effect has been recently applied to clinical sites. With regard to animal models as well, the anti-tumor effect of irinotecan hydrochloride on mouse models, into which various types of human tumor cells including colon cancer as a typical example had been transplanted, has been reported (Cancer Chemother Pharmacol. (1991); 28(3):192-8). Thus, the recurrence-preventing effect of the anti-hTROP-2 antibody clone K5-70 (mouse IgG2a) on recurrent tumor after administration of irinotecan hydrochloride has been examined with xenograft models using a human colon cancer cell line SW480. SW480 cells ($5 \times 10^6$ cells) were subcutaneously transplanted into the right flank of 8-week-old female NOD-scid mice. Eleven days after the transplantation (Day 11) at which the mean tumor volume reached 100 mm$^3$, the mice were divided into a non-treat group (normal saline administration group, N=8, 130.7±16 2 mm$^3$) and an irinotecan hydrochloride (CPT-11, Topotecin, Daiichi Sankyo Co., Ltd.) administration group (N=16, 123.0±21.4 mm$^3$) Thereafter, irinotecan hydrochloride was intraperitoneally administered to the mice at a dosage of 40 mg/kg body weight, once every 3 days, total 3 times (Days 11, 14, and 17). On the third day after the final administration of irinotecan hydrochloride (Day 20), the tumor volume of the non-treat group reached 232.1±21.1 mm$^3$. On the other hand, the tumor volume of the irinotecan hydrochloride administration group was 126.6±26.6 mm$^3$ (P<0.01 by Student's t-test), and thus, an apparent tumor-suppressing effect was observed. At this stage, the irinotecan hydrochloride administration group was divided into two groups based on tumor size. One group was defined as a K5-70 antibody administration group (10 mg/kg body weight, N=8, tumor volume on Day 20: 126.0±28 0 mm$^3$), and the other group was defined as a mouse IgG administration group (10 mg/kg body weight, N=8, tumor volume on Day 20: 127.2±27.0 mm$^3$) Intraperitoneal administration of the antibodies and the measurement of a tumor volume were carried out on each group once every 3 days, so that the recurrence of a tumor was evaluated (FIG. 32). In the mouse IgG administration group, from the 18$^{th}$ day after the final administration of irinotecan hydrochloride (Day 35), several mice having an apparent recurrent tumor with a tumor volume of greater than 300 mm$^3$ were observed. On the 30$^{th}$ day after the final administration of irinotecan hydrochloride (Day 47), a tumor with a tumor volume of greater than 300 mm$^3$ was observed in 5 out of the 8 mice (mean tumor volume: 401.7±172.7 mm$^3$) In contrast, in the K5-70 antibody administration group, tumor recurrence was significantly suppressed, and the mean tumor volume was 180.5±142.1 mm$^3$ (P<0.05 by Student's t-test) (FIG. 32). In particular, in the K5-70 antibody administration group, the tumor volume on Day 47 became smaller than the tumor volume when the mice were divided into groups (126.0±28.0 mm$^3$) The tumor volume became less than 100 mm$^3$ in 4 out of the 8 mice. From these results, it became clear that the anti-hTROP-2 antibody K5-70 has extremely strong suppressive action even on recurrent tumor after administration of irinotecan hydrochloride.

Example 30

[Epitope Mapping Using CLIPS Technology]
<Materials and Methods>
Peptide Synthesis 15-mer and 30-mer of linear peptides derived from TROP-2 extracellular domains, which were used in the present experiment, were obtained by solid-phase synthesis according to a Fmoc (9-Fluorenylmethoxycarbonyl) method. In addition, for discontinuous epitope analysis, a 17-mer peptides derived from a TROP-2 extracellular domain, to both ends of which cysteine residues had been added, was synthesized, and a conformation having one or two loop structures was reconstructed by CLIPS technology (Chemically Linked Peptides on Scaffolds technology). When another cysteine residue was present close to the added cysteine residue, it was substituted with alanine.

Epitope Screening ELISA 5034 types of the synthesized peptides were covalently bound to PEPSCAN cards (455 peptides/card), and the binding of the synthesized peptides to antibodies was then analyzed by the ELISA method. The PEPSCAN cards were allowed to react with anti-human TROP-2 monoclonal antibodies (K5-70, K5-107, K5-116-2-1, T5-86, and T6-16) that had been diluted to a concentration of 1 μg/mL with a blocking buffer (a phosphate buffer containing 4% horse serum, 5% ovalbumin, and 1% TWEEN). After washing, the resultant was allowed to react with a 1000-fold diluted peroxidase-secondary antibody complex at 25° C. for 1 hour. After washing, a substrate solution (a solution containing 2,2'-azino-di-3-ethylbenzthiazoline sulfonate (ABTS) and 2 μL of 3% hydrogen peroxide solution) was added to the reaction solution, followed by a chromogenic reaction for 1 hour. The binding activity of the antibodies was quantified by photographing with a CCD camera and then performing an image analysis.

<Results>

The anti-hTROP-2 monoclonal antibodies K5-70, K5-107, K5-116-2-1, T5-86 and T6-16, which exhibited beneficial effects, were subjected to epitope analysis using CLIPS (Chemically Linked Peptides on Scaffolds) technology. It is to be noted that the term "amino acid number" is used in the present examples to mean the amino acid number in the amino acid sequence shown in SEQ ID NO: 2 (hTROP-2 protein (323 amino acid residues)).

The result of analysis for the K5-70 antibody is shown in Table 7 below. As a result, it was found that 33 peptides exhibit strong binding activity to the K5-70 antibody. In these 33 peptides, a sequence comprising VCSPDGPGGRCQCRALGSGMAVD (amino acid numbers 43-65 of SEQ ID NO: 2) (peptide Nos. 1-7 and 9 shown in Table 7), a sequence comprising HHILIDLRHRPTAG (amino acid numbers 152-165 of SEQ ID NO: 2) (peptide Nos. 14, 22-24 and 28 shown in Table 7), a sequence comprising VHYEQPTIQIELRQ (amino acid numbers 194-207 of SEQ ID NO: 2) (peptide Nos. 10, 12, 13, 18, 20, 21, 23, 26-28, 30 and 32 shown in Table 7), and a sequence comprising DLDLDAELRRLFRER (amino acid numbers 171-183 of SEQ ID NO: 2) (peptide Nos. 11, 16, 18, 19, 21, 22, 29, 31 and 33 shown in Table 7) appeared repeatedly. The K5-70 antibody particularly strongly bound to the sequence comprising VCSPDGPGGRCQCRALGSGMAVD (amino acid numbers 43-65 of SEQ ID NO: 2). From these results, it was suggested that, in the hTROP-2 protein, the aforementioned 4 types of peptide sequence regions are likely to be epitopes of the K5-70 antibody.

TABLE 7

Binding of K5-70 antibody to CLIPS peptides derived from human TROP-2 extracellular domains

| number | peptide | binding of K5-70 | SEQ ID No. |
| --- | --- | --- | --- |
| 1 | NKMTVCSPDGPGGRCQCRALGSGMAVDCST | 2742 | 101 |
| 2 | TVCSPDGPGGRCQCRALGSGMAVDCSTLTS | 2604 | 102 |
| 3 | TNKMTVCSPDGPGGRCQCRALGSGMAVDCS | 2562 | 103 |
| 4 | MTVCSPDGPGGRCQCRALGSGMAVDCSTLT | 2402 | 104 |
| 5 | KMTVCSPDGPGGRCQCRALGSGMAVDCSTL | 1770 | 105 |
| 6 | PTNKMTVCSPDGPGGRCQCRALGSGMAVDC | 1391 | 106 |
| 7 | VCSPDGPGGRCQCRALGSGMAVDCSTLTSK | 932 | 107 |
| 8 | CAAVHYEQPTIQIELRCAAVHYEQPTIQIELRC | 876 | 108 |
| 9 | CPTNKMTVCSPDGPGGRCQCRALGSGMAVD | 839 | 109 |
| 10 | CVHYEQPTIQIELRQNCVHYEQPTIQIELRQNC | 825 | 110 |
| 11 | HSDLDAELRRLFRERCHSDLDAELRRLFRERC | 725 | 111 |
| 12 | RLFRERYRLHPKFVAAVHYEQPTIQIELRQ | 687 | 112 |
| 13 | AVHYEQPTIQIELRQ | 642 | 113 |
| 14 | CAGAFNHSDLDAELRRCHHILIDLRHRPTAGC | 624 | 114 |
| 15 | CPKFVAAVHYEQPTIQCGLDLRVRGEPLQVERC | 579 | 115 |
| 16 | CHSDLDAELRRLFRERCGLDLRV | 538 | 116 |
| 17 | FQGRGGLDLRVRGEP | 538 | 117 |
| 18 | CVHYEQPTIQIELRQNCDLDAELRRLFRERYRC | 524 | 118 |
| 19 | CHSDLDAELRRLFRERCRGEPLQ | 519 | 119 |
| 20 | CFIQIELRQNTSQKAACVHYEQPTIQIELRQNC | 513 | 120 |

TABLE 7-continued

Binding of K5-70 antibody to CLIPS peptides derived from human TROP-2 extracellular domains

| number | peptide | binding of K5-70 | SEQ ID No. |
|---|---|---|---|
| 21 | CVHYEQPTIQIELRQNCHSDLDAELRRLFRERC | 511 | 121 |
| 22 | CHHILIDLRHRPTAGACHSDLDAELRRLFRERC | 489 | 122 |
| 23 | CHHILIDLRHRPTAGACVHYEQPTIQIELRQNC | 489 | 123 |
| 24 | CHHILIDLRHRPTAGACGLDLRVRGEPLQVERC | 488 | 124 |
| 25 | CDAELRRLFRERYRLHCDELVRTHHILIDLRHC | 483 | 125 |
| 26 | CVHYEQPTIQIELRQNC | 483 | 126 |
| 27 | CAFNHSDLDAELRRLFCVHYEQPTIQIELRQNC | 478 | 127 |
| 28 | CVHYEQPTIQIELRQNCHHILIDLRHRPTAGAC | 473 | 128 |
| 29 | CDLDAELRRLFRERYRCDELVRTHHILIDLRHC | 472 | 129 |
| 30 | VHYEQPTIQIELRQNCGLDLRVRGEPLQVERC | 470 | 130 |
| 31 | CDELVRTHHILIDLRHCDLDAELRRLFRERYRC | 469 | 131 |
| 32 | AVHYEQPTIQIELRQCAVHYEQPTIQIELRQC | 468 | 132 |
| 33 | CHSDLDAELRRLFRERCDELVRTHHILIDLRHC | 466 | 133 |

The result of analysis for the K5-107 antibody is shown in Table 8 below. As a result, it was found that a sequence comprising VCSPDGPGGRCQCRALGSGMAVD (amino acid numbers 43-65 of SEQ ID NO: 2) was comprised in 9 out of the 20 peptides (peptide Nos. 1-6, 8, 9 and 17 shown in Table 8) (Table 8).

Accordingly, it was suggested that, in the hTROP-2 protein, the aforementioned peptide sequence region consisting of VCSPDGPGGRCQCRALGSGMAVD (amino acid numbers 43-65 of SEQ ID NO: 2) may be an epitope of the K5-107 antibody.

TABLE 8

Binding of K5-107 antibody to CLIPS pevides derived from human TROP-2 extracellular domains

| number | peptide | binding K5-107 | SEQ ID No |
|---|---|---|---|
| 1 | TNKMTVCSPDGPGGRCQCRALGSGMAVDCS | 2763 | 134 |
| 2 | NKMTVCSPDGPGGRCQCRALGSGMAVDCST | 2761 | 135 |
| 3 | KMTVCSPDGPGGRCQCRALGSGMAVDCSTL | 2752 | 136 |
| 4 | MTVCSPDGPGGRCQCRALGSGMAVDCSTLT | 272 | 137 |
| 5 | CPTNKMTVCSPDGPGGRCQCRALGSGMAVD | 2723 | 138 |
| 6 | TVCSPDGPGGRCQCRALGSGMAVDCSTLTS | 2720 | 139 |
| 7 | TCPTNKMTVCSPDGPGGRCQCRALGSGMAV | 2716 | 140 |
| 8 | VCSPDGPGGRCQCRALGSGMAVDCSTLTSK | 2689 | 141 |
| 9 | CSPDGPGGRCQCRALGSGMAVDCSTLTSKC | 2655 | 142 |
| 10 | CTCPTNKMTVCSPDGPGGRCQCRALSGSMA | 2655 | 143 |
| 11 | NCTCPTNKMTVCSPDGPGGRCQCRALGSGM | 2207 | 144 |
| 12 | DNCTCPTNKMTVCSPDGPGGRCQCRALGSG | 1816 | 145 |
| 13 | TNKMTVCSPDGPGGRCQCRALSGSMAVDCS | 1525 | 146 |
| 14 | CTVCSPDGPGGRCQCRALGSGMAVDASTLTSKC | 1118 | 147 |
| 15 | QDNCTCPTNKMTVCSPDGPGGRCQCRALGS | 574 | 148 |

TABLE 8-continued

Binding of K5-107 antibody to CLIPS pevides derived from human TROP-2 extracellular domains

| number | peptide | binding K5-107 | SEQ ID No |
|---|---|---|---|
| 16 | SPDGPGGRCQCRALGSGMAVDCSTLTSKCL | 561 | 149 |
| 17 | CTNKMTVCSPDGPGGRCQCRALGSGMAVDASTC | 380 | 150 |
| 18 | TVCSPDGPGGRCQCR | 312 | 151 |
| 19 | CAPKNARTLVRPSEHACARTLVRPSHEALVDNC | 284 | 152 |
| 20 | HSDLDAELRRLFRFRCHSDLDAELRRLFRERC | 272 | 153 |

The result of analysis for the K5-116-2-1 antibody is shown in Table 9 below. In this analysis, three types of peptide sequences, namely, a sequence comprising VCSPDGPGGRCQCRALGSGMAVD (amino acid numbers 43-65 of SEQ ID NO: 2) (peptide Nos. 1-7, and 15 shown in Table 9), a sequence comprising HHILIDLRHRPTAG (amino acid numbers 152-165 of SEQ ID NO: 2) (peptide Nos. 8-11, 16, 20, 22, 24, and 27-28 shown in Table 9), and a sequence comprising DLDAELRRLFRER (amino acid numbers 171-183 of SEQ ID NO: 2) (peptide Nos. 11-13, 17, 21, and 29 shown in Table 9) appeared several times (Table 9). Accordingly, it was suggested that, in the hTROP-2 protein, these three types of peptide sequence regions may be epitopes of the K5-116-2-1 antibody.

TABLE 9

Binding of K5-116-2-1 antibody to CLIPS peptides derived from human TROP-2 extracellular domains

| number | peptide | binding of K5-116-2-1 | SEQ ID No. |
|---|---|---|---|
| 1 | TVCSPDGPGGRCQCRALGSGMAVDCSTLTS | 2672 | 154 |
| 2 | NKMTVCSPDGPGGRCQCRALGSGMAVDCST | 2613 | 155 |
| 3 | TNKMTVCSPDGPGGRCQCRALGSGMAVDCS | 2482 | 156 |
| 4 | MTVCSPDGPGGRCQCRALGSGMAVDCSTLT | 2440 | 157 |
| 5 | KMTVCSPDGPGGRCQCRALGSGMAVDCSTL | 2423 | 158 |
| 6 | CPTNKMTVCSPDGPGGRCQCRALGSGMAVD | 2136 | 159 |
| 7 | PTNKMTVCSPDGPGGRCQCRALGSGMAVDC | 1723 | 160 |
| 8 | CAGAFNHSDLDAELRRCHHILIDLRHRPTAGAC | 1643 | 161 |
| 9 | CTHHILIDLRHRPTAGC | 1586 | 162 |
| 10 | CVHYEQPTIQIELRQNCHHILIDLRHRPTAGAC | 1504 | 163 |
| 11 | CHHILIDLRHRPTAGACHSDLDAELRRLFRERC | 1475 | 164 |
| 12 | HSDLDAELRRLFRERCHSDLDAELRRLFRERC | 1467 | 165 |
| 13 | CDAELRRLFRERYRLHCHSDLDAELRRLFRERC | 1462 | 166 |
| 14 | CDAELRRLFRERYRLHCPK | 1442 | 167 |
| 15 | VCSPDGPGGRCQCRALGSGMAVDCSTLTSK | 1432 | 168 |
| 16 | DLSLRCDELVRTHHILIDLRHRPTAGAFNH | 1421 | 169 |
| 17 | CDELVRTHHILIDLRHCDLDAELRRLFRERYRC | 1392 | 170 |
| 18 | CFQGRGGLDLRVRGEPC | 1376 | 171 |
| 19 | CDAELRRLFRERYRLHCDELVRTHHILIDLRHC | 1366 | 172 |
| 20 | CGLDLRVRGEPLQVERCHHILIDLRHRPTAGAC | 1342 | 173 |
| 21 | CHSDLDAELRRLFRERCHSDLDAELRRLFRERC | 1331 | 174 |
| 22 | CDELVRTHHILIDLRHCHHILIDLRHRPTAGAC | 1323 | 175 |

TABLE 9-continued

Binding of K5-116-2-1 antibody to CLIPS peptides derived from human TROP-2 extracellular domains

| number | peptide | binding of K5-116-2-1 | SEQ ID No. |
|---|---|---|---|
| 23 | CDAELRRLFRERYRLHCDELVRTHHILIDLRHC | 1266 | 176 |
| 24 | CHHILIDLRHRPTAGACRGEPLQVERTLIYYLC | 1229 | 177 |
| 25 | CSPDGPGGRCQCRAL | 1227 | 178 |
| 26 | CTVASPDGPGGRAQARCVHYEQPTIQIELRQNC | 1223 | 179 |
| 27 | CHHILIDLRHRPTAGACVHYEQPTIQIELRQNC | 1222 | 180 |
| 28 | LSLRCDELVRTHHILIDLRHRPTAGAFNHS | 1220 | 181 |
| 29 | CDELVRTHHILIDLRHCSDLDAELRRLFRERC | 1205 | 182 |

The results of analysis for the T5-86 and T6-16 antibodies are shown in Table 10 and Table 11 below, respectively. In these analyses, the antibodies strongly bound to a peptide comprising a sequence consisting of DPEGRFKARQCN (amino acid numbers 109-120 of SEQ ID NO: 2). The above-mentioned peptide sequence was comprised in several peptides binding to the T5-86 antibody as shown in Table 10, and it was comprised in several peptides binding to the T6-16 antibody as shown in Table 11. Moreover, in the analysis regarding the T5-86 antibody, other than the sequence comprising DPEGRFKARQCN[ ] (amino acid numbers 109-120 of SEQ ID NO: 2), a sequence comprising VCSPDGPGGRCQCRA (amino acid numbers 43-57 of SEQ ID NO: 2) appeared several times (as shown in Table 10). Furthermore, in the analysis regarding the T6-16 antibody as well, another sequence comprising HHILIDLRHRPTAG (amino acid numbers 152-165 of SEQ ID NO: 2) (shown in Table 11) was found several times. Accordingly, it was suggested that, in the hTROP-2 protein, two types of peptide sequence regions, namely, DPEGRFKARQCN (amino acid numbers 109-120 of SEQ ID NO: 2) and VCSPDGPGGRCQCRA (amino acid numbers 43-57 of SEQ ID NO: 2), may be epitopes of the K5-86 antibody. It was also suggested that, in the hTROP-2 protein, two types of peptide sequence regions, namely, DPEGRFKARQCN (amino acid numbers 109-120 of SEQ ID NO: 2) and HHILIDLRHRPTAG (amino acid numbers 152-165 of SEQ ID NO: 2), may be epitopes of the T6-16 antibody.

TABLE 10

Binding of TS-86 antibody to CLTS peptides derived from human TROP-2 extracellular domains

| number | peptide | binding of TS-86 | SEQ ID NO. |
|---|---|---|---|
| 1 | CYDPDADPEGRFKARQCADFEGRFKAPQANCTC | 2306 | 183 |
| 2 | PDCEPFGRFKARQCN | 2292 | 184 |
| 3 | CARPFGRFKARQANCPDAADPEGRFKARQANC | 2287 | 185 |
| 4 | VCSPDGPGRCQCRA | 2263 | 186 |
| 5 | CYDPDADPFGRFKARQCPFADPEGRFKARQANC | 2260 | 187 |
| 6 | CADPEGRFKARQANQTCTDPDADFEGRFKARQ | 2240 | 188 |
| 7 | CADPEGRFKARQANQTCTDPDADFEGRFKARQ | 2208 | 189 |
| 8 | DCDPEGRFKARQ | 2150 | 190 |
| 9 | CTVASPDGPGGRAQARCHSDLDAELRRLFRERC | 2086 | 191 |
| 10 | CDADPFGRFKARQANQCDADPEGRFKARQANQC | 2035 | 192 |
| 11 | DGRFKARQANQTSVAWCARTLVRPSEHALVDNC | 2019 | 193 |
| 12 | DADPEGRFKARQANQTCPDADPEDRFKARQANC | 1980 | 194 |
| 13 | CPDADPEGRFKARQANCPDADPEGFRKARQANC | 1950 | 195 |
| 14 | CSPEDGPGGRQCRAL | 1946 | 196 |

TABLE 10-continued

Binding of TS-86 antibody to CLTS peptides derived from human TROP-2 extracellular domains

| number | peptide | binding of TS-86 | SEQ ID NO. |
|---|---|---|---|
| 15 | CEGRFKARQANQTSVACEGRFKARQANQTSVAC | 1895 | 197 |
| 16 | CfVASPDGPGGRAQARCPDADPEGRFKARQANC | 1890 | 198 |
| 17 | CGLYDPDADPFGRFKACPDADPEGRFKARQANC | 1857 | 199 |
| 18 | DPDCDPEGRFKARQCNCQTSVCWCVNSVGVR | 1850 | 200 |
| 19 | CPEDRFKARQAQNQTSVCDELVRHHILIDIRHC | 1841 | 201 |
| 20 | CPDGPGGRAQARALGSCHSDLDAELRRLFRERC | 1830 | 202 |
| 21 | CTLVRPSEHALVDNDGCGRFKARQANQSVAWC | 1820 | 203 |
| 22 | CPDADPEGRFKARQANCYDPDADPEGRFKARQC | 1795 | 204 |
| 23 | CGLYDPDADPEDRFKACPEDRFKARQANQTSVC | 1793 | 205 |
| 24 | YDPDCDPEGRFKARC | 1775 | 206 |
| 25 | CPDADPDFRFKARQANCADPEFRFKARQAHQTC | 1773 | 207 |
| 26 | CDPEGRFKARQCNQ | 1772 | 208 |

TABLE 11

Binding of T6-16 antibody to CLIPS peptides derived from human TROP-2 extracellular domains

| number | peptide | binding of 16-16 | SEQ ID No. |
|---|---|---|---|
| 1 | CVNSVGVRRTDKGDLSCYDPDADPEGRFKARQC | 1072 | 209 |
| 2 | CSVGVRRTDKGDLSLRCYDPDADPEGRFKARQC | 786 | 210 |
| 3 | HSDLDAELRRLFRERCHSDLDAELRRLFRERC | 714 | 211 |
| 4 | CDELVRTHHILIDLRHCDLDAELRRLFRERYRC | 713 | 212 |
| 5 | CVNSVGVRRTDKGDLSLRCDELVRTHHILI | 688 | 213 |
| 6 | VRRTDKGDLSLRCDELVRTHHILIDLRHRP | 670 | 214 |
| 7 | CVERTLIYYLDEIPPKCHHILIDLRHRPTAGAC | 626 | 215 |
| 8 | CHHILIDLRHRPTAGACHSDLDAELRRLFRERC | 620 | 216 |
| 9 | CVNSVGVRRTDKGDLSCPDADPEGRFKARQANC | 611 | 217 |
| 10 | CVHYEQPTIQIELRQNCHHILIDLRHRPTAGAC | 602 | 218 |
| 11 | VGVRRTDKGDLSLRCDELVRTHHILIDLRH | 601 | 219 |
| 12 | CAGAFNHSDLDAELRRCHHILIDLRHRPTAGAC | 592 | 220 |
| 13 | CSVGVRRTDKGDLSLRCPDADPEGRFKARQANC | 585 | 221 |
| 14 | CVRPSEHALVDNDGLYCSVGVRRTDKGDLSLRC | 573 | 222 |
| 15 | CDAELRRLFRERYRLHCHSDLDAELRRLFRERC | 566 | 223 |
| 16 | CSVGVRRTDKGDLSLRCNDGLYDPDADPEGRFC | 559 | 224 |
| 17 | CVNSVGVRRTDKGDLSCGLYDPDADPEGRFKAC | 553 | 225 |
| 18 | CDLDAELRRLFRERYRCHSDLDAELRRLFRERC | 534 | 226 |
| 19 | CDELVRTHHILIDLRHCHHILIDLRHRPTAGAC | 534 | 227 |

TABLE 11-continued

Binding of T6-16 antibody to CLIPS peptides derived from human TROP-2 extracellular domains

| number | peptide | binding of 16-16 | SEQ ID No. |
|---|---|---|---|
| 20 | CAGAFNHSDLDAELRRCDLDAELRRLFRERYRC | 529 | 228 |
| 21 | CDAELRRLFRERYRLHCDELVRTHHILIDLRHC | 527 | 229 |
| 22 | CVHYEQPTIQIELRQNCDLDAELRRLFRERYRC | 526 | 230 |
| 23 | CHHILIDLRHRPTAGACVHYEQPTIQIELRQNC | 524 | 231 |
| 24 | CGVRRTDKGDLSLRADCGVRRTDKGDLSLRADC | 524 | 232 |
| 25 | CGLDLRVRGEPLQVERCHHILIDLRHRPTAGAC | 521 | 233 |
| 26 | CDLDAELRRLFRERYRCDELVRTHHILIDLRHC | 516 | 234 |

Example 311

[Sequencing of Variable Regions of Antibody Genes of Mouse Anti-hTROP-2 Antibodies (Clones K5-70, K5-107, K5-116-2-1 and T6-16)]

Total RNA was extracted from $3 \times 10^6$ mouse anti-TROP-2 monoclonal antibody-producing hybridomas, using TRIzol reagent (Invitrogen). With regard to the clone K5-70, clone K5-107 and clone K5-116-2-1, cDNA was synthesized employing SMARTer™ RACE cDNA Amplification kit (Clontech) according to the method included with the kit, using a mouse IgG H chain-specific primer (5'-TCCAK-AGTTCCA-3' (SEQ ID NO: 24)) and a mouse IgG L chain-specific primer (5'-GCTGTCCTGATC-3' (SEQ ID NO: 25)). With regard to the clone T6-16, cDNA was synthesized employing GeneRacer kit (Invitrogen) according to the method included with the kit, using an oligo dT primer. Genes encoding the variable regions (VH, VL) of the H and L chains of clone K5-70 (mouse IgG2a), clone K5-107 (mouse IgG1) and clone K5-116-2-1 (mouse IgG2a) were each cloned by a PCR method using the above-synthesized cDNA as a template. In this operation, 10× Universal Primer A Mix (UPM) included with SMARTer™ RACE cDNA Amplification kit was used as a 5'-primer. On the other hand, as a 3'-primer for VH amplification, a primer having a sequence specific to the mouse IgG H chain was used, and as a 3'-primer for VL amplification, a primer having a sequence specific to the mouse IgG L chain was used.

5'-Primer (10 × Universal Primer A Mix (UPM)):
Long (0.4 µM)
(SEQ ID NO: 26)
5'-CTAATACGACTCACTATAGGGCAAGCAGTGGTATCAACGCAGAGT-3'

Short (2 µM)
(SEQ ID NO: 27)
5'-CTAATACGACTCACTATAGGGC-3'

3'-Primer (R primer):
VH:
(SEQ ID NO: 28)
5'-GGGAARTARCCCTTGACCAGGCA-3'

(SEQ ID NO: 29)
5'-GGGAARTAGCCTTTGACAAGGCA-3'

VL:
(SEQ ID NO: 30)
5'-CACTGCCATCAATVCTCCACTTGACA-3'

Using each of the above-described primers, PCR was carried out under the following composition of reaction solution and reaction conditions. In addition, a R primer for amplification of VH cDNA was prepared by mixing the two above sequences with each other at an equimolar ratio and was then used.

| <Composition of reaction solution> | |
|---|---|
| Template cDNA: | 2.5 µL |
| 5 × PrimeSTAR buffer (Mg$^{2+}$ plus): | 10 µL |
| 2.5 mM dNTP: | 4 µL |
| PrimeSTAR HS DNA polymerase (2.5 U/µL): | 0.5 µL |
| 10 × Universal Primer A Mix (UPM): | 5 µL |
| R primer (10 µM): | 1 µL |
| Sterilized water: | 27 µL |
| Total: | 50 µL |

<Reaction Conditions>

A reaction was carried out at 94° C. (10 sec), and thereafter, a cycle consisting of "heat denaturation/dissociation at 98° C. (10 sec)→annealing at 60° C. (5 sec)→synthesis/elongation at 72° C. (60 sec)" was carried out 30 times in total. Finally, a reaction was carried out at 72° C. (3 min).

The synthesized VH and VL cDNAs were subcloned into a pMD20-T vector (Takara Bio Inc.), and the nucleotide sequences thereof were determined. The nucleotide sequences of a plurality of VH clones and VL clones were decoded, and nucleotide sequences specific to the variable regions of mouse H chain and L chain were identified. FIG. 33 and FIG. 34 show the consensus cDNA nucleotide sequences of the VH and VL of K5-70, and putative amino acid sequences. FIG. 35 and FIG. 36 show the consensus cDNA nucleotide sequences of the VH and VL of K5-107, and putative amino acid sequences. FIG. 37 and FIG. 38 show the consensus cDNA nucleotide sequences of the VH and VL of K5-116-2-1, and putative amino acid sequences.

Genes encoding the variable regions (VH, VL) of the H and L chains of clone T6-16 were cloned by a PCR method using the above-synthesized cDNA as a template. In this operation, a primer included with GeneRacer kit was used as a 5'-primer. On the other hand, as a 3'-primer for VH amplification, a primer having a sequence specific to the mouse IgG H chain was used, and as a 3'-primer for VL amplification, a primer having a sequence specific to the mouse IgG L chain was used.

```
5'-Primer (F primer):
                                        (SEQ ID NO: 31)
5'-CGACTGGAGCACGAGGACACTGA-3'

3'-Primer (R primer):
VH:
                                        (SEQ ID NO: 32)
5'-GCCAGTGGATAGACAGATGG-3'

VL:
                                        (SEQ ID NO: 33)
5'-GATGGATACAGTTGGTGCAGC-3'
```

Using each of the above-described primers, PCR was carried out under the following composition of reaction solution and reaction conditions.
<Composition of Reaction Solution>

| Template cDNA:                          | 1.0 μL  |
| --------------------------------------- | ------- |
| 5 × PrimeSTAR buffer (Mg$^{2+}$ plus):  | 10 μL   |
| 2.5 mM dNTP:                            | 4 μL    |
| PrimeSTAR HS DNA polymerase (2.5 U/μL): | 0.5 μL  |
| F primer (10 μM):                       | 3 μL    |
| R primer (10 μM):                       | 1.0 μL  |
| Sterilized water:                       | 30.5 μL |
| Total:                                  | 50 μL   |

<Reaction Conditions>

A cycle consisting of "heat denaturation/dissociation at 98° C. (10 sec)→annealing at 57° C. (10 sec)→synthesis/elongation at 72° C. (60 sec)" was carried out 35 times in total.

The synthesized VH and VL cDNAs were subcloned into a pCR™4 Blunt-TOPO® vector (Invitrogen), and the nucleotide sequences thereof were determined. The nucleotide sequences of a plurality of VH clones and VL clones were decoded, and nucleotide sequences specific to the variable regions of mouse H chain and L chain were identified. FIG. 39 and FIG. 40 show the consensus cDNA nucleotide sequences of the VH and VL of T6-16, and putative amino acid sequences.

Example 32

[Design of Humanized K5-70 Antibody]

Humanization of the variable regions (VH, VL) of the K5-70 antibody prepared in the previous Examples was carried out as follows according to the method of Queen et al. (Proc. Natl. Acad. Sci. USA 86: 10029-10033, 1989). First, the molecular modeling of the three-dimentional structure of each K5-70 antibody variable region was carried out using a computer. Subsequently, homology search was performed with the variable region sequences of human antibody genes. As a result, a cDNA sequence (DA980102 VH) with GenBank accession number of DA980102 was selected as an acceptor that provides a framework region (FR) necessary for humanization of the K5-70 VH (Genome Res. 16:55-65, 2006). Likewise, a cDNA sequence (L41174 VL) with GenBank accession number of L41174 was selected as an acceptor that provides a framework region (FR) necessary for humanization of the K5-70 VL (J. Biol. Chem. 270:12457-12465, 1995).

For humanization of the K5-70 VH, the CDR sequence of the K5-70 VH was substituted with the corresponding position of the DA980102 VH used as an acceptor. As a result of the analysis of the three-dimensional structure according to computer modeling, with regard to amino acid residues (isoleucine (I) at position 48, lysine (K) at position 66, alanine (A) at position 67, valine (V) at position 71 and threonine (T) at position 93) that are adjacent to the CDR of the K5-70 VH and are assumed to play important roles for the maintenance of the structure, those of the K5-70 VH were retained, and the residual FR region was substituted with the acceptor sequence. The amino acid residue position numbers in VH and VL were used in accordance with the definitions of Kabat et al. (Sequences of Proteins of Immunological Interests, Fifth edition, NIH Publication No. 91-3242, U.S. Department of Health and Human Services, 1991).

Moreover, the methionine (M) as an amino acid residue at position 82 of the acceptor sequence DA980102 VH was highly likely to be a special amino acid residue caused by somatic hypermutation. Thus, in order to decrease potential antigenicity, the aforementioned methionine was substituted with leucine (L) that is most common as an amino acid residue at position 82. An alignment of the amino acid sequences of the thus designed humanized K5-70 VH (HuK5-70 VH), K5-70 VH and DA980102 VH is shown in FIG. 41.

With regard to the design of humanized K5-70 VL as well, the same transplantation of a CDR sequence as described above was carried out. As an amino acid residue (lysine (K) at position 49) important for the maintenance of the structure of CDR, that of the K5-70 VL was retained, and the residual FR region was substituted with the acceptor sequence (HuK5-70 VL). An alignment of the amino acid sequences of the HuK5-70 VL, K5-70 VL and L41174 VL is shown in FIG. 42.

Example 33

[Design of Humanized T6-16 Antibody]

Humanization of the variable regions (VH, VL) of the T6-16 antibody prepared in the previous Examples was carried out as follows according to the method of Queen et al. (Proc. Natl. Acad. Sci. USA 86: 10029-10033, 1989). First, the molecular modeling of the three-dimentional structure of each T6-16 antibody variable region was carried out using a computer. Subsequently, homology search was performed with the variable region sequences of human antibody genes. As a result, a cDNA sequence (DA935238 VH) with GenBank accession number of DA935238 was selected as an acceptor that provides a framework region (FR) necessary for humanization of the T6-16 VH (Genome Res. 16:55-65, 2006). Likewise, a cDNA sequence (M99608 VL) with GenBank accession number of M99608 was selected as an acceptor that provides a framework region (FR) necessary for humanization of the T6-16 VL (J. Immunol. 149: 2518-2529, 1992).

For humanization of the T6-16 VH, the CDR sequence of the T6-16 VH was substituted with the corresponding position of the DA935238 VH used as an acceptor. As a result of the analysis of the three-dimensional structure according to computer modeling, with regard to amino acid residues (isoleucine (I) at position 48, alanine (A) at position 67 and lysine (K) at position 73) that are adjacent to the CDR of the T6-16 VH and are assumed to play important roles for the maintenance of the structure, those of the T6-16 VH were retained, and the residual FR region was substituted with the acceptor sequence (HuT6-16 VH1). In addition, the lysine residue (K) at position 73 was unlikely to have influence on appropriate formation of an antigen-binding site, and thus, an amino acid sequence, in which the lysine residue of the HuT6-16 VH1 was substituted with threonine (T) as a more generous amino acid residue, was designed, separately (HuT6-16 VH2). An alignment of the amino acid sequences of the thus designed humanized T6-16 VH (HuT6-16 VH1 and HuT6-16 VH2), T6-16 VH and DA935238 VH is shown in FIG. 43.

With regard to the design of humanized T6-16 VL as well, the same transplantation of a CDR sequence as described above was carried out. Amino acid residues important for the maintenance of the structure of CDR were retained also in the acceptor sequence, and as a FR sequence, the same sequence as the acceptor sequence was used (HuT6-16 VL). An alignment of the amino acid sequences of the HuT6-16 VL, T6-16 VL and L41174 VL is shown in FIG. 44.

Example 34

[Synthesis of Humanized K5-70 VH and VL Genes]

Genes encoding HuK5-70 VH and HuK5-70 VL were prepared as follows. The gene were synthesized based on an amino acid sequence in which a signal peptide sequence derived from K5-70 VH or VL had been added to the N-terminal side of each of the above-designed HuK5-70 VH and VL (Operon). In this gene synthetic operation, a Kozak sequence (ACC ACC) was added to the 5'-terminal side of the gene sequence of each of the synthesized HuK5-70 VH and HuK5-70 VL. In addition, an EcoRI site (GAA TTC) was added as a restriction enzyme site to the 5' end of the HuK5-70 VH, and an NheI site (GCT AGC) was added to the 3' end thereof. Likewise, an AgeI site (ACC GGT) was added as a restriction enzyme site to the 5' end of the HuK5-70 VL, and a BsiWI site (CGT ACG) was added to the 3' end thereof. The synthesized HuK5-70 VH gene and HuK5-70 VL gene were incorporated into a pCR2.1 vector (Invitrogen) according to TA cloning. The gene sequences of the HuK5-70 VH and VL prepared by the gene synthesis are shown in FIGS. 45 and 46, respectively.

Example 35

[Synthesis of Humanized T6-16 VH1, T6-16 VH2 and T6-16 VL Genes]

Genes encoding HuT6-16 VH1, HuT6-16 VH2 and HuT6-16 VL were prepared as follows. The gene were synthesized, based on an amino acid sequence in which a signal peptide sequence derived from T6-16 VH had been added to the N-terminal side of each of the above-designed HuT6-16 VH1 and HuT6-16 VH2, and an amino acid sequence in which a signal peptide sequence derived from T6-16 VL had been added to the N-terminal side of the HuT6-16 VL (Operon). In this gene synthetic operation, a Kozak sequence (ACC ACC) was added to the 5'-terminal side of the gene sequence of each of the synthesized HuT6-16 VH1, HuT6-16 VH2 and HuT6-16 VL. In addition, an EcoRI site (GAA TTC) was added as a restriction enzyme site to the 5' end of each of the HuT6-16 VH1 and HuT6-16 VH2, and an NheI site (GCT AGC) was added to the 3' end thereof. Likewise, an AgeI site (ACC GGT) was added as a restriction enzyme site to the 5' end of the humanized T6-16VL, and a BsiWI site (CGT ACG) was added to the 3' end thereof. The synthesized HuT6-16 VH1 gene, HuT6-16 VH2 gene and HuT6-16 VL gene were incorporated into a pCR2.1 vector (Invitrogen) according to TA cloning.

The gene sequences of the HuT6-16 VH1, HuT6-16 VH2 and HuT6-16 VL prepared by the gene synthesis are shown in FIGS. 47 to 49, respectively.

Example 36

[Construction of Gene Expression Vectors for Humanized K5-70 VH and VL Genes]

The HuK5-70 VH and VL genes, which had been each incorporated into the pCR2.1 vector (Invitrogen), were digested with the restriction enzymes EcoRI and NheI, and AgeI and BsiWI, respectively, and gene fragments were then recovered. Subsequently, the cleaved HuK5-70 VH gene was inserted into the EcoRI/NheI site of a pFUSE-CHIg-hG1 vector (InvivoGen) as an animal cell expression vector for the expression of a human IgG1 form (pFUSE-CHIg-HuK5-70), whereas the HuK5-70 VL gene was inserted into the AgeI/BsiWI site of a pFUSE2-CLIg-hk vector (Invivo-Gen) as a human Igκ form expression vector (pFUSE2-CLIg-HuK5-70). Thus, each construct was completed.

Example 37

[Construction of Gene Expression Vectors for Humanized T6-16 VH1, T6-16 VH2 and T6-16 VL Genes]

The T6-16 VH1 and T6-16 VH2 genes, which had been each incorporated into the pCR2.1 vector (Invitrogen), were digested with the restriction enzymes EcoRI and NheI, and the T6-16 VL gene was digested with the restriction enzymes AgeI and BsiWI. Then, gene fragments were recovered. Subsequently, the cleaved T6-16 VH1 gene was inserted into the EcoRI/NheI site of a pFUSE-CHIg-hG1 vector (InvivoGen) (pFUSE-CHIg-HuT6-16-1), and the T6-16 VH2 gene was also inserted into the EcoRI/NheI site of a pFUSE-CHIg-hG1 vector (pFUSE-CHIg-HuT6-16-2). The T6-16 VL gene was inserted into the AgeI/BsiWI site of a pFUSE2-CLIg-hk vector (InvivoGen) (pFUSE2-CLIg-HuT6-16). Thus, each construct was completed.

Example 38

[Establishment of 293F Cell Line Capable of Stably Expressing HuK5-70 Antibody, HuT6-16-1 Antibody and HuT6-16-2 Antibody]

293F cells (Invitrogen) were maintained and cultured in FreeStyle 293 Expression Medium (Invitrogen). Genes were introduced into the 293F cells using a 293 fectin reagent (Invitrogen) in accordance with protocols included therewith. That is, pFUSE-CHIg-HuK5-70 and pFUSE2-CLIg-HuK5-70 were both introduced into the 293F cells, and drug selection was then carried out using Zeocin (InvivoGen) and Blasticidin (InvivoGen), so as to establish a cell line capable of stably expressing a HuK5-70 antibody. Also, pFUSE-CHIg-HuT6-16-1 and pFUSE2-CLIg-HuT6-16 were both introduced into the 293F cells, and the above-mentioned drug selection was then carried out, so as to establish a cell line capable of stably expressing a HuT6-16-1 antibody. Also, pFUSE-CHIg-HuT6-16-2 and pFUSE2-CLIg-HuT6-16 were both introduced into the 293F cells, and the above-mentioned drug selection was then carried out, so as to establish a cell line capable of stably expressing a HuT6-16-2 antibody.

Example 39

[Purification of HuK5-70 Antibody, HuT6-16-1 Antibody and HuT6-16-2 Antibody Proteins]

The established antibody-expressing cell lines were each inoculated on FreeStyle 293 Expression Medium (Invitrogen) at a cell density of 1 to $2.5 \times 10^5$ cells/ml, and thereafter, roller bottle culture was carried out for 6 to 8 days. Thereafter, a culture supernatant was recovered, and each humanized antibody was then purified using rProtein A Sepharose Fast Flow (GE Healthcare) according to an ordinary method.

FIG. 50 shows the results obtained by confirming by Western blotting the expression of each humanized antibody protein in a culture supernatant of the 293F cells, in which a HuK5-70 antibody, a HuT6-16-1 antibody and a HuT6-16-2 antibody were expressed. Specifically, after completion of SDS-PAGE, each protein was transferred on a PVDF membrane (Immobilon-P, Millipore, IPVH00010). The membrane was blocked at room temperature for 30 minutes using TBS (Tris-buffered saline) containing 5% skim milk. The resultant was washed with 0.1% TBST (TBS containing 0.1% TWEEN 20) for 5 minutes three times, and was then allowed to react with a primary antibody.

Lane 1 indicates a culture supernatant of 293F cells into which no genes had been introduced (negative control), and lane 2 indicates a culture supernatant of 293F cells into which pFUSE-CHIg-HuK5-70 and pFUSE2-CLIg-HuK5-70 had been introduced. For detection of the heavy chain and light chain proteins of the HuK5-70 antibody, a biotin-labeled anti-human IgG F(ab')$_2$ antibody (Rockland) was used. Lane 3 indicates a culture supernatant of 293F cells into which pFUSE-CHIg-HuT6-16-1 and pFUSE2-CLIg-HuT6-16 had been introduced, and lane 4 indicates a culture supernatant of 293F cells into which pFUSE-CHIg-HuT6-16-2 and pFUSE2-CLIg-HuT6-16 had been introduced. The heavy chain proteins of the HuT6-16-1 antibody and the HuT6-16-2 antibody were detected with a biotin-labeled anti-human IgG Fc antibody (Rockland), whereas the light chain proteins of the HuT6-16-1 antibody and the HuT6-16-2 antibody were detected with a biotin-labeled anti-human IgG F(ab')$_2$ antibody (Rockland).

As a result, in all cases of the HuK5-70 antibody, the HuT6-16-1 antibody and the HuT6-16-2 antibody, the expression of heavy chain and light chain proteins was confirmed in each culture supernatant.

Moreover, FIG. 51 shows the results obtained by loading the purified HuK5-70 antibody, HuT6-16-1 antibody and HuT6-16-2 antibody on SDS-PAGE and then staining them with CBB. In all of the cases, a heavy chain of approximately 50 kD and a light chain of approximately 25 kD were detected under reducing conditions, and bands were confirmed in the same positions as the heavy chain and light chain detected by the above-described Western blotting. From these results, it was confirmed that a HuK5-70 antibody protein, a HuT6-16-1 antibody protein and a HuT6-16-2 antibody protein were generated.

Example 40

[Antigen Affinity of Humanized K5-70 Antibody (HuK5-70) and Humanized T6-16 Antibodies (HuT6-16-1 and HuT6-16-2)]

The antigen affinity of the purified HuK5-70 antibody, HuT6-16-1 antibody and HuT6-16-2 antibody was examined by methods using FACS and ELISA.

FACS was carried out, using HEK293-hTROP-2 cells in which a full-length human TROP-2 gene was stably expressed in HEK293 cells, and a pancreatic cancer cell line PK-59 which endogenously expressed a human TROP-2 protein on the cell surface. 100 µl of an antibody solution used as a primary antibody, which had been diluted to 1 µg/ml with a medium containing 10% FCS, was added to a suspension ($5 \times 10^5$ cells) of cells (HEK293-hTROP-2 cells or PK-59 cells), which had been removed from a culture dish by treatment with trypsin, and the obtained mixture was then incubated at 4° C. for 20 minutes. Thereafter, the resultant was washed with 1 ml of a medium containing 10% FCS. Then, secondary antibody (100 µl each), in which a phycoerythrin (PE)-labeled anti-mouse IgG antibody (BD Pharmingen) or a biotin-labeled anti-human IgG Fc antibody (Rockland) was diluted up to 200 times or 2000 times, respectively, was added to the resultant. The obtained mixture was incubated at 4° C. for 20 minutes, and was then washed with 1 ml of a medium containing 10% FCS again. In a case in which the biotin-labeled anti-human IgG Fc antibody was used as a secondary antibody, 100 µl of a labeling solution, in which streptavidin-labeled PE (BD Pharmingen) was diluted up to 400 times, was added thereto as a fluorescence labeling reagent. Thereafter, the obtained mixture was incubated at 4° C. for 20 minutes, and was then washed with 1 ml of a medium containing 10% FCS. Subsequently, the sample containing labeled cells was suspended in 1 ml of PBS containing 1% FCS and 2 mM EDTA, and the obtained suspension was then analyzed using FACSCalibur (Becton Dickinson). As a result, it was found that the HuK5-70 antibody showed reactivity equivalent to that of a mouse K5-70 antibody both in the HEK293-hTROP-2 cells and in the PK-59 cells. Likewise, the HuT6-16-1 antibody and the HuT6-16-2 antibody showed reactivity equivalent to that of a T6-16 antibody (FIG. 52).

Furthermore, antigen affinity was also examined by an ELISA method. ELISA was carried out using an ELISA plate which was coated with the recombinant protein of the hTROP-2 extracellular region as described in Example 3. Specifically, a 96-well plate (BD FALCON) was coated with a 50 µl/well recombinant protein of a hTROP-2 extracellular region that had been diluted with PBS to 0.5 µg/ml (at 4° C. overnight). Thereafter, the resultant was washed with a washing buffer (PBS containing 0.05% TWEEN 20), and a blocking buffer (PBS containing 2% skim milk and 0.05% TWEEN 20) was then added thereto (200 µl/well) to block it (at room temperature for 1 hour). The resultant was washed with a washing buffer. Thereafter, a HuK5-70 antibody, a HuT6-16-1 antibody, a HuT6-16-2 antibody, a K5-70 antibody and a T6-16 antibody were diluted with an ELISA buffer (PBS containing 1% skim milk and 0.025% TWEEN 20) in a concentration range from $3.05 \times 10^{-4}$ to 5 µg/ml, so as to prepare a series of two-fold dilution samples. The obtained dilution samples were each added in an amount of 50 µl/well to the above-described ELISA plate (at room temperature for 2 hours). The reaction product was washed with a washing buffer, and thereafter, a HRP-labeled goat anti-human κ chain antibody (SouthernBiotech) or a HRP-labeled sheep anti-mouse IgG antibody (GE Healthcare), each of which had been diluted to 2000 times with an ELISA buffer, was added (50 µl/well) as a detection antibody to the reaction product (at room temperature for 1 hour). After the mixture had been washed with a washing buffer, a TMB (3,3',5,5'-tetramethylbenzidine: SIGMA) substrate solution was added (50 µl/well) to the resultant to carry out a color reaction. Then, 1 M sulfuric acid (25 µl/well) was added to the reaction product to terminate the reaction. Using Microplate reader Model 550 (BioRad), an absorbance at 450 nm was measured with an absorbance at 655 nm used as a reference. As a result, the reaction curves of K5-70 and HuK5-70 were almost overlapped with each other, and the EC50 values thereof were 27 ng/ml and 22 ng/ml, respectively (FIG. 53). Also, the reaction curves of T6-16, HuT6-16-1 and HuT6-16-2 were almost overlapped with one another, and the EC50 values thereof were 30 ng/ml, 27 ng/ml and 27 ng/ml, respectively (FIG. 54). From these results, it became clear that all of the HuK5-70 antibody, the HuT6-16-1 antibody and the HuT6-16-2 antibody exhibit antigen affinity equivalent to that of the K5-70 or T6-16 antibody that is a parent antibody before humanization.

Example 41

[Anti-Tumor Activity of Humanized Anti-hTROP-2 Antibody (HuK5-70) In Vivo]

Subsequently, the anti-tumor activity of a HuK5-70 antibody in vivo was examined with xenograft treatment models using a human colon cancer cell line SW480, which endogenously expresses human TROP-2 on the cell surface. SW480 cells ($5 \times 10^6$ cells) were subcutaneously transplanted into the right flank of each of 7-week-old female NOD-scid mice (Day 1). When the mean tumor volume reached 100 mm$^3$, grouping was carried out (Day 9). From Day 9, intraperitoneal administration of the antibody was carried out at administration intervals of once every three days. On the $39^{th}$ day after the cancer cell transplantation (Day 39), the tumor volume of a control group (PBS administration, N=8) was 824.3±188.8 mm$^3$. On the other hand, the tumor volume of a HuK5-70 antibody administration group (10 mg/kg body weight, N=8) was 455.5±208.6 mm$^3$ (P<0.01 by Student's t-test), and thus, tumor formation was significantly inhibited in the HuK5-70 antibody administration group (inhibitory rate: 44.7%) (FIG. 55A). With regard to tumor weight, the tumor weight of the control group was 0.509±0.161 g. In contrast, in the HuK5-70 antibody administration group, the tumor weight of the control group was 0.272±0.162 g (P<0.05 by Student's t-test), showing an inhibitory rate of 46.6% (FIG. 55B).

Example 42

[Dose-Dependent Anti-Tumor Activity of Humanized Anti-hTROP-2 Antibodies (HuK5-70 and HuT6-16-2) on Xenograft Treatment Models Using Human Colon Cancer Cell Line SW480]

The dose-dependent anti-tumor activity of HuK5-70 and HuT6-16-2 antibodies was examined with xenograft treatment models using a human colon cancer cell line SW480. SW480 cells ($5 \times 10^6$ cells) were subcutaneously transplanted into the right flank of each of 7-week-old female NOD-scid mice (Day 1). On the $9^{th}$ day after the cancer cell transplantation (Day 9) at which the mean tumor volume reached 100 mm$^3$, the mice were divided into a control group (PBS administration group, N=8, 101.65±8.35 mm$^3$), a 1 mg/kg body weight HuK5-70 antibody administration group (N=8, 103.18±9.86 mm$^3$), a 5 mg/kg body weight HuK5-70 antibody administration group (N=8, 101.34±8.94 mm$^3$), a 10 mg/kg body weight HuK5-70 antibody administration group (N=8, 101.53±8.98 mm$^3$), a 1 mg/kg body weight HuT6-16-2 antibody administration group (N=8, 103.18±9.86 mm$^3$), a 5 mg/kg body weight HuT6-16-2 antibody administration group (N=8, 101.34±8.94 mm$^3$), and a 10 mg/kg body weight HuT6-16-2 antibody administration group (N=8, 101.53±8.98 mm$^3$) Then, from Day 9, intraperitoneal administration of each antibody was carried out at administration intervals of once every three days. On the $48^{th}$ day after the cancer cell transplantation (Day 48), the tumor volume of the control group was 754.67±276.05 mm$^3$. On the other hand, in the HuK5-70 antibody administration groups, the tumor volume of the 1 mg/kg body weight administration group was 521.81±183.45 mm$^3$ (inhibitory rate: 30.9%), the body volume of the 5 mg/kg body weight administration group was 258.78±137.02 mm$^3$ (inhibitory rate: 65.7%, P<0.01 by Student's t-test), and the tumor volume of the 10 mg/kg body weight administration group was 314.60±152.89 mm$^3$ (inhibitory rate: 58.3%, P<0.01 by Student's t-test) (FIG. 56A). In the HuT6-16-2 antibody administration groups, the tumor volume of the 1 mg/kg body weight administration group was 600.41±319.84 mm$^3$ (inhibitory rate: 20.4%), the tumor volume of the 5 mg/kg body weight administration group was 315.32±189.02 mm$^3$ (inhibitory rate: 58.2%, P<0.01 by Student's t-test), and the tumor volume of the 10 mg/kg body weight administration group was 270.79±266.71 mm$^3$ (inhibitory rate: 64.1%, P<0.01 by Student's t-test) (FIG. 57A). With regard to tumor weight on Day 48, the tumor weight of the control group was 0.422±0.201 g. On the other hand, in the HuK5-70 antibody administration groups, the tumor weight of the 1 mg/kg body weight administration group was 0.301±0.160 g (inhibitory rate: 28.7%), the tumor weight of the 5 mg/kg body weight administration group was 0.115±0.083 g (inhibitory rate: 72.7%, P<0.01 by Student's t-test), and the tumor weight of the 10 mg/kg body weight administration group was 0.244±0.181 g (inhibitory rate: 42.2%) (FIG. 56B). In the HuT6-16-2 antibody administration groups, the tumor weight of the 1 mg/kg body weight administration group was 0.422±0.255 g (inhibitory rate: 0%), the tumor weight of the 5 mg/kg body weight administration group was 0.247±0.151 g (inhibitory rate: 41.5%), and the tumor weight of the 10 mg/kg body weight administration group was 0.190±0.190 g (inhibitory rate: 53.1%, P<0.01 by Student's t-test) (FIG. 57B). From these results, it was confirmed that the HuK5-70 and HuT6-16-2 antibodies have dose-dependent anti-tumor activity.

Example 43

[Anti-Tumor Activity of Anti-hTROP-2 Mouse Monoclonal Antibodies K5-70 and T6-16 on Xenograft Treatment Models Using Human Ovarian Cancer Cell Line SK-OV-3]

The anti-tumor activity of K5-70 and T6-16 antibodies as parent antibodies in vivo was examined with xenograft treatment models using a human ovarian cancer cell line SK-OV-3, which endogenously expresses hTROP-2 on the cell surface. SK-OV-3 cells ($5 \times 10^6$ cells) were subcutaneously transplanted into the right flank of each of 7-week-old female nude mice (Day 1). On the $11^{th}$ day after the cancer cell transplantation (Day 11), individuals mice, in which clear tumor formation was observed (mean tumor volume: approximately 50 mm$^3$), were divided into groups. Then, from Day 11, intraperitoneal administration of each antibody was carried out at administration intervals of twice a week. On the $56^{th}$ day after the cancer cell transplantation (Day 56), the tumor volume of a control group (PBS administration, N=8) was 652.6±349.1 mm$^3$. On the other hand, the tumor volume of a K5-70 antibody administration group (10 mg/kg body weight, N=8) was 253.7±137.3 mm$^3$ (P<0.01 by Student's t-test), and thus, tumor formation was significantly inhibited (inhibitory rate: 61.1%); and the tumor volume of a T6-16 antibody administration group (10 mg/kg body weight, N=8) was 214.6±98.6 mm$^3$ (P<0.01 by Student's t-test), and thus, tumor formation was significantly inhibited (inhibitory rate: 67.1%) (FIG. 58A). With regard to tumor weight, the tumor weight of the control group was 0.413±0.218 g. In contrast, the tumor weight of the K5-70 antibody administration group was 0.194±0.112 (g) (P<0.05 by Student's t-test), showing an inhibitory rate of 53.0%; and the tumor weight of the T6-16 antibody administration group was 0.183±0.093 (g) (P<0.05 by Student's t-test), showing an inhibitory rate of 55.7% (FIG. 58B).

Example 44

[Anti-Tumor Activity of Anti-hTROP-2 Mouse Monoclonal Antibodies K5-70 and T6-16 on Xenograft Treatment Models Using Human Breast Cancer Cell Line MDA-MB-468]

Likewise, the anti-tumor activity of K5-70 and T6-16 antibodies in vivo was examined with xenograft treatment models using a human breast cancer cell line MDA-MB-468, which endogenously expresses hTROP-2 on the cell surface. MDA-MB-468 cells ($5 \times 10^6$ cells) were subcutaneously transplanted into the right flank of each of 7-week-old female nude mice (Day 1). On the $12^{th}$ day after the cancer cell transplantation (Day 12), individuals mice, in which clear tumor formation was observed (mean tumor volume: approximately 50 mm$^3$), were divided into groups. Then, from Day 12, intraperitoneal administration of each antibody was carried out at administration intervals of twice a week. On the $54^{th}$ day after the cancer cell transplantation (Day 54), the tumor volume of a control group (PBS administration, N=8) was 218.6±75.5 mm$^3$. On the other hand, the tumor volume of a K5-70 antibody administration group (10 mg/kg body weight, N=8) was 70.2±37.4 mm$^3$ (P<0.01 by Student's t-test), and thus, tumor formation was significantly inhibited (inhibitory rate: 67.9%); and the tumor volume of a T6-16 antibody administration group (10 mg/kg body weight, N=8) was 88.3±42.9 mm$^3$ (P<0.01 by Student's t-test), and thus, tumor formation was significantly inhibited (inhibitory rate: 59.6%) (FIG. 59A). With regard to tumor weight on Day 54, the tumor weight of the control group was 0.142±0.049 g. In contrast, the tumor weight of the K5-70 antibody administration group was 0.050±0.033 (g) (P<0.01 by Student's t-test), showing an inhibitory rate of 64.8%; and the tumor weight of the T6-16 antibody administration group was 0.077±0.046 (g) (P<0.05 by Student's t-test), showing an inhibitory rate of 45.8% (FIG. 59B).

Example 451

[Anti-Tumor Activity of Anti-hTROP-2 Mouse Monoclonal Antibodies K5-70 and T6-16 on Xenograft Treatment Models Using Human Lung Cancer Cell Line Calu-3]

Likewise, the anti-tumor activity of K5-70 and T6-16 antibodies in vivo was examined with xenograft treatment models using a human lung cancer cell line Calu-3, which endogenously expresses hTROP-2 on the cell surface. Calu-3 cells ($5 \times 10^6$ cells) were subcutaneously transplanted into the right flank of each of 7-week-old female nude mice (Day 1). On the $9^{th}$ day after the cancer cell transplantation (Day 9), individuals mice, in which clear tumor formation was observed (mean tumor volume: approximately 100 mm$^3$), were divided into groups. Then, from Day 9, intraperitoneal administration of each antibody was carried out at administration intervals of twice a week. On the $41^{st}$ day after the cancer cell transplantation (Day 41), the tumor volume of a control group (PBS administration, N=8) was 395.7±221.2 mm$^3$. On the other hand, the tumor volume of a K5-70 antibody administration group (10 mg/kg body weight, N=8) was 120.7±125.6 mm$^3$ (P<0.01 by Student's t-test), and thus, tumor formation was significantly inhibited (inhibitory rate: 69.5%); and the tumor volume of a T6-16 antibody administration group (10 mg/kg body weight, N=8) was 146.3±128.4 mm$^3$ (P<0.05 by Student's t-test), and thus, tumor formation was significantly inhibited (inhibitory rate: 63.0%) (FIG. 60A). With regard to tumor weight, the tumor weight of the control group was 0.301±0.189 g. In contrast, the tumor weight of the K5-70 antibody administration group was 0.08±0.085 (g) (P<0.01 by Student's t-test), showing an inhibitory rate of 73.5%; and the tumor weight of the T6-16 antibody administration group was 0.106±0.096 (g) (P<0.05 by Student's t-test), showing an inhibitory rate of 64.9% (FIG. 60B).

Example 46

[Anti-Tumor Activity of Anti-hTROP-2 Mouse Monoclonal Antibody K5-70 on Xenograft Prevention Models Using Human Bile Duct Cancer Cell Line TFK-1]

Likewise, the anti-tumor activity of a K5-70 antibody in vivo was examined with xenograft prevention models using a human bile duct cancer cell line TFK-1, which endogenously expresses hTROP-2 on the cell surface. TFK-1 cells ($5 \times 10^6$ cells) were subcutaneously transplanted into the right flank of each of 7-week-old female nude mice (Day 1), and from the same day, intraperitoneal administration of the antibody was initiated at administration intervals of twice a week. On the $31^{st}$ day after the cancer cell transplantation (Day 31), the tumor volume of a control group (PBS administration, N=5) was 1000.4±268.9 mm$^3$. On the other hand, the tumor volume of a K5-70 antibody administration group (10 mg/kg body weight, N=5) was 197.2±215 5 mm$^3$ (P<0.01 by Student's t-test), and thus, tumor formation was significantly inhibited (inhibitory rate: 80.3%) (FIG. 61A). With regard to tumor weight, the tumor weight of the control group was 0.443±0.070 g. In contrast, the tumor weight of the K5-70 antibody administration group was 0.063±0.052 (g) (P<0.01 by Student's t-test), showing an inhibitory rate of 85.8% (FIG. 61B).

Example 47

[Analysis of Avidity of HuK5-70 and HuT6-16-2 Antibodies]

The antigen-binding activity of HuK5-70 and HuT6-16-2 antibodies was examined according to an ELISA method (low-density antigen-coated ELISA) using a 96-well plate on which a low-density antigen has been coated. A recombinant hTACSTD2-Fc-His protein (Creative BioMart), which had been prepared to a concentration of 0.1 µg/mL with a 0.1 M acetate buffer (pH 5.3), was added in an amount of 50 µL/well to a 96-well plate, and coating was carried out at 4° C. overnight. Thereafter, the same analysis as that in Example 40 was carried out. Test antibodies were diluted with an ELISA buffer (PBS containing 1% skim milk and 0.025% TWEEN 20), so as to prepare samples with a concentration range from 20 µg/mL to a series of two-fold dilutions (15 samples) and to use them. As a result, it was found that the HuT6-16-2 antibody had binding activity that was almost equivalent to that of the T6-16 antibody (wherein their EC50 values were 49 ng/mL and 41 ng/mL, respectively), but that the EC50 value of the HuK5-70 antibody was approximately 20 times higher than that of the K5-70 antibody (wherein their EC50 values were 222 ng/mL and 12 ng/mL, respectively; FIG. 62).

Subsequently, the antigen-binding activity of HuK5-70 and K5-70 antibodies was examined by ELISA for analyzing a monovalent antigen-antibody reaction. Goat anti-human IgG (Fcγ specific) (Southern Biotech) which had been diluted to 1 μg/mL with a 0.1 M acetate buffer (pH 5.3) and Goat anti-mouse IgG (γ chain specific) (Southern Biotech) which had been diluted to 3 μg/mL were added in each amount of 50 μL/well to a 96-well plate. Thereafter, coating was carried out at 4° C. overnight. Thereafter, the reaction product was washed with a washing buffer (PBS containing 0.05% TWEEN 20), and a blocking buffer (PBS containing 2% skim milk and 0.05% TWEEN 20) was then added thereto (200 μL/well) to block it (at room temperature for 1 hour). The resultant was washed with a washing buffer. Thereafter, the test antibody, which had been diluted to 1 μg/mL with an ELISA buffer (PBS containing 1% skim milk and 0.025% TWEEN 20), was added in an amount of 50 μL/well to the above-described plate. During this operation, a HuK5-70 antibody was added to a well coated with Goat anti-human IgG (Fcγ specific), and a K5-70 antibody was added to a well coated with Goat anti-mouse IgG (γ chain specific). The mixture was left at rest at room temperature for 1 hour, and the reaction product was then washed with a washing buffer. The recombinant protein of the hTROP-2 extracellular region described in Example 3 (hTROP-2 EC) was diluted with an ELISA buffer to prepare samples with a concentration range from 5 μg/mL to a series of three-fold dilutions (10 samples). The thus obtained sample was added in each amount of 50 μL/well to the plate. The mixture was left at rest at room temperature for 1 hour, and the reaction product was then washed with a washing buffer. Then, anti-His (G-18) (Santa Cruz), which had been diluted to 2 μg/mL with an ELISA buffer, was added as a primary antibody to the reaction product (50 μL/well). The obtained mixture was left at rest at room temperature for 1 hour, and it was then washed with a washing buffer. Thereafter, HRP-labeled anti-rabbit IgG (GE Healthcare), which had been diluted to 1000 times with an ELISA buffer, was added as a secondary antibody to the reaction product (50 μL/well). The obtained mixture was left at rest at room temperature for 1 hour, and it was then washed with a washing buffer. Thereafter, a TMB (3,3',5,5'-tetramethylbenzidine: SIGMA) substrate solution was added in an amount of 50 μL/well to the resultant to carry out a color reaction. Then, 1 M sulfuric acid (25 μL/well) was added to the reaction product to terminate the reaction. Using Microplate reader Model 550 (BioRad), an absorbance at 450 nm was measured with an absorbance at 655 nm used as a reference. As a result, the EC50 values calculated from the binding curves of the hTROP-2EC protein with the K5-70 and HuK5-70 antibodies were 7 ng/mL and 6 ng/mL, respectively (FIG. 63). These results demonstrated that the HuK5-70 antibody and the K5-70 antibody have equivalent antigen affinity in a monovalent antigen-antibody reaction.

As described in Example 40, in an ELISA method using a 96-well plate on which a high-density antigen (0.5 μg/mL) had been coated (antigen-coated ELISA), the antigen affinity of the K5-70 antibody was equivalent to the antigen affinity of the HuK5-70 antibody (FIG. 53). Thus, it was considered that the antigen-binding activity of the HuK5-70 antibody that is relatively lower than that of the K5-70 antibody in an ELISA method, in which a low-density antigen (0.1 μg/mL) has been coated on a plate, may be caused by the fact that flexibility of the movement of two antigen-binding arms, namely, "avidity" is relatively lower in the HuK7-50 antibody than that in the K5-70 antibody.

Example 48

[Preparation and Characterization of Humanized K5-70 Antibody Mutants]

For the purpose of improving the "avidity" of a HuK5-70 antibody, the following experiment was carried out.

Whether the above-mentioned relatively low "avidity" of the HuK5-70 antibody is caused by VH or by VL was examined by the following experiment. First, genes encoding the H chain variable region (K5-70 VH) and L chain variable region (K5-70 VL) of a K5-70 antibody as a parent antibody were prepared by gene synthesis (Operon). During the gene synthesis, a Kozak sequence (ACC ACC) was added to the 5'-terminal side of the gene sequence of each of the K5-70 VH and the K5-70 VL. Further, an EcoRI site (GAA TTC) was added as a restriction enzyme site to the 5' end of the K5-70 VH, and an NheI site (GCT AGC) was added as a restriction enzyme site to the 3' end thereof. Likewise, an AgeI site (ACC GGT) was added as a restriction enzyme site to the 5' end of the K5-70 VL, and a BsiWI site (CGT ACG) was added as a restriction enzyme site to the 3' end thereof. The thus synthesized K5-70 VH gene and K5-70 VL gene were each incorporated into a pCR2.1 vector (Invitrogen). The gene sequences of the K5-70 VH and VL prepared by the gene synthesis are shown in FIG. 64 and FIG. 65, respectively. The K5-70 VH and K5-70 VL genes incorporated into the pCR2.1 vector were digested with the restriction enzymes EcoRI and NheI, and AgeI and BsiWI, respectively, and gene fragments were then recovered. Subsequently, the cleaved K5-70 VH gene was inserted into the EcoRI/NheI site of a pFUSE-CHIg-hG1 vector (InvivoGen) as an expression vector for the expression of a human IgG1 form, whereas the K5-70 VL gene was inserted into the AgeI/BsiWI site of a pFUSE2-CLIg-hk vector (InvivoGen) as a human Igκ form expression vector, thereby completing mouse-human chimeric constructs (pFUSE-CHIg-MuK5-70 and pFUSE2-CLIg-MuK5-70).

The thus prepared constructs, and the HuK5-70 H chain expression vector (pFUSE-CHIg-HuK5-70) and the HuK5-70 L chain expression vector (pFUSE2-CLIg-HuK5-70), which had been prepared in Example 36, were allowed to co-express in 293F cells (Invitrogen) by combinations 1 to 4 in the following table.

|   | H chain | L chain | Antibody generated | Remarks |
|---|---------|---------|--------------------|---------|
| 1 | pFUSE-CHIg-HuK5-70 | pFUSE2-CLIg-HuK5-70 | HuK5-70 antibody | Humanized K5-70 antibody |
| 2 | pFUSE-CHIg-HuK5-70 | pFUSE2-CLIg-MuK5-70 | HuVH/MuVL antibody | Humanized K5-70 VH/ Mouse K5-70 VL |

| H chain | L chain | Antibody generated | Remarks |
|---|---|---|---|
| 3 pFUSE-CHIg-MuK5-70 | pFUSE2-CLIg-HuK5-70 | MuVH/HuVL antibody | Mouse K5-70 VH/ Humanized K5-70 VL |
| 4 pFUSE-CHIg-MuK5-70 | pFUSE2-CLIg-MuK5-70 | ChK5-70 antibody | Chimeric K5-70 antibody |

Transfection of the expression vectors described above into 293F cells (Invitrogen) was carried out using NeoFection reagent (Astec) in accordance with the method described in instructions included therewith. After completion of the transfection, the resultant was cultured for 5 days using FreeStyle 293 Expression Medium (Invitrogen) at 37° C. in a $CO_2$ incubator with a $CO_2$ concentration of 8%. Thereafter, a culture supernatant was recovered. The antibody concentration in the culture supernatant was measured by a sandwich ELISA method. Specifically, Goat anti-human IgG (Fcγ specific) (Southern Biotech), which had been diluted to 1 µg/mL with PBS, was added in an amount of 50 µL/well to a 96-well plate. Thereafter, coating was carried out at 4° C. overnight. Thereafter, the reaction product was washed with a washing buffer (PBS containing 0.05% TWEEN 20), and a blocking buffer (PBS containing 2% skim milk and 0.05% TWEEN 20) was then added thereto (200 µL/well) to block it at room temperature for 1 hour. The resultant was washed with a washing buffer. Thereafter, a culture supernatant, which had been diluted to an appropriate dilution magnification with an ELISA buffer (PBS containing 1% skim milk and 0.025% TWEEN 20), was added in an amount of 50 µL/well to the above-described plate, and a reaction was then carried out at room temperature for 2 hours. As a standard preparation, a HuK5-70 antibody was used. The reaction product was then washed with a washing buffer. As a detection antibody, HRP-labeled Goat anti-human kappa (κ chain specific) (Southern Biotech), which had been diluted to 1,000 times with an ELISA buffer, was added in an amount of 50 µL/well to the reaction product, and a reaction was then carried out at room temperature for 1 hour. The reaction product was washed with a washing buffer, and thereafter, a TMB (3,3',5,5'-tetramethylbenzidine: SIGMA) substrate solution was added in an amount of 50 µL/well to the resultant to carry out a color reaction. Then, 1 M sulfuric acid (25 µL/well) was added to the reaction product to terminate the reaction. Using iMark Microplate reader (BioRad), an absorbance at 450 nm was measured with an absorbance at 655 nm used as a reference. The binding of the 4 types of antibodies contained in the culture supernatants to hTROP-2 was measured by the above-described low-density antigen-coated ELISA. As a result, it was found that the binding activity of a MuVH/HuVL antibody constituted with mouse K5-70 VH and HuK5-70 VL to hTROP-2 was equivalent to that of a ChK5-70 antibody, but that the binding activity of a HuVH/MuVL antibody constituted with HuK5-70 VH and mouse K5-70 VL was relatively lower than that of the ChK5-70 (FIG. 66). These results suggested that HuK5-70 VH be involved in the "avidity" of HuK5-70. Hence, in order to prepare modified antibodies, in which the "avidity" of the Huk5-70 antibody has been improved, amino acid substitution was carried out on the HuK5-70 VH. As is found from a alignment of the amino acid sequences of HuK5-70 VH and K5-70 VH as shown in FIG. 41, a total of 17 amino acids with amino acid numbers 5, 7, 11, 12, 13, 20, 38, 40, 44, 73, 75, 81, 82c, 83, 87, 108 and 109 are different between HuK5-70 VH and K5-70 VH (wherein the amino acid numbers are used in accordance with the definitions of Kabat et al. (1991)). The aforementioned amino acids of HuK5-70 VH were substituted with the corresponding amino acids of K5-70 VH, so that mutants were prepared according to gene synthesis. Then, an expression vector (a pFUSE-CHIg-HuK5-70 mutant) was prepared. According to the report by Landolfi et al. (J. Immunol. 166:1748, 2001), it has been reported that the amino acids at positions 11 and 38 of VH are involved in the avidity of a humanized antibody, and that avidity and biological activity are improved by substituting the two above amino acids with the corresponding amino acids derived from mouse. Hence, a double mutant comprising substitution of the amino acids at positions 11 and 38 was also prepared. The names of the thus prepared 18 types of HuK5-70 VH mutants and their amino acid sequences are shown in FIG. 67.

The prepared 18 types of HuK5-70 VH mutants (expression vectors for pFUSE-CHIg-HuK5-70 mutants) were each combined with a HuK5-70 L chain expression vector (pFUSE2-CLIg-HuK5-70), and the thus obtained expression vectors were each transfected into HEK293 cells. Then, using the obtained culture supernatant, the binding activity of each amino acid substitution antibody to hTROP-2 was examined by low-density antigen-coated ELISA. As a result, among the 18 types of HuK5-70 VH mutants, an R44G mutant, in which the R (arginine) at position 44 of HuK5-70 VH had been substituted with G (glycine) (HuK5-70 R44G; which is hereafter referred to as HuK5-70-2), was observed to have an apparently improved antigen-binding activity (FIG. 68). The sequence of a HuK5-70 VH R44G (hereinafter referred to as HuK5-70 VH2) gene is shown in FIG. 69.

Example 49

[Purification and Characterization of HuK5-70-2 Antibody]
The HuK5-70-2 antibody that is a HuK5-70 R44G mutant antibody was purified as follows. That is, pFUSE-CHIg-HuK5-70 R44G and pFUSE2-CLIg-HuK5-70 were transfected into 293F cells, and the resultant was then cultured for 5 days. Thereafter, a culture supernatant was recovered. The HuK5-70-2 antibody was purified from the recovered culture supernatant, using rProtein A sepharose Fast Flow (GE Healthcare). The purified HuK5-70-2 antibody was loaded on SDS-PAGE under reducing conditions. As a result, an H chain of approximately 50 kDa and an L chain of approximately 25 kDa were found. The purity of each antibody was 95% or more (FIG. 70).

The binding activity of the purified HuK5-70-2 and HuK5-70 antibodies to hTROP-2 was examined by high-density antigen-coated ELISA and low-density antigen-coated ELISA. The affinity of the antibodies was examined by the high-density antigen-coated ELISA (using a 96-well plate which was coated with 1 µg/mL hTROP-2). As a result, it was found that the binding curve of the HuK5-70 antibody was almost overlapped with the binding curve of the HuK5-70-2 antibody, and that their affinity was equivalent to each other. Subsequently, the avidity of the antibodies was examined by the low-density antigen-coated ELISA (using a 96-well plate which was coated with 0.1 µg/mL hTROP-2). As a result, it was found that, as same the case with using a culture supernatant, the antigen-binding activity of the HuK5-70-2 antibody was clearly higher than the antigen-binding activity of the HuK5-70 antibody (FIG. 71). Specifically, the $EC_{50}$ value of a K5-70 antibody was 11.4 ng/mL, that of a HuK5-70 antibody was 33.4 ng/mL, and that of a HuK5-70-2 antibody was 11.4 ng/mL. Thus, it was demonstrated that the HuK5-70-2 antibody has an improved avidity in comparison with the HuK5-70 antibody, and that the HuK5-70-2 antibody has activity equivalent to that of the K5-70 antibody.

Example 50

[Measurement of Antibody-Dependent Cellular Cytotoxicity (ADCC) Activity of Humanized Anti-hTROP-2 Antibodies]
(1) Preparation of Target Cell Solution As target cells, a human colon cancer cell line SW480, a human pancreatic cancer cell line PK-59, and a human prostate cancer cell line PC-3, each of which endogenously expresses hTROP-2, were used. Target cells cultured on a 10-cm cell culture dish were harvested from the plate by treatment with trypsin, and were then suspended in an assay medium. A Leivovitz L-15 medium (for SW480 cells) or an RPMI-1640 medium (for PK-59 and PC-3 cells), to which 0.5% FBS had been added, was used for ADCC assay. After completion of centrifugation (at 1000 rpm for 3 minutes at room temperature), pellets were prepared at a cell density of $2 \times 10^5$ cells/mL with the same medium as that used above, and thus a target cell solution was prepared.
(2) Separation of Human Peripheral Blood Mononuclear Cells Healthy venous blood was collected with heparin, and was then diluted to 2 times with PBS. Thereafter, the diluted blood was layered on Lymphoprep (Daiichi Kagaku Yakuhin K. K.) and was then centrifuged (at room temperature at 750 rpm for 5 minutes, and then at 2000 rpm for 20 minutes). After completion of the centrifugation, mononuclear cells (healthy peripheral blood monocytes) were recovered from an intermediate layer fraction, and were then washed with PBS three times. Thereafter, a cell suspension was prepared with an assay medium, and the prepared cells were used as effector cells.
(3) ADCC Activity of Humanized Anti-hTROP-2 Antibodies (HuK5-70, HuK5-70-2 and HuT6-16-2 Antibodies)

100 µL ($2 \times 10^4$ cells/well) of the prepared target cell solution was dispensed in a 96-well flat bottom plate (manufactured by FALCON). Subsequently, human peripheral blood mononuclear cells (effector cells) were added to the plate, so that the ratio between the effector cells and the target cells could be 40:1. Thereafter, humanized anti-hTROP-2 antibodies (HuK5-70, HuK5-70-2 and HuT6-16-2 antibodies) were each added as test antibodies to the plate to a final concentration of 0.1 to 30 µg/mL. The mixture was adjusted to a total amount of 200 µL, and it was then cultured in a $CO_2$ incubator (at 37° C. in 5% $CO_2$) for 6 hours. After completion of the culture, the activity of lactate dehydrogenase released from the cytoplasm of the target cells damaged by the effector cells was measured using Cytotoxicity Detection Kit (LDH) (Roche, Cat. No. 11 644 793 001) in accordance with protocols included with the kit, and ADCC activity was then evaluated using the measurement result as an indicator.

As shown in FIGS. 72A to 72C, it became clear that the HuK5-70 and HuT6-16-2 antibodies dose-dependently exhibit ADCC activity on a human colon cancer cell line SW480 (FIG. 72A), a human pancreatic cancer cell line PK-59 (FIG. 72B) and a human prostate cancer cell line PC-3 (FIG. 72C), each of which expresses hTROP-2 on the cell surface. In addition, as shown in FIGS. 72B and 72C, it became clear that the HuK5-70-2 antibody exhibits ADCC activity on the pancreatic cancer cell line PK-59 and the human prostate cancer cell line PC-3, wherein the above-mentioned ADCC activity is stronger than that of the HuK5-70 antibody. As mentioned above, the HuK5-70-2 antibody is an antibody whose binding ability (avidity) to hTROP-2 has been improved by substituting the R (arginine) at position 44 of HuK5-70 VH with G (glycine). It was demonstrated that the avidity of the HuK5-70-2 antibody, which had been improved when compared with the HuK5-70 antibody, is reflected in ADCC activity. Therefore, it is assumed that the HuK5-70-2 antibody has excellent anti-tumor activity even in vivo, as with the HuK5-70 antibody (wherein the HuK5-70-2 antibody can preferably have anti-tumor activity higher than that of the HuK5-70 antibody). From the above-described results, it was suggested that the HuK5-70, HuK5-70-2 and HuT6-16-2 antibodies become therapeutic antibodies useful for cancer that expresses hTROP-2 on the cell surface.

INDUSTRIAL APPLICABILITY

The present invention is able to provide an antibody, which specifically reacts with hTROP-2 and has high anti-tumor activity in vivo, and specifically, a monoclonal antibody having high anti-tumor activity in vivo at a low dose, and particularly, such an antibody, which is a humanized antibody. In addition, the present invention is able to provide a hybridoma, which produces the antibody, a fragment of the antibody, a complex of the antibody or the like and various types of drugs, a pharmaceutical composition for diagnosing or treating a tumor, a method for detecting a tumor, and a kit for detecting or diagnosing a tumor.

SEQUENCE LISTING FREE TEXT

SEQ ID NO: 3 Synthetic DNA
SEQ ID NO: 4 Synthetic DNA
SEQ ID NO: 5 Synthetic DNA
SEQ ID NO: 6 Synthetic DNA
SEQ ID NO: 7 Synthetic DNA
SEQ ID NO: 8 Synthetic DNA
SEQ ID NO: 9 Synthetic DNA
SEQ ID NO: 10 Synthetic DNA
SEQ ID NO: 11 Synthetic DNA
SEQ ID NO: 12 Synthetic DNA
SEQ ID NO: 13 Synthetic DNA
SEQ ID NO: 14 Synthetic DNA
SEQ ID NO: 15 Synthetic DNA
SEQ ID NO: 16 Synthetic DNA
SEQ ID NO: 17 Synthetic DNA
SEQ ID NO: 18 Synthetic DNA
SEQ ID NO: 19 Synthetic DNA
SEQ ID NO: 20 Synthetic DNA
SEQ ID NO: 21 Synthetic DNA
SEQ ID NO: 22 Synthetic DNA
SEQ ID NO: 23 Synthetic DNA
SEQ ID NO: 24 Synthetic DNA
SEQ ID NO: 25 Synthetic DNA
SEQ ID NO: 26 Synthetic DNA SEQ ID NO: 27 Synthetic DNA
SEQ ID NO: 28 Synthetic DNA
SEQ ID NO: 29 Synthetic DNA
SEQ ID NO: 30 Synthetic DNA
SEQ ID NO: 31 Synthetic DNA
SEQ ID NO: 32 Synthetic DNA
SEQ ID NO: 33 Synthetic DNA
SEQ ID NO: 74 Recombinant DNA
SEQ ID NO: 75 Synthetic construct (recombinant protein)
SEQ ID NO: 76 Recombinant DNA
SEQ ID NO: 77 Synthetic construct (recombinant protein)
SEQ ID NO: 78 Recombinant DNA
SEQ ID NO: 79 Synthetic construct (recombinant protein)
SEQ ID NO: 80 Recombinant DNA
SEQ ID NO: 81 Synthetic construct (recombinant protein)
SEQ ID NO: 82 Recombinant DNA
SEQ ID NO: 83 Synthetic construct (recombinant protein)
SEQ ID NO: 92 Recombinant protein
SEQ ID NO: 93 Recombinant protein
SEQ ID NO: 94 Recombinant protein
SEQ ID NO: 95 Recombinant protein
SEQ ID NO: 96 Recombinant protein
SEQ ID NO: 97 Recombinant protein
SEQ ID NO: 98 Recombinant protein
SEQ ID NO: 99 Recombinant DNA
SEQ ID NO: 100 Recombinant DNA

The invention claimed is:

1. An isolated antibody that binds human TROP-2 comprising a heavy chain variable region comprising the amino acid sequence of SEQ ID NO: 92 or SEQ ID NO: 98, and a light chain variable region comprising the amino acid sequence of SEQ ID NO: 93, wherein the heavy chain variable region and the light chain variable region together form an antigen-binding site.

2. The isolated antibody of claim 1, wherein said antibody comprises the heavy chain variable region comprising the amino acid sequence of SEQ ID NO:92.

3. The isolated antibody of claim 1, wherein the antibody comprises the heavy chain variable region comprising the amino acid sequence of SEQ ID NO:98.

4. The isolated antibody of claim 1, wherein the antibody is a monoclonal antibody.

5. The isolated antibody of claim 1 conjugated to an agent having anti-tumor activity and/or tumor cell killing activity.

6. An antibody antigen-binding fragment, comprising (i) the amino acid sequence of SEQ ID NO: 92 or SEQ ID NO: 98 and (ii) the amino acid sequence of SEQ ID NO: 93, wherein (i) and (ii) together form an antigen-binding site.

7. The antibody antigen-binding fragment of claim 6 conjugated to an agent having anti-tumor activity and/or tumor cell killing activity.

8. A pharmaceutical composition comprising an antibody that binds human TROP-2 and a pharmaceutically acceptable carrier, wherein said antibody comprises (i) a heavy chain variable region consisting of the amino acid sequence of SEQ ID NO: 92 or SEQ ID NO: 98, and (ii) a light chain variable region consisting of the amino acid sequence of SEQ ID NO: 93, wherein the heavy chain variable region and the light chain variable region together form an antigen-binding site.

9. The pharmaceutical composition of claim 8, wherein the antibody is conjugated to an agent having anti-tumor activity and/or tumor cell killing activity.

10. A pharmaceutical composition comprising an antibody antigen-binding fragment and a pharmaceutically acceptable carrier, wherein said antibody antigen-binding fragment comprises (i) the amino acid sequence of SEQ ID NO: 92 or SEQ ID NO: 98 and (ii) the amino acid sequence of SEQ ID NO: 93, wherein (i) and (ii) together form an antigen-binding site.

11. The pharmaceutical composition of claim 10, wherein the antibody antigen-binding fragment is conjugated to an agent having anti-tumor activity and/or tumor cell killing activity.

12. A diagnostic agent comprising an antibody that binds human TROP-2, said antibody comprising (1) a heavy chain variable region consisting of the amino acid sequence of SEQ ID NO: 92 or SEQ ID NO: 98 and (2) a light chain variable region consisting of the amino acid sequence of SEQ ID NO: 93, and a detectable label, wherein the heavy chain variable region and the light chain variable region together form an antigen-binding site.

13. A diagnostic agent comprising an antibody antigen-binding fragment comprising (i) the amino acid sequence of SEQ ID NO: 92 or SEQ ID NO: 98 and (ii) the amino acid sequence of SEQ ID NO: 93, and a detectable label, wherein (i) and (ii) together form an antigen-binding site.

14. A kit for treating, diagnosing or detecting a tumor, comprising the isolated antibody of claim 1.

* * * * *